United States Patent [19]
Blizzard et al.

[11] Patent Number: 5,496,816
[45] Date of Patent: Mar. 5, 1996

[54] CARBAPENEM ANTIBACTERIAL COMPOUNDS, COMPOSITIONS CONTAINING SUCH COMPOUNDS AND METHODS OF TREATMENT

[75] Inventors: Timothy A. Blizzard, Rahway; Ronald W. Ratcliffe, Matawan; Sherman T. Waddell, Wetfield; Sandra P. Szumiloski, Edison; Robert R. Wilkening, Maplewood; Kenneth J. Wildonger, Bridgewater, all of N.J.

[73] Assignee: Merck & Co., Inc., Rahway, N.J.

[21] Appl. No.: 359,770

[22] Filed: Dec. 20, 1994

Related U.S. Application Data

[63] Continuation-in-part of Ser. No. 213,314, Mar. 14, 1994, abandoned.

[51] Int. Cl.⁶ .................... A61K 31/40; C07D 487/04
[52] U.S. Cl. ................................. 514/210; 540/350
[58] Field of Search ........................ 540/350; 514/210

[56] References Cited

U.S. PATENT DOCUMENTS

| | | |
|---|---|---|
| 3,950,357 | 4/1976 | Kahan et al. . |
| 4,122,086 | 10/1978 | Hall et al. . |
| 4,150,145 | 4/1979 | Christensen et al. . |
| 4,168,314 | 9/1979 | Christensen et al. . |
| 4,194,047 | 3/1980 | Christensen et al. . |
| 4,212,807 | 7/1980 | Ratcliffe . |
| 4,217,453 | 8/1980 | Christensen et al. . |
| 4,218,462 | 8/1980 | Christensen et al. . |
| 4,232,036 | 11/1980 | Christensen et al. . |
| 4,235,917 | 11/1980 | Christensen et al. . |
| 4,235,922 | 11/1980 | Ratcliffe et al. . |
| 4,260,618 | 4/1981 | Christensen et al. . |
| 4,262,010 | 4/1981 | Christensen et al. . |
| 4,269,772 | 5/1981 | Melillo et al. . |
| 4,273,709 | 6/1981 | Christensen et al. . |
| 4,275,207 | 6/1981 | Ratcliffe et al. . |
| 4,282,148 | 8/1981 | Liu et al. . |
| 4,290,947 | 9/1981 | Christensen et al. . |
| 4,298,741 | 11/1981 | Christensen et al. . |
| 4,309,346 | 1/1982 | Christensen et al. . |
| 4,310,538 | 1/1982 | Christensen et al. . |
| 4,312,871 | 1/1982 | Christensen et al. . |
| 4,318,912 | 3/1982 | Christensen et al. . |
| 4,335,043 | 6/1982 | Christensen et al. . |
| 4,347,367 | 8/1982 | Christensen et al. . |
| 4,357,342 | 11/1982 | Christensen et al. . |
| 4,369,187 | 1/1983 | Christensen et al. . |
| 4,378,315 | 3/1983 | Christensen et al. . |
| 4,383,946 | 5/1983 | Christensen et al. . |
| 4,397,861 | 8/1983 | Christensen et al. . |
| 4,424,230 | 1/1984 | Christensen et al. . |
| 4,428,960 | 1/1984 | Heck . |
| 4,565,808 | 1/1986 | Andrus et al. . |
| 4,610,820 | 9/1986 | Christensen et al. . |
| 4,650,794 | 3/1987 | Christensen et al. . |
| 4,680,292 | 7/1987 | Christensen et al. . |
| 4,707,547 | 11/1987 | Christensen et al. . |
| 4,725,594 | 2/1988 | Christensen et al. . |
| 4,729,993 | 3/1988 | Christensen et al. . |
| 4,736,025 | 4/1988 | Christensen et al. . |
| 4,739,048 | 4/1988 | Christensen et al. . |
| 4,745,188 | 5/1988 | Christensen et al. . |
| 4,748,162 | 5/1988 | Leanza et al. . |
| 4,782,051 | 11/1988 | Christensen et al. . |
| 4,783,453 | 11/1988 | Christensen et al. . |
| 4,820,817 | 5/1989 | Christensen et al. . |
| 4,833,167 | 5/1989 | Christensen et al. . |
| 4,840,946 | 6/1989 | Habich et al. . |
| 4,892,869 | 1/1990 | Christensen et al. . |
| 4,952,397 | 8/1990 | Heck et al. . |
| 4,992,542 | 2/1991 | Christensen et al. . |
| 5,021,565 | 6/1991 | Ratcleffe et al. . |
| 5,021,566 | 6/1991 | Christensen et al. . |
| 5,077,287 | 12/1991 | Ternansky . |
| 5,140,030 | 8/1992 | Christensen et al. . |

FOREIGN PATENT DOCUMENTS

| | | |
|---|---|---|
| 0010316 | 4/1980 | European Pat. Off. . |
| 0010317 | 4/1980 | European Pat. Off. . |
| 017992A1 | 10/1980 | European Pat. Off. . |
| 0030031 | 6/1981 | European Pat. Off. . |
| 0054917B1 | 6/1982 | European Pat. Off. . |
| 0071908A1 | 7/1982 | European Pat. Off. . |
| 060612A1 | 9/1982 | European Pat. Off. . |
| 0061231 | 9/1982 | European Pat. Off. . |
| 0167139A1 | 1/1986 | European Pat. Off. . |
| 170073A1 | 2/1986 | European Pat. Off. . |
| 0184842A2 | 6/1986 | European Pat. Off. . |
| 0184843A1 | 6/1986 | European Pat. Off. . |
| 0230792B1 | 8/1987 | European Pat. Off. . |
| 0235823A2 | 9/1987 | European Pat. Off. . |
| 0268963A1 | 6/1988 | European Pat. Off. . |
| 0472062A1 | 2/1992 | European Pat. Off. . |
| 0050334B1 | 4/1992 | European Pat. Off. . |
| 0495584A2 | 7/1992 | European Pat. Off. . |
| 0504612A2 | 9/1992 | European Pat. Off. . |
| 0527686A1 | 2/1993 | European Pat. Off. . |
| 0560365A1 | 9/1993 | European Pat. Off. . |
| 0587436A1 | 3/1994 | European Pat. Off. . |
| 3640715A1 | 6/1988 | Germany . |
| 59-46288A2 | 3/1984 | Japan . |

OTHER PUBLICATIONS

Abstract from the 33rd ICAAC, Oct. 1993.
J. Med. Chem. 1993, vol. 36, pp. 2332–2334.
J. Med. Chem. 1993, vol. 36, pp. 1971–1976.
Tetrahedron Letter, vol. 39(15), pp. 2531–2549 (1983).
08/213,314 Mar, 14, 1994 Blizzard, et al.

*Primary Examiner*—Rebecca Cook
*Attorney, Agent, or Firm*—Richard C. Billups; Mark R. Daniel

[57] ABSTRACT

Carbapenems of the formula:

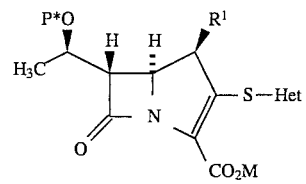

are disclosed as useful antibacterial agents.

Pharmaceutical compositions and methods of use are also disclosed.

34 Claims, No Drawings

CARBAPENEM ANTIBACTERIAL COMPOUNDS, COMPOSITIONS CONTAINING SUCH COMPOUNDS AND METHODS OF TREATMENT

CROSS REFERENCE TO RELATED APPLICATIONS

This application is a continuation in pan of application Ser. No. 08/213,314, filed on Mar. 14, 1994, now abandoned, priority of which is claimed hereunder.

BACKGROUND OF THE INVENTION

The present invention relates to antibacterial agents of the carbapenem class in which the five membered pyrroline ring of the carbapenem nucleus is substituted by various cationic —S—heteroaryl substituents.

Thienamycin was an early carbapenem antibacterial agent having a broad spectrum; it has the following formula:

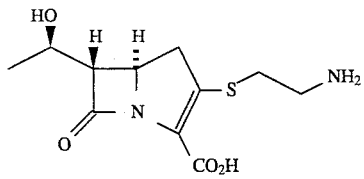

Later, N-formimidoyl thienamycin was discovered; it has the formula:

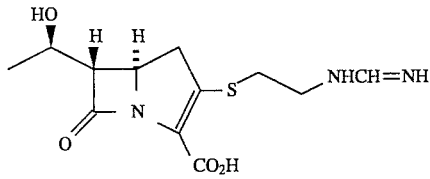

The carbapenems of the present invention are useful against gram positive microorganisms, especially methicillin resistant *Staphylococcus aureus* (MRSA), methicillin resistant *Staphylococcus epidermidis* (MRSE), and methicillin resistant coagulase negative Staphylococci (MRCNS). Additionally, strains of vancomycin resistant enterococcus (VRE) have recently been reported. The antibacterial compounds of the present invention comprise an important contribution to therapy of these difficult to control pathogens. There is an increasing need for agents effective against such pathogens (MRSA/MRCNS and VRE) which are at the same time safe, i.e., relatively free from undesirable side effects.

Also, certain carbapenems of the present invention have a relatively low level of inactivation by dehydropeptidase and penicillinase, two enzymes known to reduce the serum levels of conventional beta lactam antibiotics.

SUMMARY OF THE INVENTION

The compounds of the invention are represented by formula I:

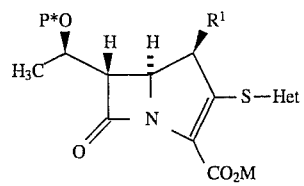

wherein:

$R^1$ represents H or methyl;

$CO_2M$ represents a carboxylic acid, a carboxylate anion, a pharmaceutically acceptable ester group or a carboxylic acid protected by a protecting group;

$P^*$ represents H or a hydroxyl protecting group;

Het has substituent groups which contain from one to three positively charged atoms and is selected from:

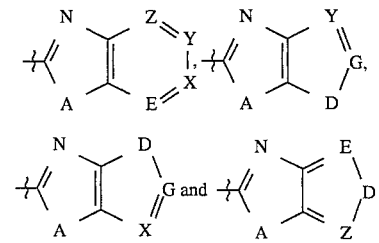

wherein:

A is O or S;

D is O, S or $NR^a$;

E, G, X, Y and Z represent CR or N;

each R is independently selected from: —$R^*$; hydrogen; halo; —CN; —$NO_2$; —$OR^c$; —$SR^c$; —$CONR^aR^b$; —$COOR^h$; —$SOR^c$; —$SO_2R^c$; —$SO_2NR^aR^b$; —$NR^aSO_2R^b$; —$COR^a$; —$OCOR^a$; —$OCONR^aR^b$; —$NR^aCONR^bR^c$; —$NR^aCO_2R^h$; —$OCO_2R^h$; —$C_{1-6}$ straight- or branched-chain alkyl, unsubstituted or substituted with one to four $R^d$ groups; and —$C_{3-7}$ cycloalkyl, unsubstituted or substituted with one to four $R^d$ groups, with the proviso that from one to three R groups are present which contain $R^*$ or Q, said $R^*$ and Q being defined below;

$R^a$, $R^b$ and $R^c$ represent hydrogen, —$C_{1-6}$ straight- or branched-chain alkyl, unsubstituted or substituted with one to four $R^d$ groups; —$C_{3-7}$ cycloalkyl, unsubstituted or substituted with one to four $R^d$ groups; or—$R^*$ or $R^a$ and $R^b$ taken together with any intervening atoms represent a 4–6 membered saturated ring optionally interrupted by one or more of O, S, $NR^c$, with $R^c$ as defined above, or —C(O)—, said ring being unsubstituted or substituted with one to four $R^i$ groups;

or $R^b$ and $R^c$ taken together with any intervening atoms represent a 4–6 membered saturated ring optionally interrupted by one to three of O, S, $NR^a$, with $R^a$ as defined above, or —C(O)—, said ring being unsubstituted or substituted with one to four $R^i$ groups;

each $R^d$ independently represents halo; —CN; —$NO_2$; —$NR^eR^f$; —$OR^g$; —$SR^g$; —$CONR^eR^f$; —$COOR^g$; —$SOR^g$; —$SO_2R^g$; —$SO_2NR^e R^f$; —$NR^eSO_2R^f$; —$COR^e$; —$NR^eCOR^f$; —$OCOR^e$; —$OCONR^eR^f$; —$NR^eCONR^fR^g$; —$NR^eCO_2R^h$; —$OCO_2R^h$; —C(N-$R^e$)$NR^fR^g$; —$NR^eC(NH)NR^fR^g$; —$NR^eC(NR^f)R^g$; —$R^*$ or —Q;

$R^e$, $R^f$ and $R^g$ represent hydrogen; —$C_{1-6}$ straight- or branched-chain alkyl unsubstituted or substituted with one to four $R^i$ groups, or —$R^*$;

or $R^e$ and $R^f$ taken together with any intervening atoms represent a 4–6 membered saturated ring optionally interrupted by one to three of O, S, —C(O)— or $NR^g$ with $R^g$ as defined above, said ring being unsubstituted or substituted with one to four $R^i$ groups;

each $R^i$ independently represents halo; —CN; —$NO_2$; phenyl; —$NHSO_2R^h$; —$OR^h$; —$SR^h$; —$N(R^h)_2$; —$N+(Rh)3$; —$C(O)N(R^h)_2$; —$SO_2N(Rh)_2$; heteroaryl; heteroarylium; —$CO_2R^h$; —$C(O)R^h$; —$OCOR^h$; —$NHCOR^h$; guanidinyl; carbamimidoyl or ureido;

each $R^h$ independently represents H, a —$C_{1-6}$ straight or branched-chain alkyl group, a —$C_3$-$C_6$ cycloalkyl group or phenyl, or when two $R^h$ groups are present, said $R^h$ groups may be taken in combination and represent a 4–6 membered saturated ring, optionally interrupted by one or two of O, S, $SO_2$, —C(O)—, NH and $NCH_3$;

Q is selected from the group consisting of:

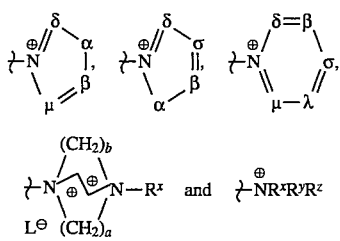

wherein:

a and b are 1, 2 or 3;

L– is a pharmaceutically acceptable counterion;

α represents O, S or $NR^s$;

β, δ, λ, μ and σ represent $CR^t$, N or $N^+R^s$, provided that no more than one of β, δ, λ, μ and σ is $N^+R^s$;

R* is selected from the group consisting of:

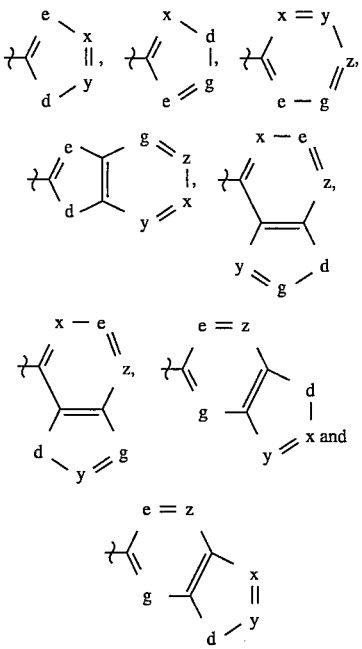

wherein:

each d independently represents O, S or $NR^k$;

e, g, x, y and z represent $CR^m$, N or $N^+R^k$, provided that no more than one of e, g, x, y and z in any given structure represents $N^+R^k$;

$R^k$: represents hydrogen; —$C_{1-6}$ straight- or branched-chain alkyl, unsubstituted or substituted with one to four $R^i$ groups; or —$(CH_2)_nQ$ where n=1, 2 or 3 and Q is as previously defined;

each $R^m$ independently represents a member selected from the group consisting of: hydrogen; halo; —CN; —$NO_2$; —$NR^nR^o$; —$OR^n$; —$SR^n$; —$CONR^nR^o$; —$COOR^h$; —$SOR^n$; —$SO_2R^n$; —$SO_2NR^nR^o$; —$NR^nSO_2R^o$; —$COR^n$; —$NR^nCOR^o$; —$OCOR^n$; —$OCONR^nR^o$; —$NR^nCO_2R^h$; —$NR^nCONR^oR^h$; —$OCO_2R^h$; —$CNR^nNR^oR^h$; —$NR^nCNHNR^oR^h$; —$NR^nC(NR^o)R^h$; —$C_{1-6}$ straight- or branched-chain alkyl, unsubstituted or substituted with one to four $R^i$ groups; —$C_{3-7}$ cycloalkyl, unsubstituted or substituted with one to four $R^i$ groups; and —$(CH_2)_nQ$ where n and Q are as defined above;

$R^n$ and $R^o$ represent hydrogen, phenyl; —$C_{1-6}$ straight- or branched-chain alkyl unsubstituted or substituted with one to four $R^i$ groups;

each $R^s$ independently represents hydrogen; phenyl; —$C_{1-6}$ straight- or branched-chain alkyl, unsubstituted or substituted with one to four $R^i$ groups;

each $R^t$ independently represents hydrogen; halo; phenyl; —CN; —$NO_2$; —$NR^uR^v$; —$OR^u$; —$SR^u$; —$CONR^uR^v$; —$COOR^h$; —$SOR^u$; —$SO_2R^u$; —$SO_2NR^uR^v$; —$NR^uSO_2R^v$; —$COR^u$; —$NR^uCOR^v$; —$OCOR^u$; —$OCONR^uR^v$; —$NR^uCO_2R^v$; —$NR^uCONR^vR^w$; —$OCO_2R^v$; heteroaryl; heteroarylium; —$C_{1-6}$ straight- or branched-chain alkyl, unsubstituted or substituted with one to four $R^i$ groups;

$R^u$ and $R^v$ represent hydrogen or —$C_{1-6}$ straight- or branched-chain alkyl, unsubstituted or substituted with one to four $R^i$ groups;

or $R^u$ and $R^v$ together with any intervening atoms represent a 4–6 membered saturated ring optionally interrupted by one or more of O, S, $NR^w$ or —C(O)—, said ring being unsubstituted or substituted with one to four $R^i$ groups;

each $R^w$ independently represents hydrogen or —$C_{1-6}$ straight- or branched-chain alkyl, unsubstituted or substituted with one to four $R^i$ groups; $C_{3-6}$ cycloalkyl optionally substituted with one to four $R^i$ groups; phenyl optionally substituted with one to four $R^i$ groups and heteroaryl optionally substituted with one to four $R^i$ groups.

or $R^h$ and $R^w$ taken together with any intervening atoms represent a 5–6 membered saturated ring, optionally interrupted by one or two of O, S, $SO_2$, NH or $NCH_3$;

$R^x$ represents hydrogen or a $C_{1-8}$ straight- or branched-chain alkyl, optionally interrupted by one or two of O, S, SO, $SO_2$, $NR^w$, $N^+R^hR^w$, or —C(O)—, said chain being unsubstituted or substituted with one to four of halo, CN, $NO_2$, $OR^w$, $SR^w$, $SOR^w$, $SO_2R^w$, $NR^hR^w$, $N^+(R^h)_2R^w$, —C(O)—$R^w$, $C(O)NR^hR^w$, $SO_2NR^hR^w$, $CO_2R^w$, $OC(O)R^w$, $OC(O)NR^hR^w$, $NR^hC(O)R^w$, $NR^hC(O)NR^hR^w$, or a phenyl or heteroaryl group which is in turn optionally substituted with from one to four $R^i$ groups or with one to two $C_{1-3}$ straight- or branched-chain alkyl groups, said alkyl groups being unsubstituted or substituted with one to four $R^i$ groups;

$R^y$ and $R^z$ represent hydrogen; phenyl; —$C_{1-6}$ straight or branched chain alkyl, unsubstituted or substituted with one to four $R^i$ groups, and optionally interrupted by O, S, $NR^w$, $N^+R^hR^w$ or —C(O)—;

or $R^x$ and $R^y$ together with any intervening atoms represent a 4–6 membered saturated ring optionally interrupted by O, S, SO$_2$, NR$^w$, N$^+$R$^h$R$^w$ or —C(O)—, unsubstituted or substituted with 1–Ri groups, and when R$^x$ and R$^y$ together represent a 4–6 membered ring as defined above, R$^z$ is as defined above or R$^z$ represents an additional saturated 4–6 membered ring fused to the ring represented by R$^x$ and R$^y$ taken together, optionally interrupted by O, S, NR$^w$ or —C(O)—, said rings being unsubstituted or substituted with one to four R$^i$ groups.

Pharmaceutical compositions, intermediates, processes of manufacture and methods of treatment are also disclosed.

DETAILED DESCRIPTION OF THE INVENTION

The invention is described herein in detail using the terms defined below unless otherwise specified.

Carboxylate anion refers to a negatively charged group —COO—.

The term "alkyl" refers to a monovalent alkane (hydrocarbon) derived radical containing from 1 to 10 carbon atoms unless otherwise defined. It may be straight, branched or cyclic. Preferred alkyl groups include methyl, ethyl, propyl, isopropyl, butyl, t-butyl, cyclopentyl and cyclohexyl. When substituted, alkyl groups may be substituted with up to four substituent groups, R$^i$ as defined, at any available point of attachment. When the alkyl group is said to be substituted with an alkyl group, this is used interchangeably with "branched alkyl group".

Cycloalkyl is a specie of alkyl containing from 3 to 15 carbon atoms, without alternating or resonating double bonds between carbon atoms. It may contain from 1 to 4 rings which are fused.

The term "alkenyl" refers to a hydrocarbon radical straight, branched or cyclic containing from 2 to 10 carbon atoms and at least one carbon to carbon double bond. Preferred alkenyl groups include ethenyl, propenyl, butenyl and cyclohexenyl.

The term "alkynyl" refers to a hydrocarbon radical straight or branched, containing from 2 to 10 carbon atoms and at least one carbon to carbon triple bond. Preferred alkynyl groups include ethynyl, propynyl and butynyl.

Aryl refers to aromatic rings e.g., phenyl, substituted phenyl and the like, groups as well as rings which are fused, e.g., naphthyl, phenanthrenyl and the like. An aryl group thus contains at least one ring having at least 6 atoms, with up to five such rings being present, containing up to 22 atoms therein, with alternating (resonating) double bonds between adjacent carbon atoms or suitable heteroatoms. The preferred aryl groups are phenyl, naphthyl and phenanthrenyl. Aryl groups may likewise be substituted as defined. Preferred substituted aryls include phenyl and naphthyl.

The term "heteroaryl" refers to a monocyclic aromatic hydrocarbon group having 5 or 6 ring atoms, or a bicyclic aromatic group having 8 to 10 atoms, containing at least one heteroatom, O, S or N, in which a carbon or nitrogen atom is the point of attachment, and in which one or two additional carbon atoms is optionally replaced by a heteroatom selected from O or S, and in which from 1 to 3 additional carbon atoms are optionally replaced by nitrogen heteroatoms, said heteroaryl group being optionally substituted as described herein. Examples of this type are pyrrole, pyridine, oxazole, thiazole and oxazine. Additional nitrogen atoms may be present together with the first nitrogen and oxygen or sulfur, giving, e.g., thiadiazole. Examples include the following:

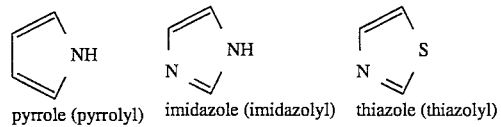
pyrrole (pyrrolyl)   imidazole (imidazolyl)   thiazole (thiazolyl)

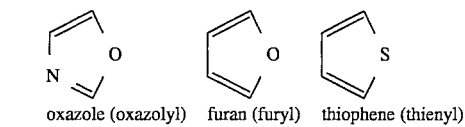
oxazole (oxazolyl)   furan (furyl)   thiophene (thienyl)

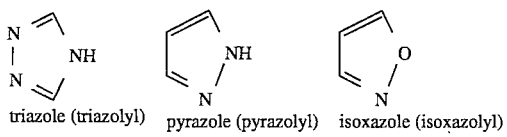
triazole (triazolyl)   pyrazole (pyrazolyl)   isoxazole (isoxazolyl)

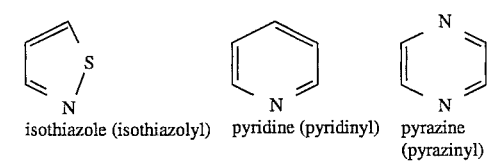
isothiazole (isothiazolyl)   pyridine (pyridinyl)   pyrazine (pyrazinyl)

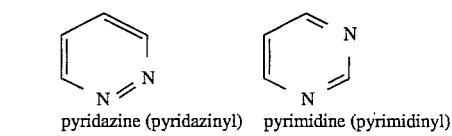
pyridazine (pyridazinyl)   pyrimidine (pyrimidinyl)

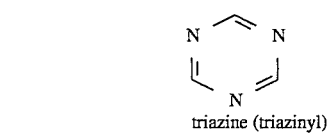
triazine (triazinyl)

Heteroarylium refers to heteroaryl groups bearing a quaternary nitrogen atom and thus a positive charge. Examples include the following:

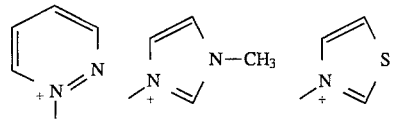

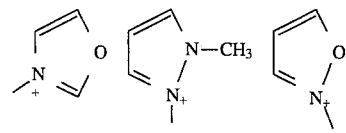

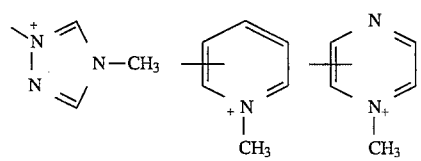

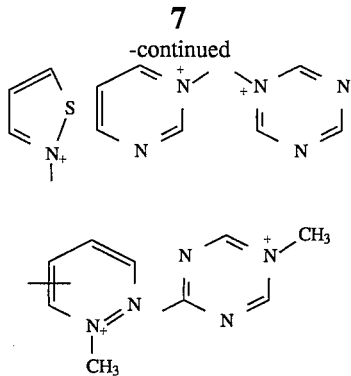

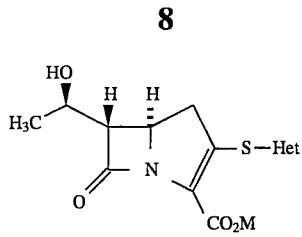

The term "heterocycloalkyl" refers to a cycloalkyl group (nonaromatic) in which one of the carbon atoms in the ring is replaced by a heteroatom selected from O, S or N, and in which up to three additional carbon atoms may be replaced by said hetero atoms.

The term "quaternary nitrogen" refers to a tetravalent positively charged nitrogen atom including, e.g., the positively charged nitrogen in a tetraalkylammonium group (eg. tetramethylammonium, N-methylpyridinium), the positively charged nitrogen in protonated ammonium species (eg. trimethylhydroammonium, N-hydropyridinium), the positively charged nitrogen in amine N-oxides (eg. N-methylmorpholine-N-oxide, pyridine-N-oxide), and the positively charged nitrogen in an N-amino-ammonium group (eg. N-aminopyridinium).

The term "heteroatom" means O, S or N, selected on an independent basis.

Halogen and "halo" refer to bromine, chlorine, fluorine and iodine.

Alkoxy refers to $C_1$–$C_4$ alkyl-O—, with the alkyl group optionally substituted as described herein.

An "alkoxycarbonyl" radical is represented by the formula: —C(O)O$R^h$, where the $R^h$ group is a straight or branched $C_{1-6}$ alkyl group. When referring to $R^d$, the group —COO$R^g$ represents an alkoxycarbonyl group where $R^g$ is a $C_{2-6}$ straight or branched alkyl group. When referring to $R^m$ and $R^t$, the group —COO$R^h$ is an alkoxycarbonyl group.

When a group is termed "substituted", unless otherwise indicated, this means that the group contains from 1 to 4 substituents thereon. With respect to R, $R^a$, $R^b$ and $R^c$, the substituents available on alkyl groups are selected from the values of $R^d$. Many of the variable groups are optionally substituted with up to four $R^i$ groups. With respect to $R^e$, $R^f$ and $R^g$, when these variables represent substituted alkyl, the substituents available thereon are selected from the values of $R^i$.

When a functional group is termed "protected", this means that the group is in modified form to preclude undesired side reactions at the protected site. Suitable protecting groups for the compounds of the present invention will be recognized from the present application taking into account the level of skill in the art, and with reference to standard textbooks, such as Greene, T. W. et al. *Protective Groups in Organic Synthesis* Wiley, N.Y. (1991). Examples of suitable protecting groups are contained throughout the specification.

A. A preferred subset of compounds (the 1H subset of compounds) is represented by formula Ia:

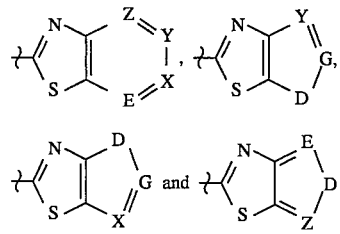

wherein:
 $CO_2M$ represents a carboxylic acid, a carboxylate anion or a pharmaceutically acceptable ester group;
 Het has substituent groups which contain from one to three positively charged atoms and is selected from:

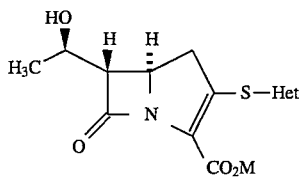

wherein:
 D is O, S or $NR^a$;
 E, G, X, Y and Z represent CR or N;
 each R is independently selected from: —R*; hydrogen; halo; —CN; —$OR^c$; —$SR^c$; —CON$R^aR^b$; —COO$R^h$; —SO$R^c$; —SO$_2R^c$; —SO$_2NR^aR^b$; —CO$R^a$; —OCO$R^a$; —OCON$R^aR^b$; —OCO$_2R^h$; —$C_{1-6}$ straight- or branched-chain alkyl, unsubstituted or substituted with one to four $R^d$ groups; —$C_{3-7}$ cycloalkyl, unsubstituted or substituted with one to four $R^d$ groups, with the proviso that one to three R groups contain R* or Q;
 and R* and Q are as defined above.

B. Within the 1H subset of compounds, the preferred subset of 1H compounds includes compounds of formula Ia:

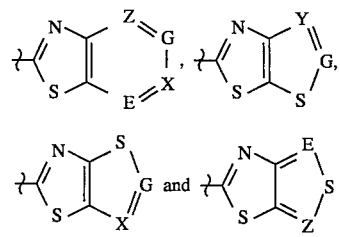

wherein:
 $CO_2M$ represents a carboxylic acid or a carboxylate anion;
 Het has substituent groups which contain one or two positively charged atoms and is selected from:

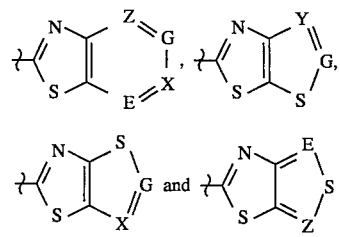

wherein:
 E, G, X, Y and Z represent CR or N;
 each R is independently selected from the group consisting of —R*; hydrogen; halo; —CN; —CON$R^aR^b$;

—COOR$^h$;—SOR$^c$;    —SO$_2$R$^c$;    —SO$_2$NR$^a$R$^b$;
—OC(O)R$^a$; —COR$^a$; —C$_{1-6}$ straight- or branched-chain alkyl, unsubstituted or substituted with one to three R$^d$ groups; —C$_{3-7}$ cycloalkyl, unsubstituted or substituted with one to three R$^d$ groups, with the proviso that one or two R groups contain R* or Q;

R$^a$, R$^b$ and R$^c$ independently represent —R*; hydrogen, —C$_{1-6}$ straight- or branched-chain alkyl, unsubstituted or substituted with one to four R$^d$ groups; —C$_{3-7}$ cycloalkyl, unsubstituted or substituted with one to four R$^d$ groups;

or R$^a$ and R$^b$ taken together with any intervening atoms represent a 4–6 membered saturated ring optionally interrupted by one or more of O, S, NR$^c$ with R$^c$ as defined above, or —C(O)—, said ring being unsubstituted or substituted with one to four R$^i$ groups;

Q represents a member selected from the group consisting of:

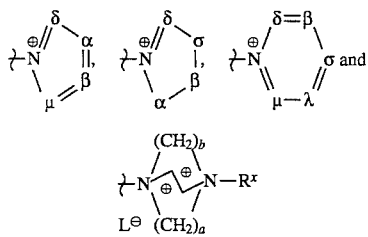

wherein:

a and b are 2 or 3;

L– is a pharmaceutically acceptable counterion;

α represents O, S or NR$^s$;

β, δ, λ, μ and σ represent CR$^t$, N or N$^+$R$^s$, provided that no more than one of β, δ, λ, μ and σ is N$^+$R$^s$;

R* is selected from:

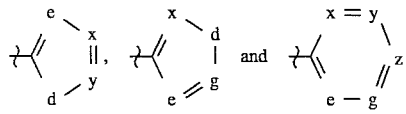

wherein each d independently represents O, S or NR$^k$;

e, g, x, y and z represent CR$^m$, N or N$^+$R$^k$, provided that no more than one of e, g, x, y and z in any given structure represents N$^+$R$^k$;

and R$^k$ is as previously defined.

C. Within the preferred subset of 1H compounds, a more preferred subset of compounds (the more preferred 1H compounds) includes compounds of formula Ic:

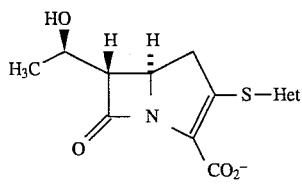

wherein:

Het has substituent groups which contain one or two positively charged atoms and is selected from the group consisting of:

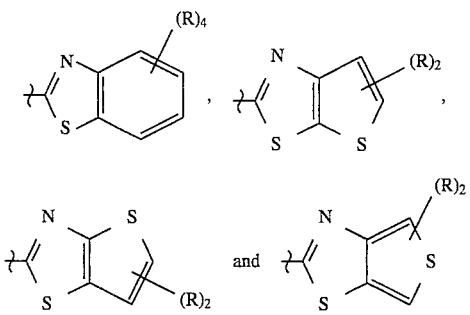

each R is independently selected from: hydrogen, —C$_{1-6}$ straight- or branched-chain alkyl, unsubstituted or substituted with one to three R$^d$ groups; and —R*, with the proviso that one or two R groups contain R* or Q;

R$^d$ represents —CN; —NR$^e$R$^f$; —OR$^g$; —CONR$^e$R$^f$; —COOR$^g$; —SOR$^g$; —SO$_2$R$^g$; —SO$_2$NR$^e$R$^f$; —NR$^e$SO$_2$R$^f$; —COR$^e$; —NR$^e$COR$^f$; —OCONR$^e$R$^f$; —NR$^e$CONR$^f$R$^g$; —NR$^e$CO$_2$R$^h$; —C(NR$^e$)NR$^f$R$^g$; —NR$^e$C(NH)NR$^f$R$^g$;—NR$^e$C(NR$^f$)R$^g$; —R* or —Q;

R$^e$, R$^f$ and R$^g$ represent hydrogen; —C$_{1-6}$ straight- or branched-chain alkyl or —R*;

or R$^e$ and R$^f$ taken together represent a 4–6 membered saturated ring optionally interrupted by one or more of O, S, —C(O)— or NR$^g$ with R$^g$ as defined above, said ring being unsubstituted or substituted with one to four R$^i$ groups;

each R$^h$ independently represents H, a —C$_{1-6}$ straight or branched-chain alkyl group, a —C$_3$–C$_6$ cycloalkyl group or phenyl, or when two R$^h$ groups are present, said R$^h$ groups may be taken in combination and represent a 4–6 membered saturated ring, optionally interrupted by one or two of O, S, SO$_2$, —C(O)—, NH and NCH$_3$;

each R$^i$ independently represents halo; —CN; —NO$_2$; phenyl; —NHSO$_2$R$^h$; —OR$^h$, —SR$^h$; —N(Rh)$_2$; —N$^+$(R$^h$)$_3$; —C(O)N(R$^h$)$_2$; —SO$_2$N(Rh)$_2$; heteroaryl; heteroarylium; —CO$_2$R$^h$; —C(O)R$^h$; —OCOR$^h$; —NHCOR$^h$; guanidinyl; carbamimidoyl or ureido;

Q is selected from:

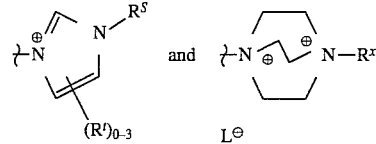

wherein:

L– is as previously defined;

R$^x$ represents hydrogen or a C$_{1-8}$ straight- or branched-chain alkyl, optionally interrupted by one or two of O, S, SO, SO$_2$, NR$^w$, N$^+$R$^h$R$^w$, or —C(O)—, said chain being unsubstituted or substituted with one to four of halo, CN, NO$_2$, OR$^w$, SR$^w$, SOR$^w$, SO$_2$R$^w$, NR$^h$R$^w$, N$^+$(R$^h$)$_2$R$^w$, —C(O)—R$^w$, C(O)NR$^h$R$^w$, SO$_2$NR$^h$R$^w$, CO$_2$R$^w$, OC(O)R$^w$, OC(O)NR$^h$R$^w$, NR$^h$C(O)R$^w$, NR$^h$C(O)NR$^h$R$^w$, or a phenyl or heteroaryl group which is in turn optionally substituted with from one to four R$^i$ groups or with one to two C$_{1-3}$ straight- or branched-chain alkyl groups, said alkyl groups being unsubstituted or substituted with one to four R$^i$ groups;

$R^s$ represents hydrogen; phenyl; —$C_{1-6}$ straight- or branched-chain alkyl, unsubstituted or substituted with one to four $R^i$ groups;

$R^t$ is selected from the group consisting of: halo; phenyl; —CN; —$NO_2$; —$NR^uR^v$; —$OR^u$; —$SR^u$; —$CONR^uR^v$; —$COOR^h$; —$SOR^u$; —$SO_2R^u$; —$SO_2NR^uR^v$; —$NR^uSO_2R^v$; —$COR^u$; —$NR^uCOR^v$; —$OCOR^u$; —$OCONR^uR^v$; —$NR^uCO_2R^v$; —$NR^uCONR^vR^w$; —$OCO_2R^v$; —$C_{1-6}$ straight- or branched-chain alkyl, unsubstituted or substituted with one to four $R^i$ groups, and the remaining $R^t$ groups are hydrogen;

$R^*$ is

<chemical structure: phenyl ring with $(R^m)_{0-3}$ substituents> wherein each $R^m$ is selected from the group consisting of: halo; —CN; —$NR^nR^o$; —$OR^n$; —$SR^n$; —$CONR^nR^o$; —$COOR^h$; —$SOR^n$; —$SO_2R^n$; —$SO_2NR^nR^o$; —$NR^nSO_2R^o$; —$COR^n$; —$NR^nCOR^o$; —$OCOR^n$; —$OCONR^nR^o$; , —$NR^nCO_2R^h$; —$NR^nCONR^oR^h$; —$OCO_2R^h$; —$C_{1-6}$ straight- or branched-chain alkyl, unsubstituted or substituted with one to four $R^i$ groups; —$C_{3-7}$ cycloalkyl, unsubstituted or substituted with one to four $R^i$ groups; or —$(CH_2)_nQ$ where n=1–3;

$R^n$ and $R^o$ represent hydrogen, phenyl; —$C_{1-6}$ straight- or branched-chain alkyl unsubstituted or substituted with one to four $R^i$ groups;

$R^u$ and $R^v$ independently represent hydrogen; —$C_{1-6}$ straight- or branched-chain alkyl, unsubstituted or substituted with one to four $R^i$ groups;

or $R^u$ and $R^v$ together with any intervening atoms represent a 4–6 membered saturated ring optionally interrupted by one or more of O, S, $NR^w$ or —C(O)—, said ring being unsubstituted or substituted with one to four $R^i$ groups, and $R^w$ represents hydrogen or —$C_{1-6}$ straight- or branched-chain alkyl, unsubstituted or substituted with one to four $R^i$ groups; $C_{3-6}$ cycloalkyl optionally substituted with one to four $R^i$ groups; or phenyl optionally substituted with one to four $R^i$ groups, or $R^h$ and $R^w$ taken together with any intervening atoms represent a 5–6 membered saturated ring, optionally interrupted by one or two of O, S, $SO_2$, NH or $NCH_3$.

D. Another subset of compounds of the invention (the 1-methyl compounds) which is preferred includes compounds of formula Ib:

<chemical structure Ib: carbapenem with HO, $H_3C$, H, H, $CH_3$, S—Het, N, O, $CO_2M$> wherein:

$CO_2M$ represents a carboxylic acid, a carboxylate anion or a pharmaceutically acceptable ester group;

and Het is as previously defined with respect to the compounds of formula I.

E. Within the 1-methyl compounds, a subset of compounds which is preferred (the preferred 1 methyl compounds) is represented by formula Ib:

<chemical structure Ib: carbapenem with HO, $H_3C$, H, H, $CH_3$, S—Het, N, O, $CO_2M$> wherein:

$CO_2M$ represents a carboxylic acid or a carboxylate anion;

Het has substituent groups which contain one to three positively charged atoms and is selected from the group consisting of:

<chemical structures: three fused bicyclic heterocycles with N, S, Z, Y, X, E, G>

<chemical structure: bicyclic with N, E, S, Z> wherein:

E, G, X, Y and Z independently represent CR or N;

each R is selected from the group consisting of hydrogen; halo; —CN; —$CONR^aR^b$; —$COOR^h$; —$SOR^c$; —$SO_2R^c$; —$SO_2NR^aR^b$; —$COR^a$; —$C_{1-6}$ straight- or branched-chain alkyl, unsubstituted or substituted with one to three $R^d$ groups; —$C_{3-7}$ cycloalkyl, unsubstituted or substituted with one to three $R^d$ groups; and —$R^*$, with the proviso that one to three R groups contain $R^*$ or Q;

Q is selected from the group consisting of:

<chemical structures: three 6-membered positively charged rings with δ, α, β, σ, μ, λ>

<chemical structure: bicyclic diazonium with $(CH_2)_b$, $(CH_2)_a$, N, $N—R^x$, $L^\ominus$> wherein:

L– represents a pharmaceutically acceptable counterion;

a and b independently represent 2 or 3;

α represents O, S or $NR^s$;

β, δ, λ, μ and σ independently represent $CR^t$, N or $N^+R^s$ provided that no more than one of β, δ, λ, μ and σ is $N^+R^s$;

$R^*$ is selected from the group consisting of:

<chemical structures: three 5-membered heterocycles with e, x, y, d, g, z> wherein:

d represents O, S or $NR^k$;

e, g, x, y and z independently represent $CR^m$, N or $N^+R^k$, provided that no more than one of e, g, x, y and z represents $N^+R^k$;

$R^a$, $R^b$ and $R^c$ independently represent hydrogen, —$C_{1-6}$ straight- or branched-chain alkyl, unsubstituted or substituted with one to four $R^d$ groups; —$C_{3-7}$ cycloalkyl, unsubstituted or substituted with one to four $R^d$ groups, or —$R^*$;

or $R^a$ and $R^b$ taken together with any intervening atoms represent a 4–6 membered saturated ring optionally interrupted by one or more of O, S, $NR^c$, with $R^c$ as defined above, or —C(O)—, said ring being unsubstituted or substituted with one to four $R^i$ groups; and each $R^d$ independently represents halo; —CN; —$NO_2$; —$NR^eR^f$; —$OR^g$; —$SR^g$; —$CONR^eR^f$; —$COOR^g$; —$SOR^g$; —$SO_2R^g$; —$SO_2NR^eR^f$; —$NR^eSO_2R^f$; —$COR^e$; —$NR^e$ $COR^f$; —$OCOR^e$; —$OCONR^eR^f$; —$NR^eCONR^fR^g$; —$NR^eCO_2R^h$; —$OCO_2R^h$; —C(N-$R^e$)$NR^fR^g$; —$NR^eC(NH)NR^fR^g$; —$NR^eC(NR^f)R^g$;—$R^*$ or —Q;

$R^e$, $R^f$ and $R^g$ represent hydrogen; —$C_{1-6}$ straight- or branched-chain alkyl unsubstituted or substituted with one to four $R^i$ groups, or —$R^*$;

or $R^e$ and $R^f$ taken together represent a 4–6 membered saturated ring optionally interrupted by one to three of O, S, —C(O)— or $NR^g$ with $R^g$ as defined above, said ring being unsubstituted or substituted with one to four $R^i$ groups;

each $R^i$ independently represents halo; —CN; —$NO_2$; phenyl; —$NHSO_2R^h$; —$OR^h$; —$SR^h$; —$N(R^h)_2$; —$N^+(R^h)_3$; —$C(O)N(R^h)_2$; —$SO_2N(R^h)_2$; heteroaryl; heteroarylium; —$CO_2R^h$; —$C(O)R^h$; —$OCOR^h$; —$NHCOR^h$; guanidinyl; carbamimidoyl or ureido;

each $R^h$ independently represents H, a —$C_{1-6}$ straight or branched-chain alkyl group, a $C_{3-6}$ cycloalkyl group or phenyl, or when two $R^h$ groups are present, said $R^h$ groups may be taken in combination and represent a 4–6 membered saturated ring, optionally interrupted by one or two of O, S, $SO_2$, —C(O)—, NH or $NCH_3$;

$R^k$ represents hydrogen; —$C_{1-6}$ straight- or branched-chain alkyl, unsubstituted or substituted with one to four $R^i$ groups; or —$(CH_2)_nQ$ where n and Q are as previously defined;

each $R^m$ independently represents a member selected from the group consisting of: hydrogen; halo; —CN; —$NO_2$; —$NHR^n$; —$NR^nR^o$; —$OR^n$; —$SR^n$; —$CONR^nR^o$; —$COOR^h$; —$SOR^n$; —$SO_2R^n$; —$SO_2NR^nR^o$; —$NR^nSO_2R^o$; —$COR^n$; —$NR^nCOR^o$; —$OCOR^n$; —$OCONR^nR^o$; —$NR^nCO_2R^h$; —$NR^nCONR^oR^h$; —$OCO_2R^h$; —$CNR^nNR^oR^h$; —$NR^nCNHNR^oR^h$; —$NR^nC(NR^o)R^h$; —$C_{1-6}$ straight- or branched-chain alkyl, unsubstituted or substituted with one to four $R^i$ groups; —$C_{3-7}$ cycloalkyl, unsubstituted or substituted with one to four $R^i$ groups; and —$(CH_2)_nQ$ where n=1–3;

$R^n$ and $R^o$ represent hydrogen, phenyl; —$C_{1-6}$ straight- or branched-chain alkyl unsubstituted or substituted with one to four $R^i$ groups;

each $R^s$ independently represents hydrogen; phenyl; —$C_{1-6}$ straight- or branched-chain alkyl, unsubstituted or substituted with one to four $R^i$ groups;

each $R^t$ independently represents hydrogen; halo; phenyl; —CN; —$NO_2$; —$NHR^u$; —$NR^uR^v$; —$OR^u$; —$SR^u$; —$CONR^uR^v$; —$COOR^h$; —$SOR^u$; —$SO_2R^u$; —$SO_2NR^uR^v$; —$NR^uSO_2R^v$; —$COR^u$; —$NR^uCOR^v$; —$OCOR^u$; —$OCONR^uR^v$; —$NR^uCO_2R^v$;—$NR^u$-$CONR^vR^w$; —$OCO_2R^v$; heteroaryl; heteroarylium; —$C_{1-6}$ straight- or branched-chain alkyl, unsubstituted or substituted with one to four $R^i$ groups;

$R^u$ and $R^v$ represent hydrogen or —$C_{1-6}$ straight- or branched-chain alkyl, unsubstituted or substituted with one to four $R^i$ groups;

or $R^u$ and $R^v$ together represent a 4–6 membered saturated ring optionally interrupted by one or more of O, S, $NR^w$ or —C(O)—, said ring being unsubstituted or substituted with one to four $R^i$ groups;

each $R^w$ independently represents hydrogen or —$C_{1-6}$ straight- or branched-chain alkyl, unsubstituted or substituted with one to four $R^i$ groups; $C_{3-6}$ cycloalkyl optionally substituted with one to four $R^i$ groups; phenyl optionally substituted with one to four $R^i$ groups and $R^x$ represents hydrogen or a $C_{1-8}$ straight- or branched-chain alkyl, optionally interrupted by one or two of O, S, SO, $SO_2$, $NR^w$, $N^+R^hR^w$, or —C(O)—, said chain being unsubstituted or substituted with one to four of halo, CN, $NO_2$, $OR^w$, $SR^w$, $SOR^w$, $SO_2R^w$, $NR^hR^w$, $N^+(R^h)_2R^w$, —C(O)—$R^w$, C(O)$NR^hR^w$, $SO_2NR^hR^w$, $CO_2R^w$, $OC(O)R^w$, $OC(O)NR^hR^w$, $NR^hC(O)R^w$, $NR^hC(O)NR^hR^w$, or a phenyl or heteroaryl group which is in turn optionally substituted with from one to four $R^i$ groups or with one to two $C_{1-3}$ straight- or branched-chain alkyl groups, said alkyl groups being unsubstituted or substituted with one to four $R^i$ groups, or $R^h$ and $R^w$ taken together with any intervening atoms represent a 5–6 membered saturated ring, optionally interrupted by one or two of O, S, $SO_2$, NH or $NCH_3$.

F. A more preferred subset of 1-methyl compounds is represented by formula Ic:

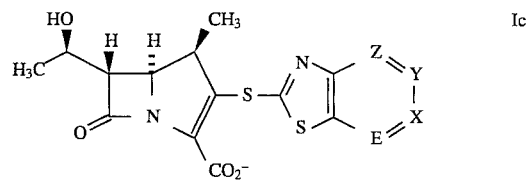

wherein:

E, X, Y and Z independently represent CR or N; and each R is independently selected from: —$R^*$; hydrogen; halo; —CN; —$NO_2$; —$OR^c$; —$SR^c$; —$CONR^aR^b$; —$COOR^h$; —$SOR^c$; —$SO_2R^c$; —$SO_2NR^aR^b$; —$NR^aSO_2R^b$; —$COR^a$; —$OCOR^a$; —$OCONR^aR^b$; —$NR^aCONR^bR^c$; —$NR^aCO_2R^h$; —$OCO_2R^h$; —$C_{1-6}$ straight- or branched-chain alkyl, unsubstituted or substituted with one to four $R^d$ groups; and —$C_{3-7}$ cycloalkyl, unsubstituted or substituted with one to four $R^d$ groups, with the proviso that from one to three positively charged atoms are contained in said R groups, and one to three R groups are present which contain $R^*$ or Q;

Q is selected from the group consisting of:

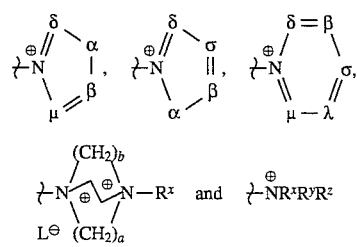

wherein:

a and b are 1, 2 or 3;

L− is a pharmaceutically acceptable counterion;

α represents O, S or NR$^s$;

β, δ, λ, μ and σ represent CR$^t$, N or N$^+$R$^s$, provided that no more than one of β, δλμ and σ is N$^+$R$^s$;

R* is selected from the group consisting of:

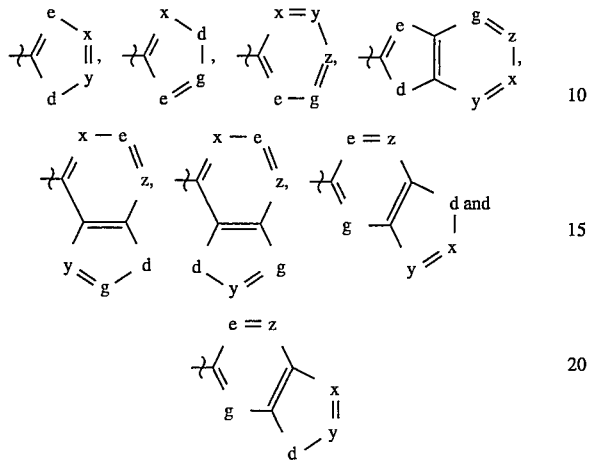

wherein:

each d independently represents O, S or NR$^k$;

e, g, x, y and z represent CR$^m$, N or N$^+$R$^k$, provided that no more than one of e, g, x, y and z in any given structure represents N$^+$R$^k$;

R$^a$, R$^b$ and R$^c$ represent hydrogen, —C$_{1-6}$ straight- or branched-chain alkyl, unsubstituted or substituted with one to four R$^d$ groups; —C$_{3-7}$ cycloalkyl, unsubstituted or substituted with one to four R$^d$ groups; or —R*;

or R$^a$ and R$^b$ taken together with any intervening atoms represent a 4–6 membered saturated ring optionally interrupted by one or more of O, S, NR$^c$, with R$^c$ as defined above, or —C(O)—, said ring being unsubstituted or substituted with one to four R$^i$ groups;

or R$^b$ and R$^c$ taken together with any intervening atoms represent a 4–6 membered saturated ring optionally interrupted by one to three of O, S, NR$^a$, with R$^a$ as defined above, or —C(O)—, said ring being unsubstituted or substituted with one to four R$^i$ groups;

each R$^d$ independently represents halo; —CN; —NO$_2$; —NR$^e$R$^f$; —OR$^g$; —SR$^g$; —CONR$^e$R$^f$; —COOR$^g$; —SOR$^g$; —SO$_2$R$^g$; —SO$_2$NR$^e$R$^f$; —NR$^e$SO$_2$R$^f$; —COR$^e$; —NR$^e$ COR$^f$; —OCOR$^e$; —OCONR$^e$R$^f$; —NR$^e$CONR$^f$R$^g$; —NR$^e$CO$_2$R$^h$; —OCO$_2$R h; —C(N-R$^e$)NR$^f$R$^g$; —NR$^e$C(NH)NR$^f$R$^g$; —NR$^e$C(NR$^f$)R$^g$; —R* or —Q;

R$^e$, R$^f$ and R$^g$ represent hydrogen; —C$_{1-6}$ straight- or branched-chain alkyl unsubstituted or substituted with one to four R$^i$ groups, or —R*;

or R$^e$ and R$^f$ taken together represent a 4–6 membered saturated ring optionally interrupted by one to three of O, S, —C(O)— or NR$^g$ with R$^g$ as defined above, said ring being unsubstituted or substituted with one to four R$^i$ groups;

each R$^i$ independently represents halo; —CN; —NO$_2$; phenyl; —NHSO$_2$R$^h$; —OR$^h$, —SR$^h$; —N(R$^h$)$_2$; —N$^+$(R$^h$)$_3$; —C(O)N(R$^h$)$_2$; —SO$_2$N(R$^h$)$_2$; heteroaryl; heteroarylium; —CO$_2$R$^h$; —C(O)R$^h$; —OCOR$^h$; —NHCOR$^h$; guanidinyl; carbamimidoyl or ureido;

each R$^h$ independently represents H, a —C$_{1-6}$ straight or branched-chain alkyl group, a —C$_3$-C$_6$ cycloalkyl group or phenyl, or when two R$^h$ groups are present, said R$^h$ groups may be taken in combination and represent a 4–6 membered saturated ring, optionally interrupted by one or two of O, S, SO$_2$, —C(O)—, NH and NCH$_3$;

R$^k$ represents hydrogen; —C$_{1-6}$ straight- or branched-chain alkyl, unsubstituted or substituted with one to four R$^i$ groups; or —(CH$_2$)$_n$Q where n and Q are as previously defined;

each R$^m$ independently represents a member selected from the group consisting of: hydrogen; halo; —CN; —NO$_2$; —NHR$^n$; —NR$^n$R$^o$; —OR$^n$; —SR$^n$; —CONR$^n$R$^o$; —COOR$^h$; —SOR$^n$; —SO$_2$R$^n$; —SO$_2$NR$^n$R$^o$; —NR$_n$SO$_2$R$^o$; —COR$^n$; —NR$^n$COR$^o$; —OCOR$^n$; —OCONR$^n$R$^o$; —NR$^n$CO$_2$R$^h$; —NR$^n$CONR$^o$R$^h$; —OCO$_2$R$^h$; —CNR$^n$NR$^o$R$^h$; —NR$^n$CNHNR$^o$R$^h$; —NR$^n$C(NR$^o$)R$^h$; —C$_{1-6}$ straight- or branched-chain alkyl, unsubstituted or substituted with one to four R$^i$ groups; —C$_{3-7}$ cycloalkyl, unsubstituted or substituted with one to four R$^i$ groups; and —(CH$_2$)$_n$Q where n=1-3;

R$^n$ and R$^o$ represent hydrogen, phenyl; —C$_{1-6}$ straight- or branched-chain alkyl unsubstituted or substituted with one to four R$^i$ groups;

each R$^s$ independently represents hydrogen; phenyl; —C$_{1-6}$ straight- or branched-chain alkyl, unsubstituted or substituted with one to four R$^i$ groups;

each R$^t$ independently represents hydrogen; halo; phenyl; —CN; —NO$_2$; —NHR$^u$; —NR$^u$R$^v$; —OR$^u$; —SR$^u$; —CONR$^u$R$^v$; —COOR$^h$; —SOR$^u$; —SO$_2$R$^u$; —SO$_2$NR$^u$R$^v$; —NR$^u$SO$_2$R$^v$; —COR$^u$; —NR$^u$COR$^v$; —OCOR$^u$; —OCONR$^u$R$^v$; —NR$^u$CO$_2$R$^v$;—NR$^u$CONR$^v$R$^w$; —OCO$_2$R$^v$; heteroaryl; heteroarylium; —C$_{1-6}$ straight- or branched-chain alkyl, unsubstituted or substituted with one to four R$^i$ groups;

R$^u$ and R$^v$ represent hydrogen or —C$_{1-6}$ straight- or branched-chain alkyl unsubstituted or substituted with one to four R$^i$ groups;

or R$^u$ and R$^v$ together represent a 4–6 membered saturated ting optionally interrupted by one or more of O, S, NR$^w$ or —C(O)—, said ring being unsubstituted or substituted with one to four R$^i$ groups;

each R$^w$ independently represents hydrogen or —C$_{1-6}$ straight- or branched-chain alkyl, unsubstituted or substituted with one to four R$^i$ groups; C$_{3-6}$ cycloalkyl optionally substituted with one to four R$^i$ groups; phenyl optionally substituted with one to four R$^i$ groups and R$^x$ represents hydrogen or a C$_{1-8}$ straight- or branched-chain alkyl, optionally interrupted by one or two of O, S, SO, SO$_2$, NR$^w$, N$^+$R$^h$R$^w$, or —C(O)—, said chain being unsubstituted or substituted with one to four of halo, CN, NO$_2$, OR$^w$, SR$^w$, SOR$^w$, SO$_2$R$^w$, NR$^h$R$^w$, N$^+$(R$^h$)$_2$R$^w$, —C(O)—R$^w$, C(O)NR$^h$R$^w$, SO$_2$NR$^h$R$^w$, CO$_2$R$^w$, OC(O)R$^w$, OC(O)NR$^h$R$^w$, NR$^h$C(O)R$^w$, NR$^h$C(O)NR$^h$R$^w$, or a phenyl or heteroaryl group which is in turn optionally substituted with from one to four R$^i$ groups or with one to two C$_{1-3}$ straight- or branched-chain alkyl groups, said alkyl groups being unsubstituted or substituted with one to four R$^i$ groups;

or R$^h$ and R$^w$ taken together with any intervening atoms represent a 5–6 membered saturated ring, optionally interrupted by one or two of O, S, SO$_2$, NH or NCH$_3$;

R$^y$, and R$^z$ represent hydrogen; phenyl; —C$_{1-6}$ straight- or branched-chain alkyl, unsubstituted or substituted with one to four $R^i$ groups and optionally interrupted by O, S, $NR^w$, $N^+R^hR^w$ or —C(O)—;

or $R^x$ and $R^y$ together with any intervening atoms represent a 4–6 membered saturated ring optionally interrupted by O, S, $SO_2$, $NR^w$, $N^+R^hR^w$ or —C(O)—, and, when $R^x$ and $R^y$ together represent a 4–6 membered ring as defined above, $R^z$ is as defined above or $R^z$ represents an additional saturated 4–6 membered ring fused to the ring represented by $R^x$ and $R^y$ taken together, optionally interrupted by O, S, $NR^w$ or —C(O)—, said rings being unsubstituted or substituted with one to four $R^i$ groups.

G. A still more preferred subset of 1-methyl compounds is represented by formula Id:

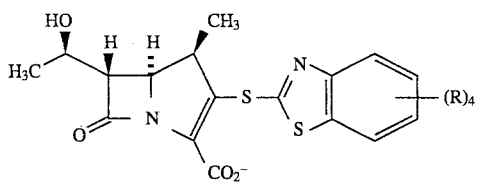

wherein:

$(R)_4$ contains from one to three positively charged atoms, and each R is selected from the group consisting of hydrogen; halo; —CN; $—CONR^aR^b$; $—COOR^h$; $—SOR^c$; $—SO_2R^c$; $—SO_2NR^aR^b$; $—COR^a$; $—C_{1-6}$ straight- or branched-chain alkyl, unsubstituted or substituted with one to three $R^d$ groups; or —R*, with the proviso that one to three R groups are present which contain R* or Q;

$R^a$, $Rb$ and $R^c$ independently represent hydrogen, $—C_{1-6}$ straight- or branched-chain alkyl, unsubstituted or substituted with one to four $R^d$ groups; or —R*;

or $R^a$ and $R^b$ taken together with any intervening atoms represent a 4–6 membered saturated ring optionally interrupted by one or more of O, S, $NR^c$, with $R^c$ as defined above, or —C(O)—, said ring being unsubstituted or substituted with one to four $R^i$ groups;

each $R^d$ independently represents halo; —CN; $—NO_2$; $—NR^eR^f$; $—OR^g$; $—SR^g$; $—CONR^eR^f$; $—COOR^g$; $—SOR^g$; $—SO_2R^g$; $—SO_2NR^eR^f$; $—NR^eSO_2R^f$; $—COR^e$; $—NR^e COR^f$; $—OCOR^e$; $—OCONR^eR^f$; $—NR^eCONR^fR^g$; $—NR^eCO_2R^h$; $—OCO_2R^h$; $—C(NR^e)NR^fR^g$; $—NR^eC(NH)NR^fR^g$; $—NR^eC(NR^f)R^g$; —R* or —Q;

Q represents

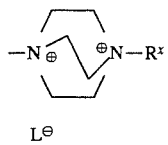

wherein L– is a pharmaceutically acceptable counterion;

Rx represents hydrogen or a $C_{1-8}$ straight- or branched-chain alkyl, optionally interrupted by one or two of O, S, SO, $SO_2$, $NR^w$, $N^+R^hR^w$, or —C(O)—, said chain being unsubstituted or substituted with one to four of halo, CN, $NO_2$, $OR^w$, $SR^w$, $SOR^w$, $SO_2R^w$, $NR^hR^w$, $N^+(R^h)_2R^w$, $—C(O)—R^w$, $C(O)NR^hR^w$, $SO_2NR^hR^w$, $CO_2R^w$, $OC(O)R^w$, $OC(O)NR^hR^w$, $NR^hC(O)R^w$, $NR^hC(O)NR^hR^w$, or a phenyl or heteroaryl group which is in turn optionally substituted with from one to four $R^i$ groups or with one to two $C_{1-3}$ straight- or branched-chain alkyl groups, said alkyl groups being unsubstituted or substituted with one to four $R^i$ groups;

each $R^h$ independently represents H, a $—C_{1-6}$ straight or branched-chain alkyl group, a $—C_3-C_6$ cycloalkyl group or phenyl, or when two $R^h$ groups are present, said $R^h$ groups may be taken in combination and represent a 4–6 membered saturated ring, optionally interrupted by one or two of O, S, $SO_2$, —C(O)—, NH and $NCH_3$;

$R^i$ independently represents halo; —CN; $—NO_2$; phenyl; $—NHSO_2R^h$; $—OR^h$, $—N(R^h)_2$; $—N^+(R^h)_3$; $—C(O)N(R^h)_2$; $—SO_2N(R^h)_2$; heteroaryl; heteroarylium; $—CO_2R^h$; $—C(O)R^h$; $—OCOR^h$; $—NHCOR^h$; guanidinyl; carbamimidoyl or ureido;

$R^w$ represents hydrogen or $—C_{1-6}$ straight- or branched-chain alkyl, unsubstituted or substituted with one to four $R^i$ groups; $C_{3-6}$ cycloalkyl optionally substituted with one to four $R^i$ groups; phenyl optionally substituted with one to four $R^i$ groups;

or $R^h$ and $R^w$ taken together with any intervening atoms represent a 5–6 membered saturated ring, optionally interrupted by one or two of O, S, $SO_2$, NH or $NCH_3$;

R* is selected from the group consisting of:

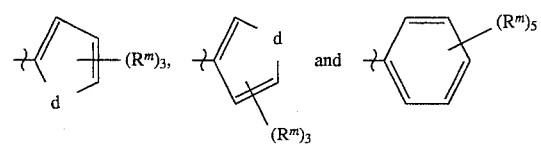

wherein:

d is O, S or $NR^k$;

$R^k$ represents hydrogen; $—C_{1-6}$ straight- or branched-chain alkyl, unsubstituted or substituted with one to four $R^i$ groups; or $—(CH_2)n—Q$;

$R^m$ is selected from the group consisting of: hydrogen; halo; —CN; $—NO_2$; $—NHR^n$; $—NR^nR^o$; $—OR^n$; $—SR^n$; $—CONR^nR^o$; $—SOR^n$; $—SO_2R^n$; $—SO_2NR^nR^o$; $—NR^nSO_2R^o$; $—COR^n$; $—NR^nCOR^o$; $—NR^nCO_2R^h$; $—NR^nCONR^oR^h$; $—C_{1-6}$ straight- or branched-chain alkyl, unsubstituted or substituted with one to four $R^i$ groups; and $—(CH_2)_n-Q$;

$R^d$ represents —R* as defined above or Q; and $R^n$ and $R^o$ represent hydrogen, phenyl; $—C_{1-6}$ straight- or branched-chain alkyl unsubstituted or substituted with one to four $R^i$ groups.

H. Another preferred subset of 1-methyl compounds is represented by formula Id:

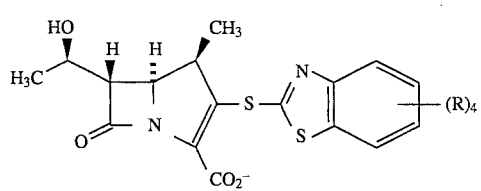

wherein:

each R is selected from the group consisting of hydrogen; halo; —CN; $—CONR^aR^b$; $—COOR^h$; $—SOR^c$; $—SO_2R^c$; $—SO_2NR^aR^b$; $—COR^a$; $—C_{1-6}$ straight- or branched-chain alkyl, unsubstituted or substituted with one to three $R^d$ groups; and —R*, with the proviso that one or two R groups contain R* or Q and $—(R)_4$ contains from one to two positively charged atoms;

Q represents a member selected from the group consisting of:

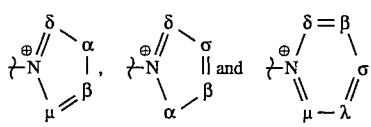

wherein:

α represents O, S or $NR^s$;

β, δ, λ, μ and σ independently represent $CR^t$, N or $N^+R^s$ provided that no more than one of β, δ, λ, μ and σ may be $N^+R^s$;

R* is selected from the group consisting of:

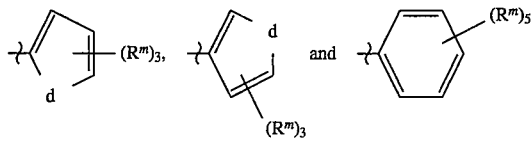

wherein:

d represents O, S or $NR^k$;

$R^a$, $R^b$ and $R^c$ independently represent hydrogen, $-C_{1-6}$ straight- or branched-chain alkyl, unsubstituted or substituted with one to four $R^d$ groups; or —R*;

or $R^a$ and $R^b$ taken together with any intervening atoms represent a 4–6 membered saturated ring optionally interrupted by one or more of O, S, $NR^c$, with $R^c$ as defined above, or —C(O)—, said ring being unsubstituted or substituted with one to four $R^i$ groups;

$R^d$ represents —R* or —Q;

each $R^h$ independently represents H, a $-C_{1-6}$ straight or branched-chain alkyl group, a $-C_3-C_6$ cycloalkyl group or phenyl, or when two $R^h$ groups are present, said $R^h$ groups may be taken in combination and represent a 4–6 membered saturated ring, optionally interrupted by one or two of O, S, $SO_2$, —C(O)—, NH and $NCH_3$;

$R^k$ represents hydrogen; $-C_{1-6}$ straight- or branched-chain alkyl, unsubstituted or substituted with one to four $R^i$ groups; or $-(CH_2)_n-Q$;

$R^i$ represents halo; —CN; $-NO_2$; phenyl; $-NHSO_2R^h$; $-OR^h$, $-N(R^h)_2$; $-N^+(R^h)_3$; $-C(O)N(R^h)_2$; $-SO_2N(R^h)_2$; heteroaryl; heteroarylium; $-CO_2R^h$; $-C(O)R^h$; $-OCOR^h$; $-NHCOR^h$; guanidinyl; carbamimidoyl or ureido;

$R^m$ is selected from the group consisting of: hydrogen; halo; —CN; $-NO_2$; $-NHR^n$; $-NR^nR^o$; $-OR^n$; $-SR^n$; $-CONR^nR^o$; $-SOR^n$; $-SO_2R^n$; $-SO_2NR^nR^o$; $-NR^nSO_2R^o$; $-COR^n$; $-NR^nCOR^o$; $-NR^nCO_2R^h$; $-NR^nCONR^oR^h$; $-C_{1-6}$ straight- or branched-chain alkyl, unsubstituted or substituted with one to four $R^i$ groups; and $-(CH_2)_n-Q$;

$R^n$ and $R^o$ represent hydrogen, phenyl; $-C_{1-6}$ straight- or branched-chain alkyl unsubstituted or substituted with one to four $R^i$ groups;

$R^s$ represents hydrogen; phenyl; $-C_{1-6}$ straight- or branched-chain alkyl, unsubstituted or substituted with one to four $R^i$ groups;;

$R^t$ represents hydrogen; halo; phenyl; —CN; $-NHR^u$; $NR^uR^v$; $-OR^u$; $-SR^u$; $-CONR^uR^v$; $-COOR^h$; $-SOR^u$; $-SO_2R^u$; $-SO_2NR^uR^v$; $-NR^uSO_2R^v$; $-COR^u$; $-NR^uCOR^v$; $-OCOR^u$; $-OCONR^uR^v$; $-NR^uCO_2R^v$; $-NR^uCONR^vR^w$; $-OCO_2R^v$; $-C_{1-6}$ straight- or branched-chain alkyl, unsubstituted or substituted with one to four $R^i$ groups;

$R^u$ and $R^v$ represent hydrogen or $-C_{1-6}$ straight- or branched-chain alkyl, unsubstituted or substituted with one to four $R^i$ groups;

or $R^u$ and $R^v$ together represent a 4–6 membered saturated ring optionally interrupted by one or more of O, S, $NR^w$ or —C(O)—, said ring being unsubstituted or substituted with one to four $R^i$ groups;

each $R^w$ independently represents hydrogen or $-C_{1-6}$ straight- or branched-chain alkyl, unsubstituted or substituted with one to four $R^i$ groups; $C_{3-6}$ cycloalkyl optionally substituted with one to four $R^i$ groups; phenyl optionally substituted with one to four $R^i$ groups.

I. Another preferred subset of 1-methyl compounds is defined in accordance with formula Ie:

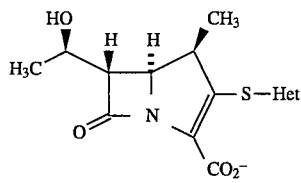

wherein:

Het has substituents which contain one to three positively charged atoms and is selected from the group consisting of:

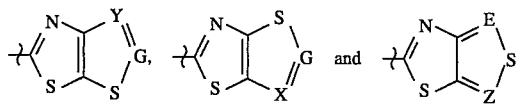

wherein:

E, G, X, Y and Z independently represent CR or N;

each R is selected from the group consisting of hydrogen; halo; —CN; $-CONR^aR^b$; $-COOR^h$; $-SOR^c$; $-SO_2R^c$; $-SO_2NR^aR^b$; $-COR^a$; $-C_{1-6}$ straight- or branched-chain alkyl, unsubstituted or substituted with one to three $R^a$ groups; $-C_{3-7}$ cycloalkyl, unsubstituted or substituted with one to three $R^d$ groups, and —R*, with the proviso that one or two R groups are present which contain R* or Q;

Q is selected from the group consisting of:

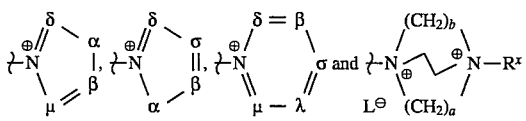

wherein:

L– represents a pharmaceutically acceptable counterion;

and b independently represent 2 or 3;

α represents O, S or $NR^s$;

β, δ, λ, μ and σ independently represent $CR^t$, N or $N^+R^s$ provided that no more than one of β, δ, λ, μ and σ is $N^+R^s$;

R* is selected from the group consisting of:

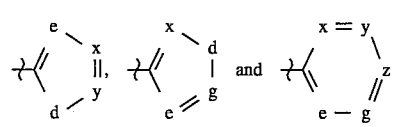

wherein:

d represents O, S or $NR^k$;

e, g, x, y and z independently represent $CR^m$, N or $N^+R^k$, provided that no more than one of e, g, x, y and z represents $N^+R^k$;

$R^a$, $R^b$ and $R^c$ independently represent hydrogen, —$C_{1-6}$ straight- or branched-chain alkyl, unsubstituted or substituted with one to four $R^d$ groups; —$C_{3-7}$ cycloalkyl, unsubstituted or substituted with one to four $R^d$ groups; or —R*;

or $R^a$ and $R^b$ taken together with any intervening atoms represent a 4–6 membered saturated ring optionally interrupted by one or more of O, S, $NR^c$, with $R^c$ as defined above, or —C(O)—, said ring being unsubstituted or substituted with one to four $R^i$ groups; and each $R^d$ independently represents halo; —CN; —$NO_2$; —$NR^eR^f$; —$OR^g$; —$SR^g$; —$CONR^eR^f$; —$COOR^g$; —$SOR^g$; —$SO_2R^g$; —$SO_2NR^eR^f$; —$NR^eSO_2R^f$; —$COR^e$; —$NR^e$ $COR^f$; —$OCOR^e$; —$OCONR^eR^f$; —$NR^eCONR^fR^g$; —$NR^eCO_2R^h$; —$OCO_2R^h$; —$C(NR^e)NR^fR^g$; —$NR^eC(NH)NR^fR^g$; —$NR^eC(NR^f)R^g$; —R* or —Q;

$R^e$, $R^f$ and $R^g$ represent hydrogen; —$C_{1-6}$ straight- or branched-chain alkyl unsubstituted or substituted with one to four $R^i$ groups, or —R*;

or $R^e$ and $R^f$ taken together represent a 4–6 membered saturated ring optionally interrupted by one to three of O, S, —C(O)— or $NR^g$ with $R^g$ as defined above, said ring being unsubstituted or substituted with one to four $R^i$ groups;

each $R^h$ independently represents H, a —$C_{1-6}$ straight or branched-chain alkyl group, a —$C_3$-$C_6$ cycloalkyl group or phenyl, or when two $R^h$ groups are present, said $R^h$ groups may be taken in combination and represent a 4–6 membered saturated ring, optionally interrupted by one or two of O, S, $SO_2$, —C(O)—, NH and $NCH_3$;

$R^i$ represents halo; —CN; —$NO_2$; phenyl; —$NHSO_2R^h$; —$OR^h$, —$N(R^h)_2$; —$N^+(R^h)_3$; —$C(O)N(R^h)_2$; —$SO_2N(R^h)_2$; heteroaryl; heteroarylium; —$CO_2R^h$; —$C(O)R^h$; —$OCOR^h$; —$NHCOR^h$; guanidinyl; carbamimidoyl or ureido;

$R^k$ represents hydrogen; —$C_{1-6}$ straight- or branched-chain alkyl, unsubstituted or substituted with one to four $R^i$ groups; or —$(CH_2)_n$—Q where n=1–3;

$R^s$ represents hydrogen; phenyl; —$C_{1-6}$ straight- or branched-chain alkyl, unsubstituted or substituted with one to four $R^i$ groups;

$R^t$ represents hydrogen; halo; phenyl; —CN; —$NR^uR^v$; —$OR^u$; —$SR^u$; —$CONR^uR^v$; —$COOR^h$; —$SOR^u$; —$SO_2R^u$; —$SO_2NR^uR^v$; —$NR^uSO_2R^v$; —$COR^u$; —$NR^uCOR^v$; —$OCOR^u$; —$OCONR^uR^v$; —$NR^uCO_2R^v$; —$NR^uCONR^vR^w$; —$OCO_2R^v$; —$C_{1-6}$ straight- or branched-chain alkyl, unsubstituted or substituted with one to four $R^i$ groups;

$R^u$ and $R^v$ represent hydrogen or —$C_{1-6}$ straight- or branched-chain alkyl unsubstituted or substituted with one to four $R^i$ groups;

or $R^u$ and $R^v$ together represent a 4–6 membered saturated ring optionally interrupted by one or more of O, S, $NR^w$ or —C(O)—, said ring being unsubstituted or substituted with one to four $R^i$ groups, and each $R^w$ independently represents hydrogen or —$C_{1-6}$ straight- or branched-chain alkyl, unsubstituted or substituted with one to four $R^i$ groups; $C_{3-6}$ cycloalkyl optionally substituted with one to four $R^i$ groups; phenyl optionally substituted with one to four $R^i$ groups;

or $R^h$ and $R^w$ taken together with any intervening atoms represent a 5–6 membered saturated ring, optionally interrupted by one or two of O, S, $SO_2$, NH or $NCH_3$;

and $R^x$ represents hydrogen or a $C_{1-8}$ straight- or branched- chain alkyl, optionally interrupted by one or two of O, S, SO, $SO_2$, $NR^w$, $N^+R^hR^w$, or —C(O)—, said chain being unsubstituted or substituted with one to four of halo, CN, $NO_2$, $OR^w$, $SR^w$, $SOR^w$, $SO_2R^w$, $NR^hR^w$, $N^+(R^h)_2R^w$, —C(O)—$R^w$, $C(O)NR^hR^w$, $SO_2NR^hR^w$, $CO_2R^w$, $OC(O)R^w$, $OC(O)NR^hR^w$, $NR^hC(O)R^w$, $NR^hC(O)NR^hR^w$, or a phenyl or heteroaryl group which is in turn optionally substituted with from one to four $R^i$ groups or with one to two $C_{1-3}$ straight- or branched-chain alkyl groups, said alkyl groups being unsubstituted or substituted with one to four $R^i$ groups.

J. Another preferred subset of 1 methyl compounds includes compounds of formula Ie:

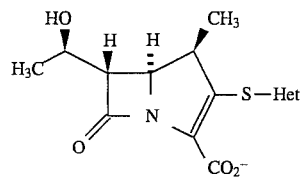

wherein:

Het has substituents which contain from one to three positively charged atoms and is selected from the group consisting of:

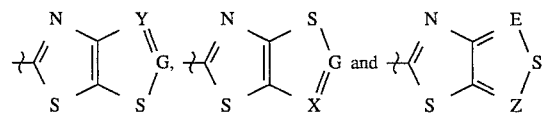

wherein:

E, G, X, Y and Z independently represent CR or N;

each R is selected from the group consisting of hydrogen; halo; —CN; —$CONR^aR^b$; —$COOR^h$; —$SOR^c$; —$SO_2R^c$; —$SO_2NR^aR^b$; —$COR^a$; —$C_{1-6}$ straight- or branched-chain alkyl, unsubstituted or substituted with one to three $R^d$ groups; —$C_{3-7}$ cycloalkyl, unsubstituted or substituted with one to three $R^d$ groups; and —R*;

with the proviso that one R group contains Q;

R* is selected from the group consisting of:

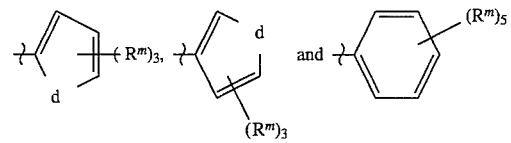

wherein:

d is O, S or $NR^k$;

Q represents

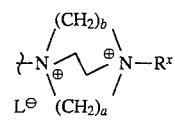

wherein a and b are 2,

L– is a pharmaceutically acceptable counterion, and $R^x$ represents hydrogen or a $C_{1-8}$ straight- or branched-chain alkyl, optionally interrupted by one or two of O, S, SO, SO₂, NR^w, N⁺R^hR^w, or —C(O)—, said chain being unsubstituted or substituted with one to four of halo, CN, NO₂, OR^w, SR^w, SOR^w, SO₂R^w, NR^hR^w, N⁺(R^h)₂R^w, —C(O)—R^w, C(O)NR^hR^w, SO₂NR^hR^w, CO₂R^w, OC(O)R^w, OC(O)NR^hR^w, NR^hC(O)R^w, NR^hC(O)NR^hR^w, or a phenyl or heteroaryl group which is in mm optionally substituted with from one to four R^i groups or with one to two C_{1-3} straight- or branched-chain alkyl groups, said alkyl groups being unsubstituted or substituted with one to four R^i groups;

each R^h independently represents H, a —C_{1-6} straight or branched-chain alkyl group, a —C₃-C₆ cycloalkyl group or phenyl, or when two R^h groups are present, said R^h groups may be taken in combination and represent a 4–6 membered saturated ring, optionally interrupted by one or two of O, S, SO₂, —C(O)—, NH and NCH₃;

R^i independently represents halo; —CN; —NO₂; phenyl; —NHSO₂R^h; —OR^h, —N(R^h)₂; —N⁺(R^h)₃; —C(O)N(R^h)₂; —SO₂N(R^h)₂; heteroaryl; heteroarylium; —CO₂R^h; —C(O)R^h; —OCOR^h; —NHCOR^h; guanidinyl; carbamimidoyl or ureido;

R^k represents hydrogen; —C_{1-6} straight- or branched-chain alkyl, unsubstituted or substituted with one to four R^i groups; or —(CH₂)_n—Q, wherein n=1, 2 or 3 and Q is as defined above;

R^m is selected from the group consisting of: hydrogen; halo; —CN; —NO₂; —NHR^n; —NR^nR^o; —OR^n; —SR^n; —CONR^nR^o; —SOR^n; —SO₂R^n; —SO₂NR^nR^o; —NR^nSO₂R^o; —COR^n; —NR^nCOR^o; —NR^nCO₂R^h; —NR^nCONR^oR^h; —C_{1-6} straight- or branched-chain alkyl, unsubstituted or substituted with one to four R^i groups; and —(CH₂)1-3—Q;

R^a, R^b and R^c independently represent hydrogen, —C_{1-6} straight- or branched-chain alkyl, unsubstituted or substituted with one to four R^d groups; or —R*;

or R^a and R^b taken together with any intervening atoms represent a 4–6 membered saturated ring optionally interrupted by one or more of O, S, NR^c, with R^c as defined above, or —C(O)—, said ring being unsubstituted or substituted with one to four R^i groups;

R^d represents R* or Q;

R^n and R^o represent hydrogen, phenyl; —C_{1-6} straight- or branched-chain alkyl unsubstituted or substituted with one to four R^i groups, and R^w represents hydrogen or —C_{1-6} straight- or branched-chain alkyl, unsubstituted or substituted with one to four R^i groups; C_{3-6} cycloalkyl optionally substituted with one to four R^i groups; or phenyl optionally substituted with one to four R^i groups.

K. Another preferred subset of 1 methyl compounds is represented by formula Ie:

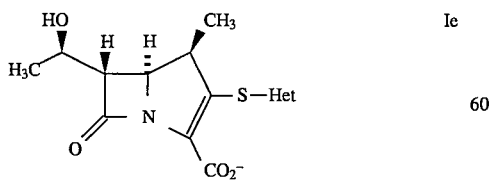

Ie wherein:

Het has substituent groups which contain from one to three positively charged atoms and is selected from the group consisting of:

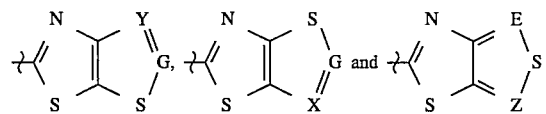

wherein:

E, G, X, Y and Z independently represent CR or N;

R represents a member selected from the group consisting of hydrogen; halo; —CN; —CONR^aR^b; —COOR^h; —SOR^c; —SO₂R^c; —SO₂NR^aR^b; —COR^a; —C_{1-6} straight- or branched-chain alkyl, unsubstituted or substituted with one to three R^d groups; and —R*, with the proviso that one or two R groups contain R* or Q;

Q represents a member selected from the group consisting of:

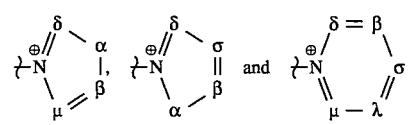

wherein:

α represents O, S or NR^s;

β, δ, λ, μ and σ independently represent CR^t, N or N⁺R^s provided that no more than one of β, δ, λ, μ and σ may be N⁺R^s;

R* is selected from the group consisting of:

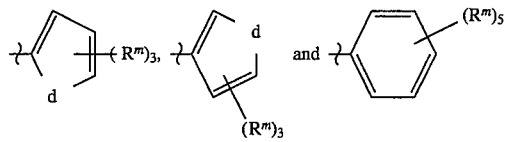

wherein:

d represents O, S or NR^k;

R^a, R^b and R^c independently represent hydrogen, —C_{1-6} straight- or branched-chain alkyl, unsubstituted or substituted with one to four R^d groups; or —R*;

or R^a and R^b taken together with any intervening atoms represent a 4–6 membered saturated ring optionally interrupted by one or more of O, S, NR^c, with R^c as defined above, or —C(O)—, said ring being unsubstituted or substituted with one to four R^i groups;

R^d represents —R* or —Q;

each R^h independently represents H, a —C_{1-6} straight or branched-chain alkyl group, a —C₃-C₆ cycloalkyl group or phenyl, or when two R^h groups are present, said R^h groups may be taken in combination and represent a 4–6 membered saturated ring, optionally interrupted by one or two of O, S, SO₂, —C(O)—, NH and NCH₃;

R^i represents halo; —CN; —NO₂; phenyl; —NHSO₂R^h; —OR^h, —N(R^h)₂; —N⁺(R^h)₃; —C(O)N(R^h)₂; —SO₂N(R^h)₂; heteroaryl; heteroarylium; —CO₂R^h; —C(O)R^h; —OCOR^h; —NHCOR^h; guanidinyl; carbamimidoyl or ureido;

R^k represents hydrogen; —C_{1-6} straight- or branched-chain alkyl, unsubstituted or substituted with one to four R^i groups; or —(CH₂)_n—Q, wherein n and Q are as previously defined;

R^m is selected from the group consisting of: hydrogen; halo; —CN; —NO₂; —NHR^n; —NR^nR^o; —OR^n; —SR^n; —CONR^nR^o; —SOR^n; —SO₂R^n;

—SO₂NRⁿRᵒ; —NRⁿSO₂Rᵒ; —CORⁿ; —NRⁿCORᵒ; —NRⁿCO₂Rʰ; —NRⁿCONRᵒRʰ; —C₁₋₆ straight- or branched-chain alkyl, unsubstituted or substituted with one to four Rⁱ groups; and —(CH₂)ₙ—Q, wherein n and Q are as previously defined;

Rⁿ and Rᵒ represent hydrogen, phenyl; —C₁₋₆ straight- or branched-chain alkyl unsubstituted or substituted with one to four Rⁱ groups;

Rˢ represents hydrogen; phenyl; —C₁₋₆ straight- or branched-chain alkyl, unsubstituted or substituted with one to four Rⁱ groups;

Rᵗ represents hydrogen; halo; phenyl; —CN; —NHRᵘ; —NRᵘRᵛ; —ORᵘ; —SRᵘ; —CONRᵘRᵛ; —COORʰ; —SORᵘ; —SO₂Rᵘ; —SO₂NRᵘRᵛ; —NRᵘSO₂Rᵛ; —CORᵘ; —NRᵘCORᵛ; —OCORᵘ; —OCONRᵘRᵛ; —NRᵘCO₂Rᵛ; —NRᵘCONRᵛRʷ; —OCO₂Rᵛ; —C₁₋₆ straight- or branched-chain alkyl, unsubstituted or substituted with one to four Rⁱ groups;

Rᵘ and Rᵛ represent hydrogen or —C₁₋₆ straight- or branched-chain alkyl, unsubstituted or substituted with one to four Rⁱ groups;

or Rᵘ and Rᵛ together represent a 4–6 membered saturated ring optionally interrupted by one or more of O, S, NRʷ or —C(O)—, said ring being unsubstituted or substituted with one to four Rⁱ groups;

each Rʷ independently represents hydrogen or —C₁₋₆ straight- or branched-chain alkyl, unsubstituted or substituted with one to four Rⁱ groups, or C₃₋₆ cycloalkyl optionally substituted with one to four Rⁱ groups; phenyl optionally substituted with one to four Rⁱ groups.

L. Yet another preferred subset of 1-methyl compounds is represented by the formula If:

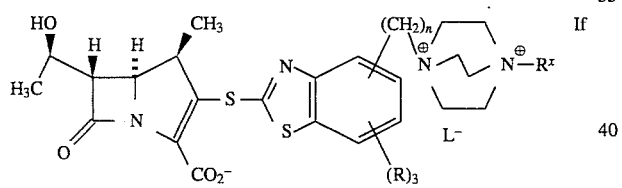

wherein:
L⁻ is a pharmaceutically acceptable counterion;
n is 1–3;
Rˣ represents hydrogen or a C₁₋₈ straight- or branched-chain alkyl, optionally interrupted by one or two of O, S, SO, SO₂, NRʷ, N⁺RʰRʷ, or —C(O)—, said chain being unsubstituted or substituted with one to four of halo, CN, NO₂, ORʷ, SRʷ, SORʷ, SO₂Rʷ, NRʰRʷ, N⁺(Rʰ)₂Rʷ, —C(O)—Rʷ, C(O)NRʰRʷ, SO₂NRʰRʷ, CO₂Rʷ, OC(O)Rʷ, OC(O)NRʰRʷ, NRʰC(O)Rʷ, NRʰC(O)NRʰRʷ, or a phenyl or heteroaryl group which is in turn optionally substituted with from one to four Rⁱ groups or with one to two C₁₋₃ straight- or branched-chain alkyl groups, said alkyl groups being unsubstituted or substituted with one to four Rⁱ groups;

each R is independently selected from: hydrogen; halo; —CN; —NO₂; —ORᶜ; —SRᶜ; —CONRᵃRᵇ; —COORʰ; —SORᶜ; —SO₂Rᶜ; —SO₂NRᵃRᵇ; —NRᵃSO₂Rᵇ; —CORᵃ; —OCORᵃ; —OCONRᵃRᵇ; —NRᵃCONRᵇRᶜ; —NRᵃCO₂Rʰ; —OCO₂Rʰ; —C₁₋₆ straight- or branched-chain alkyl, unsubstituted or substituted with one to four Rᵈ groups; and —C₃₋₇ cycloalkyl, unsubstituted or substituted with one to four Rᵈ groups, each Rᵈ independently represents halo; —CN; —NO₂; —NRᵉRᶠ; —ORᵍ; —SRᵍ; —CONRᵉRᶠ; —COORᵍ; —SORᵍ; —SO₂Rᵍ; —SO₂NRᵉRᶠ; —NRᵉSO₂Rᶠ; —CORᵉ; —NRᵉCORᶠ; —OCORᵉ; —OCONRᵉRᶠ; —NRᶜCONRᶠRᵍ; —NRᶜCO₂Rʰ; —OCO₂Rʰ; —C(NRᵉ)NRᶠRᵍ; —NRᵉC(NH)NRᶠRᵍ; or —NRᵉC(NRᶠ)Rᵍ;

Rᵉ, Rᶠ and Rᵍ represent hydrogen; or —C₁₋₆ straight- or branched-chain alkyl unsubstituted or substituted with one to four Rⁱ groups;

or Rᵉ and Rᶠ taken together with any intervening atoms represent a 4–6 membered saturated ring optionally interrupted by one to three of O, S, —C(O)— or NRᵍ with Rᵍ as defined above, said ring being unsubstituted or substituted with one to four Rⁱ groups;

each Rʰ independently represents H, a —C₁₋₆ straight or branched-chain alkyl group, a —C₃–C₆ cycloalkyl group or phenyl, or when two Rʰ groups are present, said Rʰ groups may be taken in combination and represent a 4–6 membered saturated ring, optionally interrupted by one or two of O, S, SO₂, —C(O)—, NH and NCH₃;

Rⁱ independently represents halo; —CN; —NO₂; phenyl; —NHSO₂Rʰ; —ORʰ, —N(Rʰ)₂; —N⁺(Rʰ)₃; —C(O)N(Rʰ)₂; —SO₂N(Rʰ)₂; heteroaryl; heteroarylium; —CO₂Rʰ; —C(O)Rʰ; —OCORʰ; —NHCORʰ; guanidinyl; carbamimidoyl or ureido, and Rʷ represents hydrogen or —C₁₋₆ straight- or branched-chain alkyl, unsubstituted or substituted with one to four Rⁱ groups; C₃₋₆ cycloalkyl optionally substituted with one to four Rⁱ groups; or phenyl optionally substituted with one to four Rⁱ groups.

M. A more preferred subset of 1-methyl compounds is represented by formula Ig:

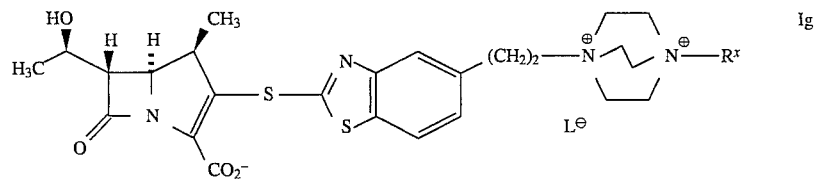

wherein:
L⁻ is a pharmaceutically acceptable counterion;
Rˣ represents hydrogen or a C₁₋₈ straight- or branched-chain alkyl, optionally interrupted by one or two of O, S, SO, SO₂, NRʷ, N⁺RʰRʷ, or —C(O)—, said chain being unsubstituted or substituted with one to four of halo, CN, NO₂, ORʷ, SRʷ, SORʷ, SO₂Rʷ, NRʰRʷ, N⁺(Rʰ)₂Rʷ, —C(O)—Rʷ, C(O)NRʰRʷ, SO₂NRʰRʷ, CO₂Rʷ, OC(O)Rʷ, OC(O)NRʰRʷ, NRʰC(O)Rʷ, NRʰC(O)NRʰRʷ, or a phenyl or heteroaryl group which is in mm optionally substituted with from one to four Rⁱ groups or with one to two C₁₋₃ straight- or branched-chain alkyl groups, said alkyl groups being unsubstituted or substituted with one to four Rⁱ groups;

each $R^h$ independently represents H, a —$C_{1-6}$ straight or branched-chain alkyl group, a —$C_3$-$C_6$ cycloalkyl group or phenyl, or when two $R^h$ groups are present, said $R^h$ groups may be taken in combination and represent a 4–6 membered saturated ring, optionally interrupted by one or two of O, S, $SO_2$, —C(O)—, NH and $NCH_3$;

$R^w$ represents hydrogen or —$C_{1-6}$ straight- or branched-chain alkyl, unsubstituted or substituted with one to four $R^i$ groups, $C_{3-6}$ cycloalkyl optionally substituted with one to four $R^i$ groups; phenyl optionally substituted with one to four $R^i$ groups, or $R^h$ and $R^w$ taken together with any intervening atoms represent a 5–6 membered saturated ring, optionally interrupted by one or two of O, S, $SO_2$, NH or $NCH_3$; and $R^i$ independently represents halo; —CN; —$NO_2$; phenyl; —$NHSO_2R^h$; —$OR^h$, —$N(R^h)_2$; —$N^+(R^h)_3$; —$C(O)N(R^h)_2$; —$SO_2N(R^h)_2$; heteroaryl; heteroarylium; —$CO_2R^h$; —$C(O)R^h$; —$OCOR^h$; —$NHCOR^h$; guanidinyl; carbamimidoyl or ureido.

N. Another more preferred subset of 1-methyl compounds is represented by formula Ih:

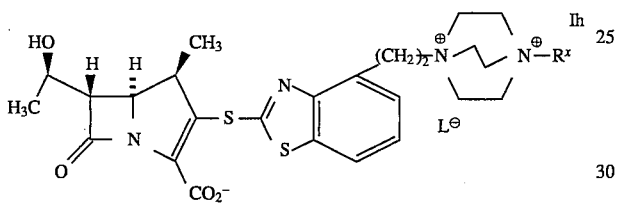

wherein:

L– is a pharmaceutically acceptable counterion;

$R^x$ represents hydrogen or a $C_{1-8}$ straight- or branched-chain alkyl, optionally interrupted by one or two of O, S, SO, $SO_2$, $NR^w$, $N^+R^hR^w$, or —C(O)—, said chain being unsubstituted or substituted with one to four of halo, CN, $NO_2$, $OR^w$, $SR^w$, $SOR^w$, $SO_2R^w$, $NR^hR^w$, $N^+(R^h)_2R^w$, —C(O)—$R^w$, $C(O)NR^hR^w$, $SO_2NR^hR^w$, $CO_2R^w$, $OC(O)R^w$, $OC(O)NR^hR^w$, $NR^hC(O)R^w$, $NR^hC(O)NR^hR^w$, or a phenyl or heteroaryl group which is in mm optionally substituted with from one to four $R^i$ groups or with one to two $C_{1-3}$ straight- or branched-chain alkyl groups, said alkyl groups being unsubstituted or substituted with one to four $R^i$ groups;

each $R^h$ independently represents H, a —$C_{1-6}$ straight or branched-chain alkyl group, a —$C_3$-$C_6$ cycloalkyl group or phenyl, or when two $R^h$ groups are present, said $R^h$ groups may be taken in combination and represent a 4–6 membered saturated ring, optionally interrupted by one or two of O, S, $SO_2$, —C(O)—, NH and $NCH_3$;

$R^w$ represents hydrogen or —$C_{1-6}$ straight- or branched-chain alkyl, unsubstituted or substituted with one to four $R^i$ groups, $C_3$cycloalkyl optionally substituted with one to four $R^i$ groups; phenyl optionally substituted with one to four $R^i$ groups, or $R^h$ and $R^w$ taken together with any intervening atoms represent a 5–6 membered saturated ring, optionally interrupted by one or two of O, S, $SO_2$, NH or $NCH_3$; and $R^i$ independently represents halo; —CN; —$NO_2$; phenyl; —$NHSO_2R^h$; —$OR^h$, —$N(R^h)_2$; —$N^+(R^h)_3$; —$C(O)N(R^h)_2$; —$SO_2N(R^h)_2$; heteroaryl; heteroarylium; —$CO_2R^h$; —$C(O)R^h$; —$OCOR^h$; guanidinyl; carbamimidoyl or ureido.

O. Another preferred subset of 1-methyl compounds is represented by formula Ii:

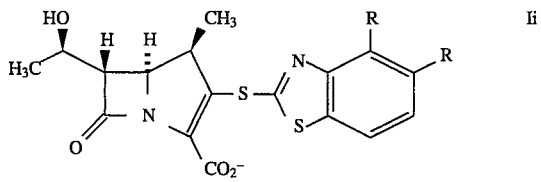

wherein:

each R independently represents a member selected from the group consisting of hydrogen or —$C_{1-6}$ straight- or branched-chain alkyl, unsubstituted or substituted with one to three $R^d$ groups;

$R^d$ represents —Q ;

Q represents a member selected from the group consisting of:

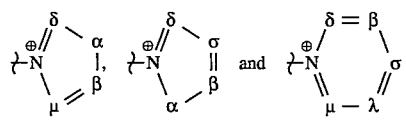

wherein:

represents O, S or $NR^s$;

β, δ, λ, μ and σ independently represent $CR^t$, N or $N^+R^s$ provided that no more than one of β, δ, λ, μ and σ may be $N^+R^s$ and further provided that from one to three positively charged atoms are contained in the R groups;

$R^s$ represents hydrogen; phenyl; —$C_{1-6}$ straight- or branched-chain alkyl, unsubstituted or substituted with one to four $R^i$ groups;;

$R^t$ represents hydrogen; halo; phenyl; —CN; —$NHR^u$; —$NR^uR^v$; —$OR^u$; —$SR^u$; —$CONR^uR^v$; —$COOR^h$; —$SOR^u$; —$SO_2R^u$; —$SO_2NR^uR^v$; —$NR^uSO_2R^v$; —$COR^u$; —$NR^uCOR^v$; —$OCOR^u$; —$OCONR^uR^v$; —$NR^uCO_2R^v$; —$NR^uCONR^vR^w$; —$OCO_2R^v$; —$C_{1-6}$ straight- or branched-chain alkyl, unsubstituted or substituted with one to four $R^i$ groups;

$R^i$ represents halo; —CN; —$NO_2$; phenyl; —$NHSO_2R^h$; —$OR^h$, —$N(R^h)_2$; —$N^+(R^h)_3$; —$C(O)N(R^h)_2$; —$SO_2N(R^h)_2$; heteroaryl; heteroarylium; —$CO_2R^h$; —$C(O)R^h$; —$OCOR^h$; —$NHCOR^h$; guanidinyl; carbamimidoyl or ureido;

each $R^h$ independently represents H, a —$C_{1-6}$ straight or branched-chain alkyl group, a —$C_3$-$C_6$ cycloalkyl group or phenyl, or when two $R^h$ groups are present, said $R^h$ groups may be taken in combination and represent a 4–6 membered saturated ring, optionally interrupted by one or two of O, S, $SO_2$, —C(O)—, NH and $NCH_3$;

$R^u$ and $R^v$ represent hydrogen or —$C_{1-6}$ straight- or branched-chain alkyl, unsubstituted or substituted with one to four $R^i$ groups;

or $R^u$ and $R^v$ together represent a 4–6 membered saturated ting optionally interrupted by one or more of O, S, $NR^w$ or —C(O)—, said ring being unsubstituted or substituted with one to four $R^i$ groups;

and each $R^w$ independently represents hydrogen or —$C_{1-6}$ straight- or branched-chain alkyl, unsubstituted or substituted with one to four $R^i$ groups, $C_{3-6}$ cycloalkyl optionally substituted with one to four $R^i$ groups; or phenyl optionally substituted with one to four $R^i$ groups.

P. A further subset of 1-methyl compounds which is preferred is represented by the formula Ie:

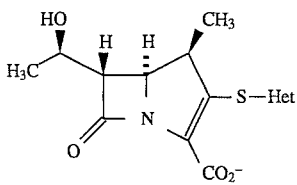

wherein:

Het has substituent groups which contain from two to three positively charged atoms and is selected from the group consisting of:

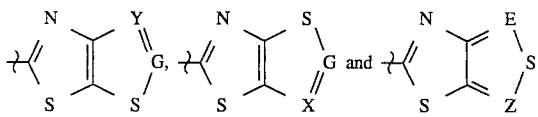

wherein:

E, G and Y independently represent CR or N;

X and Z independently represent CH or N;

R represents a member selected from the group consisting of hydrogen; —$C_{1-6}$ straight- or branched-chain alkyl, unsubstituted or substituted with $R^d$;

with the proviso that one R group is present which contains Q;

$R^d$ represents Q;

Q represents

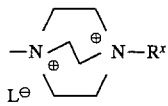

wherein

L– is a pharmaceutically acceptable counterion;

$R^x$ represents hydrogen or a $C_{1-8}$ straight- or branched-chain alkyl, optionally interrupted by one or two of O, S, SO, $SO_2$, $NR^w$, $N^+R^hR^w$, or —C(O)—, said chain being unsubstituted or substituted with one to four of halo, CN, $NO_2$, $OR^w$, $SR^w$, $SOR^w$, $SO_2R^w$, $NR^hR^w$, $N^+(R^h)_2R^w$, —C(O)—$R^w$, C(O)$NR^hR^w$, $SO_2NR^hR^w$, $CO_2R^w$, $OC(O)R^w$, $OC(O)NR^hR^w$, $NR^hC(O)R^w$, $NR^hC(O)NR^hR^w$, or a phenyl or heteroaryl group which is in turn optionally substituted with from one to four $R^i$ groups or with one to two $C_{1-3}$ straight- or branched-chain alkyl groups, said alkyl groups being unsubstituted or substituted with one to four $R^i$ groups;

each $R^h$ independently represents H, a —$C_{1-6}$ straight or branched-chain alkyl group, a —$C_3$-$C_6$ cycloalkyl group or phenyl, or when two $R^h$ groups are present, said $R^h$ groups may be taken in combination and represent a 4–6 membered saturated ring, optionally interrupted by one or two of O, S, $SO_2$, —C(O)—, NH and $NCH_3$;

$R^i$ independently represents halo; —CN; —$NO_2$; phenyl; —$NHSO_2R^h$; —$OR^h$, —$N(R^h)_2$; —$N^+(R^h)_3$; —C(O)$N(R^h)_2$; —$SO_2N(R^h)_2$; heteroaryl; heteroarylium; —$CO_2R^h$; —C(O)$R^h$; —$OCOR^h$; —$NHCOR^h$; guanidinyl; carbamimidoyl or ureido, and $R^w$ represents hydrogen or —$C_{1-6}$ straight- or branched-chain alkyl, unsubstituted or substituted with one to four $R^i$ groups, $C_{3-6}$ cycloalkyl optionally substituted with one to four $R^i$ groups; phenyl optionally substituted with one to four $R^i$ groups.

or $R^h$ and $R^w$ taken together with any intervening atoms represent a 5–6 membered saturated ring, optionally interrupted by one or two of O, S, $SO_2$, NH or $NCH_3$.

Q. Another preferred subset of the 1-methyl compounds of the invention is defined in accordance with formula Ie:

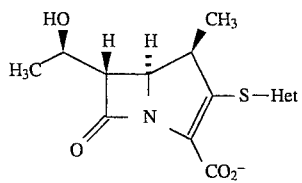

wherein:

Het has substituents which contain from one to three positively charged atoms and is selected from the group consisting of:

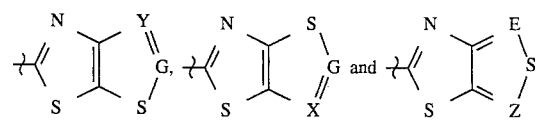

wherein:

E, G, X, Y and Z independently represent CR or N;

R represents a member selected from the group consisting of hydrogen; —$C_{1-6}$ straight- or branched-chain alkyl, unsubstituted or substituted with one to three $R^d$ groups;

with the proviso that from one to three R groups are present which contains Q;

$R^d$ represents Q;

Q is selected from the group consisting of:

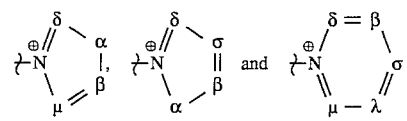

wherein:

α represents O, S or $NR^s$;

β, δ, λ, μ and σ independently represent $CR^t$, N or $N^+R^s$ provided that no more than one of β, δ, λ, μ and σ may be $N^+R^s$;

$R^s$ represents hydrogen; phenyl; —$C_{1-6}$ straight- or branched-chain alkyl, unsubstituted or substituted with one to four $R^i$ groups;

$R^i$ represents halo; —CN; —$NO_2$; phenyl; —$NHSO_2R^h$; —$OR^h$, —$N(R^h)_2$; —$N^+(R^h)_3$; —C(O)$N(R^h)_2$; —$SO_2N(R^h)_2$; heteroaryl; heteroarylium; —$CO_2R^h$; —C(O)$R^h$; —$OCOR^h$; —$NHCOR^h$; guanidinyl; carbamimidoyl or ureido;

each $R^h$ independently represents H, a —$C_{1-6}$ straight or branched-chain alkyl group, a —$C_3$-$C_6$ cycloalkyl group or phenyl, or when two $R^h$ groups are present, said $R^h$ groups may be taken in combination and represent a 4–6 membered saturated ring, optionally interrupted by one or two of O, S, $SO_2$, —C(O)—, NH and $NCH_3$;

$R^t$ represents hydrogen; halo; phenyl; —CN; —$NHR^u$; —$NR^uR^v$; —$OR^u$; —$SR^u$; —$CONR^uR^v$; —$COOR^h$; —$SOR^u$; —$SO_2R^u$; —$SO_2NR^uR^v$; —$NR^uSO_2R^v$; —$COR^u$; —$NR^uCOR^v$; —$OCOR^u$; —$OCONR^uR^v$; —$NR^uCO_2R^v$; —$NR^uCONR^vR^w$; —$OCO_2R^v$; —$C_{1-6}$ straight- or branched-chain alkyl, unsubstituted or substituted with one to four $R^i$ groups;

$R^u$ and $R^v$ represent hydrogen or —$C_{1-6}$ straight- or branched-chain alkyl, unsubstituted or substituted with one to four $R^i$ groups;

or $R^u$ and $R^v$ together represent a 4–6 membered saturated ring optionally interrupted by one or more of O, S, $NR^w$ or —C(O)—, said ring being unsubstituted or substituted with one to four $R^i$ groups;

and each $R^w$ independently represents hydrogen or —$C_{1-6}$ straight- or branched-chain alkyl, unsubstituted or substituted with one to four $R^i$ groups, $C_{3-6}$ cycloalkyl optionally substituted with one to four $R^i$ groups; or phenyl optionally substituted with one to four $R^i$ groups;

or $R^h$ and $R^w$ taken together with any intervening atoms represent a 5–6 membered saturated ring, optionally interrupted by one or two of O, S, $SO_2$, NH or $NCH_3$.

Representative compounds of the invention are as described above with respect to formula I, wherein Het is selected from the group consisting of:

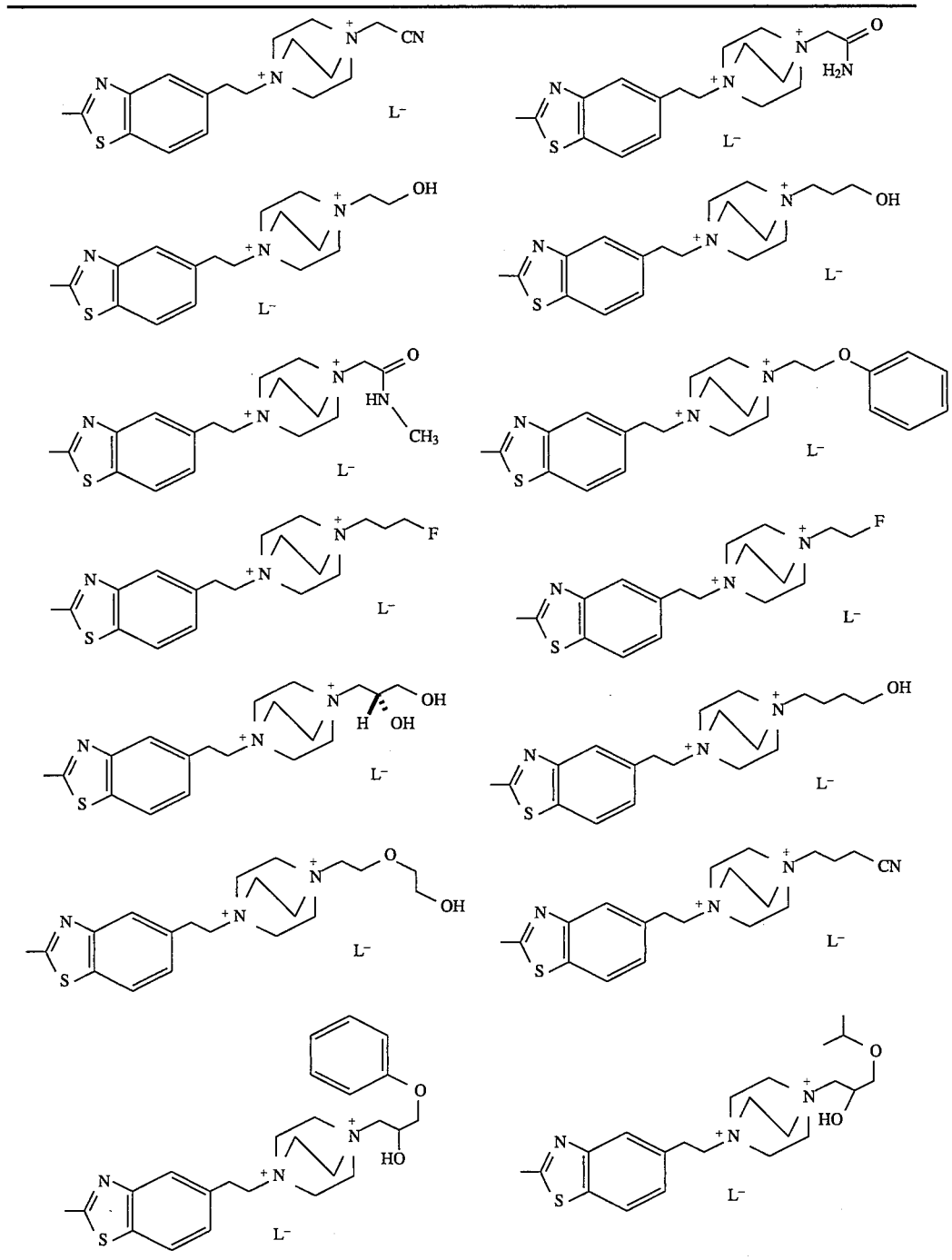

Additional representative compounds of the invention are as described above with respect to formula I wherein Het is selected from the following:

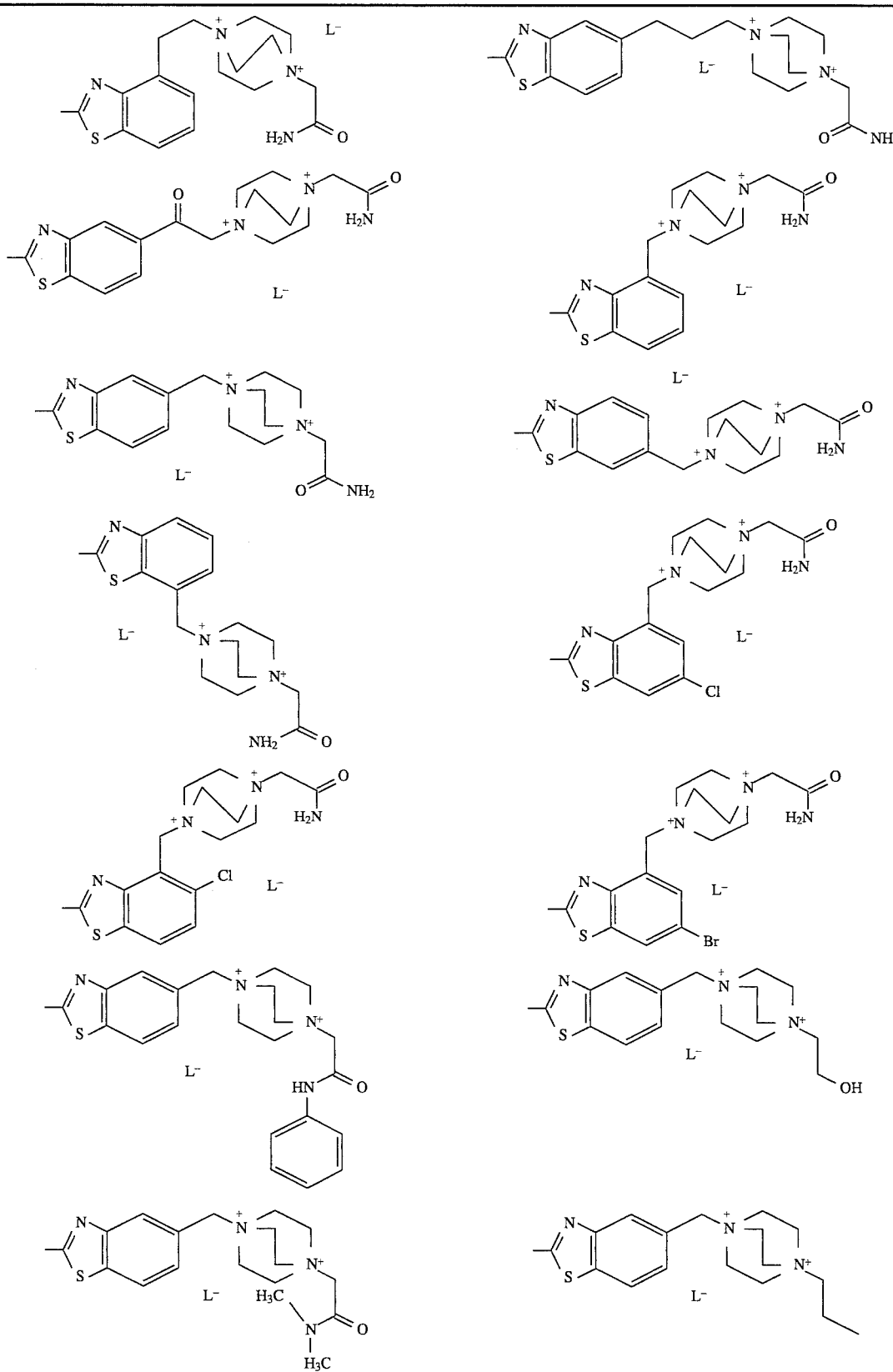

35 36
-continued
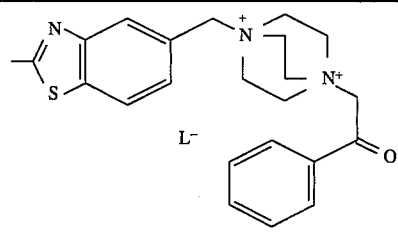
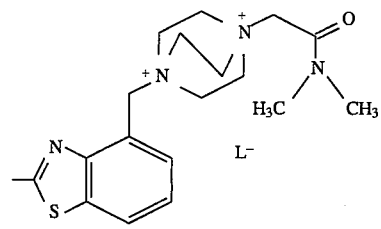
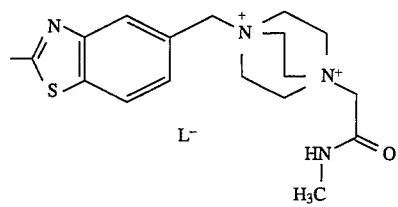
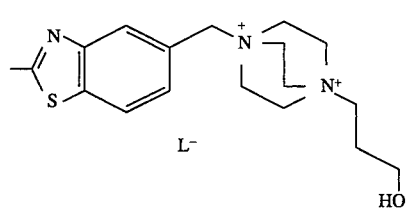
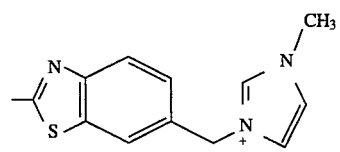
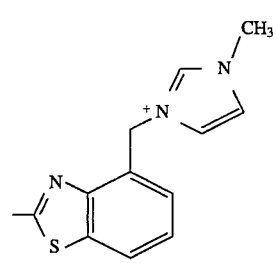
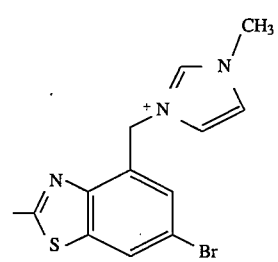
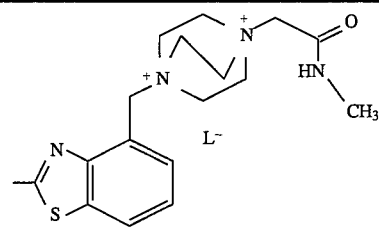
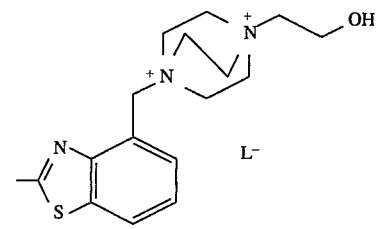
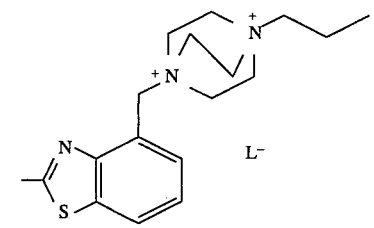
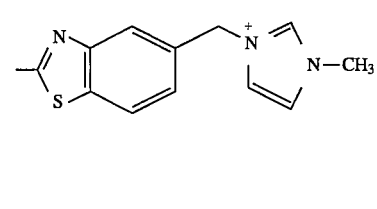
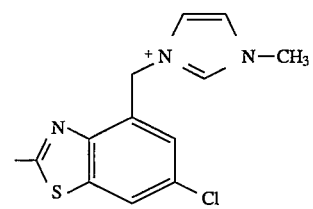
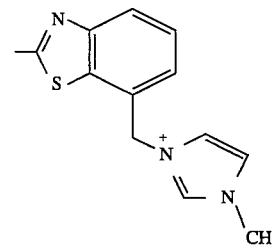
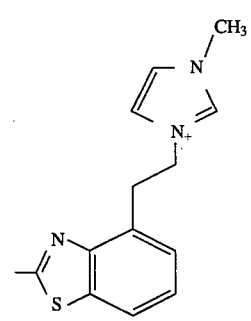

5,496,816
| 37 | 38 |
|---|---|
| 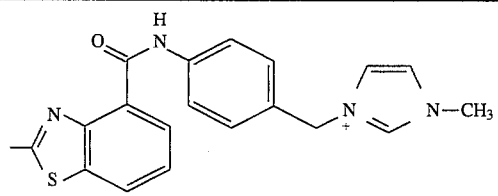 | 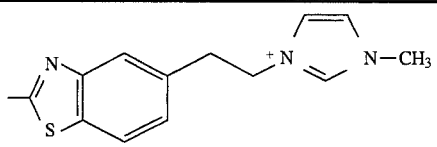 |
| 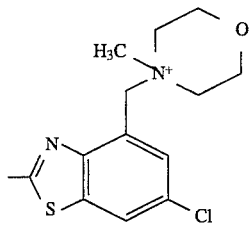 | 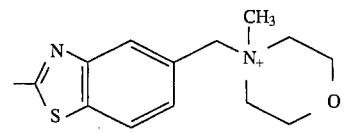 |
| 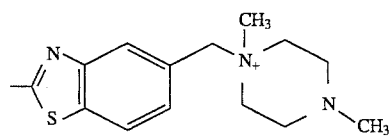 | 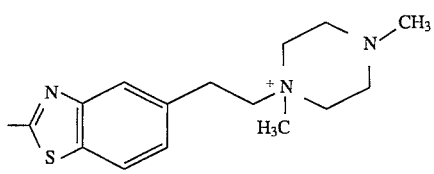 |
| 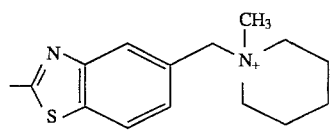 | 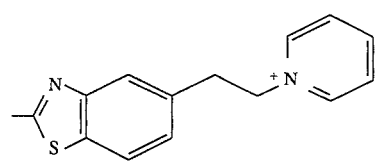 |
| 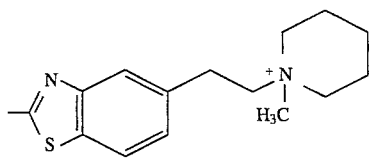 | 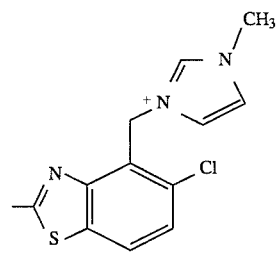 |
| 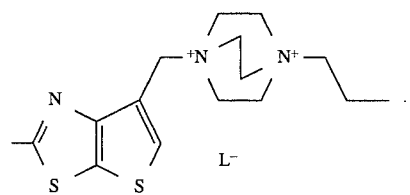 | 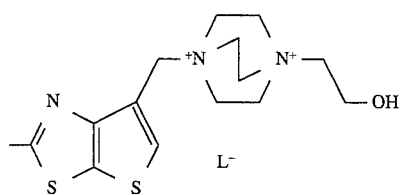 |
| 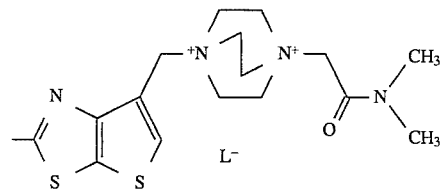 | 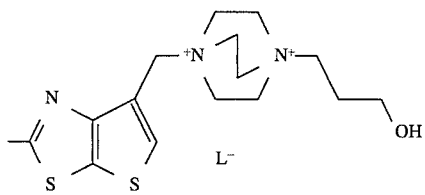 |
| 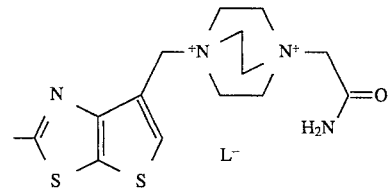 | 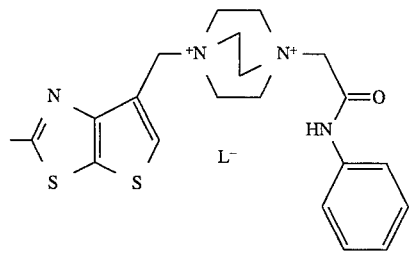 |
-continued

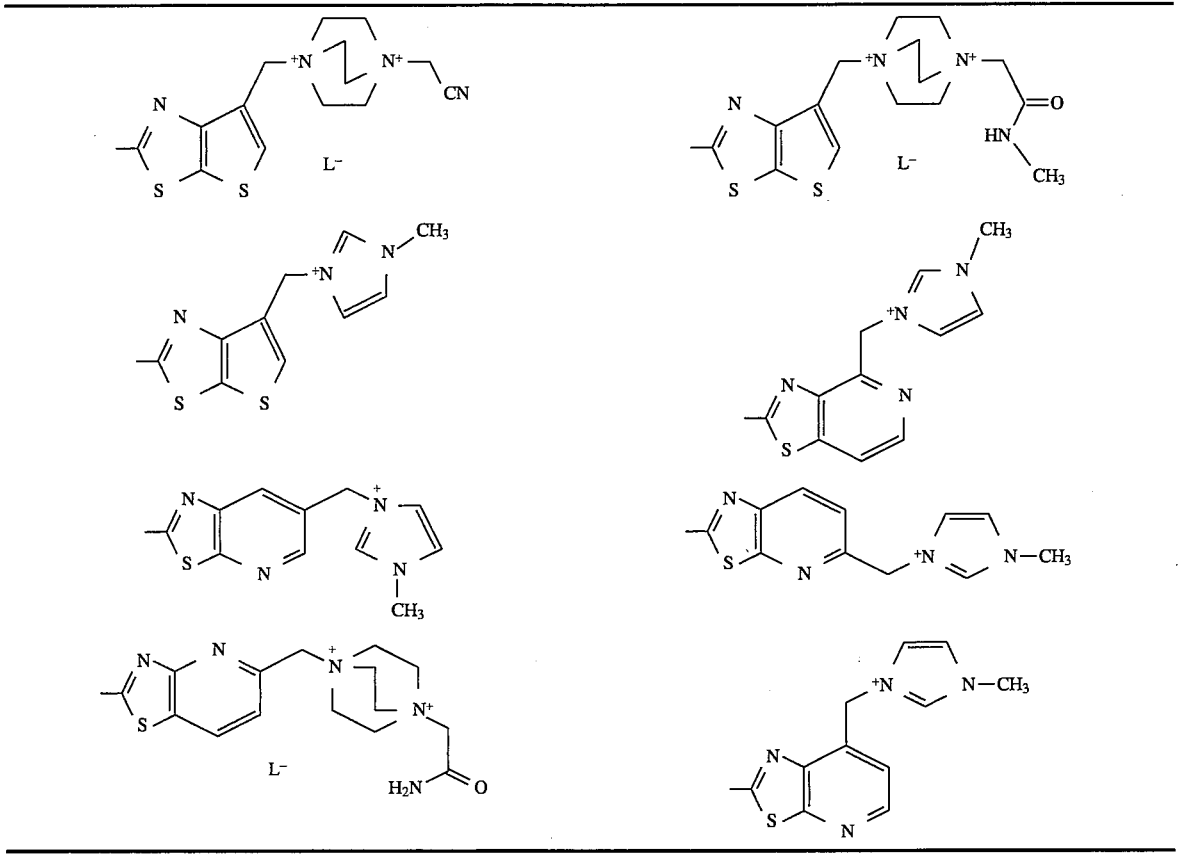

A preferred compound described herein is represented by the formula:

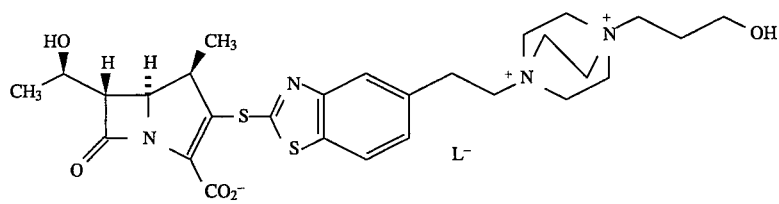

wherein L– represents a pharmaceutically acceptable counterion.

The compounds of the invention can be synthesized in accordance with the following general schemes and examples.

The compounds of the present invention are prepared by reacting a suitably protected carbapen-2-em-3-carboxylate having a suitable leaving group at the 2-position with a heterocyclic thiolate, modifying the thus-introduced side chain (if desired), and then removing any protecting groups which are present to afford the desired final product. The process is illustrated by the following generic scheme:

FLOW SHEET A

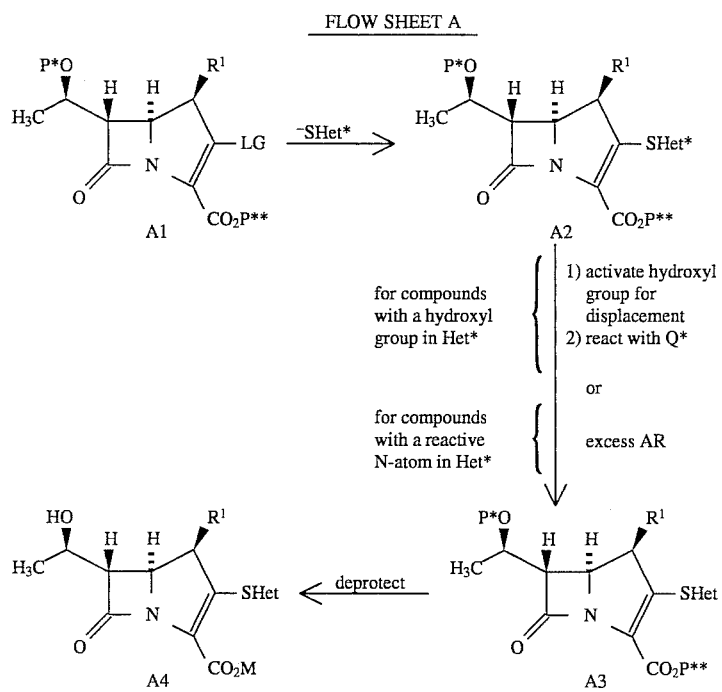

With reference to Flow Sheet A, P*, $R^1$, Het, and M, are as defined with respect to the compounds of formula I.

P** represents a carboxyl protecting group.

Het* represents a heterocyclic group which may or may not be selected from the group comprising Het as defined above and is modified as necessary in the course of the synthesis of a compound of formula I to afford a member of that group, thus Het* may be viewed as a precursor for Het.

Q* represents a group which reacts with intermediate A2 (upon activation of A2) in a manner which results in the incorporation in the final product of a member of the group defined as Q above, thus Q* may be viewed as a precursor for Q.

LG represents a suitable leaving group such as trifluoromethanesulfonate (triflate), diethyl phosphonate, diphenyl phosphonate, di-(p-chlorophenyl) phosphonate, methanesulfonate (mesylate), benzenesulfonate, p-toluenesulfonate, chloride, bromide, iodide and the like.

AR represents a suitable alkylating reagent, such as methyl iodide, methyl bromide, benzyl trichloroacetamidate, methyl trifluoromethanesulfonate, triethyloxonium tetrafluoroborate and the like.

The heterocyclic thiols or thioxo compounds (see discussion of tautomeric equilibrium below) used to generate the heterocyclic thiolates –SHet* used in the synthesis of the compounds of the present invention are, in some cases, commercially available or can be readily prepared by following procedures described in the literature.

In cases where the requisite thiolate precursor is neither commercially available nor known in the literature it is necessary to synthesize the thiolate precursor by a newly developed synthesis. For example, 2-thioxo-2,3-dihydrobenzothiazoles (alternatively described as the tautomeric 2-mercapto-benzothiazoles; see below) can be prepared from commercially available anilines or nitrobenzenes with the appropriate substitution (Comprehensive Heterocyclic Chemistry Volume 6; K. T. Potts, ed; Pergamon Press, Oxford, 1984).

Heterocyclic compounds in which a carbon atom bearing a mercaptan functionality is adjacent to a nitrogen atom exist as an equilibrium mixture of "thioxo" and "thiol" tautomers (as exemplified by the structure of 2-thioxo-2,3-dihydrothiazole (2-mercapto-thiazole); shown below) and may, in fact, exist predominantly in the thioxo form under neutral conditions. However, on treatment with base, the equilibrium shifts to favor the salt of the thiol form (thiolate) which can then react with the carbapenem as described below.

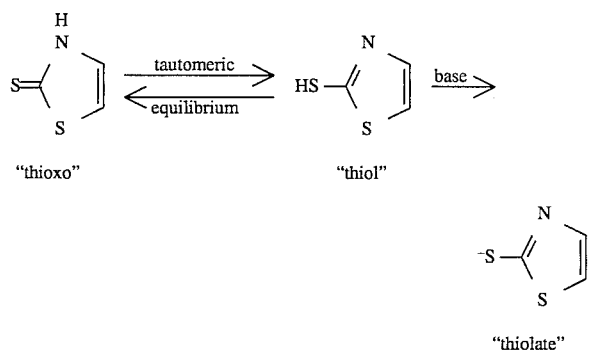

"thioxo"   "thiol"

"thiolate"

The heterocyclic thiolate –SHet* is initially reacted with a suitably protected carbapen-2-em-3-carboxylate having a suitable leaving group LG at the 2-position.

The carboxylic acid group at C-3 of the carbapenem is generally protected as a carboxyl protecting group such as p-nitrobenzyl (PNB), allyl, p-methoxybenzyl, trichloroethyl, 2-trimethhylsilylethyl, and the like. Furthermore, the hydroxyl group of the 6-(hydroxyethyl) side-chain is optionally protected with a hydroxyl protecting group such as trimethylsilyl (TMS), triethylsilyl (TES), tert-butyldimethylsilyl (TBDMS), tert-butyldiphenylsilyl (TBDPS), acetyl, allyloxycarbonyl, 2-trimethylsilylethoxy carbonyl, 2-trichloroethoxycarbonyl and the like.

The addition of the thiolate –SHet* to the carbapenem is accomplished by treating a solution of the thiol or thioxo compound in a suitable solvent such as tetrahydrofuran (THF), ether, acetonitrile, dimethylformamide (DMF), benzene, dimethylsulfoxide (DMSO), and the like with a suitable base such as sodium hydride, sodium hydroxide, lithium hydride, lithium hydroxide, lithium trimethylsilanoate, lithium hexamethyldisilazide, potassium hydride, butyl lithium, phenyl lithium, cesium hydroxide, and the like at a temperature between about −20° C. and 35° C. for about 1 to 90 minutes then combining the carbapenem, either as a solid or in solution, with the resulting mixture. The reaction is then allowed to proceed at a temperature between about 0° C. and 75° C. for about 0.25 to 24 hours.

Alternatively, the thiol or thioxo compound, base and carbapenem can be mixed together with a suitable solvent without pre-treatment of the thiol or thioxo compound with base. Once the thiol or thioxo compound, base, and carbapenem have been mixed, the reaction is allowed to proceed at a temperature between about 0° C. and 75° C. for about 0.25 to 24 hours.

The crude 2-heteroarylthio substituted carbapenem is purified by crystallization or by chromatography on silica gel, eluting with a suitable solvent or mixture of two or more solvents, such as hexane, ethyl acetate, ether, benzene, dichloromethane, chloroform, acetone, methanol and the like.

Modification of the heteroaryl side chain of compounds A2, to introduce the charged substituent of A4, is best accomplished before removal of the protecting groups. For compounds which contain a hydroxyl group in the side chain, i.e. in Het*, a positively charged substituent may be introduced into the side chain by first activating the hydroxyl group by converting it to a suitable leaving group such as a triflate, mesylate, tosylate, iodide, chloride, bromide, and the like, and then displacing the resulting leaving group with a compound Q*, such as N-methyl-imidazole, N-(2-hydroxyethyl)-imidazole, N-methyldiazabicyclooctane, 1-(carboxamidomethyl)-4-aza-1-azoniabicyclo[2.2.2.]-octane, 1-(3-hydroxyprop-1-yl)-4-aza-1-azoniabicyclo-[2.2.2.]-octane, pyridine, morpholine and the like which contains a nitrogen atom that can act as a nucleophile.

Alternatively, the charged substituent may be incorporated in the thiolate −SHet* before addition of the thiolate to the carbapenem, or may be introduced after deprotection of A2.

In some cases, activation of the hydroxyl group and displacement by Q* to produce A3 may be accomplished in a single step by taking advantage of the basic character of compound Q* and using it as a base in the activation reaction.

The conversion of the hydroxyl group to a suitable leaving group is accomplished by treating the hydroxyl substituted compound in a suitable solvent such as dichloromethane, tetrahydrofuran, ether, benzene, and the like with an activating reagent, such as trifluoromethanesulfonic anhydride, methanesulfonic anhydride, toluenesulfonic anhydride, methanesulfonyl chloride, benzenesulfonyl chloride, toluenesulfonyl chloride, and the like in the presence of a suitable base such as triethylamine, tributylamine, diisopropylethylamine, and the like at a temperature between about −100° C. and 0° C. for about 5 to 120 minutes. The intermediate thus obtained contains a leaving group, which may be convened to an alternative leaving group, iodide, by treating a solution of the intermediate in a suitable solvent such as acetone, methyl ethyl ketone, and the like at about −10° C. to 50° C. with an excess of sodium iodide or potassium iodide for about 0.25 to 24 hours.

In many cases, the iodide is obtained in sufficiently pure form that it may be used without further purification. For ease of handling, the iodide, if not crystalline, may be lyophilized from benzene to afford an amorphous, easily handled, solid.

The activated hydroxyl group or iodide is displaced by reacting the activated intermediate with reagent Q*. In some cases, activation and displacement of the hydroxyl group may be accomplished in a single step. The activating reagent is added to a solution of the hydroxyl substituted compound in the presence of a suitable base in a suitable solvent such as dichloromethane, tetrahydrofuran, ether, DMF, benzene, acetonitrile, DMSO, and the like as described in the preceding paragraphs. The resulting activated intermediate is treated with 1–3 molar equivalents of compound Q* at a temperature between about −78° C. and 50° C. for about 15 to 120 minutes. In some cases, it is desirable to form the activated intermediate in one solvent, isolate the activated intermediate, and conduct the displacement reaction in a different solvent. In other cases, the displacement may be conducted without isolation of the intermediate and, in cases where Q* is also used as a base, may even be concurrent with the formation of the activated intermediate.

In cases where the displacement reaction is best accomplished by using the iodide, a solution of the iodide is combined with an approximately equivalent amount (0.9–1.05 molar equivalents) of compound Q*. A silver salt of a non-nucleophilic acid, such as silver trifluoromethanesulfonate, silver tetrafluoroborate and the like is preferably added. The resulting mixture is then subjected to a standard work-up procedure familiar to those skilled in the an to afford a crude product which is purified, if necessary, by recrystallization or chromatography.

An alternative method for introducing a positive charge into the side chain may be applied to side chains (i.e. Het* groups) that contain a nitrogen atom which may be quaternized by reaction with a suitable alkylating reagent AR, such as methyl iodide, methyl bromide, benzyl trichloroacetimidate, methyl trifluoromethanesulfonate, triethyloxonium tetrafluoroborate, and the like. Quaternization of the nitrogen atom in the side chain is effected by treating a solution of the compound with a slight excess (1.05 to 1.2 molar equivalents) of the alkylating reagent.

Synthesis is typically completed by removing any protecting groups which are present in the penultimate intermediate. The deprotected final product is then purified, as necessary, using, e.g., ion exchange chromatography, HPLC on reverse phase silica gel, MPLC on reverse phase polystyrene gel, and the like or by recrystallization.

The final product may be characterized structurally by standard techniques such as NMR, IR, MS, and UV. For ease of handling, the final product, if not crystalline, may be lyophilized from water to afford an amorphous, easily handled solid.

In some of the carbapenem compounds of the present invention, M is a readily removable carboxyl protecting group. Such conventional groups consist of known groups which are used to protectively block the carboxyl group during the synthesis procedures described therein. These conventional blocking groups are readily removable, i.e., they can be removed, if desired, by procedures which will not cause cleavage or other disruption of the remaining portions of the molecule. Such procedures include chemical and enzymatic hydrolysis, treatment with chemical reducing or oxidizing agents under mild conditions, treatment with a transition metal catalyst and a nucleophile and catalytic hydrogenation. Examples of such ester forming protecting groups include, in addition to those noted above, benzhydryl, 2-naphthylmethyl, benzyl, silyl such as trimethylsilyl (TMS), phenacyl, p-methoxybenzyl, acetonyl, o-nitrobenzyl, p-methoxyphenyl, 4-pyridylmethyl, and t-butyl.

Furthermore, the C-6 hydroxyethyl group of the carbapenem is optionally protected with a hydroxyl protecting group such as t-butylmethoxyphenylsilyl, t-butoxydiphenylsilyl, o-nitrobenzyloxycarbonyl, p-nitrobenzyloxycarbonyl, benzyloxycarbonyl, t-butyloxycarbonyl, 2,2,2-trichloroethyloxycarbonyl and the like.

The carbapenem compounds of the present invention are useful per se and in their pharmaceutically acceptable salt and ester forms in the treatment of bacterial infections in animal and human subjects. The term "pharmaceutically acceptable ester, salt or hydrate," refers to those salts, esters and hydrated forms of the compounds of the present invention which would be apparent to the pharmaceutical chemist. i.e., those which are substantially non-toxic and which may favorably affect the pharmacokinetic properties of said compounds, their palatability, absorption, distribution, metabolism and excretion. Other factors, more practical in nature, which are also important in the selection, are cost of the raw materials, ease of crystallization, yield, stability, hygroscopicity, and flowability of the resulting bulk drug. Conveniently, pharmaceutical compositions may be prepared from the active ingredients in combination with pharmaceutically acceptable carriers. Thus, the present invention is also concerned with pharmaceutical compositions and methods of treating bacterial infections utilizing as an active ingredient the novel carbapenem compounds.

With respect to —$CO_2M$, which is attached to the carbapenem nucleus at position 3, this represents a carboxylic acid group (M represents H), a carboxylate anion (M represents a negative charge), a pharmaceutically acceptable ester (M represents an ester forming group) or a carboxylic acid protected by a protecting group (M represents a carboxyl protecting group). The pharmaceutically acceptable salts referred to above may take the form —COOM, where M is a negative charge, which is balanced by a counterion, e.g., an alkali metal cation such as sodium or potassium. Other pharmaceutically acceptable counterions may be calcium, magnesium, zinc, ammonium, or alkylammonium cations such as tetramethylammonium, terabutylammonium, choline, triethylhydroammonium, meglumine, triethanolhydroammonium, etc.

The pharmaceutically acceptable salts referred to above may also include non-toxic acid salts. Thus, the Formula I compounds can be used in the form of salts derived from inorganic or organic acids. Included among such salts are the following: bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate, and undecanoate.

The pharmaceutically acceptable esters of the present invention are such as would be readily apparent to a medicinal chemist, and include, for example, those described in detail in U.S. Pat. No. 4,309,438. Included within such pharmaceutically acceptable esters are those which are hydrolyzed under physiological conditions, such as pivaloyloxymethyl, acetoxymethyl, phthalidyl, indanyl and methoxymethyl, and others described in detail in U.S. Pat. No. 4,479,947. These are also referred to as "biolabile esters".

Biolabile esters are biologically hydrolizable, and many are suitable for oral administration, due to good absorption through the stomach or intestinal mucosa, resistance to gastric acid degradation and other factors. Examples of biolabile esters include compounds in which M represents an alkoxyalkyl, cycloalkoxyalkyl, alkenyloxyalkyl, aryloxyalkyl, alkoxyaryl, alkylthioalkyl, cycloalkylthioalkyl, alkenylthioalkyl, arylthioalkyl or alkylthioaryl group. All of these groups can be substituted in the alkyl or aryl portions thereof with acyl or halo groups. The following M species are examples of biolabile ester forming moieties: acetoxymethyl, 1-acetoxyethyl, 1-acetoxypropyl, pivaloyloxymethyl, 1-isopropyloxycarbonyloxyethyl, 1-cyclohexyloxycarbonyloxyethyl, phthalidyl and (2-oxo-5-methyl-1,3-dioxolen-4-yl)methyl L—can be present or absent as necessary to maintain the appropriate charge balance. When present, L—represents a pharmaceutically acceptable counterion. Most anions derived from inorganic or organic acids are suitable. Representative examples of such counterions are the following: acetate, adipate, aminosalicylate, anhydromethylenecitrate, ascorbate, aspartate, benzoate, benzenesulfonate, bromide, citrate, camphorate, camphorsulfonate, chloride, estolate, ethanesulfonate, fumarate, glucoheptanoate, gluconate, glutamate, lactobionate, malate, maleate, mandelate, methanesulfonate, pantothenate, pectinate, phosphate/diphosphate, polygalacturonate, propionate, salicylate, succinate, sulfate, tartrate and tosylate. Other suitable anionic species will be apparent to the ordinary skilled chemist.

Likewise, when L—represents a specie with more than one negative charge, such as malonate, tartrate, or ethylenediaminetetraacetate (EDTA), an appropriate number of carbapenem molecules can be found in association therewith to maintain the overall charge balance and neutrality.

The compounds of the present invention are valuable antibacterial agents active against various Gram-positive and to a lesser extent Gram-negative bacteria, and accordingly find utility in human and veterinary medicine.

Many of compounds of the present invention are biologically active against MRSA/MRCNS. In vitro antibacterial activity is predictive of in vivo activity, when the compounds are administered to a mammal infected with a susceptible bacterial organism.

Using standard susceptibility tests, the compounds of the invention are determined to be active against MRSA.

The compounds of the invention can be formulated in pharmaceutical compositions by combining the compound with a pharmaceutically acceptable carrier. Examples of such carriers are set forth below.

The compounds may be employed in powder or crystalline form, in liquid solution, or in suspension. They may be administered by a variety of means; those of principal interest include: topically, orally and parenterally by injection (intravenously or intramuscularly).

Compositions for injection, a preferred route of delivery, may be prepared in unit dosage form in ampules, or in multidose containers. The injectable compositions may take such forms as suspensions, solutions, or emulsions in oily or aqueous vehicles, and may contain various formulating agents. Alternatively, the active ingredient may be in powder (lyophillized or non-lyophillized) form for reconstitution at the time of delivery with a suitable vehicle, such as sterile water. In injectable compositions, the carrier is typically comprised of sterile water, saline or another injectable liquid, e.g., peanut oil for intramuscular injections. Also, various buffering agents, preservatives and the like can be included.

Topical applications may be formulated in carriers such as hydrophobic or hydrophilic bases to form ointments, creams, lotions, in aqueous, oleaginous or alcoholic liquids to form paints or in dry diluents to form powders.

Oral compositions may take such forms as tablets, capsules, oral suspensions and oral solutions. The oral compositions may utilize carriers such as conventional formulating agents, and may include sustained release properties as well as rapid delivery forms.

The dosage to be administered depends to a large extent upon the condition and size of the subject being treated, the route and frequency of administration, the sensitivity of the pathogen to the particular compound selected, the virulence of the infection and other factors. Such matters, however, are left to the routine discretion of the physician according to principles of treatment well known in the antibacterial arts. Another factor influencing the precise dosage regimen, apart from the nature of the infection and peculiar identity of the individual being treated, is the molecular weight of the compound.

The compositions for human delivery per unit dosage, whether liquid or solid, may contain from about 0.01% to as high as about 99% of active material, the preferred range being from about 10–60%. The composition will generally contain from about 15 mg to about 2.5 g of the active ingredient; however, in general, it is preferable to employ dosage amounts in the range of from about 250 mg to 1000 mg. In parenteral administration, the unit dosage will typically include the pure compound in sterile water solution or in the form of a soluble powder intended for solution, which can be adjusted to neutral pH and isotonic.

The invention described herein also includes a method of treating a bacterial infection in a mammal in need of such treatment comprising administering to said mammal a compound of formula I in an amount effective to treat said infection.

The preferred methods of administration of the Formula I antibacterial compounds include oral and parenteral, i.e., i.v. infusion, i.v. bolus and i.m. injection.

For adults, about 5–50 mg of Formula I antibacterial compound per kg of body weight given one to four times daily is preferred. The preferred dosage is 250 to 1000 mg of the antibacterial given one to four times per day. More specifically, for mild infections a dose of about 250 mg two or three times daily is recommended. For infections against highly susceptible gram positive organisms a dose of about 500 mg three or four is recommended. For severe, life-threatening infections against organisms at the upper limits of sensitivity to the antibiotic, a dose of about 1000–2000 mg three to four times daily may be recommended.

For children, a dose of about 5–25 mg/kg of body weight given 2, 3, or 4 times per day is preferred; a dose of 10 mg/kg is typically recommended.

The compounds of Formula I are of the broad class known as carbapenems. Many carbapenems are susceptible to attack by a renal enzyme known as dehydropeptidase (DHP). This attack or degradation may reduce the efficacy of the carbapenem antibacterial agent. Many of the compounds of the present invention, on the other hand, are less subject to such attack, and therefore may not require the use of a DHP inhibitor. However, such use is optional and contemplated to be part of the present invention. Inhibitors of DHP and their use with carbapenems are disclosed in, e.g., [European Patent Application Nos. 79102616.4, filed Jul. 24, 1979 (Patent No. 0 007 614); and 82107174.3, filed Aug. 9, 1982 (Publication No. 0 072 014).

The compounds of the present invention may, where DHP inhibition is desired or necessary, be combined or used with the appropriate DHP inhibitor as described in the aforesaid patents and published application. The cited European Patent Applications define the procedure for determining DHP susceptibility of the present carbapenems and disclose suitable inhibitors, combination compositions and methods of treatment. A preferred weight ratio of Formula I compound: DHP inhibitor in the combination compositions is about 1:1.

A preferred DHP inhibitor is 7-(L-2-amino-2-carboxyethylthio)-2-(2,2-dimethylcyclopropanecarboxamide)-2-heptenoic acid or a useful salt thereof.

This invention is further described in connection with the following non-limiting examples.

PREPARATIVE EXAMPLE 1

P-NITROBENZYL (1R,5R, 6S)-2- (TRIFLUOROMETHYLSULFONYL)OXY-6-[(1R)- (TRIETHYLSILYLOXY)ETHYL]-1-METHYLCARBAPEN-2-EM-3-CARBOXYLATE

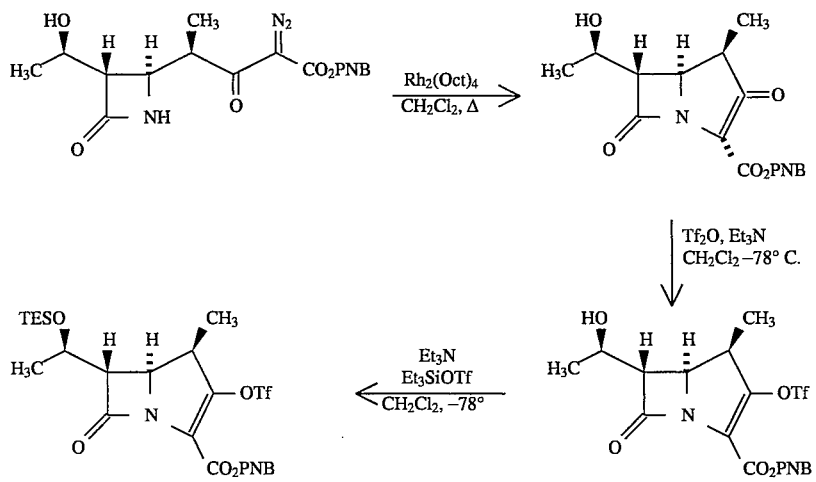

A solution of (3S,4R)-4-[2(R)-4-diazo-4-((p-nitrobenzyl)oxy)carbonyl-3-oxo-but-2-yl]-3-[1(R)-hydroxyethyl]-azetidin- 2-one(2.00 g, 5.12 mmol) and rhodium (II) octanoate dimer (20 mg, 0.026 mmol) in anhydrous dichloromethane (20 mL) was heated at reflux and under a nitrogen atmosphere for 3.25 hours. After cooling to room temperature, the reaction mixture was placed in a dry ice-acetone bath and treated dropwise with triethylamine (0.786 mL, 5.64 mmol). The resulting solution was stirred −78° C. and under a nitrogen atmosphere for 5 minutes, then treated dropwise with trifluoromethanesulfonic anhydride (0.904 mL, 5.38 mmol) and stirred at −78° C. for an additional 35 minutes. More triethylamine (1.07 mL, 7.68 mmol) was added dropwise followed by the slow, dropwise addition of triethylsilyl trifluoromethanesulfonate 1.27 mL, 5.64 mmol). After stirring an additional 75 minutes at 75 at −78° C., the reaction mixture was removed from the cooling bath, diluted with dichloromethane (75 mL), and washed with water (3×100 mL). The organic phase was dried over magnesium sulfate, filtered and evaporated under vacuum to give an oil (3.34 g). The crude product was purified by flash chromatography on a column of EM silica gel 60 (230–400 mesh, 3×19 cm, wet packed under dichloromethane). The column was eluted with dichloromethane, collecting ca. 15 mL fractions. Fractions 12–20 were combined and concentrated under vacuum to an oil that slowly deposited small, white crystalline islands on pumping under high vacuum. The oil-solid mixture (2.454 g) was treated with hexane (25 mL) and briefly solicited to give a copious crystalline precipitate. The mixture was diluted with more hexane (25 mL), then cooled in an ice bath for 20 minutes and filtered. The filter cake was washed with cold hexane (3×5 mL) and vacuum dried to provide the title compound (1.912 g) as a fluffy white solid. The filtrate and washings were concentrated under vacuum to ca. 10 mL, seeded, and stirred in an ice bath to provide additional product (0.187 g) as a white solid.

IR (KBr) 2961, 2880, 1782, 1731, 1521, 1438, 1341, 1290, 1217, 1174, 1144, 813, 738, and 609 cm$^{-1}$. UV (dioxane) $\lambda_{max}$ 273 nm ($\epsilon$ 14,300).

$^1$H NMR (CDCl$_3$, 500 MHz) δ0.61 (m, CH$_3$C$\underline{H}_2$Si), 0.95 (t, C$\underline{H}_3$CH$_2$Si), 1.25 (d, 1-CH$_3$), 1.30 (d, C$\underline{H}_3$CHOH), 3.37 (dq, H-1),3.40 (dd, H-6), 4.28 (p, CH$_3$C$\underline{H}$OH), 4.35 (dd, H-5), 5.36 and 5.43 (two d's, C$\underline{H}_2$C$_6$H$_4$NO$_2$), 7.63 and 8.23 (two m's, CH$_2$C$_6\underline{H}_4$NO$_2$).

PREPARATIVE EXAMPLE 2

(3S,4R)-4-[2(R)-4-DIAZO-4-(ALLYLOXY)CARBONYL-3-OXO-BUT-2-YL]-3-[1(R)-HYDROXYETHYL]-AZETIDIN-2-ONE

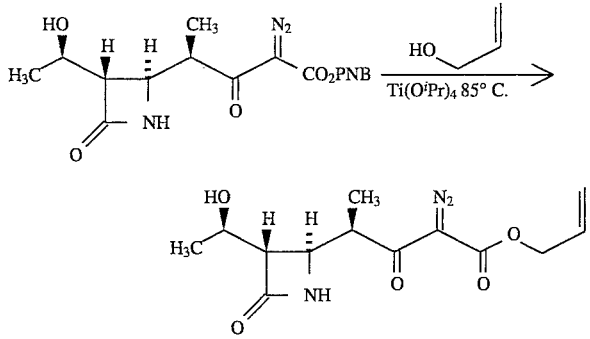

A solution of (3S,4R)-4-[2(R)-4-diazo-4-((p-nitrobenzyl)oxy)carbonyl-3-oxo-but-2-yl]-3-[1(R)-hydroxyethyl]-azetidin- 2-one(500 mg, 1.28 mmol) and titanium (IV)isopropoxide (91 mg, 0.32 mmol) in alkyl alcohol (4 mL) was heated at 85° C. for 135 minutes. The reaction mixture was concentrated and the residue was chromatographed on silica gel eluted with 2:1 hexane:acetone to afford [(3S,4R)-4-diazo-4-(allyloxy)carbonyl- 3-oxo-but-2-yl]-3-[1 (R)-hydroxyethyl]-azetidin- 2-one (300 mg) as a colorless oil.

$^1$H NMR (CDCl$_3$, 400 MHz) δ(carbapenem numbering) 6.19 (br s, NH), 5.90(m, OCH$_2$C$\underline{H}$=CH$_2$), 5.30(m, OCH$_2$CH=C$\underline{H}_2$), 4.71 (d, OC$\underline{H}_2$CH=CH$_2$), 4.11 (p, CH$_3$C$\underline{H}$OH), 3.82 (dd, H-5), 3.75 (dq, H-1), 2.88 (dd, H-6), 1.28 (d, C$\underline{H}_3$CHOH),1.19 (d, 1-CH$_3$).

PREPARATIVE EXAMPLE 3

ALLYL (1R, 5R, 6S)-2-(TRIFLUOROMETHYLSULFONYL)OXY-6-[(1R)-(TRIETHYLSILYLOXY)ETHYL]- 1-METHYLCARBAPEN-2-EM-3-CARBOXYLATE

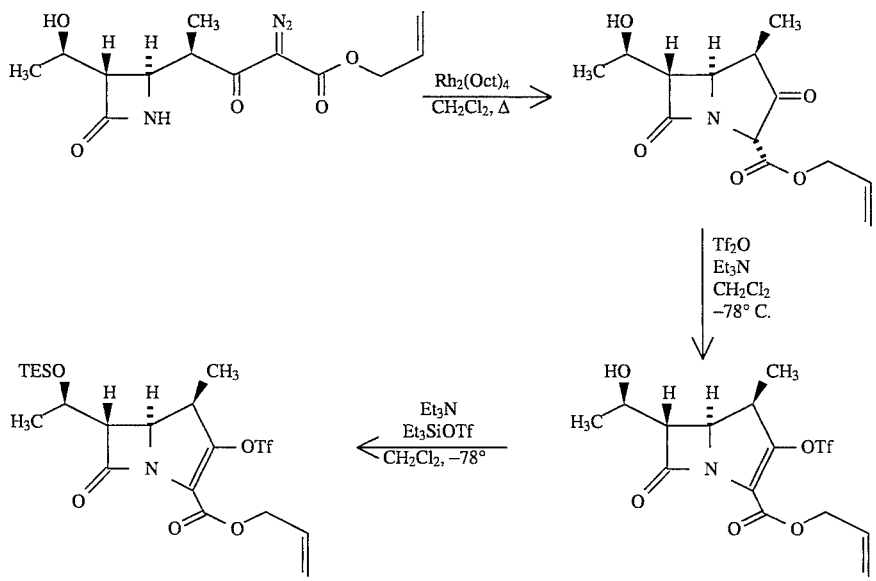

A solution of (3S,4R)-4-[2(R)-4-diazo-4-)(allyloxy) carbonyl-3-oxo-but-2-yl]-3-[1(R)-hydroxyethyl]-azetidin-2-one (213)mg,0.55 mmol) and rhodium (II) octanoate dimer (3.6 mg, 0.005 mmol) in anhydrous dichloromethane (4 mL) was heated at reflux and under a nitrogen atmosphere for 3 hours. After cooling to room temperature, the reaction mixture was placed in a dry ice-acetone bath an treated dropwise with diisopropylethylamine (0.10 mL, 0.57 mmol). The resulting solution was stirred −78° C. and under nitrogen atmosphere for 5 minutes, then treated dropwise with trifluoromethanesulfonic anhydride (0.117 mL, 0.55 mmol) and stirred at −78° C. for an additional 30 minutes. More diisopropylethylamine (0.19 mL, 1.09 mmol) was added dropwise followed by the slow, dropwise addition of triethylsilyl trifluoromethanesulfonate (0.154 mL, 0.68 mmol). After stirring an additional 75 minutes at −78° C., the reaction mixture was removed from the cooling bath, diluted with dichloromethane, and washed with water. The organic phase was dried over magnesium sulfate, filtered and evaporated under vacuum to give an oil. The crude product thus obtained was used without further purification.

PREPARATIVE EXAMPLE 4

2-THIO-4-((TRIMETHYL)SILYLOXYMETH-YL)THIAZOLO[5,4-B]PYRIDINE

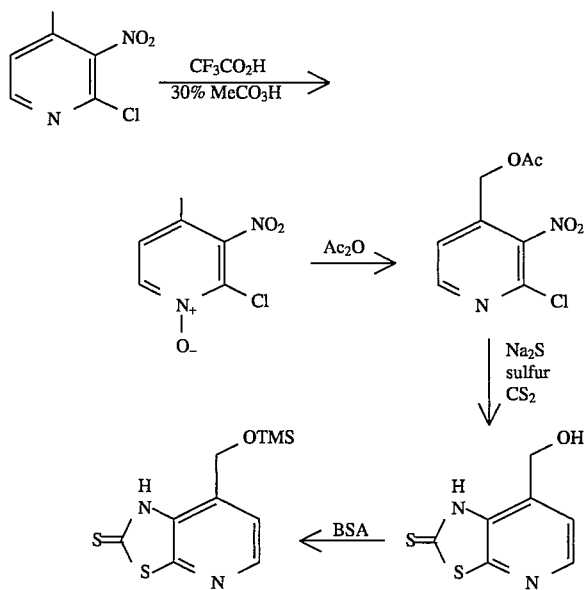

Step 1: 2-Chloro-3-nitro-4-picoline-N-oxide 2-Chloro-3-nitro-4-picoline (7 g, 0.04mol) was added to an ice cooled mixture of trifluoracetic acid (25 mL) and 30% peracetic acid in acetic acid (15 mL). The mixture was allowed to warm to room temperature over 30 minutes and was heated in a 60° C. oil bath for 5 hours. The mixture was partitioned between methylene chloride (100 mL) and water (100 mL). The pH was adjusted to 8 with 2.5 N sodium hydroxide and the aqueous layer was extracted with more methylene chloride (2×100 mL). The combined methylene chloride layers were dried with magnesium sulfate, filtered and evaporated to give 7.5 g of a 4:1 mixture of 2-Chloro-3-nitro-4-picoline-N-oxide (79%) and 2-Chloro-3-nitro-4-picoline, as determined by the integration of the NMR resonances. The two compounds could be separated by silica chromatography, but was used as is in the next reaction.

$^1$H NMR (CDCl$_3$, 300 MHz) δ2.34(s, Me), 7.16 (d, H5), 8.31 (d, H6).

Step 2: 2-Chloro-3-nitro-4-acetoxymethylpyridine

A 4:1 mixture of 2-Chloro-3-nitro-4-picoline-N-oxide and 2-Chloro-3-nitro-4-picoline (7.2 g, 0.031mol, based on the N-oxide) was dissolved i acetic anhydride (20 mL) and the solution was heated in a 80° C. oil bath for 70 minutes. The solvents were removed under vacuum and the dark residue was partitioned between methylene chloride (100 mL) and saturated aqueous potassium carbonate (200 mL). The aqueous layer was re-extracted with more methylene chloride (1× 50 mL) and the combined methylene chloride layers were dried with magnesium sulfate, filtered and evaporated under vacuum. The crude solid was dissolved in methylene chloride (20 mL) and was loaded onto a silica gel column (EMerck 60, 230–400 mesh, 4×36 cm). The column was eluted with methylene chloride collecting 25 mL fractions. Fractions 22–48 were combined and evaporated to give substantially pure 2-chloro-3-nitro-4-acetoxymethylpyridine (1.75 g) as a white solid.

$_1$H NMR (CDCl$_3$, 300 MHz) δ2.11 (s, Ac), 5.14 (s, CH$_2$OAc), 7.41 (d, H5), 8.51 (d, h6).

Step 3: 2-thio-4-hydroxymethylthiazolo[5,4-b]pyridine

A suspension of sulfur (0.5 g, 15.6 mmol) and sodium sulfide nonahydrate (1.84 g, 7.66 mmol) in water (2 mL) was heated in a 50° C. oil bath for 15 minutes. The amber colored solution was cooled to room temperature, 2-chloro-3-nitro-4acetoxymethylpyridine (0.5 g, 2.17 mmol) and carbon disulfide (0.5 mL, 8.3 mmol) were added and the mixture was heated in a 70° C. oil bath for 3.5 hours under a nitrogen atmosphere. After cooling to room temperature, the suspension was filtered and the recovered sulfur was washed with water (5 mL). The filtrate was acidified with acetic and 5% methanol/methylene chloride (20 mL) was added to the gummy precipitate. The aqueous layer was re-extracted with 5% methanol/methylene chloride (3× 10 mL) and the combined extracts were dried with magnesium sulfate, filtered and evaporated to a solid (0.58 g). The crude material was first purified on a silica column (EMerck 60, 230–400 mesh, 4×24 cm) using 5% methanol/methylene chloride as the developing solvent and collecting 8 mL fractions. Fractions 5–10 were combined and evaporated to a dark solid (220 mg). The solid was placed on preparative silica plates (analtech, 4×500 micron, 5% methanol/methylene chloride as developing solvent), the product was removed, eluted with 20% methanol/methylene chloride and evaporated to provide the title compound as a light orange sold (0.15 g).

$_1$H NMR (DMSO-d6, 300 MHz) δ4.71 (d, CH$_2$OH), 5.59 (t, CH$_2$OH), 7.45 (d, H5), 8.38 (d, H6).

Step 4: 2-thio-4-((trimethyl)silyloxymethyl)thiazolo[5,4-b] pyridine

A solution of 2-thio-4-hydroxymethylthiazolo[5,4-b] pyridine (45mg, 0.227 mmol) was dissolved in bis(trimethylsilyl) acetamide (0.5 mL) and was stirred at room temperature for 20 minutes under nitrogen. The solution was evaporated under vacuum and the residue was applied to a flash silica gel column (EMerck 60, 230–400 mesh, 2.5×10 cm). The column was eluted with 1:1 hexane/diethylether and 3 mL fractions were collected. Fractions 5–13 were combined and evaporated to give the title compound as a white solid (55mg).

$_1$H NMR (CDCl$_3$, 300 MHz) δ0.25 (s, Si(TMS)$_3$), 4.94 (s, CH$_2$O), 6.98 (d, H5), 8.31 (d, H6).

2-THIO-5-((TRIMETHYL)SILYLOXYMETHYL) THIAZOLO[5,4-B]PYRIDINE

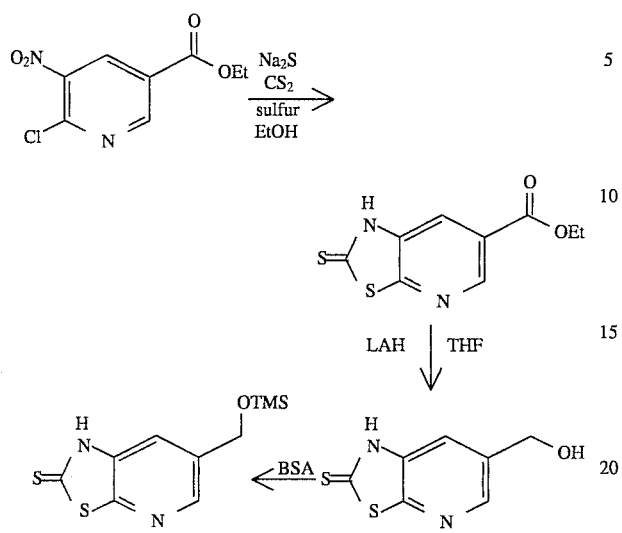

Step 1: 2-thio-5-(ethoxycarbonyl)thiazolo[5,4-b]pyridine

A suspension of sodium nonahydrate (1.5 g, 6.25 mmol) and sulfur (0.5 g, 15.6 mmol) in ethanol (20 mL) were heated in a 50° C. oil bath for 10 minutes to give an amber colored solution. After cooling to room temperature, ethyl 2-chloro-3-nitronicotinate (0.58 g, 2.5 mmol) and carbon disulfide (2 mL) were added and the mixture was heated in a 80° C. oil bath for 20 hours. The solvents were evaporate under vacuum an the residue was partitioned between methylene chloride (30 mL) and water (5 mL). The ph was adjusted to 4 with acetic acid and the aqueous layer was re-extracted with 5% methanol/methylene chloride (2×20 mL). The combined extracts were dried with magnesium sulfate, filtered and evaporated. Concentrated ammonium hydroxide was added and the precipitated sulfur was filtered and the filtrate was evaporated. The residue was placed on a silica gel column (EMerck 60, 230–400 mesh, 2.5×30cm), the column was eluted with 5% methanol/methylene chloride and 8 mL fractions were collected. Fractions 20–28 were combined and evaporated to give an impure light yellow solid (0.5 g). The collected solid was dissolve in hot ethanol (3 mL) and after cooling to room temperature the precipitate was filtered, washed with ethanol (5 mL) and provide the title compound as a white crystalline solid (0.2.65 g).

$_1$H NMR )CDCl$_3$, 300 MHz) δ1.43 (t, CH$_2$CH$_3$), 4.45(q, CH$_2$CH$_3$), 8.02 (d, H4), 9.02 (d, H6).

Step 2: 2-thio-5-(hydroxymethyl)thiazolo[5,4-b]pyridine 2-thio-5-(ethoxycarbonyl)thiazolo[5,4-b]pyridine (120 mg, 0.5 mmol) was dissolved in tetrahydrofuran (3 mL) and was treated with lithium aluminum hydride (1mL, 1 mmol, 1 molar solution in tetrahydrofuran) at room temperature under nitrogen. After 30 minutes, water (0.5 mL) was added cautiously and the granular precipitate was filtered through solka-floc. The filtrate was evaporated under vacuum and provided the title compound as a solid )120 mg)

$_1$H NMR (DMSO-d$_6$, 300 MHz) δ4.58 (s, CH$_2$OH), 7.55 (d, H4), 8.32 (d, H6).

Step 3: 2-thio-5-((trimethyl)silyloxymethyl)thiazolo[5,4-b] pyridine

A solution of 2-thio-5-hydroxymethylthiazolo[5,4-b]pyridine (120 mg, 0.61 mmol) was dissolved in a mixture of tetrahydrofuran (2 mL) and bis(trimethylsilyl) acetamide (0.5 mL) and was stirred at room temperature for 20 minutes under nitrogen. The solution was evaporated under vacuum and the residue was applied to a flash silica gel column (EMerck 60, 230–400 mesh, 2.5×5 cm). The column was eluted with methylene chloride (50 mL) and evaporated to give a white solid. The solid was triturated with hexanes, was filtered and provided the title compound as a white solid (64 mg).

$_1$H NMR (CDCl$_3$, 300 MHz) δ0.19 (s, Si(TMS)$_3$), 4.77 (s, CH$_2$O), 7.53 (s, H4), 8.36 (s, H6).

PREPARATIVE EXAMPLE 6

2-THIO-6-((TRIMETHYL)SILYLOXYMETHYL) THIAZOLO[5,4-B]PYRIDINE

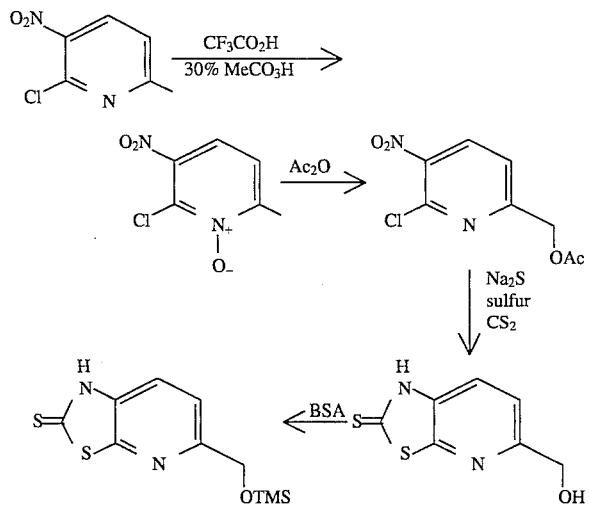

Step 1: 2-Chloro-3-nitro-6-picoline-N-oxide

Substitution of 2-Chloro-3-nitro-6-picoline (2 g, 11.6 mmol) for 2-Chloro-3-nitro-4-picoline in the procedure of Step 1 of Preparative Example 4 afforded the title compound as a white solid (1.6 g).

$_1$H NMR (CDCl$_3$, 300 MHz) δ2.62(s, Me), 7.35(d, ArH), 7.66 (d, ArH).

Step 2: 2-Chloro-3-nitro-6-acetoxymethylpyridine

2-Chloro-3-nitro-6-picoline-N-oxide (1.6 g, 8.5 mmol) was dissolved in acetic anhydride (5 mL) and the solution was heated in a 60° C. oil bath for 3 hours. Workup and chromatography as described in Step 2 of Preparative Example 4 afforded the title compound (0.42 g) as a white solid.

$_1$H NMR (CDCl$_3$, 300 MHz) δ2.19 (s, Ac), 5.24 (s, CHhd 2OAc), 7.45 (d, h5), 8.23 (d, H4).

Step 3: 2-thio-6-hydroxymethylthiazolo[5.4-b]pyridine

A suspension of sulfur (0.5 g, 15.6 mmol) and sodium sulfide nonahydrate (2.0 g, 8.3 mmol) in water (3 mL) was heated in a 50° C. oil bath for 15 minutes. The amber colored solution was cooled to room temperature, 2-chloro-3-nitro-6-acetoxymethylpyridine (0.4 g, 1.73 mmol) and carbon disulfide (1 mL, 16.7 mmol) were added and the mixture was heated in a 60° oil bath for 18 hours under a nitrogen atmosphere. Workup and chromatography as described in Step 3 of Preparative Example 4 afforded the title compound as a orange solid (240 mg).

$^1$H NMR (DMSO-d6, 300 MHz) δ4.61 (s, CH$_2$OH), 7.41 (d, ArH), 8.11 (d, ArH).

Step 4: 2-thio-6-((trimethyl)silyloxymethyl)thiazolo[5,4-b] pyridine

Substitution of 2-thio-6-hydroxymethylthiazolo[5,4-b]pyridine (230 mg, 1.16 mmol) for 2-thio-4-hydroxymethylthizolo[5,4-b]pyridine in the procedure of Step 4 of Preparative Example 6 afforded the title compound as a white solid (200 mg).

$^1$H NMR (DMSO-d$_6$, 300 MHz) δ0.05 (s, Si(TMS)$_3$), 4.56 (s, CH$_2$O), 7.48 (d, ArH), 7.63 (d, ArH).

PREPARATIVE EXAMPLE 7

6-HYDROXYMETHYL-2-THIOXO-2,3-DIHYDROBENZOTHIZOLE

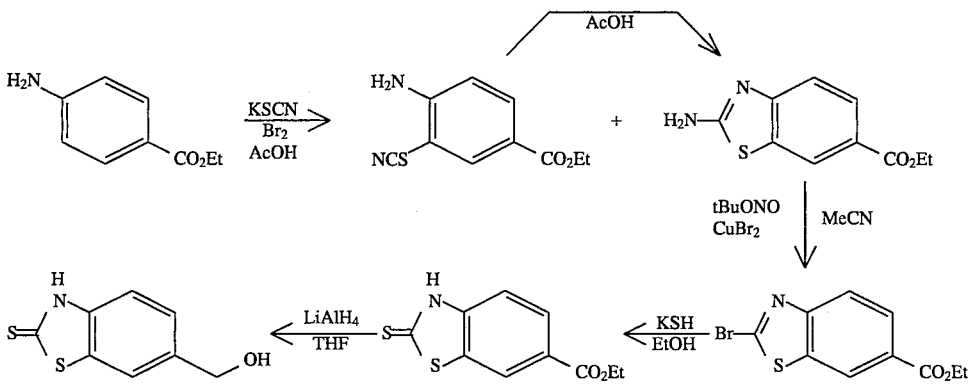

Step 1; 2-Amino-6-ethoxycarbonylbenzothiazole

A solution of ethyl 4-aminobenzoate (8.26 g, 0.005 mol) in acetic acid (100 mL) was treated with potassium thiocyanate (14.58 g, 0.15 mol) and stirred 10 minutes at room temperature to dissolve the salt. The resulting solution was cooled in an ice bath and stirred while bromine (2.6 mL, 0.05 mol) was added dropwise over 15 minutes. The cooling bath was removed and the mixture was stirred at room temperature for 2.25 hours. The mixture was stored at 5° C. for 5 hours, then filtered to remove the yellow precipitate. The filter cake was washed with ether (2×50 mL) and water (2×100 mL) and dried under vacuum to give 2-amino-6-ethoxycarbonylbenzothiazole (2.54 g, 23%) as a yellow solid. The acetic acid filtrate and ether washings were combined and evaporated under vacuum to an amber gum. The water washings from the yellow solid were added and the mixture was neutralized with solid sodium bicarbonate. The resulting precipitate was collected, washed with water and dried under vacuum to a pale tan solid (8.74 g). Proton NMR analysis of this material revealed a 65:35 mixture of ethyl 4-amino-3-thiocyanatobenzoate to 2-amino-6-ethoxycarbonylbenzothiazole. The mixture was dissolved in acetic acid (100 mL) and stirred at room temperature for 42 hours. A fine precipitate formed. The mixture was filtered and the cake washed with ether and dried under vacuum to give additional 2-amino-6-ethoxycarbonylbenzothiazole (2.28 g) as a cream colored powder.

$^1$H NMR (DMSO-d$_6$, 500 MHz) δ1.30 (t, CH$_3$), 4.28 (q, CH$_2$), 7.38 (d, H-4), 7.82 (dd, H-5), 8.07 (br s, NH$_2$), and 8.29 (d, H-7).

$^{13}$C NMR (DMSO-d$_6$, 125.7 MHz) δ14.2, 60.4, 116.8, 122.3, 122.7, 127.2, 130.5, 155.5, 165.5 and 169.8.

Step 2: 2-Bromo-6-ethoxycarbonylbenzothiazole

A mixture of copper(II) bromide (2.70 g, 12.09 mmol) and anhydrous acetonitrile (50 mL) was purged with nitrogen, cooled in an ice bath, treated with tert-butyl nitrite (1.8 mL, 15.13 mmol), stirred 10 minutes at 0°–5° C., and then treated with solid 2-amino-6 ethoxycarbonylbenzothiazole (2.24 g, 10.08 mmol). The cooling bath was removed and the mixture was stirred at room temperature for 2 hours. The mixture was diluted with water (300 mL) and extracted with ether (2×100 mL). The extracts were filtered to remove copper salts, then washed with water (100 mL) and brine (100 mL), dried over sodium sulfate, filtered and evaporated under vacuum to provide crude 2-bromo-6-ethoxycarbonylbenzothiazole (1.90 g) as an orange-tan solid.

$^1$H NMR (CDCl$_3$, 500 MHz) δ1.42 (t, CH$_3$), 4.42 (q, CH$_2$), 8.02 (d, H-4), 8.15 (dd, H-5), and 8.53 (d, H-7).

$^{13}$C NMR (CDCl$_3$, 125.7 MHz) δ14.3, 61.5, 122.5, 122.9, 127.8, 137.2, 142.3, 155.0, and 156.7.

Step 3: 6-Ethoxycarbonyl-2-thioxo-2,3-dihydrobenzothiazole

The crude 2-bromo-6-ethoxycarbonylbenzothiazole (1.90 g, 6.64 mmol) from Step 2 was suspended in absolute ethanol (35 mL) and treated with potassium, hydrogen sulfide (0.96 g, 13.3 mmol). The mixture was placed under a nitrogen atmosphere, stirred, and heated in an oil bath at 80° C. The benzothiazole starting material gradually went into solution. After heating for 20 minutes, the mixture was cooled in an ice bath, treated with 1N hydrochloric acid (13.5 mL), and evaporated under vacuum. The residue was partitioned between ethyl acetate (100 mL) and water (100 mL) and the aqueous phase extracted with more ethyl acetate (50 mL). The combined ethyl acetate solution was washed with brine (50 mL), dried over sodium sulfate, filtered and evaporated under vacuum to a yellow-tan solid (1.56 g). This material was triturated with ether and dried under vacuum to provide 6-ethoxycarbonyl-2-thioxo-2,3-dihydrobenzothiazole (1.14 g) as a pale tan powder.

$^1$H NMR (DMSO-d$_6$, 500 MHz) δ1.31 (t, CH$_3$), 4.30 (q, CH$_2$), 7.35 (d, H-4), 7.94 (d, H-5), and 8.29 (s, H-7).

$^{13}$C NMR (DMSO-d$_6$, 125.7 MHz) δ14.1, 60.9, 112.1, 123.2, 125.5, 128.4, 129.7, 144.6, 165.0, and 191.8.

Step 4: 6-Hydroxymethyl-2-thioxo-2,3-dihydrobenzothiazole 4.64 mmol) in anhydrous tetrahydrofuran (14 mL) was heated to reflux under a nitrogen atmosphere and stirred while 1M lithium aluminum hydride in tetrahydrofuran (4.7 mL) was added dropwise. The resulting mixture was stirred and heated at reflux for one hour, then cooled in an ice bath and cautiously treated with 2N hydrochloric acid. The mixture was diluted with water (20 mL) and extracted with ethyl acetate (3×25 mL). The combined extracts were washed with brine (25 mL), dried over sodium sulfate, filtered and evaporated under vacuum to provide 6-hydroxymethyl-2-thioxo-2,3-dihydrobenzo-thiazole (0.89 g) as a pale yellow solid.

$^1$H NMR (DMSO-d$_6$, 500 MHz) δ4.51 (s, CH$_2$OH), 5.28 (br s, CH$_2$OH), 7.25 (d, H-4), 7.32 (dd, H-5), and 7.60 (d, H-7).

$^{13}$C NMR (DMSO-d$_6$, 125.7 MHz) δ62.5, 112.0, 119.4, 125.7, 129.3, 139.0, 140.1 and 189.6.

PREPARATIVE EXAMPLE 8

7-HYDROXYMETHYL-2-THIOXO-2,3-DIHYDROBENZOTHIAZOLE

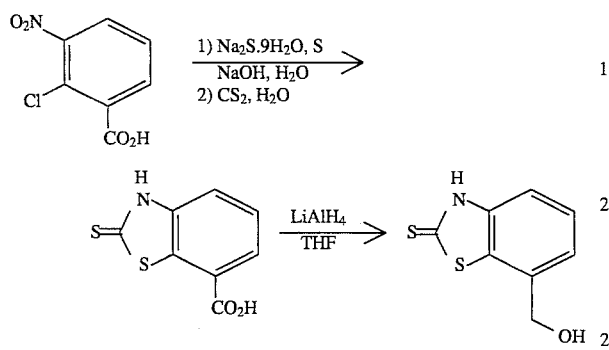

Step 1: 7-Carboxy-2-thioxo-2,3-dihydrobenzothiazole

2-Chloro-3-nitrobenzoic acid (8.06 g, 0.04 mol) in 1N sodium hydroxide (50 mL) was added to a polysulfide solution made from sodium sulfide nonahydrate (28.82 g, 0.12 mol) and sulfur (9.60 g, 0.30 mol) in water (30 mL). The resulting mixture was stirred and heated at reflux for 5.5 hours. The reaction mixture was cooled to 45° C., treated with carbon disulfide (4.81 mL), and stirred at 45° C. for 20 hours. The mixture was cooled in an ice bath and neutralized by slowly adding acetic acid (7 g). The solid precipitate was collected, washed with ice-cold water, suspended in saturated sodium carbonate solution (100 mL), and filtered to remove insolubles. The filtrate was acidified with acetic acid (33 g) and filtered to collect the insoluble material. The filter cake was dried under vacuum to afford crude 7-carboxy-2-thioxo-2,3-dihydrobenzothiazole (0.70 g) as a brownish gray solid.

IR (KBr) 1570, 1507, 1458, 1419, 1393, 1333, 1259, 1076, 1040, 984, 768, 668, 657, and 629 cm$^{-1}$.

$^1$H NMR (DMSO-d$_6$, 500 MHz) δ7.18 (t), 7.30 (d), and 7.62 (d).

$^{13}$C NMR (DMSO-d$_6$, 125.7 MHz) δ115.4, 122.8, 124.7, 131.3, 134.2, 149.0, 169.2, and 191.1.

Step 2: 7-Hydroxymethyl-2-thioxo-2,3-dihydrobenzothiazole

A mixture of crude 7-carboxy-2-thioxo-2,3-dihydrobenzothiazole (480 mg, 2.27 mmol) and anhydrous tetrahydrofuran (7 mL) was placed under a nitrogen atmosphere and sonicated for a few minutes to give a fine suspension. The mixture was stirred and heated at reflux while 1.0M lithium aluminum hydride in tetrahydrofuran (4.5 mL) was cautiously added. The resulting mixture was heated at reflux fro 60 minutes, then sonicated at room temperature for 15 minutes. The mixture was cooled in an ice bath, stirred, and acidified with 2N hydrochloric acid (18 mL). The mixture was diluted with water (18 mL) and extracted with ethyl acetate (4×20 mL). The combined extracts were washed with brine (20 mL), dried over sodium sulfate, swirled with charcoal, filtered, and evaporated under vacuum to afford 7-hydroxymethyl-2-thioxo-2,3-dihydrobenzothiazole (228 mg) as a pale yellow powder.

$^1$H NMR (DMSO-d$_6$, 500 MHz) δ4.62 (d, CH$_2$OH), 5.66 (t, CH$_2$OH), 7.13 (d, H-6), 7.19 (d, H-4), and 7.33 (t, H-5).

$^{13}$C NMR (DMSO-d$_6$, 125.7 MHz) δ61.7, 110.8, 121.2, 126.6, 127.0, 135.9, 141.9, and 190.7.

PREPARATIVE EXAMPLE 9

4-HYDROXYMETHYL-2-THIOXO-2,3-DIHYDROBENZOTHIAZOLE

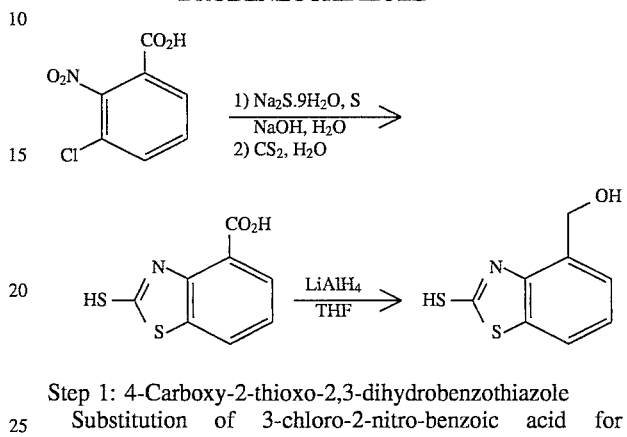

Step 1: 4-Carboxy-2-thioxo-2,3-dihydrobenzothiazole

Substitution of 3-chloro-2-nitro-benzoic acid for 2-chloro-3-nitro-benzoic acid in the procedure of Step 1 of Preparative Example 8 afforded 4-Carboxy-2thioxo-2,3-dihydrobenzothiazole as a solid. Step 2: 4-carboxybenzothiazol-2-thiol Solution of 4-carboxy-2-thioxo-2,3-dihydrobenzothiazole (1.06 g, 5 mmol) in anhydrous tetrahydrofuran (15 mL) was cooled in an ice bath under nitrogen. A solution of lithium aluminum hydride (10 mL, 10 mmol) was added dropwise over 3 minutes and the flask was removed from the ice bath and allowed to warm to room temperature. After 10 minutes, was heated in a 60° C. oil bath for one hour. After cooling in an ice bath, hydrochloric acid (40 mL, 2N) was carefully added and the resulting solution was partitioned between ethyl acetate (60 mL) and water (40 mL). The ethyl acetate was removed and the aqueous layer was re-extracted with more ethyl acetate (2×60 mL). The combined extracts were washed with brine (20 mL), dried with magnesium sulfate, filtered and evaporated under vacuum to give a light yellow foam. The solid was suspended in a mixture of water (5 mL) and methylene chloride (10 mL). The pH was adjusted to 10 with 1N sodium hydroxide, the aqueous layer was filtered through a 0.45 micron acrodisc and the pH of the filtrate was adjusted to 3 with 2N hydrochloric acid. The precipitate was filtered, washed with water (20 mL) and the collected solid was dried overnight under a stream of nitrogen to give the title compound as a light yellow solid (0.63 g).

$^1$H NMR (DMSO-d$_6$, 500 MHz) δ4.69 (s, CH$_2$OH), 5.29 (s, CH$_2$OH), 7.26 (t, ArH-6'), 7.38 and 7.55 (two d, ArH-5' and ArH-7')and 13.4 (s, NH).

$^{13}$C NMR (DMSO-d$_6$, 500 MHz) δ59.67, 120.44, 124.48, 125.91, 127.72, 129.55, 138.79 and 190.66.

PREPARATIVE EXAMPLE 10

5-HYDROXYMETHYL-2-THIOXO-2,3-DIHYDROBENZOTHIAZOLE

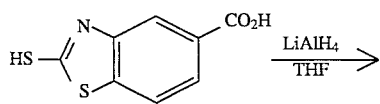

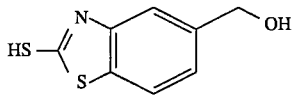

A solution of 5.04 g (23.9 mmol) of 2-thioxo-2,3-dihydrobenzothiazole-5-carboxylic acid in 25 ml of anhydrous tetrahydrofuran was stirred and heated to reflux, and 2.0 g of lithium aluminum hydride in 25 of anhydrous tetrahydrofuran was added carefully. After refluxing for two hours, the solution was cooled and added carefully to 500 ml of chilled 2N HCl. This mixture was extracted 3 times with 200 ml of ethyl acetate, and the combined organics were dried over magnesium sulfate and evaporated under reduced pressure to yield 3.67 g of the title compound.

$^1$H NMR (DMSO-$_6$, 500 MHz) δ7.59 (d, ArH), 7.29 (s, ArH), 7.19 (d, ArH), 4.52 (s, ArC$\underline{H}_2$OH).

$^{13}$C NMR (DMSO-d$_6$, 500 MHz) δ190.4, 142.8, 141.8, 127.8, 122.9, 121.7, 110.5 & 62.7.

PREPARATIVE EXAMPLE 11

4-(2-HYDROXYETHYL)-2-THIOXO-2,3-DIHYDROBENZOTHIAZOLE

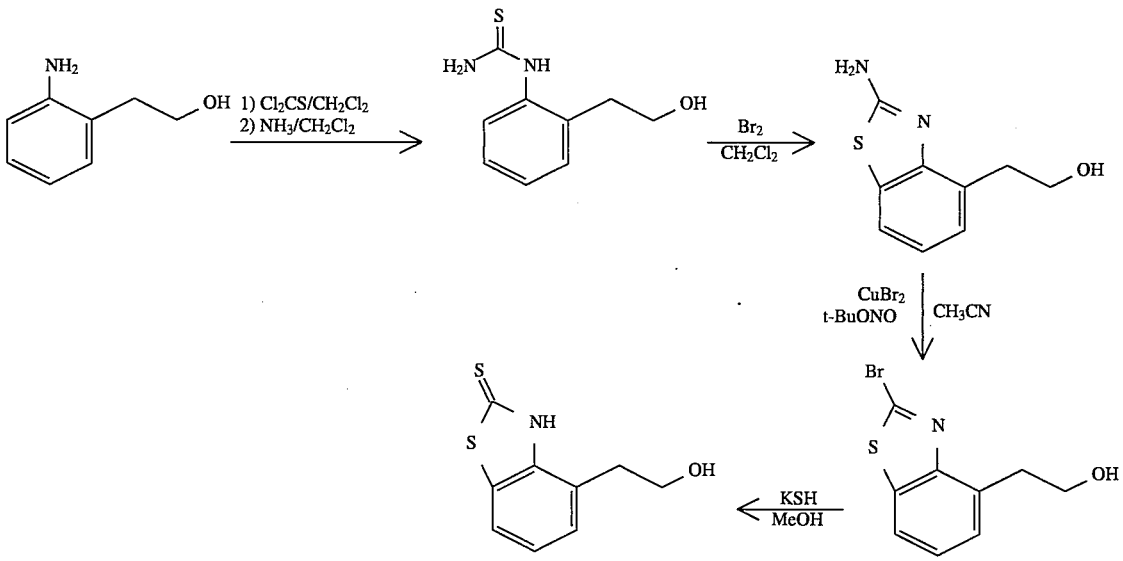

Step 1: 1-(2-(2-hydroxyethyl)phenyl)thiourea

A solution of 2-aminophenethyl alcohol (5.00 g, 36.5 mmol) in dicholormethane (100 mL) was mixed with saturated aqueous sodium bicarbonate solution (100 mL), stirred at room temperature, and treated with thiophosgene (2.80 mL, 36.7 mmol). After 35 minutes the mixture was filtered to remove some insoluble material and the organic phase recovered and washed with water (400 mL), dried over magnesium sulfate, and filtered. Ammonia was bubbled into this solution over 30 minutes at room temperature. A mixture resulted which was filtered to give a produce (6.30 g). The crude product was resuspended in water (25 mL), filtered, water washed (3×10 mL), and vacuum dried to afford the title compound as an off-white solid (6.01 g).

$^1$H NMR (DMSO-d$_6$, 500 MHz) δ2.68 (t, J=6.9 Hz,ArC$\underline{H}_2$), 3.57 (t, J=6.9 Hz, C$\underline{H}_2$OH), 4.78 (s, OH), 7.15–7.26 (m, ArH), 9.22 (s, NH).

$^{13}$C NMR (DMSO-d$_6$, 125.7 MHz) δ35.0, 39.4, 39.6, 39.8, 39.9, 40.1, 40.3, 40.4, 61.9, 127.0, 127.1, 128.2, 130.7, 136.4, 137.6, 182.1.

Step 2: 2-amino-4-(2-hydroxyethyl)benzothiazole

An ice-cold stirred suspension of 1-(2-(2-hydroxyethyl)phenyl)thiourea (3.00 g, 15.3 mmol) in chloroform (75 mL) was treated with bromine (830 µL, 16.0 mmol) and the mixture allowed to warm to room temperature. The mixture was sonicated 30 minutes to break the gummy mass which had formed, and the mixture allowed to stir overnight. The mixture was filtered, chloroform washed, and vacuum dried to afford crude product (2.64 g). The crude product was suspended in ethyl acetate (40 mL) and mixed with saturated aqueous sodium bicarbonate solution (40 mL). The organic phase was recovered, washed with water (40 mL), brine, dried over magnesium sulfate, filtered, and evaporated under vacuum to afford the title compound as a white solid (2.30 g).

$^1$H NMR (DMSO-d$_6$, 500 MHz) δ2.95 (t, J=7.2 Hz, ArC$\underline{H}_2$), 3.63 (t, J=7.2 Hz, C$\underline{H}_2$OH), 4.64 (s, OH), 6.90 (t, J=7 Hz, ArH-6), 7.03 (dd, J=1, 7 Hz, ArH-5), 7.46 (m, ArH-7).

$^{13}$C NMR ((DMSO-d$_6$6, 125.7 MHz) δ36.6, 61.7, 119.1, 121.1, 126.7, 129.1, 130.9, 151.9, 166.2.

Step 3: 2-bromo-4-(2-hydroxyethyl)benzothiazole

An ice-cold stirred suspension of CuBr$_2$ (1.89 g, 8.44 mmol) in acetonitrile (22 mL) under a nitrogen atmosphere was treated with t-butyl nitrite (1.01 mL, 8.44 mmol). After 15 minutes the mixture was treated with 2-amino-4-(2-hydroxyethyl)benzothiazole (1.10 g, 5.66 mmol) and allowed to warm to room temperature. After 16 hours the mixture was diluted with ether (75 mL) and washed with 1N hydrochloric acid (50 mL), water (50 mL), brine, dried over magnesium sulfate, filtered, and evaporated under vacuum to give the crude product as a brown oil (1.28 g). The crude produce was chromatographed on a column (3×18 cm) of EM silica gel 60 (230–400 mesh, packed in 2:1 hexane-ethyl acetate). The column was eluted with the aforementioned solvent system, collecting 12 mL fractions. Fractions 20–30 were evaporated under vacuum to afford solid title compound (656 mg).

$^1$H NMR (CDCl$_3$, 500 MHz) δ3.36 (t, J=6.2 Hz, ArC$\underline{H}_2$), 4.02 (t, J=6.2 Hz, C$\underline{H}_2$OH), 7.33 (dd, J=7 Hz, ArH-5), 7.37 (t, J=7 Hz, ArH-6), 7.70 (dd, J=1.4, 7, ArH-7).

$^{13}$C NMR (CDCl$_3$, 125.7 MHz) δ36.3, 63.1, 119.2, 125.9, 127.5, 133.9, 138.3, 151.4, 171.2.

Step 4: 2-thioxo-4(2-hydroxyethyl)-2,3-dihydrobenzothiazole

A solution of 2-bromo-4-(2-hydroxyethyl)benzothiazole (1.45 g, 5.62 mmol) in methanol (22 mL) under a nitrogen atmosphere was treated with potassium hydrogen sulfide (810 mg, 11.2 mmol) and the mixture heated at 60° C. After 1.5 hours the mixture was allowed to cool to room temperature. Additional potassium hydrogen sulfide (400 mg, 5.55 mmol) was added and heating resumed at 70° C. After 2.5 hours the mixture was allowed to cool to room temperature and concentrated under vacuum to a semi-solid. The solid was partitioned between 1m pH7.0 phosphate buffer (50 mL) and ethyl acetate (50 mL). Using 2N hydrochloric acid, the pH was adjusted to 7.0 and the organic phase recovered, washed with water (40 mL), brine, dried over magnesium sulfate, filtered, and concentrated under vacuum to ~25 mL. A precipitate formed which was recovered by filtration, and vacuum dried to afford the title compound as an off-white solid (778 mg).

$^1$H NMR (DMSO-d$_6$, 500 MHz) δ2.98 (t, J=6.3 Hz, ArCH$_2$), 3.62 (t, J=6.3 Hz, CH$_2$OH), 4.7 (br s, OH), 7.17–7.22 (m, ArH-5,6), 7.49 (dd, J=2.1, 6.9 ArH-7).

$^{13}$C NMR ((DMSO-d$_6$, 125.7 MHz) δ34.6, 61.4, 119.7, 124.5, 125.4, 128.8, 129.6, 140.6, 190.4

PREPARATIVE EXAMPLE 12

5-(2-HYDROXYETHYL)-2-THIOXO-2,3-DIHYDROBENZOTHIAZOLE

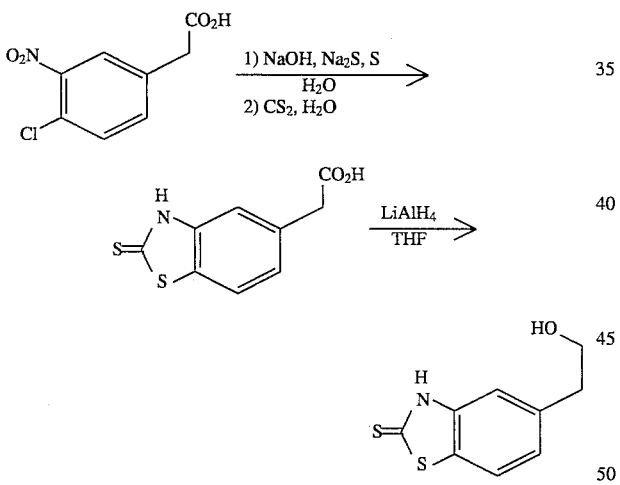

Step 1: 5-Carboxymethyl-2-thioxo-2,3-dihydrobenzothiazole

A solution of 4-chloro-3-nitro-phenylacetic acid (25.0 g, 0.116 mol) in 1N aqueous NaOH (143 mL, 0.143 ml) was added to preformed polysulfide solution (from 72.42 g, 0.301 mol of Na$_2$S.9H$_2$O, 26.87 g, 0.837 mol of S, and 74 mL of H$_2$O) at 50° C. The resulting mixture was mechanically stirred as the temperature of the oil bath was gradually increased to 115° C. over 10 min. The mixture was stirred at that temperature for two hours then allowed to cool to room temperature over two hours. Carbon disulfide (13.9 mL, 0.231 mol) was added and the reaction flask was placed in a 50° C. oil bath. The reaction mixture was stirred at that temperature for 18 hours then cooled in an ice bath, stirred, and acidified by cautious addition of glacial acetic acid (50 mL). The mixture was filtered and the filter cake was washed with water. The solid was stirred with sodium carbonate (30.7 g, 0.29 mol) in water then filtered to remove sulfur. The filtrate was cooled in an ice-bath and gradually acidified to pH 3.3 addition of 6N HCl (100 mL). The precipitate was collected, washed with ice-cold water (100 mL) and dried in vacuo to a pale brown solid (2.15 g, 82%). This crude product was recrystallized from ethanol to afford 5-carboxymethyl-2-thioxo-2,3-dihydrobenzothiazole as a pale brown solid (14.2 g).

$^1$ H NMR (DMSO-d$_6$, 500 MHz) δ3.65 (s, CH$_2$), 7.16 (d, H-6), 7.21 (s, H-4), and 7.58 (d, H-7).

$^{13}$C NMR (DMSO-d$_6$, 125.7 MHz) δ40.3 (CH$_2$), 113.2 (C-4), 121.4 (c-7), 125.7 (C-6), 127.6 (C-7a), 134.5 (C-5), 141.3 (C-3a), 172.4 (CO$_2$), and 190.1 (C-2).

Step 2; 5-(2-Hydroxyethyl)-2-thioxo-2,3-dihydrobenzothiazole

A solution of lithium aluminum hydride (65 mL of a 1M tetrahydrofuran solution, 0.065 mol) was added dropwise over 15 min to a mechanically stirred and refluxing solution of 5-carboxymethyl-2thioxo-2,3-dihydrobenzothiazole (11.27 g, 0.050 mol) in anhydrous tetrahydrofuran (150 mL). The resulting mixture was stirred at reflux for 90 min then cooled in an ice-bath and cautiously treated with 2N hydrochloric acid (250 mL). The resulting mixture was diluted with water (250 mL) and extracted three times with ethyl acetate (250, 250, and 150 mL). The combined extracts were washed with brine (2×200 mL), dried over magnesium sulfate, filtered and concentrated in vacuo to approximately 140 mL volume. Some solid was present at this point. The mixture was diluted with ether (100 mL) and filtered. The filter cake was washed with ether and dried in vacuo to afford 5-(2-hydroxyethyl)-2-thioxo-2,3-dihydrobenzothiazole (8.58 g) as pale tan crystals.

$^1$H NMR (DMSO-d$_6$, 500 MHz) δ2.76 (t, ArCH$_2$CH$_2$OH), 3.59 (t, ArCH$_2$CH$_2$OH), 7.14 (d, H-6), 7.15 (s, H-4), and 7.55 (d, H-7).

$^{13}$C NMR (DMSO-d$_6$, 125.7 MHz) δ38.7, 61.9, 112.7, 121.3, 125.3, 126.8, 139.3, 141.3, and 189.9

PREPARATIVE EXAMPLE 13

5-ACETYL-2-THIOXO-2,3-DIHYDROBENZOTHIAZOLE

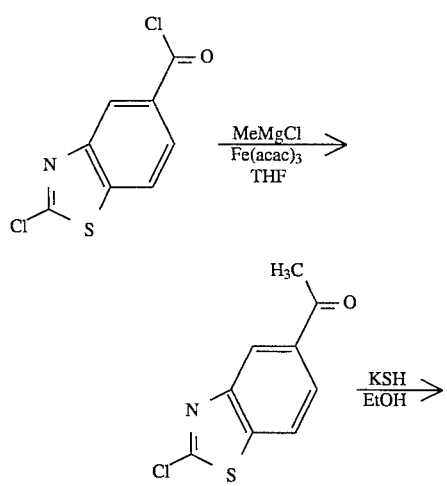

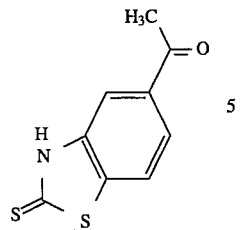

Step 1: 5-Acetyl-2-chlorobenzothiazole

A solution of 2-chloro-5-(chlorocarbonyl)benzothiazole (321 mg, 1.38 mmol, prepared according to U.S. Pat. No. 3,654,296) and ferric acetylacetonate (14.7 mg, 0.042 mmol) in anhydrous tetrahydrofuran (13.8 mL) was cooled in an ice-methanol bath (−20° C.), stirred under a nitrogen atmosphere, and treated dropwise over 5 minutes with 1M methyl magnesium chloride in tetrahydrofuran (1.38 mL). The resulting mixture was stirred at −15° C. for 15 minutes then at room temperature for 30 minutes. The mixture was treated with 2N hydrochloric acid (1.38 mL), diluted with water, and extracted with ethyl acetate. The extracts were washed with 5% aqueous sodium bicarbonate and brine, dried over magnesium sulfate, filtered, and evaporated in vacuo to white solid (299 mg). The crude product was purified by flash chromatography on silica gel (25 g, loaded as a dichloromethane solution and eluted with 2% ethyl acetate in dichloromethane) to afford 5-acetyl-2-chlorobenzothiazole (201 mg) as a white solid.

IR (KBr) 1674, 1599, 1482, 1419, 1358, 1285, 1256, 1207, 1091, 1060, 1020, 897, 818, and 650 cm$^{-1}$.

$^1$H NMR (CDCl$_3$, 500 MHz) δ2.68 (s, CH$_3$), 7.86 (d, H-7), 8.04 (dd, H-6), and 8.49 (d, H-4).

$^{13}$C NMR (CDCl$_3$ 125.7 MHz) δ26.7, 121.3, 123.2, 124.9, 136.0, 140.8, 150.9 and 197.0.

Step 2: 5-Acetyl-2-thioxo-2,3-dihydrobenzothiazole

A mixture of 5-acetyl-2-chlorobenzothiazole (137 mg, 0.65 mmol), potassium hydrogen sulfide (94 mg, 1.30 mmol) and ethanol (3.3 mL) in a capped flask was stirred in an oil bath at 80° C. for two hours. The mixture was cooled in ice, acidified with 1N hydrochloric acid (1.35 mL) and evaporated in vacuo. The residue was partitioned between water (25 mL) and ethyl acetate (50, 25 mL). The organic extracts were washed with brine, dried over magnesium sulfate, filtered and evaporated in vacuo to a solid (133 mg). This material was triturated with ether and dried to provide 5-acetyl-2-thioxo-2,3-dihydrobenzothiazole (110 mg) as a pale yellow solid.

IR (KBr) 1679, 1570, 1514, 1451, 1356, 1329, 1266, 1215, 1089, 1068, 1035, 876, 824, 730, 674, and 610 cm$^{-1}$.

$^1$H NMR (DMSO-d$_6$, 500 MHz) δ2.59 (s, CH$_3$), 7.72 (d, H-4), 7.82 (d, h-7), and 7.87 (dd, h-6).

$^{13}$C NMR (CDCl$_3$, 125.7 MHz) δ26.8, 111.0, 122.0, 124.2, 134.7, 135.6, 141.5, 190.6, and 196.9.

PREPARATIVE EXAMPLE 14

5-(3-HYDROXYPROPYL)-2-THIOXO-2,3-DIHYDROBENZOTHIAZOLE

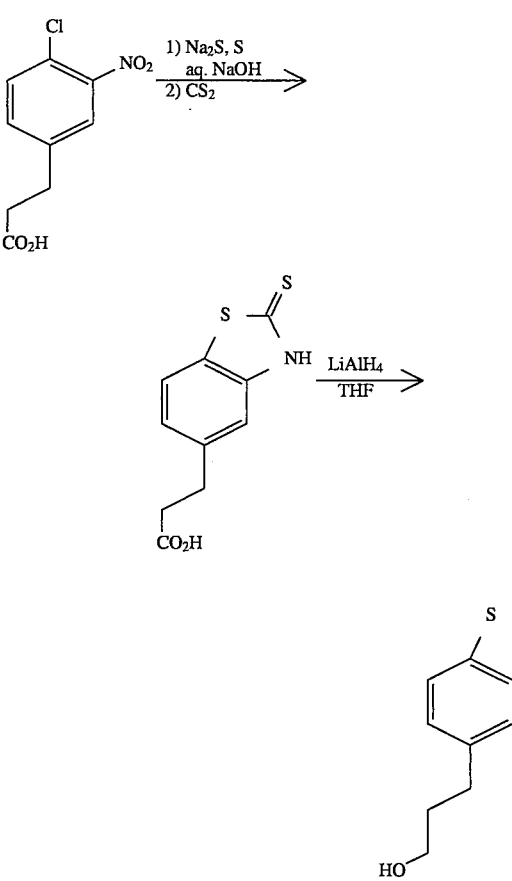

Step 1: 5-(3-carboxypropyl)-2-thioxo-2,3-dihydrobenzothiazole

A solution of 3-(4-chloro-3-nitrophenyl)propionic acid (2.40 g, 10.5 mmol) in 1N aqueous sodium hydroxide (13.6 mL) was added to a mixture of sodium sulfide nanohydrate (6.28 g, 26.1 mmol) and sulfur (2.43 g, 75.8 mmol) and the mixture heated at 100° C. After 2 hours the mixture was removed from reflux, cooled in an ice bath, treated with carbon disulfide (1.25 mL, 20.9 mmol), and again heated at 100° C. After 1.5 hours the reaction was removed from reflux and allowed to cool to room temperature. The mixture was acidified with glacial acetic acid, filtered, and the recovered solid dissolved in an aqueous (25 mL) solution of potassium carbonate (2.89 g, 20.9 mmol). The solution was again filtered and the filtrate acidified with concentrated hydrochloric acid to pH~1 and the resulting mixture filtered. The solid was dissolved in ethyl acetate (40 mL) and acetone (5 mL), washed with acidified brine, dried over magnesium sulfate, filtered, and evaporated under vacuum to give the title compound as an off-white solid (1.47 g).

IR (KBr) 3223, 1710, 1610, 1511, 1452, 1389, 1267, 1186, 1034, 884, 817 cm$_{-1}$.

$^1$H NMR (DMSO-d$_6$, 500 MHz) δ2.53(t, J=7.5 Hz, ArCH$_2$CH$_2$CO$_2$H), 2.86 (t, J=7.5 Hz, ArCH$_2$CH$_2$CO$_2$H), 7.14 (s, ArH-5), 7.15 (d, J=8.3 Hz, ArH-6), 7.56 (d, J=8.3 Hz, ArH-7), 12.18 (s, CO2H). $^{13}$C NMR (DMSO-d$_6$ 125.7 MHz) δ30.5, 35.6, 112.4, 121.9, 125.1, 127.3, 140.9, 141.8, 174.0, 190.4.

Step 2: 5-(3-hydroxypropyl)-2-thioxo-2,3-dihydrobenzothiazole

A solution of 5-(3-carboxypropyl)-2-thioxo-2,3-dihydrobenzothiazole (1.45 g, 6.06 mmol) in tetrahydrofuran (23 mL) under a nitrogen atmosphere was treated with a solution of lithium aluminum hydride (1M in tetrahydrofuran) added dropwise over 5 minutes and refluxed. After 0.75 hr the mixture was allowed to cool to room temperature and carefully treated with 2N hydrochloric acid (6 mL), mixed with ethyl acetate (50 mL), filtered, and the cake washed with ethyl acetate (5 mL). The filtrate was washed with brine, dried over magnesium sulfate, filtered and evaporated under vacuum to afford crude product as a yellow solid (1.30 g). The crude product was purified by chromatography on a column (3×12 cm) of EM silica gel 60(230–400 mesh, packed in 1:3, hexane: ethyl acetate). The column was eluted with the aforementioned solvent, collecting 11 mL fractions. Fractions 8-16 were combined and evaporated under vacuum to a solid which was crystallized from hot toluene (20 mL)-ethyl acetate (5 mL) to give the title compound as a light tan colored solid (879 mg).

IR (KBr) 3318, 2937, 1607, 1508, 1444, 1412, 1326, 1034, 915, 807 674 cm$_{-1}$.

$^1$H NMR (DMSO-d$_6$, 500 MHz) δ1.69 (m, ArCH$_2$C$\underline{H}_2$CH$_2$OH), 2.65 (t, J=7.8 Hz, ArC$\underline{H}_2$CH$_2$CH$_2$OH), 3.38 (s(br),ArCH$_2$CH$_{2C\underline{H}2}$OH), 4.47 (s, CH$_2$O$\underline{H}$), 7.10 (s, ArH-5), 7.12 (d, J=8 Hz, ArH-6), 7.55 (d, J=8 Hz, ArH-7).

$^{13}$C NMR (DMSO-d$_6$ 125.7 MHz) δ31.8, 34.8, 60.3, 112.3, 121.9, 125.2, 126.9, 141.8, 142.2, 190.3.

PREPARATIVE EXAMPLE 15

2-THIOXO -2,3-DIHYDRO-6-((TRIMETHYL)SILYLOXYMETHYL)THIAZOLO[4.5-C]PYRIDINE mL) and the combined extracts were dried with magnesium sulfate, filtered and evaporated to give the title compound as a pink solid (12.7 g).

$^1$H NMR (CDCl$_3$ 300 MHz) δ2.40(s, Me), 6.35 (d, ArH), 6.38 (s, ArH) and 8.18 (d, ArH).

Step 2: 4-amino-3-nitro-2-picoline 4-amino-2-picoline (6.0, 55.6 mmol) was cautiously added to ice cold concentrated sulfuric acid over 5 minutes. Nitric acid (4 mL, 90% HNO$_3$) was added dropwise over 10 minutes and the solution was then removed from the ice bath. After 30 minutes, the mixture was placed in a 80° C. oil bath, which over the next 15 minutes increased to 100° C. The solution was then cooled to room temperature and added to ice (300 mL). Sodium carbonate was added until the aqueous layer was basic and the suspension was extracted with methylene chloride (3×200 mL). The combined methylene chloride layers were dried with magnesium sulfate, filtered and evaporated under vacuum. The crude solid (7.6 g) was observed by $^1$H NMR to consist of a 1:2 ratio mixture of 4-amino-3-nitro-2-picoline and 4-amino-5-nitro-2-picoline. The mixture was purified by repeated silica gel chromatography (E.Merck 60,230–400 mesh, 3x(2.5×24 cm)). The columns were eluted with 5% methanol in methylene chloride and the third column gave the title compound as an off white solid (1.5 g).

$^1$H NMR (CDCl$_3$, 300 MHz) δ2.71 (s, Me), 6.57 (d,ArH) and 8.09 (d, ArH).

Step 3: 4-hydroxy-3-nitro-2-picoline 4-amino-3-nitro-2-picoline (1.5 g, 9.8 mmol) was dissolved in a mixture of water (27 mL) and concentrated sulfuric acid (4 mL), which was then cooled in an ice bath. A solution of sodium nitrite (1.2 g, 17.4 mmol) in water (4

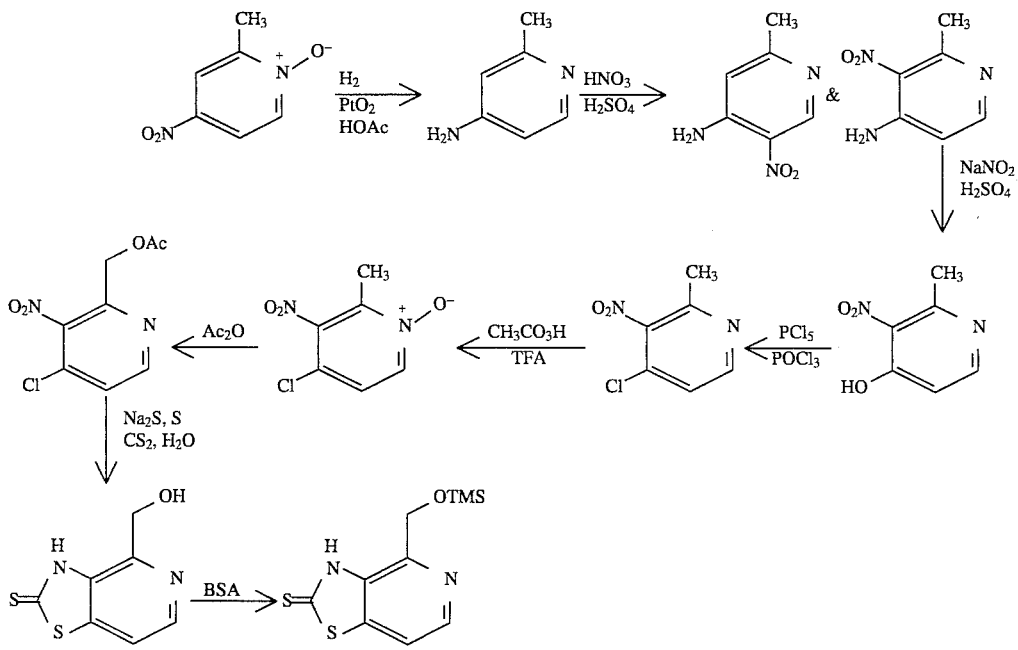

Step 1: 4-amino-2-picoline

4-Nitro-2-picoline N-oxide (19.8 g, 143.4 mmol) was hydrogenated in acetic acid (100 mL) for 2.5 hours at 50 psi in the presence of platinum oxide (0.4 g). (caution: reaction is very exothermic!) The mixture was filtered and the filtrate was evaporated to an oil. Saturated aqueous potassium carbonate was added to form a paste. The paste was extracted with 5% methanol in methylene chloride (6×50 mL) was added over 2 minutes and the solution was stirred for 2.5 hours. The mixture was then removed from the ice bath and was stirred at room temperature for 72 hours. The pH was adjusted to 6 with sodium carbonate and the solution was extracted with 5% methanol in methylene chloride (5×100 mL). The combined extracts were dried with magnesium sulfate, filtered and evaporated to a foam (2 g). Examination of the foam by $^1$H NMR showed it to consist of a 60:40 ratio mixture of 4-hydroxy-3-nitro-2-picoline and 4-amino-3-nitro-2-picoline. The above conditions were repeated by dissolving the solid in an ice cold mixture of water (17 mL) and concentrated sulfuric acid (3 mL). A solution of sodium nitrite (2 g, 29 mmol) in water (6 mL) was added over 2 minutes and the solution was then placed in a 60° C. oil bath. Over the next 15 minutes the bath temperature rose to 80° C. and the reaction was continued at this temperature for an additional hour. Work-up as above gave the title compound as a white solid (820 mg).

$^1$H NMR (DMSO-d$_6$, 300 MHz) δ2.28(s, Me), 6.32 (d, ArH) and 7.71(m, ArH).

Step 4: 4-chloro-3-nitro-2-picoline

A mixture of 4-hydroxy-3-nitro-2-picoline (820 mg, 5.32 mmol) and phosphorous pentachloride (1.11 g, 5.32 mmol) in phosphorous oxychloride (6 mL) was heated for 2 hours in a 100° C. oil bath. The phosphorous oxychloride was removed under vacuum and after cooling to room temperature, the residue was partitioned between ice (10 mL) and methylene chloride (10 mL). The aqueous layer was re-extracted with additional methylene chloride (2×10 mL) and the combined extracts were dried with magnesium sulfate, filtered and gave the title compound as a light brown solid upon evaporation (0.787 g).

$^1$H NMR (CDCl$_3$, 300 MHz) δ2.60 (s, Me),7.35 (d, ArH) and 8.51 (d, ArH).

Step 5: 4-chloro-3-nitro-2-picoline N-oxide 4-chloro-3-nitro-2-picoline (0.787 g, 4.6 mmol) was dissolved in a mixture of trifluoroacetic acid (3 mL) and 32% peracetic acid (2 mL) and was heated in a 60° C. oil bath for 4 hours, with an addition of 32% peracetic acid at 2 hours (2 mL). The solution was cooled to room temperature and was partitioned between methylene chloride (30 mL) and saturated aqueous potassium carbonate (30 mL). The aqueous layer was re-extracted with more methylene chloride (2×20 mL) and the combined extracts were dried with magnesium sulfate, filtered and evaporated to give a 45:55 mixture of the title compound and 4-chloro-3-nitro-2-picoline(0.5 g).

$^1$H NMR (CDCl$_3$, 300 MHz) δ2.60 (s, Me), 7.35 (d, ArH) and 8.51 (d, ArH).

Step 6: 4-chloro-3-nitro-2-(acetoxymethyl)pyridine

A 45:55 mixture of 4-chloro-3-nitro-2-picoline N-oxide and 4-chloro-3-nitro-2-picoline (0.48 g, 1.15 mmol) in acetic anhydride (5 mL, 53 mmol) was placed in a 60° C. oil bath for 1 hour. The temperature of the oil bath was then increased to 70° C. over the next 1.5 hours. The solution was cooled to room temperature, evaporated and partitioned between methylene chloride (20 mL) and saturated aqueous potassium carbonate (120 mL). The aqueous layer was re-extracted with more methylene chloride (2×20 mL) and the combined extracts were dried with magnesium sulfate, filtered and evaporated to a foam (0.43 g), The foam was dissolved in methylene chloride and was placed on preparative silica plates (5×1000 micron, analtech, 20×20 cm) which were developed with 5% ethyl acetate in methylene chloride and eluted with ethyl acetate to give an approximately 1:2 mixture of the title compound and 4-chloro-3-nitro-2-picoline(0.25 g).

$^1$H NMR (CDCl$_3$, 400 MHz) δ2.15 (s, OAc), 5.16 (s, CH$_2$OAc),7.38 (d, ArH) and 8.47 (d, ArH).

Step 7: 6-hydroxymethyl-2-thioxo-2,3-dihydrothiazolo[4,5-c]pyridine

A suspension of sulfur (0.5 g, 15.6 mmol) and sodium sulfide nonahydrate (1.84 g, 7.66 mmol) in water (5 mL) was heated in a 50° C. oil bath for 15 minutes. The amber colored solution was cooled to room temperature and the 2:1 mixture of 4-chloro-3-nitro-2-acetoxymethylpyridine/4-chloro-3-nitro-2-picoline (0.25 g, 0.36 mmol) and carbon disulfide (2mL, 33.4mmol) were added, and the mixture was heated in a 70° C oil bath for 18 hours under a nitrogen atmosphere. Workup and chromatography as described in Step 3 of Preparative Example 4 afforded an approximately 4:1 ratio mixture of the title compound and 6-methyl-2-thioxo-2,3-dihydrothiazolo[4,5-c]pyridine (88mg), as observed by $^1$H NMR.

$^1$H NMR (DMSO-d6, 300 MHz) δ4.83 (s, CH$_2$OH), 7.75 (d, ArH) and 8.21 (d, ArH).

Step 8: 6-((trimethyl)silyloxymethyl)-2-thioxo-2,3-dihydrothiazolo[4,5-c]pyridine A 4:1 mixture of 6-hydroxymethyl-2-thioxo-2,3-dihydrothiazolo[4,5-c]pyridine and 6-methyl-2-thioxo-2,3-dihydrothiazolo[4,5-c]pyridine (86mg, 0.35mmol) was dissolved in a mixture of tetrahydrofuran (1 mL) and bis(trimethylsilyl) acetamide (0.5mL) and was stirred at room temperature for 30 minutes under nitrogen. The solution was evaporated under vacuum and the residue was applied to a flash silica gel column (EMerck 60, 230–400 mesh, 2.5×6 cm). The column was eluted with 1:1 ether:hexane collecting 8 mL fractions. Fractions 1–8 were combined and provided the title compound as a solid upon evaporation (62mg, 70%).

$^1$H NMR (DMSO-d$_6$, 300 MHz) δ0.26 (s, Si(TMS)$_3$), 5.05 (s, CH$_2$O), 7.30 (d, ArH) and 8.30 (d, ArH).

PREPARATIVE EXAMPLE 16

4-HYDROXYMETHYL-6-BROMO-2-THIOXO-2,3-DIHYDROBENZOTHIAZOLE

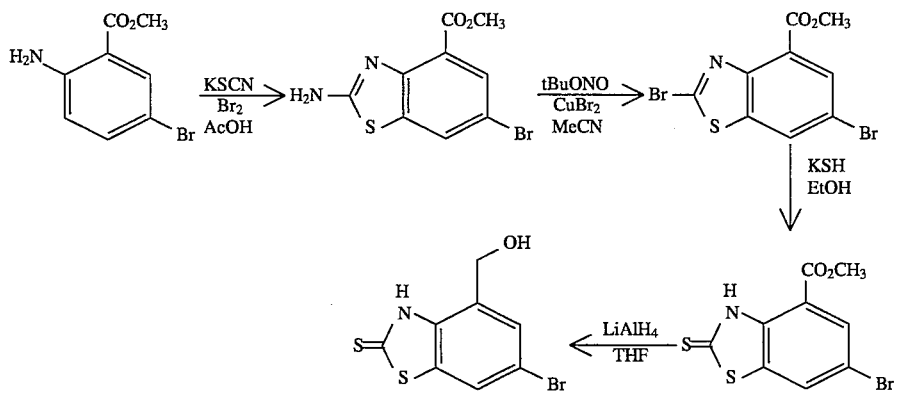

Step 1: methyl 2-amino-6-bromobenzothiazole-4-carboxylate

To 8.46 g (4.85 mmol) of methyl 2-amino-5-bromobenzoate in 150 ml of acetic acid was added 8.8 grams of potassium thiocyanate. The mixture was stirred and sonicated until all solids had gone into solution, and then 2.2 ml of bromine was added dropwise. The resulting mixture was stirred for five hours, after which time the acetic acid was

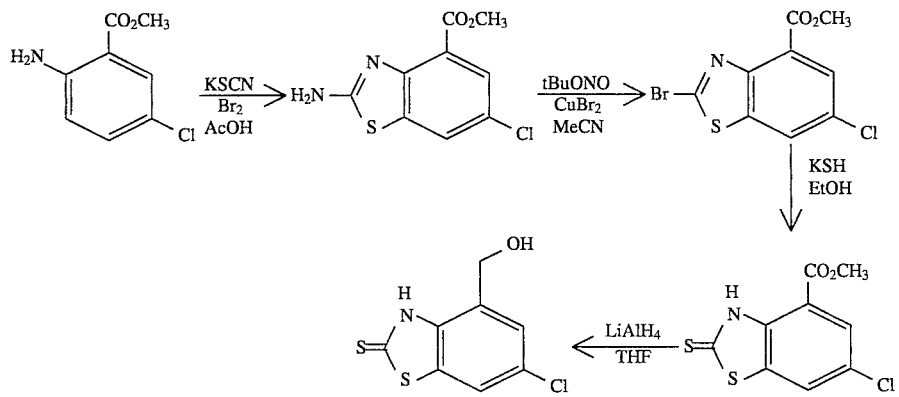

removed under reduced pressure. The residue was partitioned between saturated aq. sodium bicarbonate and tetrahydrofuran. The organic layer was separated and the solvent was removed under reduced pressure. The residue was chromatographed on silica eluting with 3:1 hexane/ethyl acetate to bring off the impurities, then with 1:1 hexane/ethyl acetate to elute the title compound (4.06 g).

Step 2: methyl 2,6-dibromobenzothiazole-4-carboxylate

Methyl 2-amino-6-bromobenzothiazole-4-carboxylate (3.86 g) was added as a solid to a mixture of 4.31 g of copper (II) bromide and 2.88 ml of tert-butyl nitrite in 90 ml of anhydrous acetonitrile stirring at 0° C. The mixture was allowed to stir and warm to room temperature over 6 hours, and was then partitioned between 600 ml of ether and 300 ml of 2N HCl. The organic layer was extracted twice with 100 ml of 2N HCl, then dried over sodium sulfate and evaporated under reduced pressure to give 3.00 g of crude methyl 2,6-dibromobenzothiazole-4-carboxylate (used without further purification in the next step).

Step 3: methyl 6-bromo-2-thioxo-2,3-dihydrobenzothiazole-4-carboxylate

To the 3.00 g of crude methyl 2,6-dibromobenzothiazole-4-carboxylate obtained in the previous step was added 60 ml of ethanol and 3.0 g of KSH, and the resulting mixture was stirred at 80° C. After 30 min the reaction was cooled and the solvent was removed under reduced pressure. The residue was taken up in ethyl acetate and extracted with water and brine. The organic layer was separated and the solvent was removed under reduced pressure. The residue was chromatographed on silica eluting with 3:1 hexane/ethyl acetate to give the title compound (0.909 g).

Step 4: 6-bromo-4-hydroxymethyl-2-thioxo-2,3-dihydrobenzothiazole

Methyl 6-bromo-2-thioxo-2,3-dihydrobenzothiazole-4-carboxylate (640 mg) in 13 ml of anhydrous tetrahydrofuran was stirred and cooled to 0° C, then 80 mg of lithium aluminum hydride was added. The reaction was stirred and allowed to warm to room temperature over 5 hours, and was then partitioned between ethyl acetate and 2 N hydrochloric acid. The organic layer was separated, dried over sodium sulfate, and evaporated under reduced pressure to give 573 mg of the title compound.

$^1$H NMR (CD$_3$COCD$_3$, 400 MHz) δ7.84 (s, ArH), 7.52 (s, ArH), 4.67 (s, ArCH$_2$OH).

PREPARATIVE EXAMPLE 17

4-HYDROXYMETHYL-6-CHLORO-2-THIOXO-2,3-DIHYDROBENZOTHIAZOLE

Substitution of methyl 2-amino-5-chlorobenzoate for methyl 2-amino-5-bromobenzoate in the procedure of Preparative Example 16 afforded 4-hydroxymethyl-6-chloro-2-thioxo-2,3-dihydrobenzothiazole $^1$H NMR (DMSO-d$_6$, 500 MHz) δ7.71 (s, ArH), 7.40 (s, ArH), 5.43 (s, OH), 4.67 (s, ArCH$_2$OH).

PREPARATIVE EXAMPLE 18

5-CHLORO-4-HYDROXYMETHYL-2-THIOXO-2,3-DIHYDROBENZOTHIAZOLE

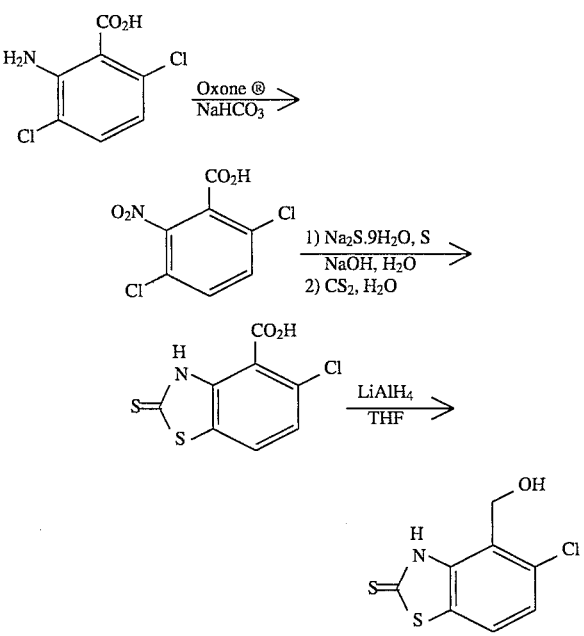

Step 1: 3,6-dichloro-2-nitrobenzoic acid

To 1.0 g (4.85 mmol) of 2-amino-3,6-dichlorobenzoic acid in 25 ml of acetone and 5 ml of water at 0° C. was added 10 g of sodium bicarbonate then 20 g of oxone® in portions over 15 minutes. The resulting mixture was stirred and allowed to warm to room temperature over 2 hours, after which time the solvent was removed under reduced pressure. The residue was triturated with 5 ml of acetone, filtered, and the acetone was evaporated under reduced pressure to give 1.16 g of the title compound.

Step 2: 5-chloro-2-thioxo-2,3-dihydrobenzothiazole-4-carboxylic acid:

To 3,6-dichloro-2-nitrobenzoic acid (1.16 g) was added 6 ml of water and 0.245 g of sodium hydroxide. The mixture was stirred at room temperature until all solids had dissolved. A solution of polysulfide was prepared by combining 3.1 g of $Na_2S \cdot 9 H_2O$, 1.2 g S, and 4 ml $H_2O$ and stirring and warming until a translucent solution was obtained. This polysulfide solution was added to the reaction and the resulting mix was heated at 100° C. for 2 hours, after which time 5 ml of carbon disulfide was added and heating was continued for 6 more hours. The solution was cooled and acidified to pH 3 with acetic acid, then filtered. The solid thus obtained was sonicated with 100 ml of 5% sodium carbonate for 15 minutes then refiltered. The filtrate was acidified with hydrochloric acid, and the resulting precipitate was collected by filtration and dried under high vacuum to give 246 mg of the title compound.

Step 3: 5-chloro-4-hydroxymethyl-2-thioxo-2,3-dihydrobenzothiazole

Lithium aluminum hydride (200 mg) was added to a solution of 5-chloro-2-thioxo-2,3-dihydrobenzothiazole-4-carboxylic acid (246 mg) in 5 ml tetrahydrofuran and the resulting mixture was heated at 50° C. for 6 hours, then partitioned between ethyl acetate and 2 N HCl. The organic layer was separated, dried over sodium sulfate, and evaporated under reduced pressure to give 138 mg of 5-chloro-4hydroxymethyl- 2-thioxo-2,3-dihydrobenzothiazole.

$^1$H NMR ($CD_3COCD_3$, 400 MHz) δ7.52 (d, ArH), 7.30 (d, ArH), 5.05 (s, Ar$CH_2$OH).

PREPARATIVE EXAMPLE 19

4-HYDROXYMETHYL-2-THIOXO-2,3-DIHYDROTHIENO[3,2-D]THIAZOLE

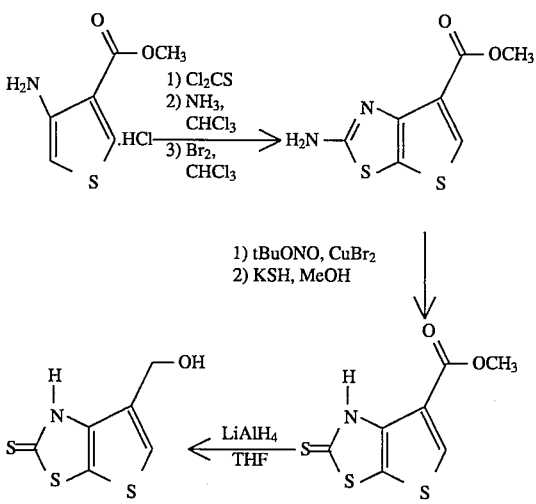

Step 1: Methyl 2-Aminothieno[3,2-d]thiazole-4-carboxylate

To 6.0 g (31.0 mmol) of 3-aminothiophene-4-carboxylate hydrochloride in 215 ml of chloroform and 100 ml of saturated aq. sodium bicarbonate, stirred vigorously at room temperature, was added 2.50 ml of thiophosgene (32.6 mmol). After 30 minutes 100 ml of brine was added and the organic layer was separated and bubbled with ammonia gas with vigorous stirring. After 30 minutes, the reaction was evaporated under reduced pressure. To the residue was added 250 ml of chloroform and the mixture was sonicated to produce a fine suspension. This mix was stirred vigorously and cooled to 0° C., then 1.92 ml (37.2 mmol) bromine was added. Stirring was continued for one hour, after which time the solvent was removed under reduced pressure. To the residue was added 180 ml of methanol and 180 ml of water containing 6.24 g of sodium bicarbonate. The mixture was cooled to 0° C. for several hours and then filtered. The solid thus obtained was dissolved in tetrahydrofuran and precipitated with hexanes to yield, after drying under high vacuum, 3.08 g of the reddish powdery title compound. The methanol/water mixture from the filtration was rotovapped to about 50 ml, cooled to 0° C. and filtered to give an additional 3.63 g of yellow solid title compound.

$^1$H NMR ($CD_3OD$, 500 MHz) δ8.12 (s, thiophene H), 3.88 ($H_3$CCO). $^{13}$C NMR ($CD_3OD$, 500 MHz) δ173.4, 162.5, 153.5, 133.7, 121.7, 120.3, 50.7.

Step 2: Methyl 2-thioxo-2,3-dihydrothieno[3,2-d]thiazole-4-carboxylate

To 3.8 g of copper (II) bromide (17.0 mmol) in 90 ml of anhydrous acetonitrile, stirred vigorously at at 0° C., was added 2.53 ml of t-butyl nitrite (21.3 mmol). After 5 minutes, 3.05 g (14.2 mmol) of methyl 2-aminothieno[3,2-d]thiazole-4-carboxylate was added as a solid. The reaction was allowed to stir at 0° C. for three hours and then was partitioned between 500 ml of ethyl acetate and 200 ml of 4 N HCl. The organic layer was separated and washed with an additional 150 ml of 4 N HCl, then dried over sodium sulfate and evaporated under reduced pressure. To the crude residue in 100 ml of methanol was added 5.0 g KSH, and the reaction was stirred at 80° C. for 2.5 hours. The methanol was removed under reduced pressure, and the residue was partitioned between 100 ml brine and 250 ml ethyl acetate. The brine was washed twice with 100 ml of ethyl acetate. The combined organics were evaporated, and the residue was chromatographed on silica eluting with 1 to 1 hexane/tetrahydrofuran. In this manner was obtained 1.55 g of the title compound.

$^1$H NMR ($CDCl_3$, 400 MHz) δ.

Step 3: 4-Hydroxymethyl-2-thioxo-2,3-dihydrothieno[3,2-d]thiazole

To 1.55 g (6.69 mmol) of methyl 2-thioxo-2,3-dihydrothieno[3,2-d]thiazole-4-carboxylate in 40 ml of anhydrous tetrahydrofuran at 0° C. was added 0.325 g (8.55 mmol) of lithium aluminum hydride. The reaction was stirred at 0° C. for 1.5 hours and then allowed to warm to room temperature over 30 minutes. To the reaction was recooled to 0° C. and 15 ml of water then 14 ml of 2 N HCl was added carefully. The reaction was then transferred to a separatory funnel with 200 ml of ethyl acetate. The organic layer was separated and the aqueous layer was washed twice with 50 ml of ethyl acetate. The combined organics were evaporated under reduced pressure and the residue was chromatographed on silica eluting with 1:1 hexane/tetrahydrofuran to obtain 1.12 g of the title compound.

$^1$H NMR ($CD_3COCD_3$, 400 MHz) δ7.15 (s, thiophene H), 4.79 ($CH_2$OH).

PREPARATIVE EXAMPLE 20

4-((4-HYDROXYMETHYLPHENYL)AMINOCARBONYL)-2-THIOXO-2,3-DIHYDROBENZTHIAZOLE

Step 1: 4-chlorocarbonyl-2-chlorobenzothiazole 4-carboxy-2-thioxo-2,3-dihydrobenzothiazole (1.68 g, 7.95mmol) was added to a mixture of phosphorous pentachloride (5.0 g, 24mmol) and dimethylformamide (3.7mL, 48mmol) in phosphorous oxychloride (50mL). The solution was heated in a 105° C. oil bath for 2 hours and the excess phosphorous oxychloride was distilled under vacuum. The black viscous liquid was cooled to room temperature and was extracted with benzene (3×50mL). The combined extracts were treated with carbon, filtered and evaporated to give the title compound as a yellow solid (1.7 g).

$^1$H NMR (CDCl$_3$, 500 MHz) δ7.60 (dd, ArH), 8.11 (d, ArH) and 8.33 (d, ArH).

$^{13}$C NMR (CDCl$_3$, 500 MHz) δ164.3, 157.3, 148.5, 138.2, 13 1.9, 127.4, 127.3 and 125.4 ppm.

Step 2: 4-(4-hydroxymethylphenyl)aminocarbonyl)-2-chlorobenzothiazole

A solution of 4-chlorocarbonyl-2-chlorobenzothiazole (0.232 g, 1 mmol) in chloroform (5mL) was cooled in an ice bath and treated with p-aminobenzylalcohol (0.246 g, 2mmol). After 5 minutes, the mixture was partitioned between methylene chloride (5mL) and saturated aqueous potassium carbonate (10mL). The aqueous layer was re-extracted with more methylene chloride (1×10mL) and the combined methylene chloride layers were dried with magnesium sulfate, s filtered and evaporated under vacuum. The crude solid was dissolved in methylene chloride (1 mL) and was loaded onto preparative silica gel plates (5×1000 micron, analtech, 20×20 cm)). The plates were developed with 5% methanol in methylene chloride and the product band was eluted with 10% methanol in methylene chloride.

Evaporation of the o eluent gave the title compound (0.22 g) as a white solid.

$^1$H NMR (CDCl$_3$, 500 MHz) δ4.66 (s, C$\underline{H}_2$OH), 7.36 (d, 2ArH), 7.54 (dd, ArH), 7.72 (d, 2ArH), 7.89 (d, ArH) and 8.43 (d, ArH).

$^{13}$C NMR (CDCl$_3$, 500 MHz) δ161.6, 155.2, 147.2, 137.6, 137.1, 136.4, 129.3, 127.7, 126.2, 126.1, 124.6, 120.3, and 64.8 ppm.

Step 3: 4-((4-hydroxymethylphenyl)aminocarbonyl)-2-thioxo-2,3-dihydrobenzothiazole A solution of 4-((4-hydroxymethylphenyl)aminocarbonyl)-2-chlorobenzothiazole (0.22 g, 0.69 mmol) and potassium hydrosulfide (0.1 g, 1.38 mmol) in methanol (3 mL) was heated in a 60° C. oil bath for 15 hours under an atmosphere of nitrogen. After cooling to room temperature, the mixture was partitioned between methylene chloride (10 mL) and water (10 mL), the pH was adjusted to 4 with 2N hydrochloric acid and the resulting thick emulsion was filtered. The collected solid was washed with water (5 mL) and methylene chloride (5 mL) and gave the title compound as a white solid after drying under vacuum (0.137 g).

$^1$H NMR (DMSO-d6, 500 MHz) δ4.45 (s, C$\underline{H}_2$OH), 7.30(d, 2ArH), 7.40 (dd, ArH), 7.40 (d, 2ArH), and 7.85 (d, 2ArH).

$^{13}$C NMR (DMSO-d6, 500 MHz) δ190.8, 164.4, 138.7, 137.6, 131.1, 127.1, 126.4, 124.7, 124.2, 120.9, 120.4, and 63.0 ppm.

PREPARATIVE EXAMPLE 21

5-HYDROXYMETHYL-2-THIOXO-2,3-DIHYDROTHIAZOLO[4,5-B]PYRIDINE

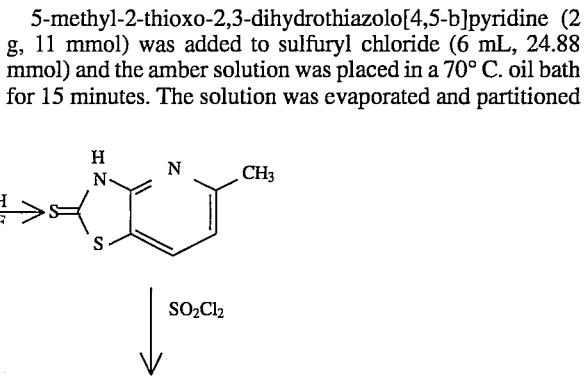
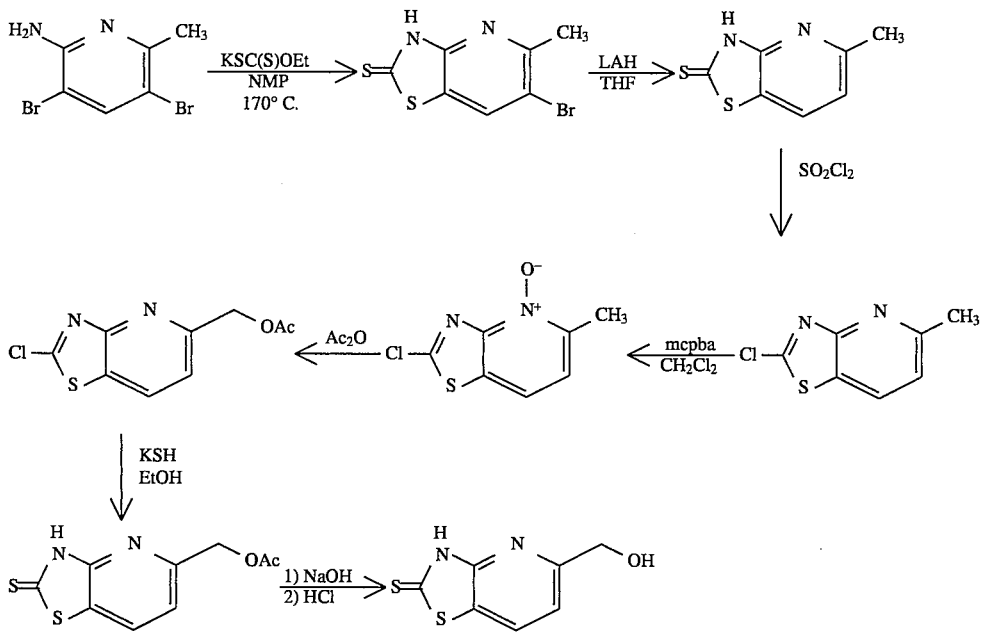

Step 1: 5-methyl-6-bromo-2-thioxo-2,3-dihydrothiazolo[4,5-b]pyridine

Potassium ethyl xanthate (4.8 g, 30 mmol) and 2-amino-3,5-dibromo-6-picoline (2.66 g, 10 mmol) were dissolved in N-methylpyrrolidinone (10 mL) and the solution was placed in a 170° C. oil bath for 4.5 hours under nitrogen. The dark solution was cooled to room temperature, diluted with water (50 ml) and acidified with acetic acid (5 mL). The suspension was filtered and the collected solid was washed with water (20 mL) and dried under vacuum to give the title compound as a light yellow solid (2.16 g, 83%).

$^1$H NMR (DMSO-$d_{6,\ 500}$ MHz) $\delta$2.50 (s, Me) and 8.22 (s, ArH).

$^{13}$C NMR (DMSO-$d_{6,\ 500}$ MHz) $\delta$191.2, 154.2, 152.6, 130.7, 123.1, 9.3, and 24.5 ppm.

Step 2: 5-methyl-2-thioxo-2,3-dihydrothiazolo[4,5-b]pyridine

An ice cooled solution of 5-methyl-6-bromo-2-thioxo-2,3-dihydrothiazolo[4,5-b]pyridine (5.0 g, 19.14 mmol) in tetrahydrofuran (50 mL) was treated with lithium aluminum hydride (1.5 g, 39.47 mmol). The mixture was removed from the ice bath, and after warming to room temperature, was stirred in a 70° C. oil bath for 1 hour. Upon cooling to room temperature, water (1 mL) was added cautiously to consume the excess hydride. The resulting suspension was partitioned between methylene chloride (300 ml) and water (200 mL). The mixture was acidified with acetic acid (5 mL) and the aqueous layer was re-extracted with more methylene chloride (2×200 mL). The combined extracts were dried with magnesium sulfate, filtered and evaporated to a solid (2.89 g). The solid was filtered with ethanol (30 mL) and dried under vacuum to give the title compound (2.0 g).

$^1$H NMR (10% CD$_3$OD in CDCl$_3$, 500 MHz) $\delta$2.65 (s, Me), 7.05 (d, ArH), and 7.65 (d, ArH).

$^{13}$C NMR (10% CD$_3$OD in CDCl$_3$, 500 MHz) $\delta$191.3, 156.6, 152.9, 130.0, 119.4, 116.0, 115.0 and 23.8 ppm.

Step 3: 5-methyl-2-chloro-thiazolo[4,5-b]pyridine 5-methyl-2-thioxo-2,3-dihydrothiazolo[4,5-b]pyridine (2 g, 11 mmol) was added to sulfuryl chloride (6 mL, 24.88 mmol) and the amber solution was placed in a 70° C. oil bath for 15 minutes. The solution was evaporated and partitioned between methylene chloride (50 mL) and aqueous potassium carbonate (50 mL). The aqueous layer was re-extracted with more methylene chloride (3×50 mL) and the combined methylene chloride layers were dried with magnesium sulfate, filtered and evaporated to a foam (2.7 g). The foam was dissolved in 5% ethyl acetate in methylene chloride (10 mL) and filtered through a plug of silica gel (10 mL). The silica was eluted with 5% ethyl acetate in s methylene chloride (150 mL) and gave the title compound as a foam upon evaporation (1.4 g).

$^1$H NMR (CDCl$_3$, 500 MHz) $\delta$2.75 (s, Me), 7.28 (d, ArH) and 8.06 (d, ArH).

Step 4: 5-methyl-2-chloro-thiazolo[4,5-b]pyridine N-oxide m-Chloroperbenzoic acid (1.87 g, 10.8 mmol, apprx. 90%) was added to a solution of 5-methyl-2-chloro-thiazolo[4,5-b]pyridine (1.0 g, 5.4 mmol) in methylene chloride (15 mL). The mixture was stirred for 5 hours at room temperature and was then partitioned between methylene chloride (30 mL) and saturated aqueous potassium carbonate (50 mL). The aqueous layer was re-extracted with more methylene chloride (6×20 mL) and the combined extracts were dried with magnesium sulfate, filtered and evaporated to a foam (1.2 g). Diethyl ether (20 mL) was added and the title compound was obtained as a white solid in two crops (0.475 g).

$^1$H NMR (CDCl$_3$, 500 MHz) $\delta$2.71 (s, Me), 7.35 (d, ArH) and 7.58(d, ArH).

Step 5: 5-(acetoxymethyl)-2-chloro-thiazolo[4,5-b]pyridine 5-methyl-2-chloro-thiazolo[4,5-b]pyridine N-oxide (450mg, 2.24 mmol) was suspended in acetic anhydride (5 mL) and was heated in a 70° C. oil bath for 45 minutes. The solution was evaporated to give the title compound as a solid.

$^1$H NMR (CDCl$_3$, 500 MHz) $\delta$2.16 (s, OAc), 5.33 (s, CH$_2$OAc), 7.43 (d, ArH) and 8.17(d, ArH).

Step 6: 5-acetoxymethyl-2-thioxo-2,3-dihydrothiazolo[4,5-b]pyridine 5-(acetoxymethyl)-2-chloro-thiazolo[4,5-b]pyridine (500mg, 2.06 mmol) was added to a suspension of potassium hydrosulfide (400 mg, 5.55 mmol) in ethanol (5 mL). After 70 minutes at room temperature the mixture was partitioned between ethyl acetate (20 mL) and water (10 mL), the pH was adjusted from 7.9 to 4.0 with 2N hydrochloric acid and the aqueous layer was extracted with additional ethyl acetate (3×20 mL). The combined ethyl acetate layers were washed with saturated aqueous sodium chloride (1×40 mL), were dried with magnesium sulfate, filtered and evaporated to an orange foam (550 mg). The foam was dissolved in methylene chloride (ca. 1 mL) and was placed on (5×1000 micron, 20×20cm, Analtech-).preparative silica plates. The plates were developed with 5% methanol in methylene chloride and the product band was removed and eluted with 5%methanol in methylene chloride to give the title compound upon evaporation (300 mg).

$^1$H NMR (CDCl$_3$, 500 MHz) δ2.16 (s, OAc), 5.47 (s, CH$_2$OAc)$_{7.32}$ (d, ArH) and 7.80 (d, ArH).

$^{13}$C NMR (CDCl$_3$, 500 MHz) δ191.0, 170.6, 154.1,152.8, 130.5, 124.2, 117.9, 66.0 and 20.9 ppm.

Step 7: 5-hydroxymethyl-2-thioxo-2,3-dihydrothiazolo[4,5-b]pyridine 5-acetoxymethyl-2-thioxo-2,3-dihydrothiazolo[4,5b]pyridine (216 mg, 0,90 mmol) was suspended in water (3 mL) and treated with 5N sodium hydroxide (0.36 mL, 1.798 mmol). The solid rapidly dissolved and after 10 minutes 2N hydrochloric acid (0.9 mL, 1.8 mmol) was added. The suspension was filtered and the collected solid was washed with water (3 mL) and after drying overnight under vacuum gave the title compound as an off white solid (169 mg).

$^1$H NMR (DMSO-d$_6$ 500 MHz) δ8.07 (d, ArH), 7.36 (d, ArH) and 4.54 (s, CH$_2$OH).

$^{13}$C NMR (DMSO-d$_6$, 500 MHz) δ191.4, 160.7, 153.4, 131.2, 122.3, 116.6, and 64.1 ppm.

PREPARATIVE EXAMPLE 22

1-(3-HYDROXYPROPYL)-4-AZA-1-AZONIABICYCLO[2.2.2]OCTANE TRIFLUOROMETHANE-SULFONATE

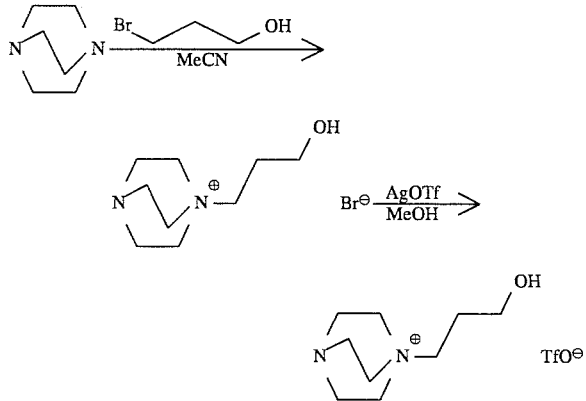

A solution of 3-bromo-1-propanol (5.56 g, 0.040 mol) in anhydrous acetonitrile (20 mL) was added dropwise over 5 minutes to a solution of 1,4-diazabicyclo[2.2.2]octane (DABCO; 5.39 g, 0.048 mol) in anhydrous acetonitrile (100 mL) The resulting solution was stirred at room temperature for 19 hours. The mixture was concentrated in vacuo to a clear oil which was triturated with anhydrous ether (3×50 mL). The oily residue was dried in vacuo to afford 1-(3-hydroxypropyl)- 4-aza-1-azoniabicyclo[2.2.2]octane bromide as a white solid (10.27 g). The bromide salt was dissolved in methanol (100 mL) and treated with solid silver trifluoromethanesulfonate (10.25 g, 0.040 mol). A voluminous yellow precipitate formed immediately. The mixture was stirred at room temperature in the dark for 30 minutes then filtered through a methanol-washed Celite pad. The filter cake was washed with methanol and the combined filtrate was concentrated in vacuo to an oil. The oil was triturated with ether (50 mL) and dried in the dark to afford a white solid (12.74 g). The crude product thus obtained was recrystallized from isopropanol-ether to afford the desired triflate salt as a white, crystalline solid (10.89 g).

$^1$H NMR (DMSO-d$_6$, 500 MHz) δ1.80 (m, NCH$_2$C$\underline{H}_2$CH$_2$OH), 3.01 (t, N(C$\underline{H}_2$CH$_2$)$_3$N), 3.21–3.28 (m, NC$\underline{H}_2$CH$_2$CH$_2$OH+N(CH$_2$ C$\underline{H}_2$)$_3$N), 3.47 (q, NCH$_2$CH$_2$C$\underline{H}_2$OH), and 4.77 (t, OH).

$^{13}$C NMR (DMSO-d$_6$, 125.7 MHz) δ24.5, 44.7, 51.6, 57.7, and 61.5.

PREPARATIVE EXAMPLE 23

1-((N-METHYL)CARBAMOYLMETHYL)-4-AZA-1-AZONIABICYCLO[ 2.2.2]OCTANE TRIFLUOROMETHANE-SULFONATE

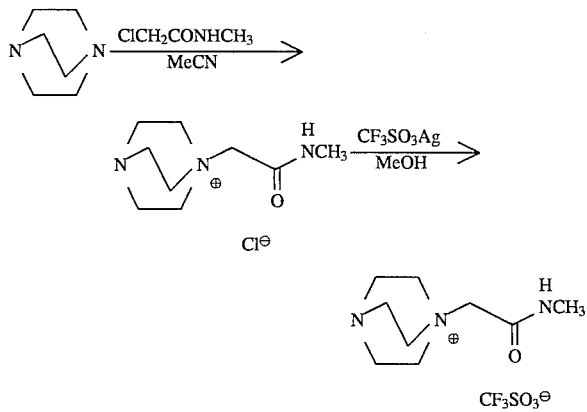

1,4-diazabicyclo[2.2.2]octane (2.64 g, 24 mmol) was dissolved in acetonitrile (20 mL) and was treated with 2-chloro-(N-methyl)acetamide (2.64 g, 21 mmol). The mixture was stirred for 1 hour and the resulting suspension was filtered. The collected solid was washed with acetonitrile (20 mL) and was dried under vacuum to give 1-((N-methyl)carbamoylmethyl)- 4-aza-1-azoniabicyclo[2.2.2]octane chloride as a very hygroscopic white solid (4.0 g, 85%). The chloride salt was dissolved in methanol (20 mL) and was treated with silver trifluoromethanesulfonate (4.68 g, 18.2 mmol). After 30 minutes the yellow suspension was filtered and the collected solid was washed with methanol (20 mL). The filtrate was concentrated under vacuum and the resulting oil was triturated with isopropanol (25 mL). The precipitated solid was filtered and dried under vacuum to give the title compound as a white solid (5.66 g).

$^1$H NMR (DMSO-d$_6$, 500 MHz) δ2.63 and 2.64 (s, NHC$\underline{H}_3$), 3.03 and 3.45 (two m, N(CH$_2$CH$_2$)$_3$N), 3.90 (s C$\underline{H}_2$CONHCH$_3$) and 8.45(s, N$\underline{H}$CH$_3$).

PREPARATIVE EXAMPLE 24

1-CYANOMETHYL-4-AZA-1-AZONIABICYCLO[2.2.2]OCTANE TRIFLUROMETHANESULFONATE

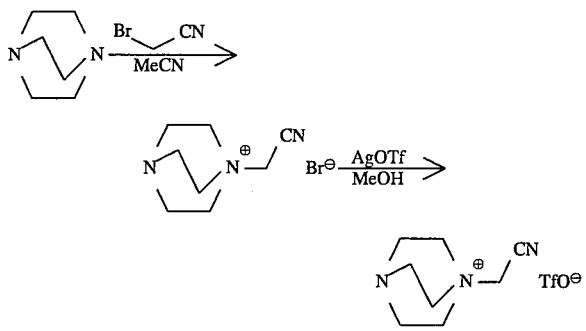

A solution of DABCO (1.345 g, 12 mmol) in acetonitrile (50 mL) was treated dropwise over two minutes with bromoacetonitrile (0.7 mL, 10 mmol). A precipitate formed during the addition. The mixture was stirred at room temperature for 30 minutes then filtered. The solid was washed with acetonitrile and dried in vacuo to afford 1-cyanomethyl- 4-aza-1-azoniabicyclo[2.2.2]octane bromide (2.302 g, 99%) as a white solid. A portion (0.928 g, 4 mmol) of the bromide salt was dissolved in methanol (40 mL) and the solution was treated with silver trifluoromethanesulfonate (1.064 g, 4 mmol). A precipitate formed immediately. The mixture was stirred at room temperature and in the dark for 4 hours, then filtered through a methanol washed, packed pad of Celite. The filtrate was evaporated in vacuo to a white solid. This material was recrystallized from isopropanol to give 1-cyanomethyl- 4-aza-1-azoniabicyclo[2.2.2]octane trifluromethanesulfonate (1.164 g) as white flakes.

$^1$H NMR (DMSO-$d_6$, 500 Mz) d 3.09 and 3.39 (two br s's, N(C$\underline{H_2}$C$\underline{H_2}$)$_3$N) and 4.78 (s, NCH$_2$CN).

$^{13}$C NMR (DMSO-$d_6$, 125.7 Mz) d 44.5, 50.3, 52.7, and 111.5.

PREPARATIVE EXAMPLES 25–40

1-SUBSTITUTED-4-AZA-1-AZONIABICYCLO[2.2.2]OCTANE SALTS

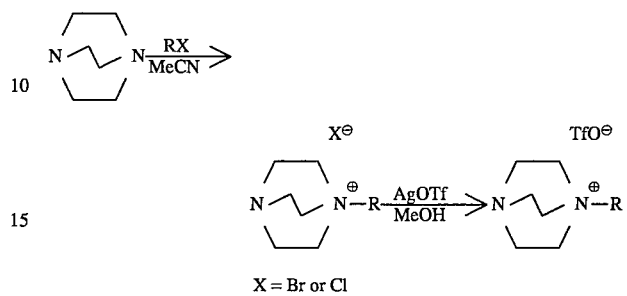

X = Br or Cl

By substitution of the appropriate alkylating reagent (RX) in the procedures of Preparative Examples 21–23, the 1-substituted-4-aza- 1-azoniabicyclo[2.2.2]octane trifluoromethanesulfonate (triflate) salts shown in the following Table were prepared:

TABLE

| Prep. Ex. | R | X | $^1$H NMR data for product (triflate salt) |
|---|---|---|---|
| 25 | CH$_2$COC$_6$H$_5$ | Br | (DMSO-$d_6$, 500Mz)δ 3.12(br s), 3.58(br s) 5.17(s), 7.61(t), 7.75(t), 7.99 (d) |
| 26 | H$_2$C—C(O)—N(CH$_2$CH$_2$)$_2$O (morpholinyl acetyl) | Cl | (D$_2$O, 500Mz)δ 3.24(m), 3.49(m), 3.58(m), 3.70(m), 3.74(m), 4.32(s) |
| 27 | H$_2$C—C(O)—N(CH$_2$CH$_2$CH$_2$CH$_2$) (pyrrolidinyl acetyl) | Cl | (DMSO-$d_6$, 500Mz)δ 1.78(p) 1.90(p), 3.06(t), 3.54(t), 3.35(m), 4.21(s) |
| 28 | CH$_2$CH$_2$F | Br | (DMSO-$d_6$, 500MHz)δ 3.02(m), 3.34(m), 3.61(m), 3.67(m), 4.89(m), 4.99 (m) |
| 29 | CH$_2$CH$_2$CH$_2$F | Br | (DMSO-$d_6$, 500MHz)δ 2.07(m), 2.12(m), 3.01(m), 3.27(m), 3.27(m), 3.31(m), 4.48(m), 4.58(m) |
| 30 | CH$_2$CH$_2$OH | Br | (DMSO-$d_6$, 500MHz)δ 3.00(br t), 3.34(br t), 3.28(t), 3.83(br s), 5.25(t) |
| 31 | CH$_2$CON(CH$_3$)$_2$ | Cl | (DMSO-$d_6$, 500MHz)δ 2.86(s), |

TABLE-continued

| Prep. Ex. | R | X | $^1$H NMR data for product (triflate salt) |
|---|---|---|---|
| 32 | CH$_2$CH$_2$CH$_3$ | Br | 2.94(s), 3.05(br t), 3.52(br t), 4.31(s) (CD$_3$CN, 500MHz)δ 3.23(m), 3.15(m), 1.78(m), 1.01(t) |
| 33 | CH$_2$CH$_2$CH$_2$CH$_2$OH | Br | (CD$_3$CN, 300MHz)δ 1.56(m), 1.85(m), 3.18(br t), 3.29(m), 3.61(t) |
| 34 | CH$_2$CH$_2$OCH$_2$CH$_2$OH | Cl | (CD$_3$CN, 300MHz)δ 3.17(br t), 3.38(br t), 3.44(m), 3.60(m), 3.68(m), 3.93(m) |
| 35 | CH$_2$CH$_2$CH$_2$CN | Cl | (CD$_3$CN, 300MHz)δ 2.14(m), 2.56(t), 3.18(br t), 3.28(br m). |
| 36 | H$_2$C—CH(OH)—CH$_2$OH | Cl | (D$_2$O, 300MHz)δ 2.75(s), 3.20(br t), 3.33(s), 3.39(s), 3.55(br m), 4.11(br m), 4.25(br m), 4.32(br m) |
| 37 | CH$_2$CONHC$_6$H$_5$ | Br | (CD$_3$CN, 300MHz)δ 3.21(br t), 3.62(br t), 4.10(s), 7.25(t), 7.42(t), 7.66(d) |
| 38 | H$_2$C—CH(OH)—CH$_2$OC$_6$H$_5$ | Cl | (CD$_3$CN, 300MHz)δ 3.19(br t), 3.37–3.58(br m), 4.05(dq), 4.62(m), 7.05(m), 7.40(m) |
| 39 | H$_2$C—CH(OH)—CH$_2$—O—CH(CH$_3$)$_2$ | Cl | (CD$_3$CN, 300MHz)δ 1.15(m), 2.00(m), 2.81(br s), 3.15(t), 3.30–3.70(m), 4.40(m) |
| 40 | CH$_2$SCH$_3$ | Cl | (D$_2$O, 500MHz)δ 2.37(s), 3.21(t), 3.48(t), 4.51(s) |

PREPARATIVE EXAMPLE 41

5-(IMIDAZOL-2-YL)-2-THIOXO-2,3-DIHYDROBENZOTHIAZOLE

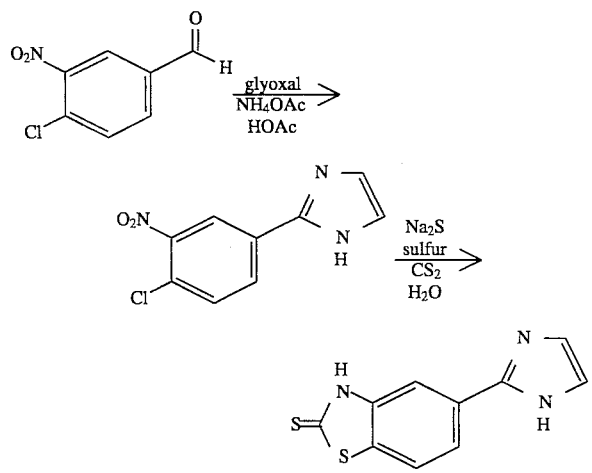

Step 1: 1-(imidazol-2-yl)-3-nitro-4-chlorobenzene 4-chloro-3-nitrobenzaldehyde (1 g, 5.39 mmol) was added to a stirred suspension of ammonium acetate (1.04 g, 13.5 mmol) in acetic acid (5 mL). Glyoxal (0.77 mL, 6.74 mmol, 40% aqueous solution) was added over 1 minute and the yellow suspension was stirred for 30 minutes at room temperature. The resulting orange solution was then placed in a 90° C. oil bath and stirred at this temperature for 7 hours, with an addition of ammonium acetate (0.5 g, 6.5 mmol) and glyoxal (0.4 mL, 3.5 mmol, 40% aqueous solution) after 30 minutes. The mixture was cooled to room temperature, was evaporated under vacuum and the residual oil was partitioned between methylene chloride (50 mL) and aqueous potassium carbonate (50 mL). The aqueous layer was re-extracted with additional methylene chloride (3×50 mL) and the combined layers were dried with magnesium sulfate, filtered and evaporated to a dark oil (1 .08 g). The oil was triturated with diethyl ether (50 mL) and the insoluble material was filtered. The filtrate was evaporated to an oil which was loaded onto preparative silica plates (5×1000 micron, analtech). The plates were developed and eluted with 5% methanol in methylene chloride to give the title compound as a yellow solid (0.36 g) upon evaporation.

$^1$H NMR (10% CD$_3$OD/CDCl$_3$, 500 MHz) δ7.06 (s, 2ImH), 7.50 (d, H$_5$), 7.97 (dd, H$_6$) and 8.31 (d, H$_2$).

$^{13}$C NMR (10% CD$_3$OD/CDCl$_3$, 500 MHz) δ121.8, 123.9, 126.1,129.4, 130.1,132.3, 143.4 and 148.0.

Step 2: 5-(imidazol-2-yl)-2-thioxo-2,3-dihydrobenzothiazole 1-(imidazol-2-yl)-3-nitro-4-chlorobenzene (0.5 g, 2 mmol) was added to a polysulfide solution, [sodium sulfide nonahydrate (1.44 g, 6 mmol) and sulfur (0.45 g, 14 mmol) in water (8 mL)], and the resulting solution was heated in a 100° C. oil bath for 18 hours. The mixture was then placed in a 50° C. oil bath and treated with carbon disulfide (1 mL, 16.6 mmol). After 2 hours the mixture was cooled to room temperature, the sulfur was filtered, the filtrate was evaporated to approximately 3 mL and was loaded onto a Amberchrom 161 resin column (8 mL). The column was washed with water (10 mL) and was eluted with 10% acetonitrile/water (25 mL). The eluent was evaporated and loaded onto preparative reverse phase plates (4×1000 micron, analtech). The plates were developed and eluted with 20% acetonitrile/water and gave the title compound as a solid upon evaporation (0.07 g).

$^1$H NMR (DMSO-d$_6$, 500 MHz) δ7.09(s, 2ImH), 7.53 (d, H$_7$), 7.62 (dd, H$_6$) and 7.82 (d, H$_4$).

$^{13}$C NMR (DMSO-d$_6$, 500 MHz) δ111.6, 119.1,120.5, 128.7, 134.2, 146.1 and 187.9.

EXAMPLE 1

(1R,5S,6S)-2-[5-[4-(2-HYDROXYETHYL)-1,4-DIAZONIABICYCLO[2.2.2]OCT-1-YLMETHYL]BENZOTHIAZOL-2-YLTHIO}-6-[1(R)-HYDROXYETHYL]-1-METHYLCARBAPEN-2-EM-3-CARBOXYLATE CHLORIDE/TRIFLUOROMETHANESULFONATE cm). The column was eluted with 8:1 dichloromethane-ethyl acetate, collecting 125 mL fractions every 2.5–3 minutes. Fractions 6–12 were combined and evaporated in vacuo to afford the title compound (2.242 g) as a white solid.

mp 158°–161° C. (micro hot stage). IR (KBr) 2957, 2876, 1781, 1711, 1607, 1560, 1523, 1458, 1417, 1380, 1340, 1278, 1206, 1147, 1055, 986, 844, 801, 738, and 688 cm$^{-1}$. UV (dioxane) $\epsilon_{max}$ 334.5 nm ($\lambda$ 21,700), 269.0 nm ($\lambda$ 17,300).

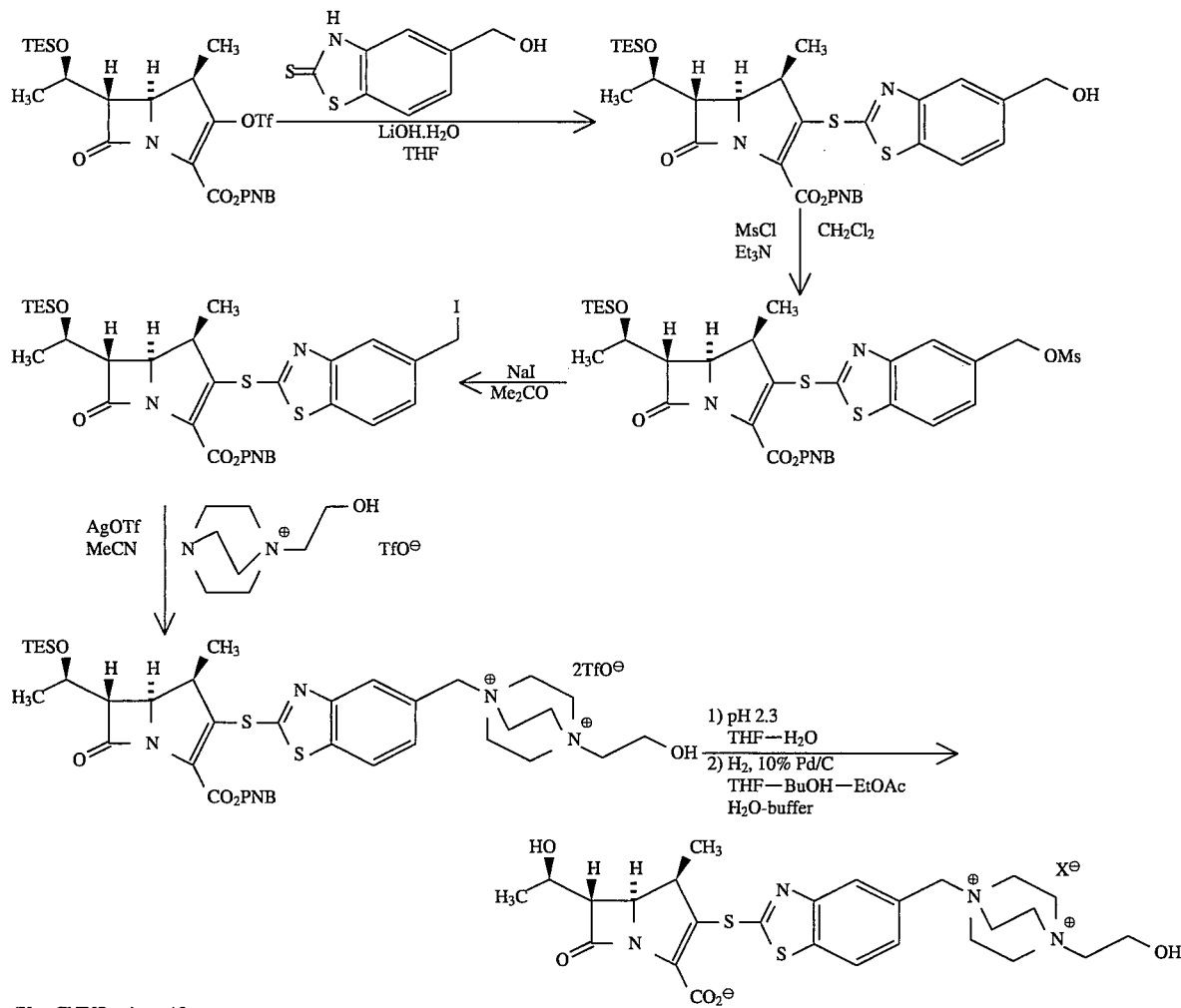

(X = Cl/TfO mixture)?

Step 1: p-Nitrobenzyl (1R,5S,6S)-2-[5-(hydroxymethyl-)benzothiazol-2-ylthio]-6-[(1R )-(triethylsilyloxy)ethyl]-1-methylcarbapen-2-em-3-carboxylate Powdered lithium hydroxide monohydrate (0.218 g, 5.2 mmol) and 5-hydroxymethyl-2-thioxo-2,3-dihydrobenzothiazole (0.868 g, 4.4 mmol) were suspended in anhydrous tetrahydrofuran (60 mL). The mixture was sonicated a few minutes then stirred at room temperature for approximately 3 minutes. Solid p-nitrobenzyl (1R,5R,6S )-2-(trifluoromethylsulfonyl)oxy-6-[(1R )-(triethylsilyloxy)ethyl]-1-methylcarbapen-2-em-3-carboxylate (2.435 g, 4 mmol) was added. The resulting mixture was stirred at room temperature for 45 minutes then diluted with ethyl acetate (400 mL), washed with water (2×200 mL) and brine (200 mL), dried over magnesium sulfate, filtered and evaporated in vacuo to an off-white solid (2.58 g). The crude product in dichloromethane was loaded onto a column of flash silica gel (250 mL dry, packed under dichloromethane, 4×20.5

$^1$H NMR (DMSO-d$_6$, 500 MHz) δ0.53 (q, CH$_3$C$\underline{H}_2$Si), 0.88 (t, C$\underline{H}_3$CH$_2$Si), 1.04 (d, 1-CH$_3$), 1.11 (d, C$\underline{H}_3$CHOSi), 3.56 (t, H-6), 3.77 (dq, H-1), 4.23 (m, CH$_3$CHOSi), 4.37 (dd, H-5), 4.64 (d, C$\underline{H}_2$OH), 5.36 (t, CH$_2$O$\underline{H}$), 5.38 and 5.49 (two d's, C$\underline{H}_2$C$_6$H$_4$NO$_2$), 7.43 (d, ArH-6'), 7.72 and 8.19 (two d's, C$_6$$\underline{H}_4$NO$_2$), 7.93 (s, ArH-4'), and 8.02 (d, ArH-7').

$^{13}$C NMR (DMSO-d$_6$, 125,7 MHz) δ4.3, 6.6, 15.8, 21.6, 42.6, 54.5, 61.0, 62.5, 64.5, 65.4, 119.9, 121.6, 123.3, 124.6, 128.30, 128.34, 134.2, 141.0, 141.9, 143.2, 147.0, 152.9, 159.5, 159.9, and 174.7.

Step 2: p-Nitrobenzyl (1R,5S,6S)-2-[5-(methanesulfonyloxymethyl)benzothiazol- 2-ylthio]-6-[(1R)-(triethylsilyloxy)ethyl]- 1-methylcarbapen-2-em-3-carboxylate A solution of p-nitrobenzyl (1R,5S,6S)-2-[5-(hydroxymethyl)benzothiazol- 2-ylthio]-6-[(1R )-(triethylsilyloxy)ethyl]-1-methylcarbapen-2-em-3-carboxylate (1.104 g, 1.68 mmol) in anhydrous dichloromethane (16.8 mL) was cooled to −55° C. (bath temperature) and stirred under a nitrogen atmosphere. Triethylamine (0.328 mL, 2.35 mmol) was added followed by the dropwise addition of methanesulfonyl chloride (0.156 mL, 2.01 mmol). The resulting solution was stirred in the cold for 90 minutes during which time the bath temperature was allowed to rise to –35° C. The solution was diluted with 1:1 ethyl acetate-diethyl ether (150 mL), washed with water (75 mL), saturated aqueous ammonium chloride (75 mL), 5% aqueous sodium bicarbonate (75 mL) and brine (75 mL), dried over magnesium sulfate, and filtered. The solvents were removed under vacuum to afford the title compound (1.29 g) as a clear oil.

$^1$H NMR (CDCl$_3$, 500 MHz) δ0.60 (q, CH$_3$CH$_2$Si), 0.94 (t, CH$_3$CH$_2$Si), 1.12(d, 1-CH$_3$), 1.23 (d, CH$_3$CHOSi), 3.01 (s, OSO$_2$CH$_3$), 3.32 (dd, H-6), 3.93 (dq, H-1), 4.30 (p, CH$_3$CHOSi), 4.43 (dd, H-5), 5.30 and 5.49 (two d's, CH$_2$C$_6$H$_4$NO$_2$), 5.38 (s, CH$_2$OSO$_2$), 7.47 (dd, ArH-6'), 7.66 and 8.21 (two d's, C$_6$H$_4$NO$_2$), 7.87 (d, ArH-7'), and 8.03 (s, ArH-4').

Step 3: p-Nitrobenzyl (1R, 5S, 6S)-2-[5-(iodomethyl)benzothiazol-2-ylthio]- 6-[(1R )-(triethylsilyloxy)ethyl]-1-methylcarbapen-2-em-3-carboxylate A solution of p-nitrobenzyl (1R,5S,6S)-2-[5-(methanesulfonyloxymethyl)benzothiazol- 2-ylthio]-6-[(1R)-(triethylsilyloxy)ethyl]- 1-methylcarbapen-2-em-3-carboxylate (1.29 g, 1.68 mmol) in acetone (17 mL) was cooled in an ice bath and treated with sodium iodide (0.756 g, 5.04 mmol). The mixture was stirred at 0–5° C. in the dark for 30 minutes and then at room temperature for an s additional 30 minutes. The mixture was diluted with 1:1 ethyl acetate diethyl ether (150 mL) and washed with water (75 mL), 5% aqueous sodium thiosulfate (75 mL), water (75 mL) and brine (75 mL). The organic solution was dried over magnesium sulfate, filtered and evaporated in vacuo to a yellow foam. The foam was lyophilized from benzene (15 mL) to afford the title compound (1.18 g) as a pale yellow, amorphous solid.

IR (KBr) 2957, 2875, 1782, 1718, 1522, 1340, 1322, 1277, 1210, 1144, 985,738 cm$^{-1}$.

$^1$H NMR (CDCl$_3$, 500 MHz) δ0.60 (q, CH$_3$CH$_2$Si), 0.94 (t, CH$_3$CH$_2$Si), 1.12 (d, 1—CH$_3$), 1.23 (d, CH$_3$CHOSi), 3.31 (dd, H-6), 3.89 (dq, H-1), 4.29 (p, CH$_3$CHOSi), 4.41 (dd, H-5), 4.60 (s, CH$_2$I), 5.30 and 5.49 (two d's, CH$_2$C$_6$H$_4$NO$_2$), 7.44 (dd, ArH-6'), 7.65 and 8.21 (two d's, C$_6$H$_4$NO$_2$), 7.75 (d, ArH-7'), and 7.98 (d, ArH-4').

$^{13}$C NMR (CDCl$_3$, 125.7 MHz) δ4.8, 4.9, 6.7, 16.3, 22.4, 43.1, 55.6, 61.4, 65.3, 65.7, 1221.6, 122.4, 123.7, 126.5, 128.2, 128.6, 135.7, 138.3, 142.3, 142.5, 153.4, 160.0, 161.3, and 174.0.

Step 4: p-Nitrobenzyl (1R,5S,6S)-2–15-[4-(2-hydroxyethyl)-1,4-diazoniabicyclo[ 2.2.2]oct-1-ylmethyl] benzothiazol-2-ylthio}-6-[1(R)-(triethylsilyloxy)ethyl]-1-methylcarbapen-2-em-3-carboxylate bis(trifluoromethanesulfonate )

p-Nitrobenzyl (1R,5S,6S)-2-[5-(iodomethyl)benzothiazol-2-ylthio]- 6-[(1R)-(triethylsilyloxy)ethyl]-1-methylcarbapen-2-em-3-carboxylate (191 mg, 0.25 mmol) and 1-(2-hydroxyethyl)-4-aza-1-azoniabicyclo[2.2.2]octane trifluoromethanesulfonate (77 mg, 0.25 mmol) were dissolved in anhydrous acetonitrile (5.0 mL). The solution deposited a white solid almost immediately. The mixture was stirred in the dark and treated dropwise over one minute with 0.986M silver trifluoromethanesulfonate in acetonitrile (0.25 mL, 0.25 mmol). The resulting mixture was stirred in the dark at room temperature for 40 minutes then filtered through an acetonitrile washed, packed pad of Celite. The filtrate was evaporated under vacuum. The residue was triturated with ether and dried under vacuum to afford substantially s pure title compound (275 mg) as a pale yellow powder.

IR (KBr) 2959, 1784, 1718, 1523, 1340, 1274, 1166, 1032, 852, 739, 641, and 519 cm$_{-1}$.

$^1$H NMR (DMSO-d$_6$, 500 MHz) δ0.55 (q, CH$_3$CH$_2$Si), 0.89 (t, CH$_3$CH$_2$Si), 1.09 (d, 1-CH$_3$), 1.13 (d, CH$_3$CHOSi), 3.56 (m, NCH$_2$CH$_2$OH), 3.64 (t, H-6), 3.79 (dq, H-1), 3.87 (m, N(CH$_2$CH$_2$)$_3$N+NCH$_2$CH$_2$OH), 4.26 (dq, CH$_3$CHOSi), 4.41 (dd, H-5), 4.92 (s, ArCH$_2$N), 5.38 and 5.47 (two d's, CH$_2$C$_6$H$_4$NO$_2$), 5.44 (t, NCH$_2$CH$_2$OH), 7.57 (d, ArH-6'), 7.70 and 8.18 (two d's, C$_6$H$_4$NO$_2$), 8.16 (s, ArH-4') and 8.28 (d, ArH-7').

Step 5: (1R,5S,6S)-2-{5-[4-(2-hydroxyethyl)-1,4-diazoniabicyclo[2.2.2]oct-1-ylmethyl]benzothiazol-2-ylthio}-6-[1(R)-hydroxyethyl]- 1-methylcarbapen-2-em-3-carboxylate chloride/trifluoromethanesulfonate A solution of p-nitrobenzyl (1R,5S,6S)-2-{5-[4-(2-hydroxyethyl)- 1,4-diazonia-bicyclo[2.2.2]oct-1-ylmethyl]benzothiazol-2-ylthio}-6-[1(R)-(triethylsilyloxy)ethyl]-1-methylcarbapen-2-em-3-carboxylate bis(trifluoromethanesulfonate) (270 mg, 0.247 mmol) in 2:1 tetrahydrofuran-water (7.5 mL) was brought to pH 2.3 by the addition of 1M aqueous trifluoromethanesulfonic acid (0.090 mL). The resulting solution was stirred at room temperature for 35 minutes to affect removal of the triethylsilyl protecting group. The reaction mixture neutralized with 1M aqueous sodium bicarbonate (0.10 mL), then added to a mixture of n-butanol (5.0 mL), ethyl acetate (2.5 mL), 1M pH 7 phosphate buffer (1.4 mL), water (6.3 mL), and 10% palladium on carbon (60 mg). The resulting mixture was stirred under a hydrogen atmosphere for 90 minutes to affect reductive cleavage of o the p-nitrobenzyl protecting group. The lower aqueous phase of the reaction mixture was separated and filtered through a tetrahydrofuran/water-washed pad of Celite. The organic portion of the reaction mixture was extracted with water (2×5 mL) and the extracts were used to wash the filter pad. The combined aqueous filtrate was washed with 1:1 ether-ethyl acetate (2×20 mL) then concentrated under vacuum to 12.7 mL volume. The aqueous solution was diluted with 20% aqueous sodium chloride (5 mL) then loaded onto a column of TosoHaas Amberchrom CG-161 resin (1×11 cm, ca. 10 mL). The column was eluted with 20% aqueous sodium chloride (5 mL), then with water (6×8.5 mL fractions) and finally with 40% aqueous acetonitrile (3×8.5 mL fractions). The second aqueous acetonitrile fraction was diluted with water, concentrated under vacuum to 7.7 mL volume, and lyophilized to afford the title compound (99 mg) as an amorphous, white solid. The product was shown to be a mixture of chloride and trifluromethanesulfonate salts by elemental analysis.

IR (KBr) 2969, 1762, 1602, 1386, 1252, 1153, 1110, 1030, 852, and 640 cm$^{-1}$. UV (0.1M pH 7.0 MOPS buffer) $\epsilon_{max}$ 307 nm (λ 12,370).

$^1$H NMR (D$_2$O, 500 MHz) δ1.05 (d, 1-CH$_3$), 1.21 (d, CH$_3$CHOH), 3.46 (dq, H-1 ), 3.51 (dd, H-6), 3.70 (m, NCH$_2$CH$_2$OH), 4.06 (m, N(CH$_2$CH$_2$)$_3$N+NCH$_2$CH$_2$OH), 4.20 (p, CH$_3$CHOH), 4.29 (dd, H-5), 4.91 (s, ArCH$_2$N), 7.48 (dd, ArH-6'), 7.87 (d, ArH-4'), and 7.99 (d, ArH-7').

EXAMPLE 2

(1R,5S,6S)-2-{5-[4-(3-HYDROXYPROPYL)-1,4-DIAZONIABICYCLO[2.2.2]OCT-1-YLM-ETHYL]BENZOTHIAZOL-2-YLTHIO}-6-[1(R)-HYDROXYETHYL]-1-METHYLCARBAPEN-2-EM-3-CARBOXYLATE CHLORIDE

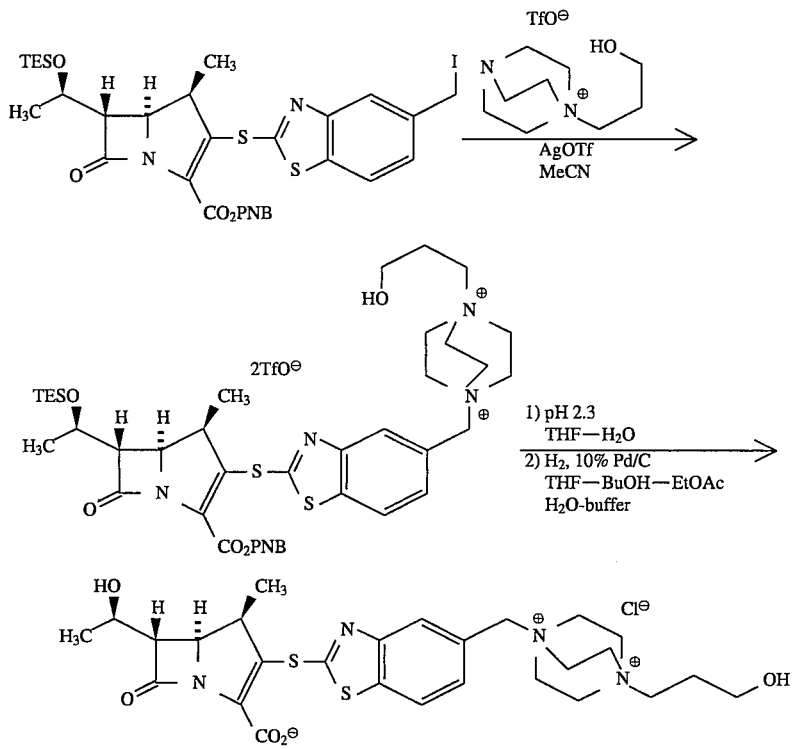

Step 1: p-Nitrobenzyl (1R,5S,6S)-2-{5-[4-(3-hydroxypropyl)-1,4-diazoniabicyclo[2.2.2]oct-1-ylmethyl]benzothiazol-2-ylthio}-6-[1(R)-(triethylsilyloxy)ethyl]-1-methylcarbapen-2-en-3-carboxylate bis(trifluoromethanesulfonate)

Substitution of 1-(3-hydroxypropyl)-4-aza-1-azoniabicyclo[2.2.2]octane trifluoromethanesulfonate for 1-(2-hydroxyethyl)- 4-aza-1-azoniabicyclo[2.2.2]octane trifluoromethanesulfonate in the procedure of Step 4 of Example 1 afforded the title compound.

Step 2: (1R,5S,6S)-2-5-[4-(3-hydroxypropyl)-1,4-diazoniabicyclo[2.2.2]oct-1-ylmethyl]benzothiazol-2-ylthio}-6-[1(R)-hydroxyethyl]- 1-methylcarbapen-2-em-3-carboxylate chloride/trifluoromethanesulfonate Substitution of p-Nitrobenzyl (1R,5S,6S)-2-{5-[4-(3-hydroxypropyl)- 1,4-diazoniabicyclo[2.2.2]oct-1-ylmethyl]benzothiazol-2-ylthio}-6-[1(R)-(triethylsilyloxy)ethyl]-1-methylcarbapen-2-em-3-carboxylate bis(trifluoromethanesulfonate) for p-nitrobenzyl (1R, 5S,6S)-2-{5-[4-(2-hydroxyethyl)-1,4-diazonia-bicyclo [2.2.2] oct-1-ylmethyl]-benzothiazol- 2-ylthio}-6-[1(R)-(triethylsilyloxy)ethyl]-1-methylcarbapen- 2-em-3-carboxylate bis(trifluoromethanesulfonate) in the procedure of Step 5 of Example 1 afforded crude product which was purified by an improved procedure. The title compound was obtained as the chloride salt by ion exchange chroatography on Bio-Rad Macro-Prep CM resin followed by desalting on TosoHaas Amberchrom CG-161 resin. This was accomplished as follows: An aqueous solution of the crude product (ca. 100 mg in 9.5 mL) was loaded onto a column s of Macro-Prep CM resin (13 mL) and the column was eluted with water (5×13 mL fractions) followed by 5% aqueous sodium chloride (5×6.5 mL fractions). Sodium chloride fractions 2–4 were cooled in ice then loaded onto a column of Amberchrom CG-161 resin (10.5 mL). The column was eluted with ice-cold water (5×10 mL fractions) followed o by ice-cold 20% aqueous isopropanol (3×10 mL fractions). Aqueous isopropanol fractions 2 and 3 were combined, concentrated in vacuo to 11.8 mL volume, and lyophilized to provide the title compound (77 rag) as a white, amorphous solid.

IR (KBr) 3022, 2968, 1762, 1603, 1420, 1388, 1252, 1148, 1108, 1055, 994, 852, and 766 $cm^{-1}$. UV (0.1M pH 7.0 MOPS buffer) $\lambda_{max}$ 317 nm ($\lambda$ 12,350).

$^1$H NMR ($D_2O$, 500 MHz) $\delta$1.03 (d, 1-$CH_3$), 1.20 (d, $CH_3$CHOH), 2.02 (m, $NCH_2\underline{CH_2}CH_2OH$), 3.44 (dq, H-1), 3.49 (dd, H-6), 3.64 (m, $N\underline{CH_2}CH_2CH_2OH$), 3.66 (t, $NCH_2CH_2\underline{CH_2}OH$), 3.98 and 4.05 (two m's, $N(\underline{CH_2CH_2})_3N$), 4.18(p, $CH_3C\underline{H}OH$), 4.25 (dd, H-5), 4.75 (s, HOD), 4.92 (s, ArCH$_2$N), 7.47 (d, ArH-6'), 7.84 (s, ArH-4'), and 7.97 (d, ArH-7').

EXAMPLES 3–19

By appropriately modifying the procedures of Examples 1–2, compounds A1, LiSHet* and Q* as set forth in the following Table were reacted to produce compounds of formula Ia in which Het is as defined in the following Table.

TABLE

TABLE-continued

TABLE-continued

| | | | | |
|---|---|---|---|---|
| 11 | (structure) | (structure) | (structure) | a,c |
| 12 | (structure) | (structure) | (structure) | a,c |
| 13 | (structure) | (structure) | (structure) | a,c |
| 14 | (structure) | (structure) | (structure) | a,c |
| 15 | (structure) | (structure) | (structure) | a,c |

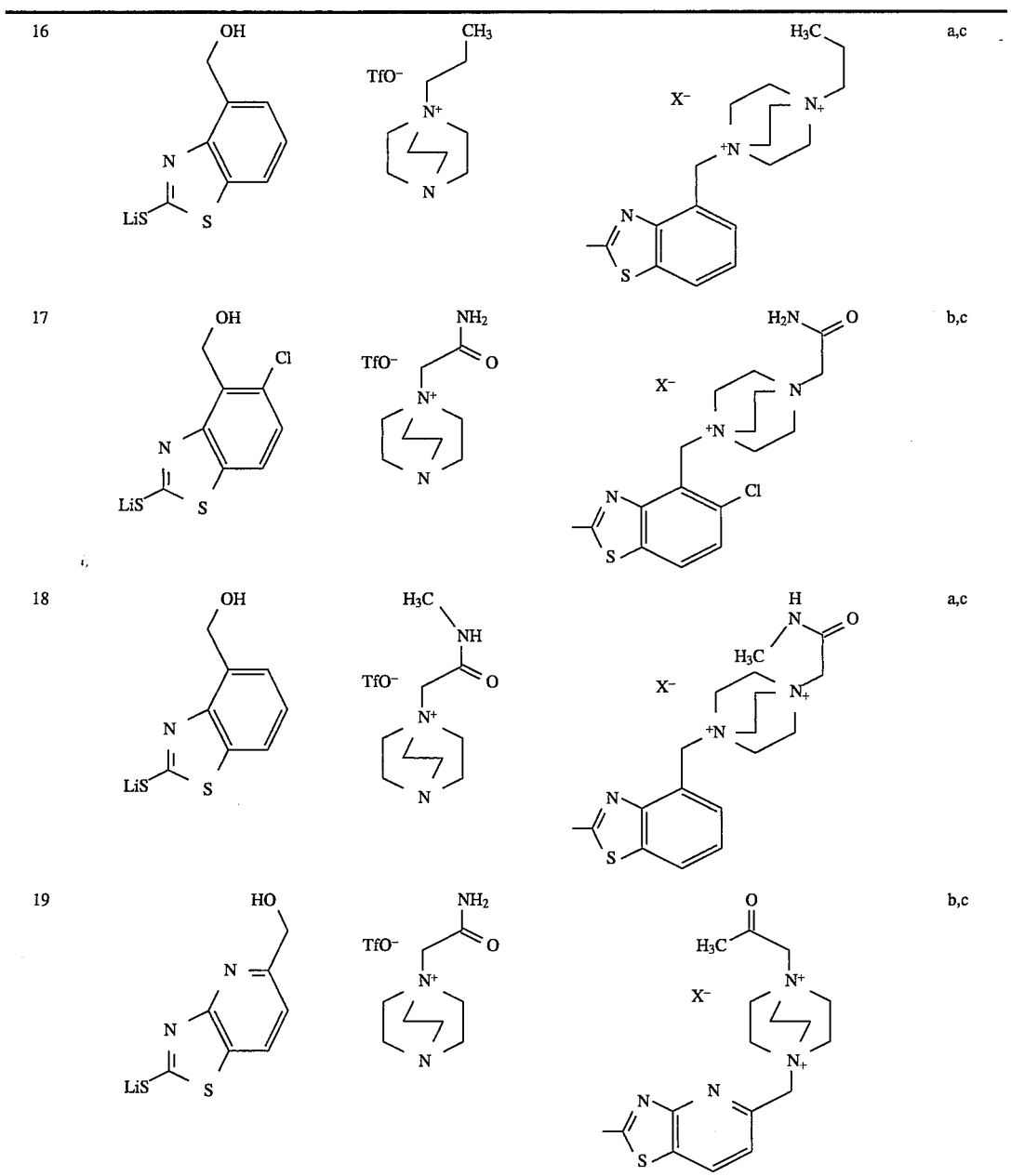

a) The final product was obtained as a mixture of chloride and trifluoromethanesulfonate salts (X = a mixture of Cl & TfO) following purification on TosoHaas Amberchrom ® CG-161 resin.
b) The final product was obtained as the chloride salt (X = Cl) by ion exchange chroatography on Bio-Rad Macro-Prep CM resin followed by desalting on TosoHaas Amberchrom CG-161 resin (see Step 2 of Example 2 for details).
c) Hydrochloric acid was substituted for trifluoromethanesulfonic acid in the step which removes the TES hydroxyl-protecting group.
d) The final product was purified by chromatography on Amberchrom ® CG-161 resin then further purified by MPLC on a column of TosoHaas Amberchrom ® CG-1000 sd resin to afford the final product as a chloride salt (X = Cl).

Data for the final product of Example 3 ((1R,5S,6S)-2-{5-[(4-n-Propyl-1,4-diazoniabicyclo[2.2.2]oct-1-yl)methyl]benzothiazol-2-ylthio}-6-1(R)-hydroxyethyl]-1-methylcarbapen-2-em-3-carboxylate chloride/trifluoromethanesulfonate):

IR (KBr) 2972, 1762, 1603, 1412, 1386, 1254, 1156, 1106, 1031, 994, 852, and 640 cm$^{-1}$. UV (0.1M pH 7.0 MOPS buffer) $\lambda_{max}$ 307 nm ($\epsilon$12,300).

$^1$H NMR (D$_2$O,500 MHz) $\delta$0.94 (t, NCH$_2$CH$_2$CH$_3$), 1.05 (d, 1-CH$_3$), 1.21 (d, CH$_3$CHOH), 1.78 (m, NCH$_2$CH$_2$CH$_3$), 3.46 (m, H-1+NCH$_2$CH$_2$CH$_3$), 3.52 (dd, H-6), 3.94 and 4.01 (two m's, N(CH$_2$CH$_2$)$_3$N), 4.20 (p CH$_3$CHOH), 4.29 (dd, H-5), 4.75 (s, HOD), 4.92 (s, ArCH$_2$N), 7.47 (d, ArH-6'), 7.87 (s, ArH-4'), and 7.99 (d, ArH-7').

Data for the final product of Example 4 ((1R,5S,6S)-2-[(5-((4-Carbamoylmethyl- 1,4-diazoniabicyclo[2.2.2 ]oct-1-yl)methyl)benzothiazol- 2-yl)thio]-6-[1(R)-hydroxyethyl]-1-methylcarbapen- 2-em-3-carboxylate chloride/trifluoromethanesulfonate):

IR (KBr) 3390 (br), 1762, 1697, 1601, 1385, 1252, 1148, 994, and 845 cm$^{-1}$. UV (0.1M pH 7.0 MOPS buffer) $\lambda_{max}$ 305 nm ($\epsilon$ 12,230).

¹H NMR (D₂O, 500 MHz) δ1.09 (d, 1-CH₃), 1.23 (d, CH₃CHOH), 3.50 (dq, H-1 ), 3.54 (dd, H-6), 4.08 and 4.24 (two t's, N(CH₂)₃N), 4.24 (m, CH₃CHOH), 4.33 (dd, H-5), 4.38 (s, NCH₂CONH₂), 4.93 (s, ArCH₂N), 7.51 (dd, ArH-6'), 7.93 (d, ArH-4'), and 8.03 (d, ArH-7').

Data for the final product of Example 5 ((1R,5S,6S)-2-{5-[(4-{ N-Methylcarbamoylmethyl}- 1,4-diazoniabicyclo[2.2.2]oct-1-yl)methyl]benzothiazol-2-ylthio}-6-[1(R)-hydroxyethyl]-1-methylcarbapen- 2-em-3-carboxylate chloride/trifluoromethanesulfonate):

IR (KBr) 3023, 2971, 1762, 1679, 1603, 1420, 1386, 1253, 1157, 1031, 866, 640 cm⁻¹. UV (0.1M pH 7.0 MOPS buffer) $\lambda_{max}$ 306 nm (ε 12,420).

¹H NMR (D₂O, 500 MHz) δ1.07 (d, 1-CH₃), 1.22 (d, CH₃CHOH), 2.74 (s, NCH₃), 3.48 (dq, H-1 ), 3.53 (dd, H-6), 4.06 (m, N(CH₂CH₂)₃N), 4.20 (m, N(CH₂CH₂)₃N+ CH₃CHOH), 4.29 (s, NCH₂CON), 4.31 (dd, H-5), 4.92 (s, ArCH₂N), 7.49 (dd, ArH-6'), 7.91 (d, ArH-4'), and 8.01 (d, ArH-7').

Data for the final product of Example 6 ((1R,5S,6S)-2-{5-[(4-{ N,N-Dimethylcarbamoylmethyl}- 1,4-diazoniabicyclo[2.2.2]oct-1yl)methyl]benzothiazol-2-ylthio}-6-[1(R)-hydroxyethyl]-1-methylcarbapen- 2-em-3-carboxylate chloride/trifluoromethanesulfonate):

IR (KBr) 2969, 1762, 1656, 1605, 1420, 1386, 1255, 1160, 1117, 1031, 867, 640 cm⁻¹. UV (0.1M pH 7.0 MOPS buffer) $\lambda_{max}$ 306 nm (ε 12,140).

¹H NMR (D₂O, 500 MHz) δ1.05 (d, 1-CH₃), 1.21 (d, CH₃CHOH), 2.90 (s, NCH₃), 2.94 (s, NCH₃), 3.47 (dq, H-1 ), 3.52 (dd, H-6), 4.07 and 4.25 (two br t's, N(CH₂CH₂)₃N), 4.21 (p, CH₃CHOH), 4.30 (dd, H-5), 4.61 (s, NCH₂CON), 4.75 (s, HOD), 4.91 (s, ArCH₂N), 7.48 (dd, ArH-6'), 7.88 (d, ArH-4'), and 7.99 (d, ArH-7').

Data for the final product of Example 7 ((1R,5S,6S)-2-{5-[(4-{ N-Phenylcarbamoylmethyl}- 1,4-diazoniabicyclo[2.2.2]oct-1-yl)methyl]benzothiazol-2-ylthio}-6-[1(R)-hydroxyethyl]-1-methylcarbapen- 2-em-3-carboxylate chloride/trifluoromethanesulfonate):

IR (KBr) 3020, 2971, 1762, 1686, 1600, 1560, 1448, 1421, 1385, 1252, 1148, 993, 869, 763, and 694 cm⁻¹. UV (0.1M pH 7.0 MOPS buffer) $\lambda_{max}$ 306 nm (ε 12,250).

¹H NMR (20% CD₃CN in D20,500 MHz) δ1.24 (d, 1-CH₃), 1.36 (d, CH₃CHOH), 3.64 (dd, H-6), 3.68 (dq, H-1), 4.19 and 4.39 (two m's, N(CH₂CH₂)₃N), 4.35 (p, CH₃CHOH), 4.49 (dd, H-5), 4.61 (s, NCH₂CON), .4.74 (s, HOD), 5.06 (s, ArCH₂N), 7.40 (m, PhiI-4), 7.56 (t, PhH-3+ PhH-5), 7.60 (d, PhH-2+PhH-6), 7.69 (d, ArH-6'), 8.16 (s, ArH-4'), and 8.24 (d, ArH-7').

Data for the final product of Example 8 ((1R,5S,6S)-2-{5-[(4-Phenacyl-1,4-diazoniabicyclo[2.2.2]oct-1-yl)methyl] benzothiazol-2-ylthio}-6-[1(R)-hydroxyethyl]-1-methylcarbapen-2-em-3-carboxylate chloride):

IR (KBr) 2970, 1762, 1696, 1597, 1229, 1128, 1016, 1000, 866, 762, 688, and 658 cm⁻¹. UV (0.1M pH 7.0 MOPS buffer) $\lambda_{max}$ 305 nm (ε 12,930).

¹H NMR (D₂O, 500 MHz) δ1.09 (d, 1-CH₃), 1.23 (d, CH₃CHOH), 3.51 (dq, H-1), 3.54 (dd, H-6), 4.15 (m, N(CH₂CH₂)₃N), 4.22 (p, CH₃CHOH), 4.33 (m, N(CH₂CH₂)₃N+H-5), 4.75 (s, HOD), 4.97 (s, ArCH₂N), 7.54 (d, ArH-6'), 7.56 (t, PhH-3 +PhH-5), 7.74(t, PhH-4), 7.92 (d, PhH-2 +PhH-6), 7.96 (s, ArH-4'), and 8.06 (d, ArH-7').

Data for the final product of Example 9 ((1R,5S,6S)-2-{6-[(4-Carbamoylmethyl- 1,4-diazoniabicyclo[2.2.2]oct-1yl)methyl]benzothiazol-2-ylthio}-6-[1(R)-hydroxyethyl]-1-methylcarbapen- 2-em-3-carboxylate chloride/trifluoromethanesulfonate):

IR (KBr) 1758, 1697, 1599, 1444, 1414, 1385, 1254, 1149, 1068, 1030, 1000, 842, 764, and 641 cm⁻¹. UV (0.1M pH 7.0 MOPS buffer) $\lambda_{max}$ 305 nm (ε 14,270) and 296 nm (ε 14,490).

¹H NMR (0.8% TFA in D2O, 500 MHz) δ1.03 (d, 1-CH₃), 1.18 (d, CH₃CHOH), 3.52 (dd, H-6), 3.68 (dq, H-1), 4.05 and 4.22 (two br t's, N(CH₂CH₂)₃N), 4.30 (br d, H-5), 4.36 (s, NCH₂CONH₂), 4.92 (s, ArCH₂N), 7.65 (d, ArH-5'), 8.07 (d, ArH-4'), and 8.16 (s, ArH-7').

Data for the final product of Example 10 ((1R,5S,6S)-2-{7-[(4-Carbamoylmethyl- 1,4-diazoniabicyclo[2.2.2]oct-1-yl)methyl]benzothiazol-2-ylthio}-6-[1(R)-hydroxyethyl]-1-methylcarbapen- 2-em-3-carboxylate chloride/trifluoromethanesulfonate):

IR (KBr) 1759, 1698, 1602, 1458, 1387, 1271, 1151, and 640 cm⁻¹. UV (0.1M pH 7.0 MOPS buffer) $\lambda_{max}$ 310 nm (ε 12,460).

¹H NMR (D₂O, 500 MHz) δ1.07 (d, 1-CH₃), 1.22 (d, CH₃CHOH), 3.51 (m, H-1 ), 3.52 (dd, H-6), 4.12 (br t, N(CH₂CH₂)₃N), 4.23 (m, N(CH₂CH₂)₃N+CH₃CHOH+ NCH₂CONH₂), 4.38 (dd, H-5), 4.98 and 5.03 (two d's, ArCH₂N), 7.56 (d, ArH-6'), 7.61 (t, ArH-5'), and 7.85 (d, ArH-4').

¹³C NMR (D₂O, 125.7 MHz) δ15.5, 19.9, 42.5, 51.1, 52.1, 56.0, 59.9, 62.2, 64.7, 68.4, 115.0, 118.8, 124.5, 127.8, 128.7, 131.0, 139.1, 140.2, 153.5, 165.2, 166.4, 166.9, and 176.9.

Data for the final product of Example 11 ((1R,5S,6S)-2-{4-[(4-Carbamoylmethyl- 1,4-diazoniabicyclo[2.2.2]oct-1-yl)methyl]-6-chlorobenzothiazol- 2-ylthio}-6-[1(R)-hydroxyethyl]-1-methylcarbapen-2-em-3-carboxylate chloride/trifluoromethanesulfonate):

UV (0.1M pH 7.0 MOPS buffer) $\lambda_{max}$ 320 nm (ε 11,934).

¹H NMR (D2O, 500 MHz) δ1.16 (d), 1.26 (d), 3.46 (dq), 3.60 (dd), 4.10 (br t), 4.30 (br m), 4.38 (br m), 5.09 (s), 7.64 (s), 8.10(s).

Data for the final product of Example 12 ((1R,5S,6S)-2-[4-((4-(2-hydroxyethyl)- 1,4-diazoniabicyclo[2.2.2]oct-1-yl)methyl)benzothiazol-2-yl)thio]-6-[1(R)-hydroxyethyl]-1-methylcarbapene-2-em-3-carboxylate chloride/trifluoromethanesulfonate):

IR (KBr) 3422 (br), 1758, 1602, 1450, 1389, 1279 cm⁻¹. UV (0.1M pH₇ MOPS buffer) $\lambda_{max}$ 312 nm (ε 12,700).

¹H NMR (D₂O, 500 MHz) δ1.13 (d, J=7.3 Hz, 1-CH₃), 1.24 (d, J=6.2 Hz, CH₃CHOH), 3.45 (dq, J=7.3, 9.6 Hz, H-1 ), 3.56 (dd, J=3.0, 5.3 Hz, H-6), 3.70 (t, J=4.3 Hz, CH₂OH), 4.00–4.10 (m, N(CH₂CH₂)₃N), 4.23 (p, J=6 Hz, CH₃CHOH), 4.35 (dd, J=2.8, 9.8 Hz, H-5), 5.08 (s, ArCH₂), 7.47 (t, J=8 Hz, ArH-6'), 7.58 (d, J=8 Hz, ArH-5'), 8.02 (d, J=8 Hz, ArH-7').

Data for the final product of Example 13 ((1R,5S,6S)-2-[(4-((4-carbamoylmethyl- 1,4-diazoniabicyclo[2.2.2]oct-1-yl)methyl)benzothiazol- 2-yl )thio)-6-[(1R )-hydroxyethyl]-1-methylcarbapen- 2-em-3-carboxylate chloride/trifluoromethanesulfonate):

UV (water) $\lambda_{max}$ 312 nm (ε 12,640).

¹H NMR (D₂O, 500 MHz) δ1.14 (d, 1-CH₃), 1.25 (d, CH₃CHOH), 3.46 (dq, H-1 ), 3.58 (dd, H-6), 4.05 and 4.20 (two s, N(CH₂CH₂)₃N), 4.21 (p, CH₃CHOH), 4.36 (s, NCH₂CONH₂), 4.36 (dd, H-5), 5.11 (s, ArCH₂N), 7.49(dd, ArH), 7.60 (d, ArH) and 8.06 (s, ArH).

Data for the final product of Example 14 ((1R,5S,6S)-2-[(4-((4-carbamoylmethyl- 1,4-diazoniabicyclo[2.2.2]oct-1-yl)methyl)-6-bromobenzothiazol- 2-yl)thio]-6-[(1R)-hydroxy-ethyl]-1-methylcarbapen- 2-em-3-carboxylate chloride/trifluoromethanesulfonate):

UV (0.1M MOPS pH =7): $\lambda_{max}$ 322 nm (ε=13700)

¹H NMR (D₂O, 500 MHz) a 8.14 (s, ArH), 7.72 (s, ArH), 5.04 (dd, ArCH₂N), 4.38 (dd, H-5), 4.36 (s, NCH₂CONH₂), 4.26 (quintet, CH₃CHOH), 4.21 & 4.05 (br m's, DABCO), 3.60 (dd, H-6), 3.48 (dq, H-1), 1.26 (d, CH₃CHOH), 1.16 (d, 1-CH₃).

Data for the final product of Example 15 ((1R,5S,6S)-2-[(4-((4-(N,N-dimethyl-carbamoyl)methyl- 1,4-diazoniabicyclo[2.2.2]oct-1-yl)methyl)benzothiazol- 2-yl)thio]-6-[(1R)-hydroxyethyl]-1-methylcarbapen- 2-em-3-carboxylate chloride/trifluoromethanesulfonate):

UV (water) λ$_{max}$ 311 nm (ε 11,400).

¹H NMR (D₂O, 500 MHz) δ1.14 (d, 1-CH₃), 1.25 (d, CH₃CHOH), 2.90 and 2.94 (two s, NMe₂), 3.45 (dq, H-1), 3.58 (dd, H-6), 4.05 and 4.22 (two m, N(CH₂CH₂)₃N), 4.25 (p, CH₃CHOH), 4.36 (dd, H-5), 4.60 (s, NCH₂CONH₂), 5.11 (s, ArCH₂N), 7.49 (dd, ArH), 7.60 (d, ArH) and 8.07 (s, ArH).

Data for the final product of Example 16 ((1R,5S,6S)-2-[4-((4-propyl-(1,4-diazoniabicyclo[2.2.2]oct-1-yl)methyl)benzothiazol-2-yl)thio]-6-[1(R)-hydroxyethyl]-1-methylcarbapene-2-em-3-carboxylate chloride/trifluoromethanesulfonate):

IR (KBr) 3422 (br), 1758, 1602, 1388 cm⁻¹.

UV (0.1M pH₇ MOPS buffer) λ$_{max}$ 312 nm (ε 12,400).

¹H NMR (D₂O, 500 MHz) δ0.94 (t, J=7.3 Hz, CH₂CH₂CH₃), 1.12 (d, J=7.1 Hz, 1-CH₃), 1.24 (d, J=6.5 Hz, CH₃CHOH), 1.77 (tq, J=4.6, 7.3, CH₂CH₂CH₃), 3.45 (dq, J=7.1, 10.0 Hz, H-1), 3.46 (t, J=4.6 Hz, CH₂CH₂CH₃), 3.56 (dd, J=3.1, 5.8 Hz, H-6), 3.90 and 4.01 (t(br)'s, J=8Hz, N(CH₂CH₂)₃N), 4.23 (p, J=6 Hz, CH₃CHOH), 4.35 (dd, J=3.1, 10.0 Hz, H-5), 5.07 (s, ArCH₂), 7.47 (t, J=8 Hz, ArH-6'), 7.57 (d, J=8 Hz, ArH-5'), 8.01 (d, J=8 Hz, ArH-7').

¹³C NMR (D₂O, 125.7 MHz) δ9.5, 15.3, 15.4, 20.0, 43.0, 51.0, 51.2, 51.2, 55.9, 59.9, 64.8, 65.0, 66.5, 117.5, 125.2, 128.6, 131.6, 137.0, 141.0, 153.0, 166.2, 169.3, 177.1

Data for the final product of Example 17 ((1R,5S,6S)-2-[(4-((4-carbamoylmethyl- 1,4-diazoniabicyclo[2.2.2]oct-1-yl)methyl)-5-chlorobenzothiazol- 2-yl)thio]-6-[(1R)-hydroxyethyl]-1-methylcarbapen- 2-em-3-carboxylate chloride):

UV (0.1M MOPS pH=7): λ$_{max}$ 322 nm (ε=13300)

¹H NMR (D₂O, 500 MHz) δ8.06 (d, ArH), 7.60 (d, ArH), 5.30 (dd, ArCH₂N), 4.38 (dd, H-5), 4.36 (s, NCH₂CONH₂), 4.26 (quintet, CH₃CHOH), 4.19 (br m, DABCO), 3.62 (dd, H-6), 3.47 (dq, H-1), 1.26 (d, CH₃CHOH), 1.16 (d, 1-CH₃).

Data for the final product of Example 18 ((1R,5S,6S)-2-[(4-((4-(N-methyl)carbamoyl)methyl- 1,4-diazoniabicyclo[2.2.2]oct-1-yl)methyl)benzothiazol- 2-yl)thio]-6-[(1R)-hydroxyethyl]-1-methylcarbapen- 2-em-3-carboxylate chloride/trifluoromethanesulfonate):

UV (water) λ$_{max}$ 311 nm (ε 11,714).

¹H NMR (D₂O, 500 MHz) δ1.15 (d, 1-CH₃), 1.26 (d, CH₃CHOH), 2.73 (s, NHCH₃), 3.46 (dq, H-1), 3.59 (dd, H-6), 4.05 and 4.16 (two m, N(CH₂CH₂)₃N), 4.25 (p, CH₃CHOH), 4.28 (s, NCH₂CONH₂), 4.36 (dd, H-5), 5.13 (s, ArCH₂N), 7.50 (dd, ArH), 7.61 (d, ArH) and 8.09 (s, ArH).

Data for the final product of Example 19 ((1R,5S,6S)-2-[(4-((4-carbamoylmethyl- 1,4-diazoniabicyclo[2.2.2]oct-1-yl)methyl)thiazolo[4,5-b]pyrid-2-yl)thio]-6-[(1R)-hydroxyethyl]-1-methylcarbapen- 2-em-3-carboxylate chloride):

UV (water) λ$_{max}$ 319 nm (ε 18,320).

¹H NMR (D₂O, 500 MHz) δ1.11 (d, 1-CH₃), 1.24 (d, CH₃CHOH), 3.59 (dd, H-6), 3.62 (dq, H-1), 4.21 and 4.24 (two s, N(CH₂CH₂)₃N), 4.39 (s, NCH₂CONH₂), 4.40 (dd, H-5), 4.95 (AB$_q$, ArCH₂N), 7.60 (d, ArH) and 8.45 (d, ArH).

EXAMPLE 20

(1R,5S,6S)-2-{5-[(3-METHYLIMIDAZOLIUM-1-YL)METHYL]BENZOTHIAZOL- 2-YLTHIO-6-[1(R)-HYDROXYETHYL]- 1-METHYLCARBAPEN-2-EM-3-CARBOXYLATE

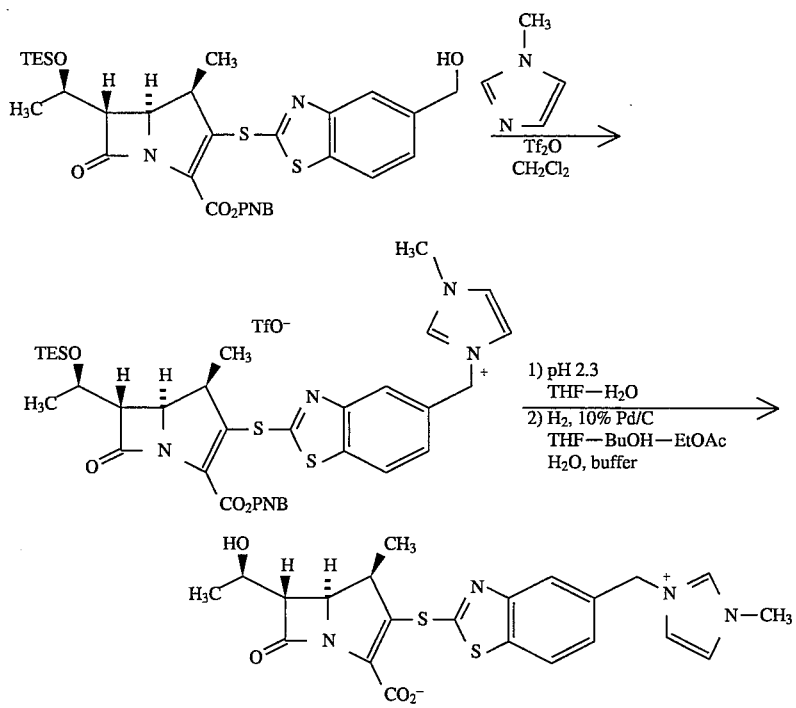

ethyl]-1-methylcarbapen- 2-em-3-carboxylate chloride):

Step 1: p-Nitrobenzyl (1R,5S,6S)-2-{5-[(3-methylimidazolium-1yl)methyl]benzothiazol-2-ylthio}-6-[1(R)-(triethylsilyloxy)ethyl]-1-methylcarbapen- 2-em-3-carboxylate trifluoromethanesulfonate A solution of p-nitrobenzyl (1R,5S,6S)-2-[5-(hydroxymethyl)-benzothiazol- 2-ylthio]-6-[(1R)-(triethylsilyloxy)ethyl]- 1-methylcarbapen-2-em-3-carboxylate (196 mg, 0.299 mmol) in anhydrous dichloromethane (14.9 mL) was treated with 1methylimidazole (0.072 mL, 0.903 mmol)then cooled in a dry-ice acetone bath and stirred under a nitrogen atmosphere. Trifluoromethanesulfonic anhydride (0.060 mL, 0.357 mmol) was added dropwise over 30 seconds. The cooling bath was removed and the mixture was stirred at room temperature for 30 minutes. The resulting solution was diluted with dichloromethane (75 mL), washed with 0.2N hydrochloric acid (25 mL), 5% aqueous sodium bicarbonate (25 mL) and brine (25 mL), dried over sodium sulfate, filtered and evaporated under vacuum to afford crude p-nitrobenzyl (1R,5S,6S)-2-{5-[(3-methylimidazolium-1-yl)methyl]benzothiazol-2-ylthio}-6-[1-(R)(triethylsilyloxy)ethyl]- 1-methylcarbapen-2-em-3-carboxylate trifluoromethanesulfonate as a white foam (250 mg).

$^1$H NMR (CDCl$_3$, 500 MHz) δ0.61 (q, CH$_3$CH$_2$Si), 0.95 (t, CH$_3$CH$_2$Si), 1.13 (d, 1-CH$_3$), 1.23 (d, CH$_3$CHOSi), 3.34 (dd, H-6), 3.92 (dq, H-1), 4.03 (s, NCH$_3$), 4.31 (dq, CH$_3$CHOSi), 4.46 (dd, H-5), 5.30 and 5.48 (two d's, CH$_2$C$_6$H$_4$NO$_2$), 5.62 (s, ArCH$_2$N), 7.19 (m, ImH-4" and ImH-5"), 7.53 (dd, ArH-6'), 7.64 and 8.19 (two m's, C$_6$H$_4$NO$_2$), 7.89 (d, ArH-7'), 7.93 (d, ArH-4'), and 9.91 (s, ImH-2").

Step 2: (1R,5S,6S)-2-{5-[(3-methylimidazolium-1-yl)methyl]benzothiazol-2-ylthio-6-[1(R)-hydroxyethyl]-1-methylcarbapen- 2-em-3-carboxylate A solution of p-nitrobenzyl (1R,5S,6S)-2-{5-[(3-methylimidazolium- 1-yl)methyl]benzothiazol-2-ylthio}-6-[1(R)-(triethylsilyloxy)ethyl]- 1-methylcarbapen-2-em-3-carboxylate trifluoromethanesulfonate (250 mg, 0.287 mmol) in tetrahydrofuran (6.0 mL) and water (2.9 mL) was cooled in an ice-bath and stirred while the pH was adjusted to 2.3 by the addition of 1N hydrochloric acid (0.165 mL, 0.6 equiv.). The resulting solution was stirred at 0–5° C. for 2 hours to effect removal of the triethylsilyl protecting group. The solution was neutralized with sodium bicarbonate (13.9 mg, 0.165 mmol) in water (0.2 mL), then added to a mixture of n-butanol (5.8 mL), ethyl acetate (2.9 mL), 1M pH 7 phosphate buffer (1.5 mL), water (7.3 mL), and 10% palladium on carbon (120 mg). The resulting mixture was stirred under a hydrogen atmosphere for 80 minutes then filtered through a celite pad to remove the catalyst which was washed with water (10 mL). The filtrate layers were separated and the organic portion extracted with water (5 mL). The combined aqueous solution was washed with dichloromethane (15 mL) and diethyl ether (15 mL), concentrated under vacuum to 9.5 mL volume, and applied to a column of TosoHaas Amberchrom CG-161 resin (27 mL, 1.7×12 cm). The column was eluted with water (5×27 mL fractions) followed by 40% acetonitrile/water (3×27 mL fractions). Fraction 7 was diluted with water (5 mL), concentrated under vacuum to 11.3 mL volume, filtered through a Gelman 0.45 micron CR acrodisc, and lyophilized to afford the title compound (97 mg) as a faint yellow, amorphous solid.

IR (KBr) 1762, 1603, 1388, 1280, 1166, 992, and 752 cm$^{-1}$. UV (H$_2$O) $\lambda_{max}$ 319 nm (ε 13,290).

$^1$H NMR (D$_2$O, 500 MHz) δ0.96 (d, 1-CH$_3$), 1.19 (d, CH$_3$CHOH), 3.33 (dq, H-1), 3.45 (dd, H-6), 3.85 (s, NCH$_3$), 4.19 (p, CH$_3$CHOH), 4.21 (dd, H-5), 5.48 (s, ArCH$_2$N), 7.37 (dd, ArH-6'), 7.42 and 7.48 (two t's, ImH-4" and ImH-5"), 7.75 (d, ArH-4'), 7.82 (d, ArH-7'), and 8.82 (s, ImH-2").

$^{13}$C NMR (D2O, 125.7 MHz) δ15.5, 19.9, 35.7, 42.4, 52.5, 55.8, 59.6, 64.7, 80.5, 121.2, 122.2, 122.3, 122.6, 123.9, 125.6, 130.4, 132.6, 136.3, 138.5, 152.4, 167.0, and 176.9.

EXAMPLE 21

[1R,5S,6S)-2-[4-((N-METHYLIMIDAZOLIUM)METHYL)THIAZOLO[ 5,4-B]PYRIDINYL- 2-THIO-]-6-[(1R)-HYDROXYETHYL]-1-METHYLCARBAPEN- 2-EM-3-CARBOXYLATE

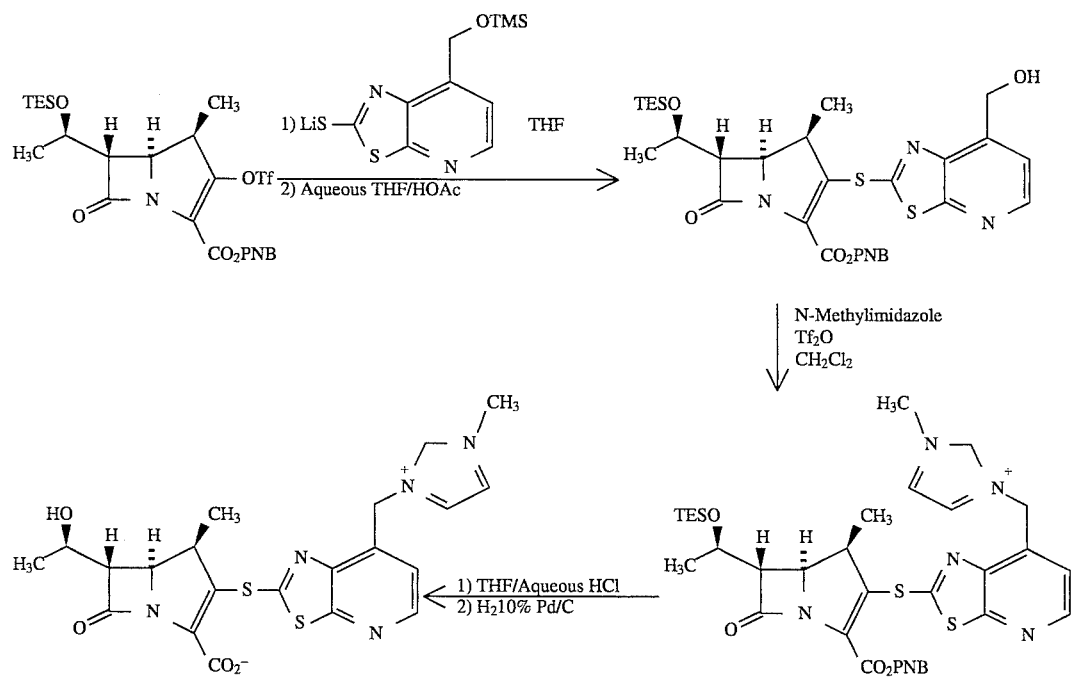

Step 1: p-Nitrobenzyl (1R,5S,6S)-2-[4-(hydroxymethyl)thiazolo[5,4-b]pyridinyl- 2-thio]-6-[(1R)-((triethyl)silyl)oxyethyl]-1-methylcarbapen-2-em-3-carboxylate An ice cooled solution of 2-thio-(5-(trimethylsilyloxymethyl)thiazolo[5,4-b]pyridine (118 mg, 0.464 mmol) in tetrahydrofuran (4 mL) was treated with lithium 25 bis(trimethylsilyl)amide (0,464 mL, of a 1.0M solution in THF, 0.464 mmol) over 1 minute to give a light yellow solution. p-Nitrobenzyl (1R,5R,6S)-2-(trifluoromethanesulfono)oxy-6-[(1R)-((triethyl)silyl)oxyethyl]- 1-methylcarbapen-2-em-3-carboxylate (282 mg, 0,464 mmol) was added after 10 minutes and after stirring an 3o additional 25 minutes, the solution was removed from the ice bath and allowed to warm to room temperature. After a total of 155 minutes, the mixture was partitioned between methylene chloride (20 mL) and 5% aqueous sodium bicarbonate (20 mL). The aqueous layer was re-extracted with more methylene chloride (2×10 mL), and the combined methylene chloride extracts were dried with magnesium sulfate, were filtered and evaporated to an oil (320 mg), which contained residual tetrahydrofuran, as observed by NMR. The oil was dissolved in a mixture of tetrahydrofuran (4 mL), water (2 mL), and acetic acid (0.5 mL) and the resulting solution was stirred at room temperature for 45 minutes. The mixture was partitioned between methylene chloride (20 mL) and 5% aqueous sodium bicarbonate (30 mL). The aqueous layer was re-extracted with more methylene chloride (2×10 mL), the combined methylene chloride extracts were dried with magnesium sulfate, were filtered and evaporated to an oil (290 mg) which contained residual tetrahydrofuran, as observed by NMR. The crude product was chromatographed on Analtech silica gel GF preparative plates (3×1000 micron, 4:1 methylene chloride/ethyl acetate). The product was removed, eluted with ethyl acetate and evaporated to give the title compound as a white solid (115 mg).

$^1$H NMR (CDCl$_3$, 400 MHz) δ0.59 (q, Si($\underline{CH_2}$CH$_3$)$_3$, 0.91 (t, Si(CH$_2\underline{CH_3}$)$_3$, 1.13 (d, 1-CH$_3$), 1.22 (d, CH$_3\underline{CHOH}$), 3.32 (dd, H-6), 3.83 (dq, H-1 ), 4.27 (p, CH$_3\underline{CHOH}$), 4.40 (dd, H-5), 5.13 (ABq, $\underline{CH_2}$OH), 5.28 and 5.47 (two d's, $\underline{CH_2}$C$_6$H$_4$NO$_2$), 7.45 (d, ArH$_5$), 7.63 and 8.19 (two m's, CH$_2$C$_6\underline{H_4}$NO$_2$), and 8.52 (d, ArH$_6$).

Step 2: p-Nitrobenzyl (1R,5S,6S)-2-[4-((N-methylimidazolium)methyl)thiazolo[ 5,4-b]pyridinyl-2-thio]-6-[(1R)-((triethyl)silyl)oxyethyl]- 1-methylcarbapen-2-em-3-carboxylate triflate p-Nitrobenzyl (1R,5S,6S)-2-[4-(hydroxymethyl)thiazolo[ 5,4-b]pyridinyl-2-thio]-6-[(1R)((triethyl)silyl)oxyethyl]-1-methylcarbapen-2-em-3-carboxylate (115 mg, 0.161 mmol) and N-methyl imidazole (0.039 mL, 0.483 mmol) were added to methylene chloride (5 mL) under a nitrogen atmosphere. The mixture was cooled in a dry ice/acetone bath and was treated with trifluoromethanesulfonic anhydride (0.041 mL, 0.242 mmol). The oily suspension was immediately removed from the cooling bath and was allowed to warm to room temperature. After a total of 30 minutes, the clear solution was partitioned between methylene chloride (10 mL) and water (5 mL). The aqueous layer was re-extracted with methylene chloride and the combined methylene chloride layers were dried with magnesium sulfate, filtered and evaporated to give the title compound as a white solid (138 mg).

$^1$H NMR (CDCl$_3$, 400 MHz) δ0.59 (q, Si($\underline{CH_2}$CH$_3$)$_3$, 0.92 (t, Si(CH$_2\underline{CH_3}$)$_3$, 1.18 (d, 1-CH$_3$), 1.21 (d, C$\underline{H^3}$CHOH), 3.39 (dd, H-6), 3.72 (dq, H-1 ), 3.96 (s, ImMe), 4.30 (p, CH$_3$CHOH), 4.46 (dd, H-5), 5.27 and 5.44 (two d's, $\underline{CH_2}$C$_6$H$_4$NO$_2$), 5.13 (s, $\underline{CH_2}$Im), 7.17 (s, ImH), 7.49 (s, ImH), 7.62 and 8.17 (two m's, CH$_2$C$_6\underline{H_4}$NO$_2$), 7.70 (d, ArH$_5$), 8.57 (d, ArH$_6$) and 9.59 (s, ImH).

Step3: (1R,5S,6S)-2-[4-((N-methylimidazolium)methyl)thiazolo[5,4-b] pyridinyl-2-thio]-6-[(1R)-(hydroxyethyl)-1-methylcarbapen-2-em-3-carboxylate The pH of a solution of p-Nitrobenzyl (1R,5S,6S)-2-[4-((N-methylimidazolium)methyl)thiazolo[ 5,4-b]pyridinyl-2-thio]-6-[(1R)-((triethyl)silyl)oxyethyl]- 1-methylcarbapen-2-em-3-carboxylate triflate (138 mg, 0.15 mmol) in a mixture of tetrahydrofuran (3 mL) and water (1.5 mL), was adjusted to 2.15 with 2N hydrochloric acid. After stirring for 35 minutes at room temperature, the pH was adjusted to 6.0 with 5% aqueous sodium bicarbonate. Butanol (3 mL), ethyl acetate (1 .5 mL), and 0.1N pH$_7$ sodium phosphate buffer (9 mL) were added and the rapidly stirred mixture was hydrogenated (atmospheric pressure) in the presence of 10% palladium on carbon (60 mg). After 2 hours, the s mixture was filtered through a 0.45 micron acrodisc, the aqueous layer was removed and the organic layer was extracted with water (1×3 mL). The combined aqueous layers were sparged with nitrogen and the volatile organics were evaporated under vacuum. The aqueous layer (ca. 5 mL) was loaded onto a amberchrom column (6 mL) and the column was eluted with water (10 mL) and then 60:40 acetonitrile/water (10 mL). The acetonitrile/water eluent was evaporated to ca. 1 mL and was placed on preparative reverse phase plates (analtech, 2×1000 micron, developing solvent 25% acetonitrile/water). The product band was removed, and eluted with 40% acetonitrile/water (30 mL). The eluent was washed with hexanes (1×20 mL), was evaporated and freeze-dried to give the title compound as a white solid (30mg).

UV (water) λ$_{max}$ 309 nm (ε 10,300).

$^1$H NMR (D$_2$O, 500 MHz) δ1.10 (d, 1-CH$_3$), 1.25 (d, CH$_3$CHOH), 3.51 (dq, H-1 ), 3.56 (dd, H-6), 3.87 (s, ImMe), 4.25 (p, CH$_3$CHOH), 4.36 (dd, H-5), 5.81 (s, CH$_2$Im), 7.46 (s, ImH), 7.52 (s, ImH), 7.70 (d, ArH$_5$), 8.49 (d, ArH$_6$) and 8.84 (s, ImH).

EXAMPLES 22-35

By appropriately modifying the procedures of Examples 20–21, compounds A1, LiSHet* and Q* as set forth in the following Table were reacted to produce compounds of formula Ia in which Het is as defined in the following Table.

TABLE

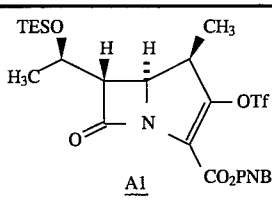

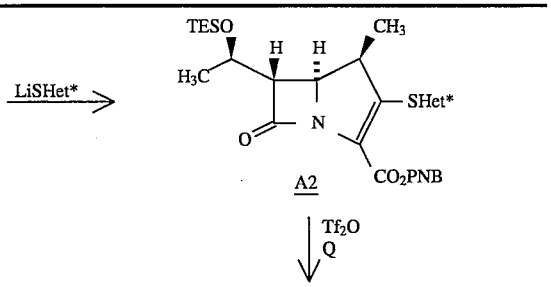

TES = triethylsilyl
PNB = p-nitrobenzyl

TABLE-continued

| Ex. # | LiSHet* | Q* | Het (of Product Ia) | Comments |
|---|---|---|---|---|
| 22 | | | | a |
| 23 | | | | a |
| 24 | | | | b |
| 25 | | | | b |
| 26 | | | | b |
| 27 | | | | a |

TABLE-continued

| # | Structure 1 | Structure 2 | Structure 3 | Notes |
|---|---|---|---|---|
| 28 | 2-lithiodithio-5-bromo-benzaldehyde alcohol derivative | N-methylimidazole | 4-((3-methylimidazolium-1-yl)methyl)-2-methyl-6-bromo-benzothiazole | a |
| 29 | 2-lithiodithio-5-chloro-benzaldehyde alcohol derivative | N-methylmorpholine | 4-((4-methylmorpholinium-4-yl)methyl)-2-methyl-6-chloro-benzothiazole | a,c |
| 30 | 2-lithiodithio-benzaldehyde alcohol derivative | N-methylmorpholine | 5-((4-methylmorpholinium-4-yl)methyl)-2-methyl-benzothiazole | a,c |
| 31 | 2-lithiodithio-benzaldehyde alcohol derivative | N-methylpiperazine (1,4-dimethyl) | 5-((1,4-dimethylpiperazinium-1-yl)methyl)-2-methyl-benzothiazole | a,c |
| 32 | 2-lithiodithio-benzaldehyde alcohol derivative | N-methylthiomorpholine-S,S-dioxide | 5-((4-methyl-1,1-dioxo-thiomorpholinium-4-yl)methyl)-2-methyl-benzothiazole | a,c |
| 33 | 2-lithiodithio-benzaldehyde alcohol derivative | N-methylpiperidine | 5-((1-methylpiperidinium-1-yl)methyl)-2-methyl-benzothiazole | a,c |

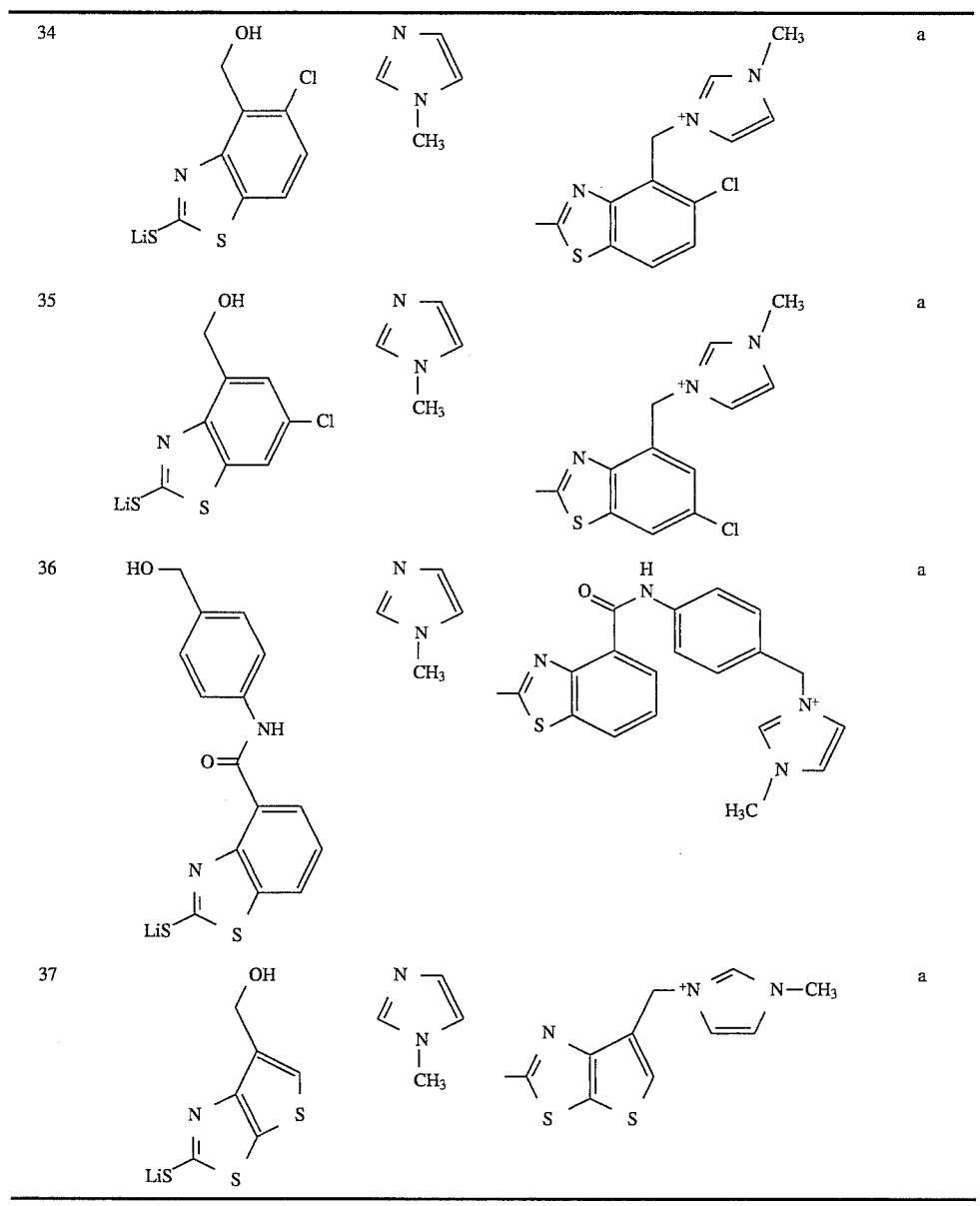

a) Prepared using the appropriately modified procedure of Example 20.
b) Prepared using the appropriately modified procedure of Example 21.
c) The final product was chromatographed on Amberchrom® CG-1000 instead of Amberchrom® CG-161.

Data for the final product of Example 22; ((1R,5S,6S)-2-{6-[(3-methylimidazolium-1-yl)methyl]benzothiazol-2-ylthio}-6-[1(R)-hydroxyethyl]-1-methylcarbapen-2-em-3-carboxylate):

IR (KBr) 2967, 1762, 1608, 1443, 1382, 1247, 1161, 999, and 764 cm$^{-1}$. UV (0.1M pH 7.0 MOPS buffer) $\lambda_{max}$ 318 nm ($\epsilon$ 14,160) and 305 nm ($\epsilon$ 14,280).

$^1$H NMR (7% DMSO-d$_6$ in D$_2$O, 500 MHz) $\delta$1.00 (d, 1-CH$_3$), 1.21 (d, CH$^3$CHOH), 3.37 (dq, H-1 ), 3.48 (dd, H-6), 3.87 (s, NCH$_3$), 4.20 (p, CH$_3$CHOH), 4.25 (dd, H-5), 5.49 (s, ArCH$_2$N), 7.44 and 7.49 (two m's, ImH-4" and ImH-5"), 7.48 (dd, ArH-5'), 7.80 (d, ArH-4'), 7.88 (d, ArH-7'), and 8.84 (s, ImH-2").

Data for the final product of Example 23 ((1R,5S,6S)-2-{7-[(3-methylimidazolium-1-yl)methyl]benzothiazol-2-ylthio}-6-[1(R)hydroxyethyl]-1-methylcarbapen-2-em-3-carboxylate)

IR (KBr) 2967, 1760, 1606, 1452, 1383, 1176, 1157, 754, and 624 cm$^{-1}$. UV (H$_2$O) $\lambda_{max}$ 306 nm ($\epsilon$ 12,640) and 319 nm ($\epsilon$ 12,640).

$^1$H NMR (D$_2$O, 500 MHz) $\delta$0.97 (d, 1-CH$_3$), 1.20 (d, CH$_3$CHOH), 3.36 (dq, H-1), 3.45 (dd, H-6), 3.86 (s, NCH$_3$), 4.19 (p, CH$_3$CHOH), 4.26 (dd, H-5), 5.45 (s, ArCH$_2$N), 7.38 (d, ArH-6'), 7.42–7.44 (m, ImH-4" and ImH-5"), 7.49 (t, ArH-5'), 7.72 (d, ArH-4'), and 8.82 (s, ImH-2").

$^{13}$C NMR (D$_2$O, 125.7 MHz) $\delta$15.4, 20.0, 35.9, 42.6, 52.1, 55.9, 59.7, 4.7, 122.3, 122.7, 124.1,126.2, 127.0, 127.6, 130.1,136.6, 139.1, 153.1,165.8, and 176.8.

Data for the final product of Example 24 ((1R,5S,6S)-2-[5-((N-methylimidazolium)-methyl)thiazolo[ 5,4-b]pyridinyl-2-thio]-6-[(1R)-hydroxyethyl]- 1-methylcarbapen-2-em-3-carboxylate)

UV (water) $\lambda_{max}$ 309 nm ($\epsilon$ 14,150).

¹H NMR (D₂O, 500 MHz) δ1.08 (d, 1-CH₃), 1.24 (d, CH₃CHOH), 3.53 (dq, H-1 ), 3.55 (dd, H-6), 3.89 (s, ImMe), 4.24 (p, CH₃CHOH), 4.36 (dd, H-5), 5.59 (s, CH₂Im), 7.47 (s, ImH), 7.54 (s, ImH), 8.15 (s, ArH4), 8.52 (s, ArH₆) and 8.89 (s, ImH).

Data for the final product of Example 25 ((1R,5S,6S)-2-[6-((N-methylimidazolium)-methyl)thiazolo[ 5,4-b]pyridinyl-2-thio]-6-[(1R)hydroxyethyl]- 1-methylcarbapen-2-em-3-carboxylate)

UV (water) λ$_{max}$ 309 nm (ε 15,200).

1H NMR (D₂O, 500 MHz) δ1.08 (d, 1-CH₃), 1.23 (d, CH₃CHOH), 3.51 (dq, H-1 ), 3.54 (dd, H-6), 3.90 (s, ImMe), 4.24 (p, CH₃CHOH), 4.33 (dd, H-5), 5.63 (s, CH₂Im), 7.47 (s, ImH), 7.51 (s, ImH), 7.59 (s, ArH₅), 8.17 (s, ArH₄) and 8.89 (s, ImH).

Data for the final product of Example 26 ((1R,5S,6S)-2-[4-((N-methylimidazolium)methyl)thiazolo[4,5-c]pyridinyl-2-thio]-6-[(1R)-hydroxyethyl]- 1-methylcarbapen-2-em-3-carboxylate)

UV (water) λ$_{max}$ 295 nm (ε 12,950).

¹H NMR (D₂O, 500 MHz) δ1.10 (d, 1-CH₃), 1.25 (d, CH₃CHOH), 3.56 (dq, H-1 ), 3.56 (dd, H-6), 3.87 (s, ImMe), 4.24 (p, CH₃CHOH), 4.38 (dd, H-5), 5.89 (s, CH₂Im), 7.44 (s, ImH), 7.49 (s, ImH), 8.0 (s, ArH), 8.33 (s, ArH) and 8.83 (s, ImH).

Data for the final product of Example 27 ((1R,5S,6S)-2-[(4-((3-methylimidazolium- 1-yl)methyl)benzothiazol-2-yl)thio]-6-[1(R)-hydroxyethyl]- 1-methylcarbapen-2-em-3-carboxylate)

UV (H₂O) λ$_{max}$ 307 nm (ε 13,380).

¹H NMR (D₂O, 500 MHz) δ0.84 (d, 1-CH₃), 1.17 (d, CH₃CHOH), 3.27 (dq, H-1 ), 3.36 (dd, H-6), 3.76 (s, NCH₃), 4.15 (p, CH₃CHOH), 4.20 (dd, H-5), 5.56 (s, ArCH₂N), 7.33 and 7.37 (two s, ImH-4" and ImH-5"), 7.33 (t, ArH-6'), 7.41 and 7.68 (two d, ArH-5' and ArH-7') and 8.68 (s, ImH-2").

¹³C NMR (D₂O, 500 MHz) δ176.6, 166.4, 166.2, 150.8, 138.6, 136.4, 136.2, 130.2, 127.8, 125.7, 125.6, 123.5, 122.9, 122.4, 64.76, 59.67, 55.92, 49.86, 42.41, 35.75, 20.13 and 15.44.

Data for the final product of Example 28 ((1R,5S,6S)-2-[(4-((3-methylimidazolium- 1-yl)methyl)-6-bromo-benzothiazol-2-yl)thio]-6-[1(R)-hydroxyethyl]-1-methylcarbapen-2-em-3-carboxylate)

UV (0.1M MOPS pH=7): λ$_{max}$ 314 nm (ε=14100)

¹H NMR (D₂O, 500 MHz) δ8.74 (s, ImH-2"), 7.76 (s, ArH), 7.55 (s, ArH), 7.43 and 7.38 (two m's, ImH-4" and ImH-5"), 5.60 (s, ArCH₂N), 4.31 (dd, H—S), 4.21 (quintet, CH₃CHOH), 3.81 (s, NCH₃), 3.49 (dd, H-6), 3.41 (dq, H-1), 1.21 (d, CH₃CHOH), 1.01 (d, 1-CH₃).

Data for the final product of Example 29 ((1R,5S,6S)-2-[(4-((4-methylmorpholin- 4-yl)methyl)-6-chloro-benzothiazol-2-yl )thio]-6-[1(R)-hydroxyethyl]-1-methylcarbapen-2-em-3-carboxylate)

UV (0.1M pH 7.0 MOPS buffer) λ$_{max}$ 319 nm (ε 13,656).

¹H NMR (D₂O, 500 MHz) δ1.12 (d), 1.24 (d), 3.13 (s), 3.45 (br t), 3.51 (br t), 3.55 (br s), 3.66 (br d), 4.10 (br t), 4.12 (br t), 4.23 (br t), 4.35 (d), 4.94 (dd), 7.64 (s), 8.01 (s).

Data for the final product of Example 30 ((1R,5S,6S)-2-[(5-((4-methylmorpholin- 4-yl)methyl)benzothiazol-2-yl)thio]-6-[1(R)-hydroxyethyl]- 1-methylcarbapen-2-em-3-carboxylate)

UV (0.1M pH 7.13 MOPS buffer) λ$_{max}$ 319 nm (ε 12,380).

¹H NMR (D₂O, 500 MHz) a 1.06 (d), 1.22 (d), 3.14 (s), 3.42 (d), 3.47 (dd), 3.52 (m), 3.66 (m), 4.06 (m), 4.22 (m), 4.32 (dd), 7.52 (d), 7.95 (s), 8.00 (d).

Data for the final product of Example 31 ((1R,5S,6S)o2-[(5-((1,4-dimethylpiperazin- 1-yl)methyl)benzothiazol-2-yl)thio]-6-[1(R)-hydroxyethyl]- 1-methylcarbapen-2-em-3-carboxylate)

UV (0.1M pH 7.0 MOPS buffer) λ$_{max}$ 315 nm (ε 11,350).

¹H NMR (D₂O, 500 MHz) δ1.04 (d), 1.17 (d), 2.55 (s), 3.10 (s), 3.33 (br d), 3.45 (dq), 3.51 (m), 3.67 (br t), 4.21 (m), 4.29 (dd), 7.50 (d), 7.90 (s), 7.96 (d).

Data for the final product of Example 32 ((1R,5S,6S)-2-[(5-((4-methylthiomorpholin- 1,1-dioxide-1-yl)methyl)benzothiazol-2-yl)thio]-6-[1(R)-hydroxyethyl]-1-methylcarbapen-2-em-3-carboxylate)

UV (0.1M pH 7.0 MOPS buffer) λ$_{max}$ 315 nm (ε 11,522).

¹H NMR (D₂O, 500 MHz) δ1.08 (d), 1.23 (d), 3.26 (s), 3.52 (m), 3.74 (br d), 3.88 (br t), 4.02 (br d), 4.22 (m), 4.34 (dd), 7.55 (d), 7.99 (s), 8.04 (d).

Data for the final product of Example 33 ((1R,5S,6S)-2-[(5-((4-methylpiperidin- 1-yl)methyl)benzothiazol-2-yl)thio]-6-[1(R)-hydroxyethyl]- 1-methylcarbapen-2-em-3-carboxylate)

UV (0.1M pH 7.0 MOPS buffer) λ$_{max}$ 315 nm (ε 12,842).

¹H NMR (D₂O, 500 MHz) δ1.05 (d), 1.22 (d), 1.58 (m), 1.73 (m), 1.93 (m), 2.97 (s), 3.33 (br m), 3.40 (br m), 3.46 (dd), 3.51 (dd), 4.22 (m), 4.31 (dd), 4.61 (s), 7.50 (d), 7.91 (s), 7.97 (d).

Data for the final product of Example 34 ((1R,5S,6S)-2-[(4-((3-methylimidazolium- 1-yl)methyl)-5-chloro-benzothiazol-2-yl)thio]-6-[1(R)-hydroxyethyl]-1-methylcarbapen-2-em-3-carboxylate)

UV (0.1M MOPS pH=7): λ$_{max}$ 322 nm (ε=13300)

¹H NMR (D₂O, 500 MHz) δ8.06 (d, ArH), 7.60 (d, ArH), 5.30 (dd, ArCH₂N), 4.38 (dd, H-5), 4.36 (s, NCH₂CONH₂), 4.26 (quintet, CH₃CHOH), 4.19 (br m, DABCO), 3.62 (dd, H-6), 3.47 (dq, H-1), 1.26 (d, CH₃CHOH), 1.16 (d, 1-CH₃).

Data for the final product of Example 35 ((1R,5S,6S)-2-[(4-((3-methylimidazolium- 1-yl)methyl)-6-chloro-benzothiazol-2-yl)thio]-6-[1(R)-hydroxyethyl]-1-methylcarbapen-2-em-3-carboxylate)

UV (0.1M pH 7.0 MOPS buffer) λ$_{max}$ 315 nm (ε 11,441).

¹H NMR (D₂O, 500 MHz) δ1.03 (d), 1.24 (d), 3.41 (m), 3.50 (q), 3.83 (s), 4.22 (m), 4.30 (q), 5.63 (s), 7.40 (s), 7.45 (s), 7.76 (s), 8.74 (s).

Data for the final product of Example 36 ((1R,5S,6S)-2-[(4-((3-methylimidazolium- 1-yl)methyl)-6-chloro-benzothiazol-2-yl)thio]-6-[1(R)-hydroxyethyl]-1-methylcarbapen-2-em-3-carboxylate)

UV (water) λ$_{max}$ 284 nm (ε 18,633).

¹H NMR (0.125 mL D2O/0.05 mL CD₃CN, 500 MHz) δ1.26 (d, 1-CH₃), 1.32 (d, CH₃CHOH), 3.66 (dd, H-6), 3.80 (dq, H-1 ), 4.09 (s, NCH₃), 4.31 (p, CH₃CHOH), 4.37 (dd, H-5), 5.52 (s, ArCH₂N), 7.31 and 7.39 (two s, ImH), 7.65 (dd, ArH), 7.68 and 7.79 (two d, ArH), 8.24 and 8.27 (two d, ArH) and 9.01 (s, ImH).

Data for the final product of Example 37 ((1R,5S,6S)-2-[(4-((3-methylimidazolium- 1-yl)methyl)-1,3-thiazolo[5,4-b]thiophen-2-yl)thio]- 6-[(1R)-hydroxyethyl]-1-methylcarbapen-2-em-3-carboxylate)

UV (0.1M pH 7 MOPS buffer) λ$_{max}$ 318 nm (ε 10900).

¹H NMR (D₂O, 500 MHz) δ8.76 (s, imidazole-H), 7.84 (s, thiophene H), 7.48 (s, imidazole-H), 7.41 (s, imidazole-H), 5.58 (s, CH₂Imidazole), 4.2 (m, H-5 & CH₃CHOH), 3.83 (s, imidazole-Me), 3.41 (dq, H-1), 3.06 (dd, H-6), 1.21 (d, CH³CHOH), 0.97 (d, 1-CH₃).

EXAMPLE 38

(1R,5S,6S)-2-(5{2-[4-(3-HYDROXYPROPYL-1,4-DIAZONIABICYCLO[2.2.2]OCT-1-YL]ETHYL}BENZOTHIAZOL-2-YLTHIO)- 6-[1(R)-HYDROXYETHYL]-1-METHYLCARBAPEN-2-EM- 3-CARBOXYLATE CHLORIDE

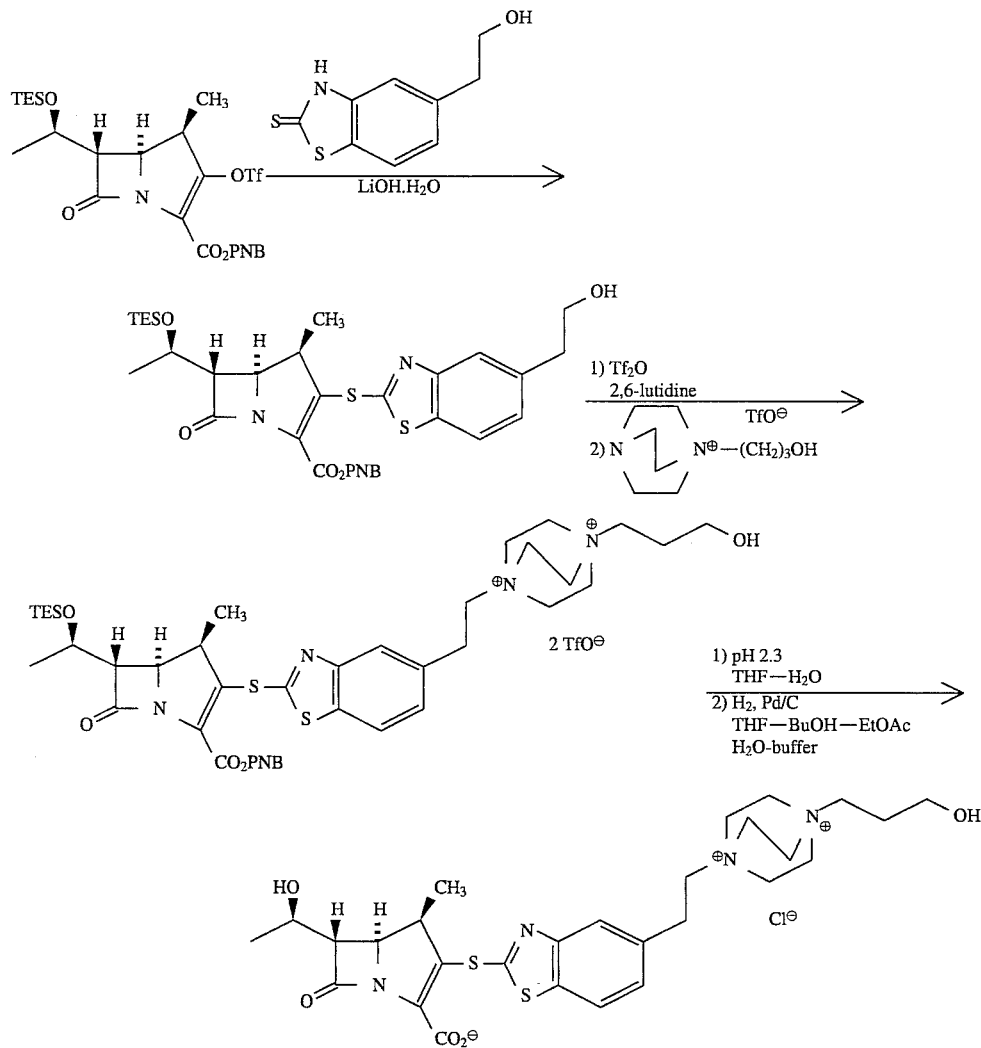

Step 1: p-Nitrobenzyl (1R,5S,6S)-2-[5-(2-hydroxyethyl)benzothiazol-2-ylthio]-6-[(1R)-(triethylsilyloxy)ethyl]-1-methylcarbapen-2-em-3-carboxylate A mixture of 5-(2-hydroxyethyl)-2-thioxo-2,3-dihydrobenzothiazole (14.51 g, 0.069 mol), powdered lithium hydroxide monohydrate (3.40 g, 0.81 mol), and tetrahydrofuran (312 mL) was stirred and sonicated for 10 min at room temperature. Solid p-nitrobenzyl (1R, 5R,6S)-2-(trifluoromethylsulfonyl)oxy-6-[(1R)-(triethylsilyloxy)ethyl]- 1-methylcarbapen-2-em-3-carboxylate (38.0 g, 0.62 mol) was added to the resulting tan solution over 2 minutes. The resulting mixture was stirred at room temperature for 40 minutes then diluted with ethyl acetate (2.2 L). The resulting solution was washed with phosphate buffer solution (150 mL 1M pH 7 phosphate buffer+750 mL H$_2$O), buffered brine solution (100 mL 1M pH 7 phosphate buffer +800 mL saturated aqueous sodium chloride), dried over magnesium sulfate, filtered, and concentrated in vacuo to a tacky, amber foam (50.43 g). A solution of the crude product in dichloromethane (200 mL) was applied to a 9×57 cm column of flash silica gel and the column was eluted with 7: 1 dichloromethane-ethyl acetate at a flow rate of 100 mL/min. After rechromatography of mixed fractions, p-nitrobenzyl (1R,5S,6S)-2-[5-(2-hydroxyethyl)benzothiazol-2-ylthio]-6-[(1R)-(triethylsilyloxy)ethyl]-1-methylcarbapen-2-em-3-carboxylate (34.1 g) was obtained as an amorphous white solid.

IR (KBr) 2956, 1782, 1607, 1523, 1442, 1379, 1340, 1277, 1211, 1144, 1055, 986, and 738 cm$^{-}$.

$^1$H NMR (CDCl$_3$, 500 MHz) δ0.59 (q, CH$_3$CH$_2$Si), 0.94 (t, CH$_3$CH$_2$Si), 1.11 (d, 1-CH$_3$), 1.22 (d, CH$_3$CHOSi), 3.02 (t, ArCH$_2$CH$_2$OH), 3.30 (dd, H-6), 3.86 (dq, H-1 ), 3.95 (t, ArCH$_2$CH$_2$OH), 4.28 (p, CH$_3$CHOSi), 4.40 (dd, H-5), 5.30 and 5.49 (two d's, CH$_2$C$_6$H$_4$NO$_2$), 7.31 (dd, ArH-6'), 7.66 and 8.21 (two m's, C$_6$H$_4$NO$_2$), 7.76 (d, ArH-7'), and 7.87 (s, ArH-4').

$^{13}$C NMR (CDCl$_3$, 125.7 MHz) δ4.9, 6.7, 16.3, 22.4, 39.0, 43.1, 53.5, 55.6, 61.3, 63.5, 65.3, 65.7, 121.1,123.0, 123.7, 127.1,128.2, 134.4, 137.8, 142.5, 143.0, 153.7, 160.0, 160.3, and 174.0.

Step 2: p-Nitrobenzyl (1 R,5S,6S)-2-(5–12-[4-( 3-hydroxypropyl-1,4-diazoniabicyclo[ 2.2.2]oct-1-yl]ethyl}benzothiazol-2-ylthio)-6-[1(R)-triethylsilyloxy- )ethyl]- 1-methylcarbapen-2-em-3-carboxylate bis(trifluoromethanesulfonate)

A solution of p-nitrobenzyl (1R,5S,6S)-2-[5-(2-hydroxyethyl)-benzothiazol- 2-ylthio]-6-[(1R)-(triethylsilyloxy)ethyl]-1-methylcarbapen- 2-em-3-carboxylate (34.67 g, 0.052 mol) in dichloromethane (500 mL) was cooled in a −20° C. (ice-methanol) bath as 2,6-lutidine (15.08 mL, 0.129 mol) was added followed by trifluoromethanesulfonic anhydride (10.88 mL, 0.065 mol). The resulting solution was stirred at −20° C. for 65 min then poured into a mixture of dichloromethane (500 mL) and water (900 mL). The layers were quickly separated and the organic portion was rapidly washed with 0.2N aqueous hydrochloric acid (2×1 L) and water (900 mL) then dried over sodium sulfate, filtered, and concentrated in vacuo to afford crude p-nitrobenzyl (1R,5S,6S)-2-(5-{2-[4-(3-{triflurormethanesulfonyloxy}propyl-1,4-diazoniabicyclo [2.2.2]oct-1-yl]ethyl}benzothiazol-2-ylthio)-6-[1(R)-(triethylsilyloxy)ethyl]-1-methylcarbapen- 2-em-3-carboxylate as a viscous liquid (ca.100 mL). The crude triflate intermediate was immediately dissolved in acetonitrile (500 mL) and the solution was treated with solid 1-(3-hydroxypropyl)-4-aza-1-azoniabicyclo[2.2.2]octane trifluoromethanesulfonate (16.58 g, 0.052 mol). The resulting solution was stirred at room temperature for one hour then concentrated in vacuo. The solid residue was recrystallized from isopropanol and the solid collected by filtration to afford p-nitrobenzyl (1R,5S,6S)-2-(5-{2-[4-(3-hydroxypropyl-1,4-diazoniabicyclo[2.2.2]oct-1-yl] ethyl}benzothiazol-2-ylthio)-6-[1(R)-(triethylsilyloxy)ethyl]- 1-methylcarbapen-2-em-3-carboxylate bis(trifluoromethanesulfonate) (50.5 g) as a white crystalline solid.

IR (KBr) 2958, 1786, 1718, 1608, 1522, 1380, 1340, 1273, 1161, 1033, 851, 738, and 641 cm$^{-1}$.

$^1$H NMR (DMSO-d$_6$, 500 MHz) δ0.54 (q, C$\underline{H}_3$CH$_2$Si), 0.89 (t, CH$_3$C$\underline{H}_2$Si), 1.07 (d, 1-CH$_3$), 1.12 (d, C$\underline{H}_3$CHOSi), 1.87 (m, NCH$_2$C$\underline{H}_2$CH$_2$OH), 3.23 (m, ArCH$_2$C$\underline{H}_2$N), 3.51 (t, NCH$_2$CH$_2$C$\underline{H}_2$OH), 3.58 (m, NC$\underline{H}_2$CH$_2$CH$_2$OH), 3.60 (t, H-6), 3.74 (dq, $\underline{H}$-1 ), 3.82 (m, ArC$\underline{H}_2$CH$_2$N), 3.85–3.97 (m, N(C$\underline{H}_2$CH$_2$)$_3$N), 4.25 (dq, CH$_3$C$\underline{H}$OSi), 4.38 (dd, H-5), 5.38 and 5.48 (two d's, C$\underline{H}_2$C$_6$H$_4$NO$_2$), 7.45 (d, ArH-6'), 7.71 and 8.18 (two d's, C$_6$H$_4$NO$_2$), 8.01 (s, ArH-4'), and 8.10 (d, ArH-7').

Step 3: (1R,5S,6S)-2-(5-{2-[4-(3-Hydroxypropyl-1,4-diazoniabicyclo-[ 2.2.2]oct-1-yl]ethyl}benzothiazol-2-ylthio)-6- [1(R)-hydroxyethyl]- 1-methylcarbapen-2-em-3-carboxylate chloride A solution of p-nitrobenzyl (1R,5S,6S)-2-(5-{2-[4-(3-hydroxypropyl- 1,4-diazoniabicyclo[2.2.2]oct-1-yl]ethyl}-benzothiazol-2-ylthio)-6-[1(R)-(triethylsilyloxy)ethyl]-1-methylcarbapen-2-em-3-carboxylate bis(trifluoromethanesulfonate) (32.6 g, 0.029 mol) in 2:1 tetrahydrofuran:water (446 mL) was stirred at room temperature while the pH of the solution was adjusted to 2.3 by addition of 1M aqueous trifluoromethanesulfonic acid (4.6 mL). The resulting solution was stirred at room temperature. Additional 1M aqueous trifluoromethanesulfonic acid (0.4 mL total) was added as necessary to maintain the pH at 2.3. After 75 min at room temperature, the removal of the triethylsilyl protecting group was judged to be complete and the pH of the mixture was raised to 6.5 by addition of 1M aqueous sodium bicarbonate (6.2 mL). The reaction mixture was added to a mixture of n-butanol (297 mL), ethyl acetate (149 mL), 1M pH 7 phosphate buffer (162 mL) and water (297 mL) in a 3 L, three-neck, round-bottom flask fitted with a mechanical stirrer, septum, and purge valve equipped with a hydrogen balloon. 10% Palladium on carbon (3.26 g) was added and the resulting mixture was stirred vigorously under a hydrogen atmosphere at room temperature. The reduction was monitored by UV (0.01 mL of the lower phase in 5.0 mL water) and judged to be complete after 75 min. The reaction mixture was filtered through a pre-washed (tetrahydrofuran/water) bed of Celite. The layers of the filtrate were separated and the organic layer was extracted with water (3×250 mL). The extracts were used to wash the filter cake and were then combined with the original aqueous layer. The resulting aqueous solution was washed with 1:1 ether-ethyl acetate (2×800 mL) then concentrated in vacuo to a volume of 849 mL. This crude product solution was loaded onto a column (5×43 cm) of the weak cation-exchange resin Bio-Rad Macro-Prep CM at a flow rate of 50 mL/min. After sample loading was complete, the column was eluted with water at 50 mL/min for 14 minutes then with water at 75 mL/min for 38 minutes and finally with 5% aqueous sodium chloride at 75 mL/min. The product began eluting 6 minutes after the eluent was changed to 5% aqueous sodium chloride and required 28 minutes to elute completely. The resulting solution of the purified product in 5% aqueous sodium chloride (total volume 2249 mL) was loaded onto a column (5×43 cm) of Amberchrom CG-161 resin at a flow rate of 65 mL/min. The column was eluted with water at 65 mL/min for 80 minutes, after which time the effluent tested negative for chloride ion by silver nitrate test. The eluent was changed to 4:1 water-isopropanol and the column was eluted with this eluent at 65 mL/min. The product began eluting 14 minutes after the eluent was changed to 4:1 water-isopropanol and required 11 minutes to elute completely. The resulting solution of desalted, purified product in 4:1 water-isopropanol (total volume ca. 700 mL) was diluted with water (500 mL) and concentrated in vacuo to a volume of 670 mL. This solution was lyophilized to afford (1R,5S,6S)-2-(5-{2-[4-(3-hydroxypropyl-1,4-diazoniabicyclo[2.2.2]-oct-1-yl] ethyl}benzothiazol-2-ylthio)-6-[1(R)-hydroxyethyl]-1-methylcarbapen- 2-em-3-carboxylate chloride (13.8 g) as an amorphous, fluffy, white solid.

IR (KBr) 2966, 1762, 1601, 1387, 1278, 1117, 1055, 995, 851, 815, and 766 cm$^{-1}$.

UV (0.1M pH 7.0 MOPS buffer) λ$_{max}$ 319.5 nm (ε 13,970)

$^1$H NMR (D$_2$O, 500 MHz) δ0.86 (d, 1-CH$_3$), 1.14 (d, CH$_3$CHOH), 2.08 (m, NCH$_2$C$\underline{H}_2$CH$_2$OH), 3.21 (dq, H-1 ), 3.30 (m, ArC$\underline{H}_2$CH$_2$N), 3.38 (dd, H-6), 3.71 (m, NCH$_2$C$\underline{H}_2$CH$_2$OH), 3.88 (m, ArCH$_2$C$\underline{H}_2$N), 4.06 (dd, H-5), 4.05–4.19 (m, CH$_3$C$\underline{H}$OH+N(C$\underline{H}_2$CH$_2$)$_3$N), 4.74 (s, HOD), 7.28(d, ArH-6'), 7.61 (s, ArH-4'), and 7.69 (d, ArH-7').

$^{13}$C NMR (D$_2$O, 125.7 MHz) 6 15.5, 20.0, 24.5, 27.9, 42.4, 51.3, 51.4, 5.6, 57.7, 59.6, 62.9, 64.5, 65.2, 121.4, 122.2, 126.5, 130.8, 133.5, 134.7, 137.8, 152.3, 165.5, 166.5, and 177.0.

EXAMPLES 39–55

By appropriately modifying the procedure of Example 38, compounds A1, LiSHet* and Q* as set forth in the following Table were reacted to produce compounds of formula Ia in which Het is as defined in the following Table.

TABLE

Reaction scheme: A1 (TESO, CH₃, OTf, CO₂PNB) + LiSHet* → A2 (SHet*) → [1) Tf₂O, base; 2) Q*] → A3 (SHet, CO₂PNB) → [1) H⁺ (de-TES); 2) H₂/cat (de-PNB)] → Ia (HO, SHet, CO₂⁻)

TES = triethylsilyl
PNB = p-nitrobenzyl

| Ex. # | LiSHet* | Q* | Het (of Product Ia) | Comments |
|---|---|---|---|---|
| 39 | 2-hydroxyethyl benzothiazole with LiS | TfO⁻ salt of DABCO-CH₂C(O)NH₂ | 2-methylbenzothiazole with ethyl-DABCO-CH₂C(O)NH₂, Cl⁻ | a,b |
| 40 | benzothiazole with LiS and hydroxyethyl substituent | TfO⁻ salt of DABCO-CH₂C(O)NH₂ | 2-methylbenzothiazole with ethyl-DABCO-CH₂C(O)NH₂, Cl⁻ | — |
| 41 | benzothiazole with LiS and 3-hydroxypropyl substituent | TfO⁻ salt of DABCO-CH₂C(O)NH₂ | 2-methylthiazolopyridine with propyl-DABCO-CH₂C(O)NH₂, Cl⁻ | — |

TABLE-continued
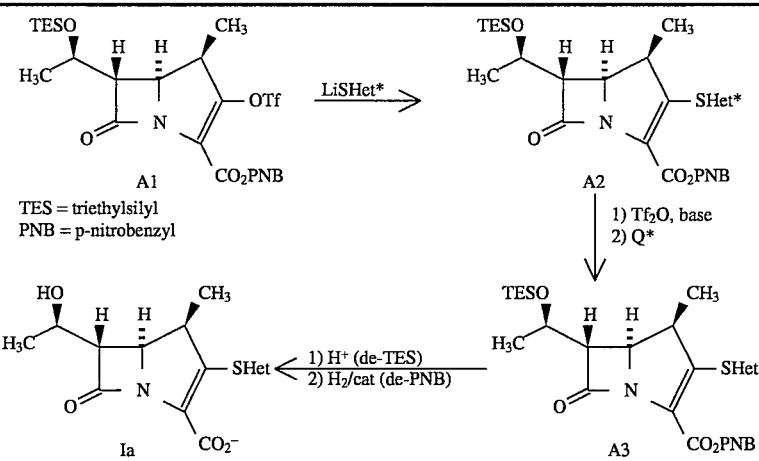

TABLE-continued

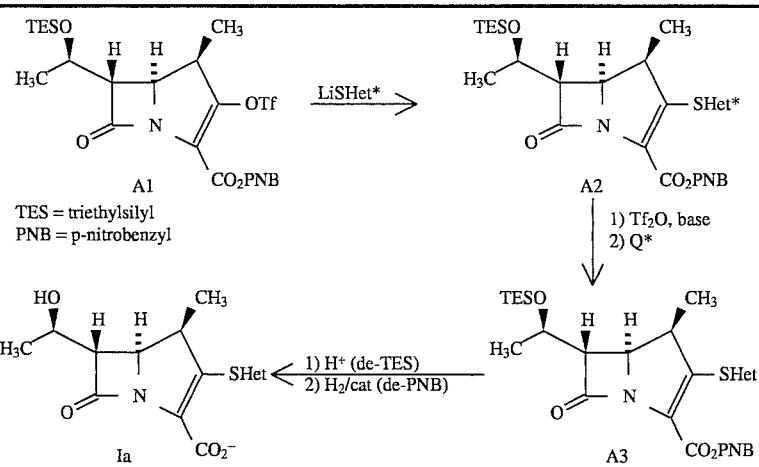

TES = triethylsilyl
PNB = p-nitrobenzyl

| Ex. # | LiSHet* | Q* | Het (of Product Ia) | Comments |
|---|---|---|---|---|
| 45 | (benzothiazole-2-thiolate Li salt with CH₂CH₂OH substituent) | 1-(2-phenoxyethyl)-DABCO triflate | 2-methylbenzothiazole with CH₂CH₂-N(DABCO)-CH₂OPh, Cl⁻ | a,c |
| 46 | (benzothiazole-2-thiolate Li salt with CH₂CH₂OH substituent) | 1-(2-fluoroethyl)-DABCO triflate | 2-methylbenzothiazole with CH₂CH₂-N(DABCO)-CH₂CH₂F, Cl⁻ | — |
| 47 | (benzothiazole-2-thiolate Li salt with CH₂CH₂OH substituent) | 1-(3-fluoropropyl)-DABCO triflate | 2-methylbenzothiazole with CH₂CH₂-N(DABCO)-CH₂CH₂CH₂F, Cl⁻ | — |

TABLE-continued
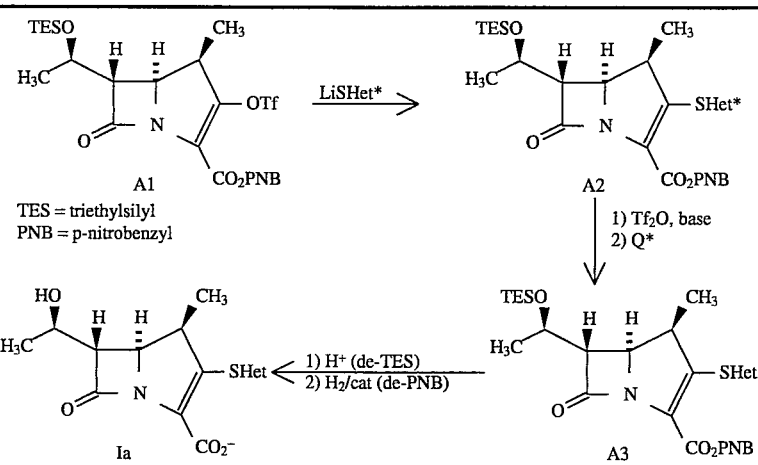
TES = triethylsilyl
PNB = p-nitrobenzyl
| Ex. # | LiSHet* | Q* | Het (of Product Ia) | Comments |
|---|---|---|---|---|
| 48 | 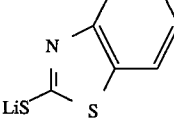 | 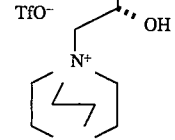 |  | a,c |
| 49 | 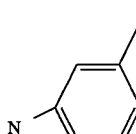 | 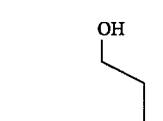 |  | a,c |
| 50 |  | 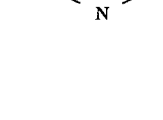 | 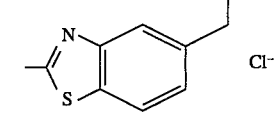 | a,c |

TABLE-continued

TABLE-continued

| Ex. # | LiSHet* | Q* | Het (of Product Ia) | Comments |
|---|---|---|---|---|
| 54 | 2-lithiothio-benzothiazole with 4-(2-hydroxyethyl) substituent | CH₃-S-CH₂-N⁺(DABCO) TfO⁻ | 2-(CH₃SCH₂-N⁺-DABCO-N⁺-CH₂CH₂-)benzothiazol-5-yl, Cl⁻ | — |
| 55 | 2-lithiothio-benzothiazole with 4-(2-hydroxyethyl) substituent | CH₃-S(=O)-CH₂-N⁺(DABCO) TfO⁻ | 2-(CH₃S(O)CH₂-N⁺-DABCO-N⁺-CH₂CH₂-)benzothiazol-5-yl, Cl⁻ | — | a) Hydrochloric acid was substituted for trifluoromethanesulfonic acid in the step which removes the TES hydroxyl-protecting group.
b) The final product was purified by chromatography on Amberchrom ® CG-161 resin then further purified by MPLC on a column of TosoHaas Amberchom ® CG-1000 sd resin to afford the final product as chloride salt (X = Cl).
c) Amberchom ® CG-1000 sd resin was substituted for Amberchrom ® CG-161 resin in the final desalting step.

Data for the final product of Example 39 ((1R,5S,6S)-2-[4-((4-carbamoylmethyl-( 1,4-diazoniabicyclo[2.2.2]oct-1-yl-)ethyl)benzothiazol- 2-yl)thio]-6-[1(R)-hydroxyethyl]-1-methylcarbapene- 2-em-3-carboxylate chloride):

IR (KBr) 3426 (br), 1757, 1697, 1600, 1390 cm⁻¹. UV (0.1M pH₇ MOPS buffer) $\lambda_{max}$295 nm (ε 13,000).
¹H NMR (D₂O, 500 MHz) δ1.10 (d, J=7.3 Hz, 1-CH₃), 1.23 (d, J=6.1 Hz, CH₃CHOH), 3.43 (dq, J=7.3, 9.7 Hz, H-1 ), 3.55 (dd, J=3.4, 5.4 Hz, H-6), 3.90 (t, J=8.2 Hz, ArCH₂CH₂),4.14 and 4.30 (t(br), J=6 Hz, N(CH₂CH₂)₃N), 4.23 (p, J=6 Hz, CH₃CHOH), 4.33 (m, H-5), 4.41 (s, NCH₂CONH₂), 7.34–7.40 (m, ArH-5', 6'), 7.82 (d, J=7.3 Hz, ArH-7').

Data for the final product of Example 40 ((1R,5S,6S)-2-[(5-((4-carbamoylmethyl- 1,4-diazoniabicyclo[2.2.2]oct-1-yl-)ethyl)benzothiazol-2-yl)thio]-6-[1(R)-hydroxyethyl]-1-methylcarbapen-2-em-3-carboxylate chloride):

IR (KBr) 3424 (br), 1762, 1696, 1599, and 1389 cm⁻¹. UV (0.1M pH₇ MOPS buffer) $\lambda_{max}$ 319 nm (ε 13,900).
¹H NMR (D₂O, 500 MHz) δ0.85 (d, J=7.1 Hz, 1-CH₃), 1.13 (d, J=6.4 Hz, CH₃CHOH), 3.21 (dq, J=7.1, 9.6 Hz, H-1), 3.30 (t(br), J=8 Hz, ArCH₂CH₂N), 3.37 (dd, J=2.9, 5.2 Hz, H-6), 3.88 (m, ArCH₂CH₂N), 4.04 (dd, J=2.5, 9.6 Hz, H-5), 4.13 (p, J=6 Hz, CH₃CHOH), 4.17 and 4.33 (two t(br)'s, J=7 Hz, N(CH₂CH₂)₃N), 4.45 (s, CH₂CONH₂), 7.27 (d, J=8.3 Hz, ArH-6'), 7.61 (s, ArH-4'), 7.68 (d, J=8.3 Hz, ArH-7').

¹³C NMR (D₂O, 125.7 MHz) δ15.5, 20.0, 27.9, 42.4, 51.3, 52.2, 55.6, 59.6, 62.2, 64.5, 65.3, 121.5, 122.2, 126.5, 131.0, 133.5, 134.7, 137.7, 152.3, 165.3, 165.5, 166.5, 177.0.

Data for the final product of Example 41 ((1R,5S,6S)-2-[(5-(3-(4-carbamoylmethyl- 1,4-diazoniabicyclo[2.2.2]oct-1-yl-)propyl)benzothiazol- 2-yl)thio]-6-[1(R)-hydroxyethyl]-1-methylcarbapen- 2-em-3-carboxylate chloride):

IR (KBr) 3423 (br), 1762, 1696, 1599, 1388, 1282, 1135 cm⁻¹. UV (0.1M pH₇ MOPS buffer) $\lambda_{max}$ 319nm (ε 13,300).

$^1$H NMR (D$_2$O, 500 MHz) δ0.79 (d, J=7.1 Hz, 1-CH$_3$), 1.12 (d, J=6.4 Hz, CH$_3$CHOH), 2.19 (p, J=8 Hz, ArCH$_2$CH$_2$CH$_2$N), 2.79 (t, J=7.5 Hz, ArCH$_2$CH$_2$CH$_2$N), 3.14 (dq, J=7.4, 9.7 Hz, H-1 ), 3.32 (dd, J=3, 5.2 Hz, H-6), 3.64 (m, ArCH$_2$CH$_2$CH$_2$N), 4.01 (dd, J=3, 9.7 Hz, H-5), 4.04 and 4.27 (two t(br)'s, J=7 Hz, N(CH$_2$CH$_2$)$_3$N)4.13 (p, J=6 Hz, CH$_3$CHOH), 4.41 (t, CH$_2$CONH$_2$), 7.22 (d, J=8.2Hz, ArH-6'), 7.57 (s, ArH-4'), 7.61 (d, J=8.2 Hz, ArH-7').

$^{13}$C NMR (D$_2$O, 125.7 MHz) δ7.4, 15.6, 20.0, 23.2, 23.7, 31.2, 42.4, 51.1, 52.2, 55.4, 59.5, 62.2, 64.4, 64.7, 115.0, 120.8, 121.7, 126.4, 131.4, 133.7, 137.3, 139.0, 152.3, 164.6, 165.3, 166.4, 177.0

Data for the final product of Example 42 ((1R,5S,6S)-2-(5-{2-[4-( 2-hydroxyethyl-1,4-diazoniabicyclo[2.2.2]oct-1-yl]ethyl}benzothiazol- 2-ylthio)-6-[1(R)-hydroxyethyl]-1-methylcarbapen-2-em-3-carboxylate chloride):

IR (KBr) 3022, 2967, 1762, 1600, 1386, 1277, 1119, 995, 862, 815, and 766 cm$^-$. UV (0.1M pH 7.0 MOPS buffer) λ$_{max}$ 318 nm (ε 13,350)

$^1$H NMR (D$_2$O, 500 MHz) δ0.90 (d, 1-CH$_3$), 1.16 (d, CH$_3$CHOH), 3.25 (dq, H-I), 3.31 (m, ArCH$_2$CH$_2$N), 3.41 (dd, H-6), 3.78 (m, NCH$_2$CH$_2$OH), 3.88 (m, ArCH$_2$CH$_2$N), 4.09 (dd, H-5), 4.10–4.22 (m, NCH$_2$CH$_2$OH+CH$_3$CHOH+N(CH$_2$CH$_2$)$_3$N), 4.74 (s, HOD), 7.29 (d, ArH-6'), 7.63 (s, ArH-4'), and 7.72 (d, ArH-7').

$^{13}$C NMR (D$_2$O, 125.7 MHz) δ15.5, 20.0, 27.9, 42.4, 51.3, 52.0, 54.9, 55.7, 59.6, 64.5, 65.2, 66.4, 121.4, 122.2, 126.4, 130.8, 133.5, 134.7, 137.9, 152.3, 165.7, 166.6, and 177.0.

Data for the final product of Example 43 ((1R,5S,6S)-2-(5-{2-[4-(cyanomethyl- 1,4-diazoniabicyclo[2.2.2]oct-1-yl]ethyl}benzothiazol-2-ylthio)- 6-[1(R)-hydroxyethyl]-1-methylcarbapen-2-em-3-carboxylate chloride):

UV (0.1M pH 7.0 MOPS buffer) λ$_{max}$ 318 nm (ε 9266).

$^1$H NMR (D$_2$O, 500 MHz) δ1.02 (d), 1.20 (d), 3.38 (m), 3.49 (dd), 3.95 (m), 4.15 (t), 4.20 (t), 4.29 (t), 5.06 (t), 7.34 (d), 7.73 (s), 7.85 (d).

Data for the final product of Example 44 ((1R,5S,6S)-2-(5-{2-[ 4-(N-methylcarbamoyl-methyl-1,4-diazoniabicyclo[2.2.2]oct- 1-yl]ethyl}benzothiazol-2-ylthio)-6-[1(R)-hydroxyethyl]-1-methylcarbapen- 2-em-3-carboxylate chloride):

UV (0.1M pH 7.0 MOPS buffer) λ$_{max}$ 318 nm (ε 12,413 ).

$^1$H NMR (D$_2$O, 500 MHz) δ0.93 (d), 1.17 (d), 2.77 (s), 3.28 (m), 3.43 (dd), 3.87 (t), 4.13 (m), 4.30 (t), 4.37 (s), 7.30 (d), 7.65 (s), 7.75 (d).

Data for the final product of Example 45 ((1R,5S,6S)-2-(5-{2-[4-( 2-phenoxyethyl-1,4-diazoniabicyclo[2.2.2]oct-1-yl]ethyl}benzothiazol- 2-ylthio)-6-[1(R)-hydroxyethyl]-1-methylcarbapen-2-em-3-carboxylate chloride):

UV (0.1M pH 7.0 MOPS buffer) λ$_{max}$ 310 nm (ε 10,380).

$^1$H NMR (D$_2$O, 500 MHz) δ0.98 (d), 1.18 (d), 3.27 (t), 3.33 (m), 3.45 (m), 3.62 (t), 3.78 (t), 3.90 (t), 4.14 (m), 4.22 (m), 4.52 (br s), 4.59 (br s), 7.02 (t), 7.08 (t), 7.32 (d), 7.38 (t), 7.69 (s), 7.80 (d).

Data for the final product of Example 46 ((1 R,5S,6S)-2-[5-(2-[4-( 2-fluoroethyl)-1,4-diazoniabicyclo[2.2.2]oct-1-yl)ethyl)benzothiazol- 2-ylthio)-6-[(1R)-hydroxyethyl]-1-methylcarbapen-2-em-3-carboxylate chloride):

UV (water) λ$_{max}$ 316 nm (ε 13,800).

$^1$H NMR (D$_2$O, 500 MHz) δ0.92 (d, 1-CH$_3$), 1.16 (d, CH$_3$CHOH), 3.28 (dq, H-1 ), 3.31 (m, CH$_2$CH$_2$Ar), 3.42 (dd, H-6), 3.89 (m, CH$_2$ CH$_2$Ar), 4.04 and 4.15 (two m, CH$_2$CH$_2$F), 4.10 (dd, H-5), 4.11 (p, CH$_3$CHOH), 4.17 (br s, N(CH$_2$CH$_2$)$_3$N), 5.00 and 5.09 (two m, CH$_2$CH$_2$F), 7.30 (dd, ArH), 7.63 (s, ArH) and 7.74 (d, ArH).

Data for the final product of Example 47 ((1R,5S,6S)-2-(5-{2-[4-( 3-fluoropropyl)-1,4-diazoniabicyclo[2.2.2]oct-1-yl)ethyl)benzothiazol- 2-yl)thio]-6-[(1R)-hydroxyethyl]-1-methylcarbapen-2-em-3-carboxylate chloride):

UV (water) λ$_{max}$ 318 nm (ε 13,300).

$^1$H NMR (D$_2$O, 500 MHz) δ0.87 (d, 1-CH$_3$), 1.14 (d, CH$_3$CHOH), 2.27 and 2.33 (two m, CH$_2$CH$_2$CH$_2$F), 3.22 (dq, H-1 ), 3.30 (m, CH$_2$ CH$_2$Ar), 3.39 (dd, H-6), 3.80 and 3.89 (two m, CH$_2$CH$_2$CH$_2$F), 4.07 (m, CH$_2$CH$_2$Ar), 4.10 (dd, H-5), 4.10 (p, CH$_3$CHOH), 4.10 and 4.14 (two m, N(CH$_2$CH$_2$)$_3$N), 4.58 and 4.67 (two m, CH$_2$CH$_2$CH$_2$F), 7.28 (dd, ArH), 7.61 (s, ArH) and 7.70 (d, ArH).

Data for the final product of Example 48 ((1R,5S,6S)-2-(5-{2-[4-(2-(R)- 2,3-dihydroxy-propyl)-1,4-diazoniabicyclo[2.2.2]oct-1-yl]ethyl)benzothiazol- 2-yl]thio]-6-[(1R)-hydroxyethyl]-1-methylcarbapen- 2-em-3-carboxylate chloride):

UV (0.1M pH 7.0 MOPS buffer) λ$_{max}$ 315 nm (ε 12,695).

$^1$H NMR (D$_2$O, 500 MHz) δ0.91 (d), 1.15 (d), 3.28 (m), 3.42 (dd), 3.60 (d), 3.69 (m), 3.88 (t), 4.11 (m), 4.28 (m), 4.38 (m), 7.29 (d), 7.64 (s), 7.73 (d).

Data for the final product of Example 49 ((1R,5S,6S)-2-(5-(2-[4-( 4-hydroxybutyl)-1,4-diazoniabicyclo[2.2.2]oct-1-yl)ethyl)benzothiazol- 2--6-[(1R)-hydroxyethyl]-1-methylcarbapen-2-em-3-carboxylate chloride):

UV (0.1M pH 7.0 MOPS buffer) λ$_{max}$ 315 nm (ε 12,134).

$^1$H NMR (D$_2$O, 500 MHz) δ0.97 (d), 1.20 (d), 1.60 (m), 1.88 (m), 3.35 (m), 3.46 (dd), 3.64 (m), 3.88 (dd), 4.05 (t), 4.16 (t), 4.19 (t), 7.31 (d), 7.67 (s), 7.80 (d).

Data for the final product of Example 50 ((1R,5S,6S)-2-[5-(2-(4-(2-( 2-hydroxyethoxy)-ethyl)-1,4-diazoniabicyclo[2.2.2]oct- 1-yl)ethyl)benzothiazol-2-ylthio)-6-[(1R)-hydroxyethyl]- 1-methylcarbapen-2-em-3-carboxylate chloride):

UV (0.1M pH 7.0 MOPS buffer) λ$_{max}$ 318 nm (ε 13,631).

$^1$H NMR (D$_2$O, 500 MHz) δ0.97 (d), 1.80 (d), 3.32 (m), 3.45 (dd), 3.64 (t), 3.73 (t), 3.87 (t), 4.03 (s), 4.13 (t), 4.18 (t), 7.31 (d), 7.67 (s), 7.78 (d).

Data for the final product of Example 51 ((1R,5S,6S)-2-[5-(2-(4-( 3-cyanopropyl)-1,4-diazoniabicyclo[2.2.2]oct-1-yl)ethyl)benzothiazol- 2-ylthio)-6-[(1R )-hydroxyethyl]-1-methylcarbapen-2-em-3-carboxylate chloride):

UV (0.1M pH 7.0 MOPS buffer) λ$_{max}$ 318 nm (ε 13,204).

$^1$H NMR (D$_2$O, 500 MHz) δ0.94 (d), 1.17 (d), 2.27 (m), 2.68 (t), 3.29 (t), 3.44 (dd), 3.74 (m), 3.89 (t), 4.14 (m), 7.30 (d), 7.64 (s), 7.75 (d).

Data for the final product of Example 52 ((1R,5S,6S)-2-[5-(2-(4-( 3-phenoxy-2-hydroxy-propyl)-1,4-diazoniabicyclo[2.2.2]oct- 1-yl)ethyl)benzothiazol-2-ylthio)-6-[(1R)-hydroxyethyl]- 1-methylcarbapen-2-em-3-carboxylate chloride):

UV (0.1M pH 7.0 MOPS buffer) λ$_{max}$ 315 nm (a 12,754).

$^1$H NMR (DMSO, 500 MHz) δ0.95 (d), 1.10 (d), 2.48 (s), 3.20 (br t), 3.39 (br d), 3.47 (br t), 3.76 (br t), 4.17 (br d), 4.56 (br d), 6.95 (t), 7.28 (m), 7.74 (s), 7.80 (d).

Data for the final product of Example 53 ((1R,5S,6S)-2-[5-(2-(4-( 3-isopropoxy-2-hydroxy-propyl)-1,4-diazoniabicyclo[2.2.2]oct- 1-yl)ethyl)benzothiazol-2-ylthio)-6-[(1R)-hydroxyethyl]- 1-methylcarbapen-2-em-3-carboxylate chloride):

UV (0.1M pH 7.0 MOPS buffer) λ$_{max}$ 318 nm (a 13,168).

$^1$H NMR (D$_2$O, 500 MHz) δ1.00 (d), 1.13 (d), 1.18 (d), 3.35 (m), 3.46 (dd), 3.53 (dd), 3.71 (m), 3.88 (t), 4.12 (s), 4.18 (m), 4.22 (br m), 4.43 (br m), 7.33 (d), 7.69 (s), 7.81 (d).

Data for the final product of Example 54 ((1R,5S,6S)-2-[5-(2-( 4-(methylthiomethyl)-1,4-diazoniabicyclo[2.2.2]oct-1-yl)ethyl)benzothiazol-2-ylthio)-6-[(1R)-hydroxyethyl]-

1-methylcarbapen-2-em-3-carboxylate chloride):

UV (0.1M pH 7.0 MOPS buffer) $\lambda_{max}$ 318 nm ($\epsilon$ 13,500).

$^1$H NMR (D$_2$O, 500 MHz) δ0.82 (d), 1.12 (d), 2.41 (s), 3.19 (dq), 3.30 (m), 3.36 (dd), 3.88 (m), 4.03 (dd), 4.13 (m), 4.89 (s), 7.27 (dd), 7.60 (d), 7.66 (d).

Data for the final product of Example 55 ((1R,5S,6S)-2-[5-(2-( 4-(methylsulfonylmethyl)-1,4-diazoniabicyclo[2.2.2]oct- 1-yl)ethyl)benzothiazol-2-ylthio]-6-[(1R)-hydroxyethyl]- 1-methylcarbapen-2-em-3-carboxylate chloride):

UV (0.1M pH 7.0 MOPS buffer) $\lambda_{max}$ 318 nm ($\epsilon$ 12,400).

$^1$H NMR (D$_2$O, 500 MHz) δ1.00 (d), 1.19 (d), 3.33 (m), 3.39 (s), 3.47 (dd), 3.92 (m), 4.19 (m), 4.48 (m), 7.32 (dd), 7.69 (d), 7.82 (d).

EXAMPLE 56

(1R,5 S, 6S )-2-[(4-( (3-METHYLIMIDAZOLIUM-1-YL)ETHYL)BENZOTHIAZOL- 2-YL)THIO]-6-[1(R)-HYDROXYETHYL]- 1-METHYLCARBAPEN-2-EM-3-CARBOXYLATE

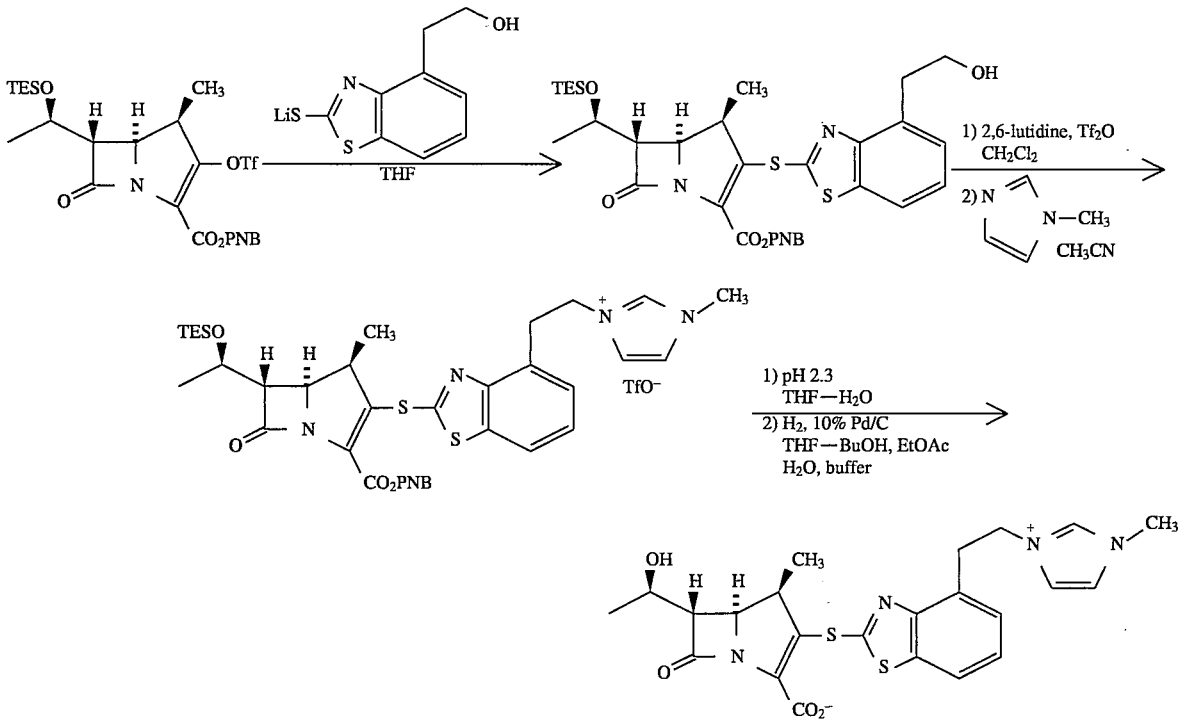

Step 1: p-Nitrobenzyl (1R,5S ,6S)-2-.[(4-(2-hydroxyethyl-)benzothiazol-2-yl)thio]-6-[1(R)-triethylsilyloxyethyl]-1-methylcarbapen-2-em-3-carboxylate A suspension of powdered lithium hydroxide monohydrate (50 mg, 1.20 mmol) in tetrahydrofuran (15 mL) under a nitrogen atmosphere was sonicated 5 minutes to give a hazy solution. The 25 solution was treated at room temperature with 4-(2-hydroxyethyl)-2-thioxo- 2,3-dihydrobenzothiazole (222 mg, 1.05 mmol) to give a light yellow solution. Crystalline p-nitrobenzyl (1R,5R,6S)-2-(trifluoromethylsulfonyl)oxy- 6-[(1R )-triethylsilyloxy)ethyl]-1-methylcarbapen- 2-em-3-carboxylate (609 mg, 1.00 mmol) was added and the resulting solution stirred at room temperature and followed by thin layer chromatography (1:1 hexane:ethyl acetate). After 60 minutes the reaction was diluted with ethyl acetate (50 mL), washed with water (2×40 mL) and brine, dried over magnesium sulfate, filtered, and evaporated under vacuum to an oil (1.221 g). The crude product was purified by chromatography on a column (2×18 cm) of EM silica gel 60 (230–400 mesh, packed in 3:2 hexane-ethyl acetate). The column was eluted with the aforementioned solvent, collecting ~5 mL fractions. Fractions 14–30 were combined and evaporated under vacuum and the residue lyophilized from benzene to afford p-nitrobenzyl (1R,5S,6S)-2-[(4-(2-hydroxyethyl)benzothiazol-2-yl)thio]-6-[1(R)-triethylsilyloxyethyl]- 1-methylcarbapen-2-em-3-carboxylate (573 mg) as a white solid.

$^1$H NMR (CDCl$_3$, 500 MHz) δ0.60 (q, J=8 Hz, C$\underline{H}_3$CH$_2$Si), 0.94 (t, J=8 Hz, CH$_3$C$\underline{H}_2$Si), 1.13 (d, J=7.3 Hz, 1-CH$_3$), 1.24 (d, J=6.2 Hz, C$\underline{H}_3$CHOSi), 3.31 (dd, J=3.1, 5.6 Hz, H-6), 3.34 (m, ArC$\underline{H}_2$CH$_2$OH), 3.80 (dq, J=7.3, 10.1 Hz, H-1), 3.98 (m, ArC$\underline{H}_2$CH$_2$OH), 4.27 (p, J=6 Hz, CH$_3$C$\underline{H}$OSi), 4.37 (dd, J=3.1, 10.1 Hz, H-5), 5.31 and 5.48 (two d's, J=13.6 Hz, C$\underline{H}_2$C$_6$H$_4$NO$_2$), 7.33–7.37 (m, ArH-5', 6'), 7.64–7.67 and 8.19–8.22 (two m's, CH$_2$C$_6\underline{H}_4$NO$_2$), 7.71 (dd, J=2.1, 7.1 Hz, ArH-7').

Step 2: p-Nitrobenzyl (1R,5S,6S)-2-[(4-(3-(methylimidazolium- 1-yl)ethyl)benzothiazol-2-yl)thio]-6-[1(R)-triethylsilyloxyethyl]- 1-methylcarbapen-2-em-3-carboxylate trifluoromethanesulfonate A solution of p-nitrobenzyl (1R,5S,6S)-2-[(4-( 2-hydroxyethyl)benzothiazol-2-yl)thio)-6-[1(R)-triethylsilyloxyethyl]- 1-methylcarbapen-2-em-3-carboxylate (250 mg, 0.373 mmol) in anhydrous dichloromethane (6.2 mL) under a nitrogen atmosphere was treated with 2,6-lutidine (109 µL, 0.933 mmol) and cooled in a dry ices acetone bath. The cold solution was treated with trifluoromethanesulfonic anhydride (78 µL, 0.466 mmol). After 45 minutes the cooling bath was removed and the reaction diluted with dichloromethane (4 mL) and washed with water (5 mL), 0.2N hydrochloric acid (5 mL), water (2×5 mL), dried over magnesium o sulfate, filtered, and evaporated under vacuum to afford crude p-nitrobenzyl (1 R,5S,6S)-2-[(4-( 2-trifluoromethanesulfonyloxyethyl)benzothiazol-2-yl)thio]- 6-[1(R)triethylsilyloxyethyl]- 1-methylcarbapen-2-em-3-carboxylate (285 mg) as a foam. The foam was dissolved in acetonitrile (6.2 mL) at room temperature under a nitrogen atmosphere and treated with 1-methylimidazole (33 μL, 0.414 mmol). After 2 hours the solution was evaporated under vacuum to an oil which was lyophilized from benzene to afford crude p-nitrobenzyl (1 R,5S,6S)-2-[(4-(2-(methylimidazolium-1-yl)ethyl)benzothiazol-2-yl)thio]-6-[1(R)-hydroxyethyl]-1-methylcarbapen- 2-em-3-carboxylate trifluoromethanesulfonate (315 mg) as an off-white solid.

Step 3: (1R,5S ,6S)-2-[(4-(3-(methylimidazolium- 1-yl)ethyl)benzothiazol-2-yl)thiol]-6-[1(R)-triethylsilyloxyethyl]-1-methylcarbapen-2-em-3-carboxylate A stirred solution of (1R,5S,6S)-2-[(4-(2-(methylimidazolium- 1-yl )ethyl )benzothiazol-2-yl)thio]-6-[1(R)-triethylsilyloxyethyl]- 1-methylcarbapen-2-em-3-carboxylate trifluoromethanesulfonate (285 mg, 0.322 mmol) in tetrahydrofuran (12 mL) and water (6 mL) at room temperature was adjusted to pH 2.3 using 2N hydrochloric acid. This pH was maintained either by the addition of additional acid or saturated aqueous sodium bicarbonate solution. After 35 minutes the solution was neutralized with saturated aqueous sodium bicarbonate solution and mixed with n-butanol (7.2 mL), ethyl acetate (3.6 mL), 0.5M pH 7.0 phosphate buffer (3.6 mL), water (7.2 mL), and 10% palladium on carbon (70 mg). The resulting mixture was stirred under a hydrogen atmosphere for 75 minutes, then filtered through a celite pad to remove catalyst which was washed with water. The filtrate layers were separated and the organic portion extracted with water (20 mL). The combined aqueous solution was washed with ethyl acetate (30 mL), concentrated under vacuum to ~10 mL, and charged onto a column (2×8 cm) of Amberchrom (Tosohaas) CG-161 resin. The column was eluted with water (~50 mL) followed by 40% acetonitrile/water. The acetonitrile/water fraction was diluted with an equal volume of water and concentrated under vacuum to ~10 mL, filtered through a Gelman 0.45 μm acrodisc, and lyopilized to afford the title compound (51.3 mg) as a yellow amorphous solid.

IR (KBr) 3424 (br), 1758, 1603, 1387, 1280, and 1176 cm$^{-1}$ UV (0.1M pH$_7$ MOPS buffer) $\lambda_{max}$ 303 nm ($\epsilon$ 11,500) and 320nm ($\epsilon$ 9,310).

$^1$H NMR (D$_2$O, 500 MHz) δ1.04 (d, J=7.1 Hz, 1-CH$_3$), 1.23 (d, J=6.2 Hz, CH$_3$CHOH), 3.42 (m, ArCH$_2$CH$_2$Im), 3.48 (dq, J=7.3, 9.8 Hz, H-1), 3.51 (dd, J=3.0, 6.0 Hz, H-6), 3.66 (s, ImCH$_3$), 4.23 (p, J=6 Hz, CH$_3$CHOH), 4.33 (dd, J=3.0, 9.8 Hz, H-5), 4.44 (t, ArCH$_2$CH$_2$Im), 7.12 (t, J=1.6 Hz, ImH-5"), 7.20 (t, J=1.6 Hz, ImH-4"), 7.23 (d, J=7.3 Hz, ArH-5'), 7.31 (t, J=7 Hz, ArH-6'), 7.73 (d, J=7.8 Hz, ArH-7'), 8.21 (s, ImH-2").

EXAMPLES 57–61

By appropriately modifying the procedure of Example 56, compounds A1, LiSHet* and Q* as set forth in the following Table were reacted to produce compounds of formula Ia in which Het is as defined in the following Table.

TABLE

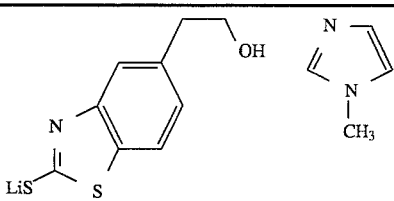

TES = triethylsilyl
PNB = p-nitrobenzyl

| Ex. # | LiSHet* | Q* | Het (of Product Ia) | Comments |
|---|---|---|---|---|
| 57 | 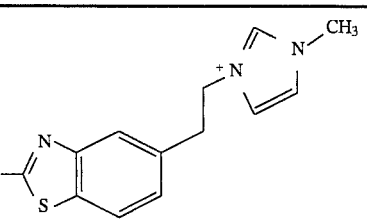 | 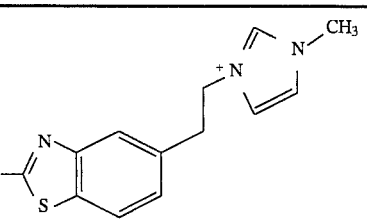 | 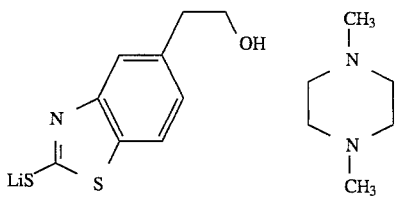 | a |
| 58 | 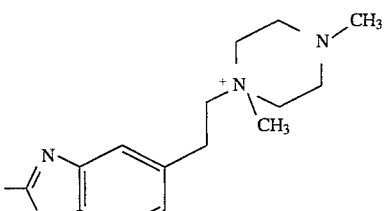 | 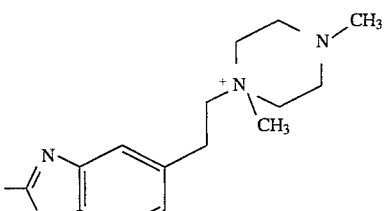 |  | a |

TABLE-continued

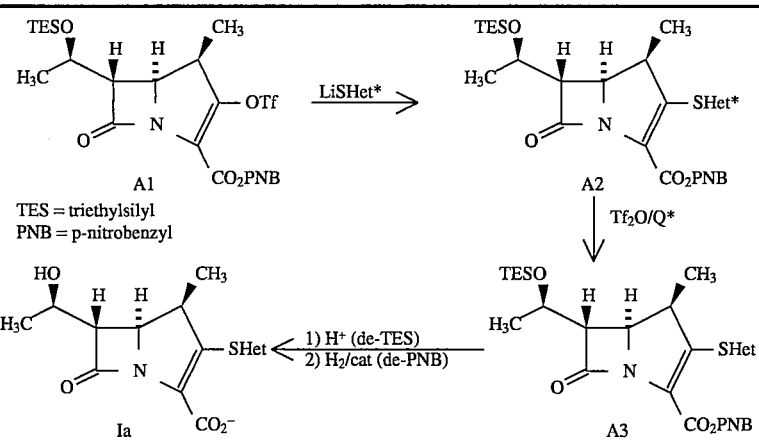

TES = triethylsilyl
PNB = p-nitrobenzyl

| Ex. # | LiSHet* | Q* | Het (of Product Ia) | Comments |
|---|---|---|---|---|
| 59 | (structure: 2-lithiothio-benzothiazole with 5-(2-hydroxyethyl) substituent) | 1,1-dioxo-4-methylthiomorpholine | 2-substituted benzothiazole with 5-(2-(4-methyl-1,1-dioxo-thiomorpholinium-4-yl)ethyl) group | a |
| 60 | (same benzothiazole) | N-methylpyridine (pyridine as Q) | benzothiazole with 5-(2-(pyridinium-1-yl)ethyl) group | b |
| 61 | (same benzothiazole) | N-methylpiperidine | benzothiazole with 5-(2-(1-methylpiperidinium-1-yl)ethyl) group | a | a) The crude product was chromatographed on Amberchrom® CG-1000 instead of Amberchrom® CG-161.
b) Trifluoromethanesulfonic acid was substituted for hydrochloric acid in the step which removes the TES hydroxyl-protecting group.

Data for the final product of Example 57 ((1R,5S,6S)-2-[(5-((3-methylimidazolium- 1-yl)ethyl)benzothiazol-2-yl)thio]-6-[1(R)-hydroxyethyl]- 1-methylcarbapen-2-em-3-carboxylate):

IR (KBr) 3424 (br), 1762, 1605, and 1384 cm$^{-1}$. UV (0.1M pH$_7$ MOPS buffer) $\lambda_{max}$ 320nm ($\epsilon$ 13,900).

$^1$H NMR (D$_2$O, 500 MHz) $\delta$0.92 (d, J=7.3 Hz, 1-CH$_3$), 1.18 (d, J=6.2 Hz, CH$_3$CHOH), 3.22 (t, J=6.8 Hz, ArCH$_2$CH$_2$Im), 3.27 (dq, J=7.3, 9.8 Hz, H-1), 3.42 (dd, J=3.0, 5.7 Hz, H-6), 3.69 (s, ImCH$_3$), 4.18 (p, J=6 Hz, CH$_3$CHOH), 4.20 (dd, J=3.0, 9.8 Hz, H-5), 4.45 (t, J=6.8 Hz, ArCH$_2$CH$_2$Im), 7.13 (dd J=1, 8.4 Hz, ArH-6'), 7.29 and 7.33(two t's, J=1.7 Hz, ImH-4", 5"), 7.40 (d, J=1 Hz, ArH-4'), 7.64 (d, J=8.2 Hz, ArH-7'), 8.43 (s, ImH-2").

Data for the final product of Example 58 ((1R,5S,6S)-2-[(5-((1,4-dimethylpiperazinium- 1-yl)ethyl)benzothiazol-2-yl)thio]-6-[1(R)-hydroxyethyl]- 1-methylcarbapen-2-em-3-carboxylate ):

UV (0.1M pH 7.0 MOPS buffer) $\lambda_{max}$ 320 nm ($\epsilon$ 12,308).

$^1$H NMR (D$_2$O, 500 MHz) $\delta$0.94 (d), 1.17 (d), 2.43 (s), 2.98 (br t), 3.25 (s), 3.42 (dd), 3.58 (s), 3.69 (br t), 4.13 (dd), 4.17 (t), 7.32 (d), 7.69 (s), 7.77 (d).

Data for the final product of Example 59 ((1R,5S,6S)-2-[(5-((4-methyl-1,1-dioxo-thiomorpholinium-1-yl)ethyl)benzothiazol-2-yl)thio]-6-[ 1(R)-hydroxyethyl]-1-methylcarbapen-2-em-3-carboxylate):

UV (0.1M pH 7.0 MOPS buffer) $\lambda_{max}$ 317 nm ($\epsilon$ 12,056).

$^1$H NMR (D$_2$O, 500 MHz) $\delta$1.00 (d), 1.19 (d), 3.35 (m), 3.42 (s), 3.46 (dd), 3.74 (br t), 3.83 (br t), 3.88 (m), 4.15 (t), 4.29 (m), 7.36 (d), 7.75 s (s), 7.85 (d).

Data for the final product of Example 60 ((1R,5S,6S)-2-[(5-(2-( 1-pyridinio)ethyl)benzothiazol-2-yl)thio]-6-[1(R)-hydroxyethyl]- 1-methylcarbapen-2-em-3-carboxylate):

IR (KBr) 3424 (br), 1758, 1604, 1384, 1278 cm$^{-1}$ UV (0.1M pH7 MOPS buffer) $\lambda_{max}$ 318nm ($\epsilon$ 13,700).

$^1$H NMR (D$_2$O, 500 MHz) $\delta$0.83 (d, J=7.1 Hz, 1-CH$_3$), 1.16 (d, J=6.4 Hz, CH$_3$CHOH), 3.20 (dq, J=7.1, 9.3 Hz, H-1), 3.37 (t, J=6.9 Hz, ArCH$_2$CH$_2$N), 3.3–3.4 (m, H-6), 4.1–4.7 (p, J=6 Hz, CH$_3$CHOH and H-5), 4.85 (t, J=6.9 Hz, ArCH$_2$CH$_2$N), 7.08 (d, J=8.4 Hz, ArH-6'), 7.31 (s, ArH-4'), 7.55 (d, J=8.4 Hz, ArH-7'), 7.86 (t, J=7.0 Hz, PyrH-3", 5"), 8.38 (dd, J=6.0, 7.0 Hz, PyrH-4"), 8.61 (d, J=6.0 Hz, PyrH-2", 6").

$^{13}$C NMR (D$_2$O, 125.7 MHz) $\delta$15.5, 20.1, 36.4, 42.4, 55.7, 59.6, 62.5, 64.6, 121.2, 122.1,126.2, 128.0, 130.3, 134.5, 134.6, 138.4, 144.1, 145.7, 52.4, 166.0, 166.2, 176.6.

Data for the final product of Example 61 ((1R,5S,6S)-2-[(5-((1-methylpiperidinium- 1-yl)ethyl)benzothiazol-2-yl)thio]- 6-[1(R)-hydroxyethyl]- 1-methylcarbapen-2-em-3-carboxylate):

UV (0.1M pH 7.0 MOPS buffer) $\lambda$max 317 nm ($\epsilon$ 13,325).

$^1$H NMR (D$_2$O, 500 MHz) $\delta$0.94 (d), 1.17 (d), 1.63 (m), 1.86 (br t), 3.13 (s), 3.20 (m), 3.31 (m), 4.10 (m), 3.56 (m), 4.16 (m), 7.32 (d), 7.70 (s), 7.77 (d).

EXAMPLE 62

(1R,5S, 6S )-2-[(4-( (4-CARBAMOYLMETHYL-1, 4-DIAZONIABICYCLO[ 2.2.2]OCT-1-YL)METH-YL)THIENO[3,2-D]THIAZOL- 2-YL)THIO]-6-[(1R)-HYDROXYETHYL]-1-METHYLCARBAPEN- 2-EM-3-CARBOXYLATE CHLORIDE

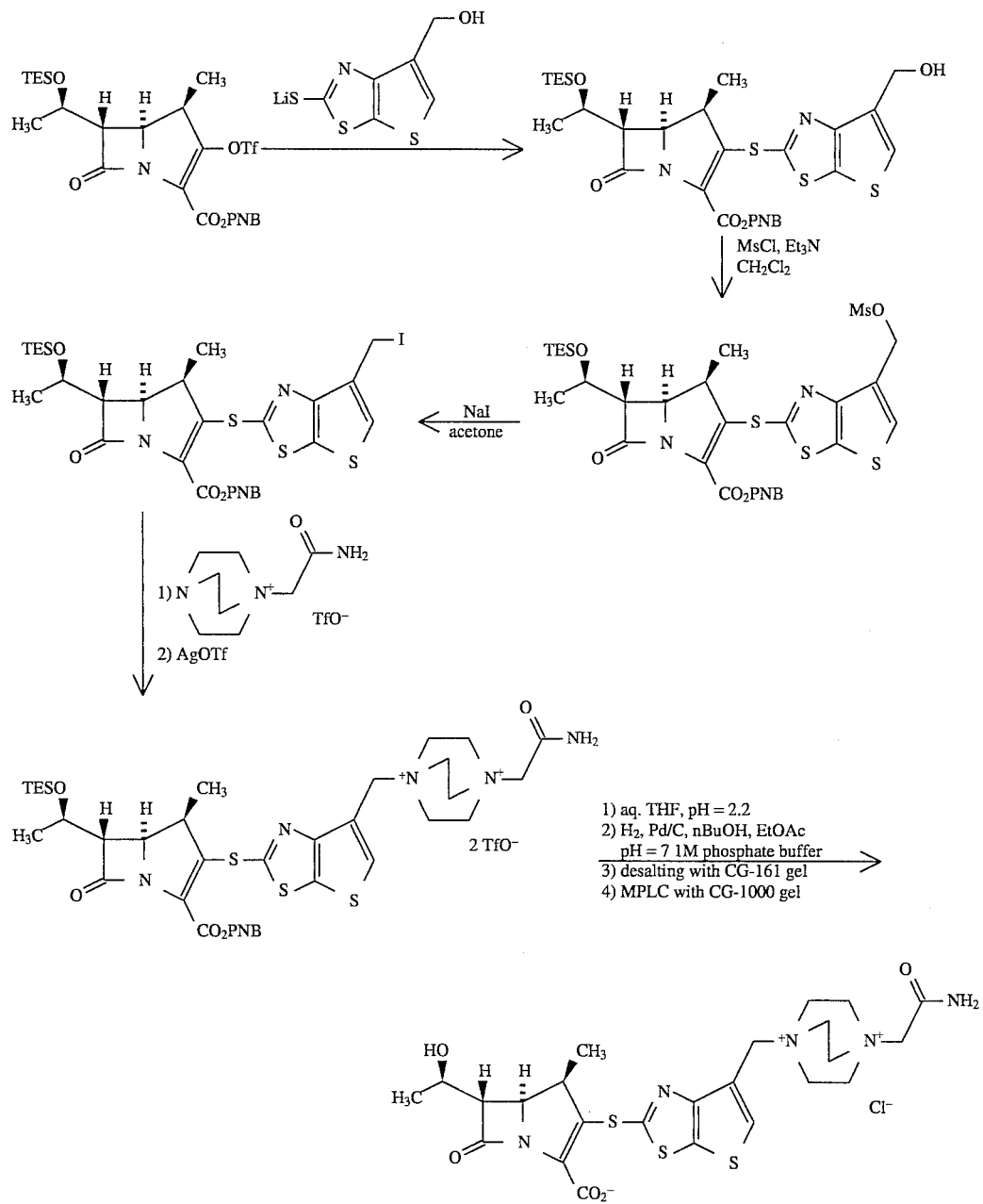

Step 1: p—Nitrobenzyl (1R,5S,6S)-2-[(4-hydroxymethylthieno[3,2-d]thiazol-2-yl)thio]-6-[(1R)-triethylsilyloxyethyl]-1-methylcarbapen-2- em-3-carboxylate To 4.0 g (19.9 mmol) of 4-hydroxymethyl-2-thioxo-2,3-dihydrothieno[3,2-d]thiazole in 200 ml of anhydrous tetrahydrofuran at room temperature was added 825 mg (19.6 mmol) of finely powdered LiOH·H$_2$O as a solid in one portion. The resulting mixture was sonicated and stirred for 10 minutes. To this mixture was added 11.5 g (18.9 mmol) of p-nitrobenzyl (1R,5S,6S)-2-trifluoromethylsulfonyloxy-6-[(1R )-triethylsilyloxyethyl]-1-methylcarbapen-2-em-3-carboxylate as a solid in a single portion. After 2 hours the solvent was removed under reduced pressure and the crude residue was chromatographed on EM silica gel 60 (230–400 mesh), eluting with 8:1 CH$_2$Cl$_2$-EtOAc. In this manner 10.8 g of the title compound was obtained as a white foam.

$^1$H NMR (CDCl$_3$, 400 MHz) δ8.21 & 7.65 (two d's, C$\underline{H}_2$C$_6$H$_4$NO$_2$), 7.41 (s, thiophene H), 5.48 & 5.29 (two d's, C$\underline{H}_2$C$_6$H$_4$NO$_2$), 4.95 (s, C$\underline{H}_2$OH), 4.29 (dd, H-5), 4.24 (quintet, CH$_3$C$\underline{H}$OTES), 3.40 (dq, H-1 ), 3.25 (dd, H-6), 1.18 (d, C$\underline{H}_3$CHOTES), 1.10 (d, 1-CH$_3$), 0.90 (t, SiCH$_2$C$\underline{H}_3$), 0.56 (q, SiC$\underline{H}_2$CH$_3$).

Step 2: p-Nitrobenzyl (1R,5S,6S)-2-[(4-methanesulfonyloxymethylthieno[3,2-d]thiazol-2-yl)thio]-6-[(1R)-triethylsilyloxyethyl]- 1-methylcarbapen-2-em-3-carboxylate To 10.8 g (16.3 mmol) of p-nitrobenzyl (1R,5S,6S)-2-[(4-hydroxymethylthieno[ 3,2-d]thiazol-2-yl)thio]-6-[(1R )triethylsilyloxyethyl]-1-methylcarbapen-2-em-3-carboxylate in 150 ml of anhydrous methylene chloride at -78° C. was added 3.16 ml (2.29 g, 22.7 mmol) of triethylamine followed by 1.57 ml of MsCl (2.32 g, 20.3 mmol). The reaction was stirred at −78° C. for 1.5 hours and then allowed to warm to room temperature over 30 minutes. The reaction was diluted with 1 liter of 1:1 ethyl acetate/dietyl ether and extracted with 300 ml each of water, saturated aqueous ammonium chloride, saturated aqueous sodium bicarbonate, and brine. The organic layer o was dried over magnesium sulfate, filtered and evaporated to give the title compound (12.5 g) as a white foam.

$^1$H NMR (CDCl$_3$, 400 MHz) δ8.20 & 7.65 (two d's, C$\underline{H}_2$C$_6$H$_4$NO$_2$), 7.64 (s, thiophene H), 5.49 (dd, C$\underline{H}_2$OMs), 5.48 & 5.29 (two d's, C$\underline{H}_2$C$_6$H$_4$NO$_2$), 4.31 (dd, H-5), 4.25 (quintet, CH$_3$C$\underline{H}$OTES), 3.49 (dq, H-1), 3.25 (dd, n-6), 1.18 (d, C$\underline{H}_3$CHOTES), 1.10 (d, 1-CH$_3$), 0.90 (t, SiCH$_2$C$\underline{H}_3$), 0.56 (q, SiC$\underline{H}_2$CH$_3$).

Step 3: p-Nitrobenzyl (1R,5S,6S)-2-[(4-iodomethylthieno[3,2-d]thiazol-2-yl)thio]-6-[(1R)-triethylsilyloxyethyl]-1-methylcarbapen-2-em-3-carboxylate To 12.5 g (16.3 mmol) of p-nitrobenzyl (1R,5S,6S)-2-[(4-methanesulfonyloxymethylthieno[3,2-d]thiazol-2-yl )thio]-6-[(1R )-triethylsilyloxyethyl]- 1-methylcarbapen-2-em-3-carboxylate in 200 ml of acetone at 0° C. was added 7.25 g (48.3 mmol) of sodium iodide. The reaction was stirred at 0° C. in the dark for 1.5 hours and then allowed to warm to room temperature over 30 minutes. The reaction was diluted with 500 ml of 1: 1 ethyl acetate/dietyl ether and extracted with 150 ml each of water, 5% aqueous sodium thiosulfate, water, and brine. The organic layer was dried over magnesium sulfate, filtered and evaporated. The residue was lyophilized from benzene to give the title compound (12.1 g).

$^1$H NMR (CDCl$_3$, 400 MHz) δ8.21 & 7.65 (two d's, C$\underline{H}_2$C$_6$H$_4$NO$_2$), 7.47 (s, thiophene H), 5.50 & 5.30 (two d's, C$\underline{H}_2$C$_6$H$_4$NO$_2$), 4.69 & 4.62 (two d's, C$\underline{H}_2$I), 4.31 (dd, H-5), 4.23 (quintet, CH$_3$C$\underline{H}$OTES), 3.68 (dq, H-1 ), 3.25 (dd, H-6), 3.04 (s, C$\underline{H}_3$SO$_3$), 1.20 (d, C$\underline{H}_3$CHOTES), 1.10 (d, 1-CH$_3$), 0.90 (t, SiCH$_2$C$\underline{H}_3$), 0.56 (q, SiC$\underline{H}_2$CH$_3$).

Step 4: p-Nitrobenzyl (1R,5S,6S)-2-[(4-((4-carbamoylmethyl-1,4-diazoniabicyclo[2.2.2]oct-1-yl)methyl)thieno[3,2-d]thiazol-2-yl)thio]-6-[(1R )-triethylsilyloxyethyl]-1-methylcarbapen-2-em-3-carboxylate bis (trifluoromethanesulfonate)

To 12.1 g (15.7 mmol) of p-nitrobenzyl (1R,5S,6S)-2-[(4-iodomethylthieno[3,2-d]thiazol-2-yl)thio]-6-[(1R)-triethylsilyloxyethyl]-1-methylcarbapen-2-em-3-carboxylate in 350 ml of anhydrous acetonitrile was added 5.24 g (16.5 mmol) of 1-carbamoylmethyl-4-aza1-azoniabicyclo[2.2.2]octane trifluoromethanesulfonate, and then 15.2 ml of 1.01M silver triflate in acetonitrile solution. The reaction was stirred in the dark for one hour, then filtered through Celite and evaporated. The viscous oil thus obtained was triturated with 200 ml of ethyl ether to give a crumbly solid which was dried under high vacuum. In this manner was obtained 17.8 g of the title compound.

$^1$H NMR (CD$_3$CN, 500 MHz) δ8.21 & 7.71 (two d's, C$\underline{H}_2$C$_6$H$_4$NO$_2$), 8.09 (s, thiophene H), 6.84 & 6.39 (two br s, CONH$_2$), 5.48 & 5.32 (two d's, C$\underline{H}_2$C$_6$H$_4$NO$_2$), 4.88 (dd, C$\underline{H}_2$DABCO), 4.36 (dd, H-5), 4.31 (quintet, CH$_3$C$\underline{H}$OTES), 4.19 (s, C$\underline{H}_2$CONH$_2$, 4.07 & 3.93 (two br t's, DAB$\underline{C}$O), 3.54 (dq, H-1), 3.44 (br t, H-6), 1.16 (d, C$\underline{H}_3$CHOTES), 1.09(d, 1-CH$_3$), 0.94 (t, SiCH$_2$C$\underline{H}_3$), 0.60 (q, SiC$\underline{H}_2$CH$_3$).

Step 5: (1R,5S,6S)-2-[(4-((4-carbamoylmethyl-1,4-diazoniabicyclo[2.2.2]oct-1-yl)methyl)thieno[3,2-d]thiazol-2-yl)thio]-6-[(1R)-hydroxyethyl]-1-methylcarbapen-2-em-3-carboxylate chloride To 17.8 g (15.7 mmol) of p-nitrobenzyl (1R,5S,6S)-2-[(4-((4-carbamoylmethyl-1,4-diazoniabicyclo[2.2.2]oct-1-yl )methyl)thieno[ 3,2-d]thiazol-2-yl)thio]-6-[(1R )-triethylsilyloxyethyl]-1-methylcarbapen-2-em-3-carboxylate bis(trifluoromethanesulfonate) in 300 ml of tetrahydrofuran and 150 ml of water was added 1 N aq. trifluoromethanesulfonic acid until the pH reached 2.3. The reaction was stirred at room temperature for 35 minutes, and then the pH was adjusted to 7 using saturated aq. sodium bicarbonate. To the reaction was added 350 ml nBuOH, 175 ml ethyl acetate, 100 ml 1M pH 7 s phosphate buffer, 400 ml of water, and 4.0 g of 10% Pd/C. This mixture was stirred vigorously at room temperature under a hydrogen atmosphere for 160 minutes. The layers were separated and the organic layer was washed with 75 ml of water. The combined aqueous layers were filtered through Celite, and the Celite was washed with 250 ml of o water. The combined aqueous layers were added to 200 ml of brine, then extracted twice with 250 ml of chloroform and once with 30 ml ether. It was then introduced to 300 ml of CG-161 resin in a large column at 4° C., which was eluted with cold water until all of the salt came off, and then with 20% acetonitrile to bring off the product. The fractions containing the product (ca. 750 ml) were evaporated under reduced pressure to a volume of approximately 200 ml, and then lyophilized to give 5.10 g of crude product. This material was purified by medium pressure liquid chromatography on a 2.5 by 15 cm column packed with CG-1000 reverse phase gel. The column was equilibrated with 0.10M aq. ammonium chloride and then a 500–600 mg sample of the crude product was introduced in 10 ml of 0.10M aq. ammonium chloride. Rate of elution was 14 ml/min. After 1 minute of eluting with 0.10M aq. ammonium chloride, the eluent was switched to straight water until the first peak (desired product, chloride salt) eluted after approximately 15 minutes. The eluent was then switched to 20% acetonitrile until the second peak (a mixture of the triflate salt of the desired product and ring opened material) eluted. In this manner, 5.06 g of crude material was purified to give, after lyophilization, 2.20 g of desired product from first peaks and 2.32 g of triflate/ring opened material from second peaks. The material from the second peaks was repurified in the same manner to give 0.95 g of desired product from first peaks and 1.34 g of second peaks, which by proton NMR and elemental analysis was shown to be a 2 to 1 mixture of the triflate salt of the desired compound to ring opened material. Thus 3.15 g of the title compound was obtained as a fluffy white lyophilate which was shown by elemental analysis to contain 8% water.

UV (0.1M MOPS pH =7): $\lambda_{max}$ 318 nm ($\epsilon$=11200)

$^1$H NMR (D$_2$O, 500 MHz) δ8.10 (s, thiophene H), 5.02 (dd, arylCH$_2$DABCO), 4.38 (s, CH$_2$CONH$_2$, 4.22 (m, DABCO, H-5 & H-8), 4.10 (m, DABCO), 3.47 (dd, H-6), 3.25 (dq, H-1 ), 1.22 (d, CH$_3$CHOH), 1.09 (d, 1-CH$_3$).

EXAMPLES 63–71

By appropriately modifying the procedure of Example 62, compounds A1, LiSHet* and Q* as set forth in the following Table were reacted to produce compounds of formula Ia in which Het is as defined in the following Table.

TABLE

TABLE-continued

TABLE-continued

| Ex. # | LiSHet* | Q* | Het (of Product Ia) | Comments |
|---|---|---|---|---|
| 70 | (thieno[3,2-d]thiazole with CH2OH, LiS) | (N-acyl-DABCO with piperidinone, TfO−) | (thienothiazole-CH2-DABCO-CH2-C(O)-piperidine, Cl−) | b |
| 71 | (thieno[3,2-d]thiazole with CH2OH, LiS) | (N-acyl-DABCO with pyrrolidinone, TfO−) | (thienothiazole-CH2-DABCO-CH2-C(O)-pyrrolidine, Cl−) | b | a) The final product was obtained as a mixture of chloride and trifluormethanesulfonate salts (X = a mixture of Cl & TfO) following purification on TosoHaas Amberchrom ® CG-161 resin.
b) The final product was obtained as the chloride salt (X = Cl) by ion exchange chroatography on Bio-Rad Macro-Prep CM resin followed by desalting on TosoHaas Amberchrom CG-161 resin (see Step 2 of Example 2 for details).
c) Hydrochloric acid was substituted for trifluoromethanesulfonic acid in the step which removes the TES hydroxyl-protecting group.
d) The final product was purified by chromatography on Amberchrom ® CG-161 resin then further purified by MPLC on a column of TosoHaas Amberchrom ® CG-1000 sd resin to afford the final product as a chloride salt (X = Cl).
e) The final product was purified by preparative HPLC on reverse-phase (C18) silica gel followed be desalting on TosoHaas Amberchrom CG-161 resin.

Data for the final product of Example 63 ((1R,5S,6S)-2-[(4-((4-(N-phenylcarbamoyl)-methyl-1,4-diazoniabicyclo[2.2.2]oct-1-yl)methyl)thieno[3,2-d]thiazol-2-yl)thio]-6-[(1R)-hydroxyethyl]-1-methylcarbapen-2-em-3-carboxylate chloride ):

UV (0.1M pH 7.0 MOPS buffer) $\lambda_{max}$ 315 nm ($\epsilon$ 10,076).

$^1$H NMR (D$_2$O, 500 MHz) δ1.09 (d), 1.21 (d), 2.02 (s), 2.50 (dq), 3.47 (dd), 4.14 (br t), 4.19 (t), 4.23 (dd), 4.29 (br t), 5.01 (dd), 7.27 (m), 7.41 (m), 8.11 (s).

Data for the final product of Example 64 ((1R,5S,6S)-2-[(4-((4-propyl-1,4-diazoniabicyclo[2.2.2]oct-1-yl)methyl)thieno[3,2-d]thiazol-2yl)thio]- 6-[(1R)-hydroxyethyl]-1-methylcarbapen-2-em-3-carboxylate chloride):

UV (0.1M MOPS pH =7): $\lambda_{max}$ 317 nm ($\epsilon$=10600)

$^1$H NMR (D$_2$O, 500 MHz) δ8.09 (s, thiophene H), 4.98 (dd, arylC$\underline{H}_2$DABCO), 4.24 (dd, H-5), 4.20 (quintet, H-8), 4.05 & 3.93 (br t's, DABCO), 3.47 (m, H-6 & CH2CH$_2$CH$_3$), 3.25 (dq, H-1), 1.78 (m, CH$_2$C$\underline{H}_2$CH$_3$), 1.22 (d, CH$_3$CHOH), 1.09 (d, 1-CH$_3$), 0.94 (t, CH$_2$CH$_2$C$\underline{H}$3).

Data for the final product of Example 65 ((1R,5S,6S)-2-[(4-((4-(3-hydroxypropyl)- 1,4-diazoniabicyclo[2.2.2]oct-1-yl )methyl)thieno[3,2-d]thiazol-2-yl)thio]-6-[(1R)-hydroxyethyl]-1-methylcarbapen-2-em-3-carboxylate chloride):

UV (0.1M MOPS pH =7): $\lambda_{max}$ 320 nm ($\epsilon$=10700)

$^1$H NMR (D$_2$O, 500 MHz) δ8.09 (s, thiophene H), 4.99 (dd, arylC$\underline{H}_2$DABCO), 4.24 (dd, H-5), 4.21 (quintet, H-8), 4.07 & 3.96 (br t's, DABCO), 3.65 (m, C$\underline{H}_2$CH$_2$CH$_2$OH), 3.48 (dd, H-6), 3.26 (dq, H-1), 2.02 (m, $CH_2C\underline{H}_2CH_2OH$), 1.22 (d, $C\underline{H}_3CHOH$), 1.10 (d, $1\text{-}CH_3$).

Data for the final product of Example 66 ((1R,5S,6S)-2-[(4-((4-(2-hydroxyethyl)- 1,4-diazoniabicyclo[2.2.2]oct-1-yl)methyl)thieno[3,2-d]thiazol-2-yl)thio]-6-[(1R )-hydroxyethyl]-1-methylcarbapen-2-em-3-carboxylate chloride):

UV (0.1M pH 7.0 MOPS buffer) $\lambda_{max}$ 315 nm ($\epsilon$ 10, 183).

$^1$H NMR ($D_2O$, 500 MHz) δ1.09 (d), 1.22 (d), 3.16 (dd), 3.26 (dq), 3.48 (rid), 3.71 (s), 4.07 (s), 4.20 (m), 4.98 (dd), 8.10 (s).

Data for the final product of Example 67 ((1R,5S,6S)-2-[(4-(( 4-(N,N-dimethyl-carbamoylmethyl)-1,4-diazoniabicyclo[2.2.2]oct- 1yl)methyl )thieno[3,2-d]thiazol-2-yl )thio]-6-[(1R )-hydroxyethyl]- 1-methylcarbapen-2-em-3-carboxylate chloride):

UV (0.1M pH 7.0 MOPS buffer) $\lambda_{max}$ 315 nm ($\epsilon$ 8511 ).

$^1$H NMR ($D_2O$, 500 MHz) δ1.09 (d), 1.22 (d), 2.93 (m), 3.25 (dq), 3.47 (dd), 4.10 (br d), 4.24 (m), 4.61 (s), 4.97 (dd), 8.10 (s).

Data for the final product of Example 68 ((1R,5S,6S)-2-[(4-((4-cyanomethyl- 1,4-diazoniabicyclo[2.2.2]oct-1-yl)methyl)thieno[3,2-d]thiazol-2-yl)thio 1–6-[(1R )-hydroxyethyl]-1-methylcarbapen-2-em-3-carboxylate chloride):

UV (0.1M pH 7.0 MOPS buffer) $\lambda_{max}$ 315 nm ($\epsilon$ 8845).

$^1$H NMR ($D_2O$, 500 MHz) δ1.09 (d), 1.22 (d), 3.26 (dq), 3.47 (dd), 4.10 (br m), 4.18 (t), 4.22 (t), 4.31 (br t), 5.05 (m), 8.11 (s).

Data for the final product of Example 69 ((1R,5S,6S)-2-[(4-(( 4-(N-methylcarbamoyl-methyl)-1,4-diazoniabicyclo[2.2.2]oct- 1-yl)methyl )thieno[3,2-d]thiazol-2-yl)thio]-6-[(1R )-hydroxyethyl]- 1-methylcarbapen-2-em-3-carboxylate chloride):

UV (0.1M pH 7.0 MOPS buffer) $\lambda_{max}$ 315 nm ($\epsilon$ 9263).

$^1$H NMR ($D_2O$, 400 MHz) δ1.13 (d), 1.26 (d), 2.78 (s), 3.31 (dq), 3.51 (dd), 4.10 (br m), 4.24 (br t), 4.28 (d), 4.34 (s), 5.03 (d), 8.14 (s).

Data for the final product of Example 70 ((1R,5S,6S)-2-{5-[( 4-{Morpholin-4-ylcarbonylmethyl}-1,4-diazoniabicyclo[2.2.2]oct- 1-yl)methyl]thieno[3,2-d]thiazol-2-ylthio}-6-[1(R)-hydroxyethyl]- 1-methylcarbapen-2-em-3-carboxylate chloride):

IR (KBr) 2969, 1756, 1654, 1598, 1387; 1274, 1245, 1113, and 849 cm$^{-1}$. UV (0.1M pH 7.0 MOPS buffer) $\lambda_{max}$ 318 nm ($\epsilon$ 11,190).

$^1$H NMR ($D_2O$, 500 MHz) δ1.07 (d, $1\text{-}CH_3$), 1.21 (d, $CH_3CHOH$), 3.25 (dq, H-1 ), 3.42 and 3.55 (two t's, morpholinyl-$NCH_2$), 3.46 (dd, H-6), 3.71 (t, morpholinyl-$OCH_2$), 4.11 and 4.26 (two t's, $N(C\underline{H}_2C\underline{H}_2)_3N$), 4.19 (p $CH_3C\underline{H}OH$), 4.22 (dd, H-5), 4.70 (s, $NCH_2CON$), 4.75 (s, HOD), 4.99 (s, $ArCH_2N$), and 8.10 (s, ArH-5').

$^{13}$C NMR ($D_2O$, 125.7 MHz) δ15.6, 20.0, 41.9, 42.7, 45.0, 51.0, 52.3, 56.0, 59.3, 61.0, 61.8, 64.9, 65.6, 66.0, 115.7, 133.6, 134.5, 136.2, 137.6, 158.0, 161.4, 165.7, 166.7, and 176.8.

Data for the final product of Example 71 ((1R,5S,6S)-2-{5-[(4-{Pyrrolidin-1-ylcarbonylmethyl}-1,4-diazoniabicyclo[2.2.2]oct-1yl)methyl]thieno[3,2-d]thiazol-2-ylthio}-6-[1(R)-hydroxyethyl]-1-methylcarbapen-2-em-3-carboxylate chloride ):

IR (KBr) 2970, 1756, 1648, 1599, 1386, 1283, 1263, 1148, 1058, 1011, 851, 766, 735, and 669 cm$^-$. UV (0.1M pH 7.0 MOPS buffer) $\lambda_{max}$ 319 nm ($\epsilon$ 11,160).

$^1$H NMR ($D_2O$, 500 MHz) δ1.08 (d, $1\text{-}CH_3$), 1.21 (d, $CH_3CHOH$), 1.84 and 1.94 (two p's, pyrrolidinyl 3-$CH_2$+ 4-$CH_2$), 3.25 (dq, H-1), 3.36 and 3.40 (two t's, pyrrolidinyl 2-$CH_2$+5-$CH_2$), 3.47 (dd, H-6), 4.10 and 4.26 (two t's, $N(C\underline{H}_2C\underline{H}_2)_3N$), 4.20 (p $CH_3C\underline{H}OH$), 4.23 (dd, H-5), 4.51 (s, $NCH_2CON$), 4.99 (ABq, $ArCH_2N$), and 8.10 (s, ArH-5').

EXAMPLE 72

(1R,5S,6S)-2-{5-[(4-CARBAMOYLMETHYL-1,4-DIAZONIABICYCLO[ 2.2.2]OCT-1-YL)ACETYL]BENZOTHIAZOL-2-YLTHIO-6-[1(R)-HYDROXYETHYL]-1-METHYLCARBAPEN-2-EM-3-CARBOXYLATE CHLORIDE

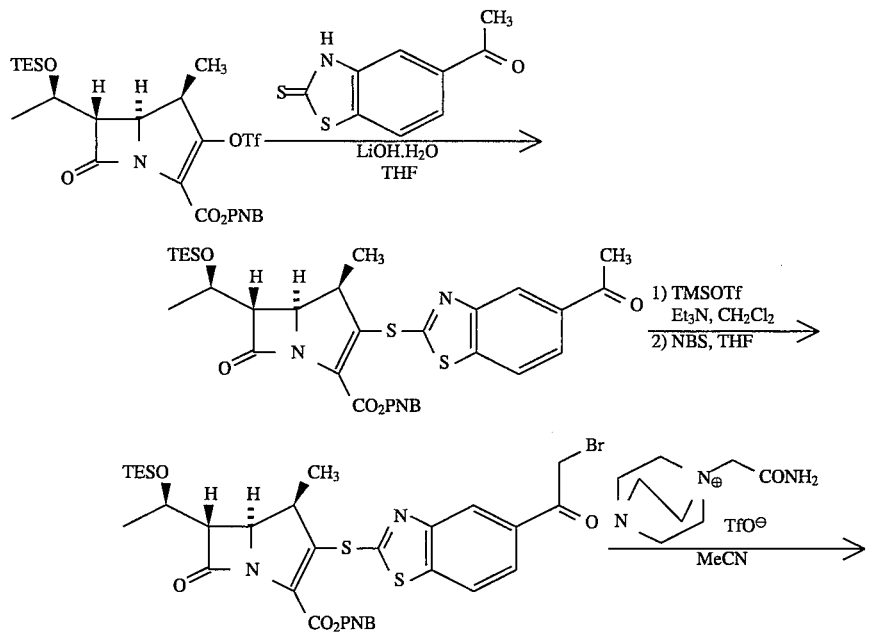

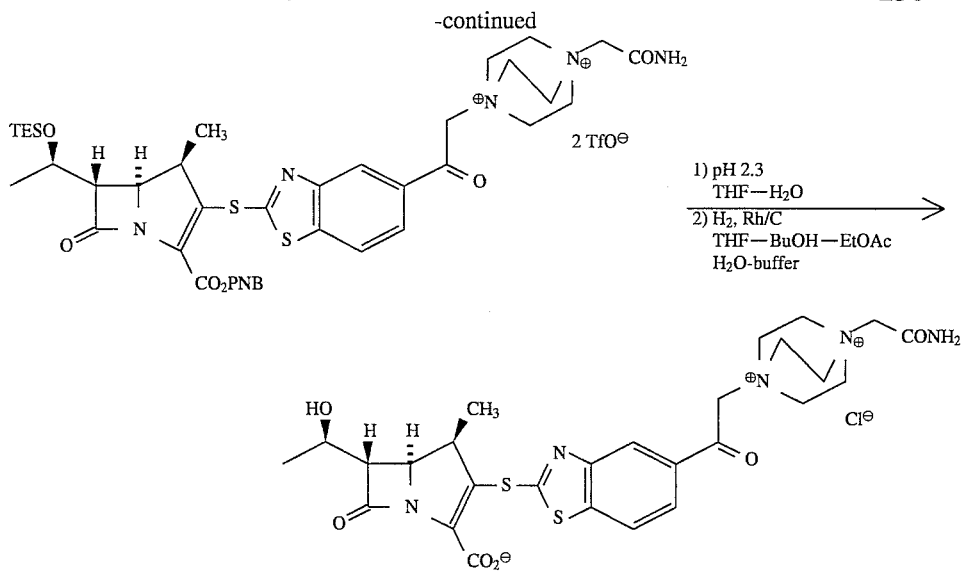

Step 1: p-Nitrobenzyl (1R,5S,6S)-2-(5-acetylbenzothiazol-2-ylthio)-6-] (1R)-(triethylsilyloxy)ethyl]-1-methylcarbapen-2-em-3-carboxylate A mixture of 5-acetyl-2-thioxo-2,3-dihydrobenzothiazole (110 mg, 0.53 mmol), powdered lithium hydroxide monohydrate (26.1 mg, 0.62 mmol) and tetrahydrofuran (4.8 mL) was sonicated a few minutes then stirred room temperature for 5 minutes. Solid p-nitrobenzyl (1R,5R,6S)-2-(trifluoromethylsulfonyl)oxy-6-[(1R)-(triethylsilyloxy)ethyl]-1-methylcarbapen-2-em-3-carboxylate (292 mg, 0.48 mmol) was added and the mixture was stirred at room temperature for 30 minutes. The mixture was diluted with ethyl acetate (50 mL), washed with water (2×25 mL) and brine (25 mL), dried over magnesium sulfate, filtered, and evaporated in vacuo to a gum (290 mg). The crude product was purified by flash chromatography on silica gel (2×12 cm column) using 7:1 dichloromethane-ethyl acetate as eluting solvent. The product containing fractions were evaporated in vacuo to a pale yellow gum which was swirled with ether to provide white crystals. After cooling in ice, the mixture was filtered and the solid portion washed with cold ether and dried in vacuo to afford p-nitrobenzyl (1R,5S,6S)-2-(5-acetylbenzothiazol-2-ylthio)-6-[(1 R)-(triethylsilyloxy)ethyl]- 1-methylcarbapen-2-em-3-carboxylate (175 mg) as a white solid.

IR (KBr) 2957, 2876, 1782, 1711, 1685, 1522, 1340, 1276, 1207, 1144, 983,739 cm⁻.

$^1$H NMR (CDCl$_3$, 500 MHz) δ0.60 (q, CH$_3$CHSi), 0.95 (t, C$\underline{H}^{13}$CH$_2$Si), 1.13 (d, 1-CH$_3$), 1.23 (d, C$\underline{H}^{13}$CHOSi), 2.70 (COCH$_3$), 3.33 (dd, H-6), 3.96 (dq, H-1 ), 4.30 (dq, CH$_3$C$\underline{H}$OSi), 4.45 (dd, H-5), 5.30 and 5.49 (two d's, C$\underline{H}_2$C$_6$H$_4$NO$_2$), 7.66 and 8.21 (two m's, C$_6$H$_4$NO$_2$), 7.90 (d, ArH-7'), 8.03 (dd, ArH-6'), and 8.53(d, ArH-4').

13C NMR (CDCl$_3$, 125.7 MHz) δ4.9, 6.8, 16.3, 22.4, 26.7, 43.1, 55.6, 61.6, 65.3, 65.8, 121.4, 122.9, 123.7, 124.8, 128.2, 129.2, 135.9, 141.3, 142.4, 153.2, 159.9, 174.0, and 197.1

Step 2: p-Nitrobenzyl (1R,5S,6S)-2-[5-(bromoacetyl)benzothiazol-2-ylthio]-6-[(1R)-(triethylsilyloxy)ethyl]-1-methylcarbapen-2-em-3-carboxylate A solution of p-nitrobenzyl (1 R,5S,6S)-2-(5-acetylbenzothiazol- 2-ylthio)-6-[(1R)-(triethylsilyloxy)ethyl]-1-methylcarbapen- 2-em-3-carboxylate (234 mg, 0.35 mmol) and triethylamine (0.086 mL, 0.62 mmol) in dichloromethane (1.75 mL) was cooled in an ice bath, stirred under a nitrogen atmosphere, and treated dropwise over 3 minutes with trimethylsilyl trifluormethanesulfonate (0.102 mL, 0.53 mmol). The resulting solution was stirred at 0–5° C. for 60 minutes then diluted with dichloromethane (20 mL), washed with water (10 mL), dilute aqueous ammonium chloride (10 mL), 5% aqueous sodium bicarbonate (10 mL) and brine. The dichloromethane solution was dried over magnesium sulfate, filtered, and evaporated under vacuum to a foam (247 mg). This material was shown to be a 78:22 mixture of the desired side-chain (trimethysilyl)enolether and side-chain ketone starting material. A solution of the crude silylenolether in anhydrous tetrahydrofuran (1.75 mL) was cooled in an ice bath, stirred under a nitrogen atmosphere, and treated with N-bromosuccinimide (62 mg, 0.35 mmol). The resulting solution was stirred at 0°–5° C. for 60 minutes then diluted with 1:1 ether-ethyl acetate (20 mL), washed with water (10 mL), 5% aqueous sodium bicarbonate (10 mL), and brine (10 mL), dried over magnesium sulfate, filtered, and evaporated in vacuo to a gum (266 mg). The crude product was purified by flash chromatography on silica gel (25 g) using dichloromethane and 0.5–1% ethyl acetate/dichlormethane as eluting solvents. The product containing fractions were evaporated in vacuo to provide p-nitrobenzyl (1R,5S ,6S)-2-[5-(bromoacetyl)benzothiazol-2-ylthio]-6-[( 1R )-(triethylsilyloxy)ethyl]-1-methylcarbapen-2-em-3-carboxylate (171 mg) as a foam.

IR (film) 2955, 2875, 1782, 1703, 1682, 1522, 1339, 1320, 1276, 1210, 1142, 982, and 738 cm⁻¹.

$^1$H NMR (CDCl$_3$, 500 MHz) δ0.61 (q, CH$_3$CH$_2$Si), 0.95 (t, CH$_3$ CH$_2$Si), 1.14 (d, 1-CH$_3$), 1.24 (d, CH$_3$CHOSi), 3.34 (dd, H-6), 3.99 (dq, H-1), 4.30 (p, CH$_3$C$\underline{H}$OSi), 4.46 (dd, H-5), 4.51 (s, CH$_2$Br), 5.31 and 5.49 (two d's, C$\underline{H}_2$C$_6$H$_4$NO$_2$), 7.66 and 8.22 (two m's, C$_6$H$_4$NO$_2$), 7.94 (d, ArH-7'), 8.04 (dd, ArH-6'), and 8.57 (d, ArH-4').

$^{13}$C NMR (CDCl$_3$, 125.7 MHz) δ4.9, 6.8, 16.3, 22.4, 30.4, 43.1, 55.6, 61.6, 65.3, 65.8, 121.8, 123.4, 123.7, 125.3, 128.3, 129.6, 132.6, 140.8, 141.7, 142.4, 153.2, 159.9, 163.2, 174.0, and 190.6.

151

Step 3: p-Nitrobenzyl (1R,5S,6S.)-2-{5-[(4-carbamoylmethyl-1,4-diazoniabicyclo[2.2.2]oct-1-yl)acetyl]benzothiazol-2-ylthio}-6-[1(R)-hydroxyethyl]-1-methylcarbapen-2-em-3-carboxylate bromide trifluoromethanesulfonate A mixture of p-nitrobenzyl (1R,5S,6S)-2-[5-(bromoacetyl)benzothiazol- 2-ylthio]-6-[(1R)-(triethylsilyloxy)ethyl]-1-methylcarbapen- 2-em-3-carboxylate (169 mg, 0.227 mmol) and 1-carbamoylmethyl- 4-aza-1-azoniabicyclo[2.2.2]octane trifluromethanesulfonate (73 mg, 0.229 mmol) in anhydrous acetonitrile (4.5 mL) was sonicated a few minutes to dissolve the DABCO salt then stirred at room temperature. A white precipitaste formed. After 6 hours the mixture was diluted with ether (5 mL), stirred a few minutes, and filtered. The solid was washed with ether and dried under vacuum to afford p-nitrobenzyl (1R,5S,6S)-2-{5-[(4-carbamoylmethyl-1,4-diazoniabicyclo[ 2.2.2]oct-1-yl)acetyl]benzothiazol-2-ylthio}-6-[1(R)-hydroxyethyl]-1-methylcarbapen-2-em-3-carboxylate bromide trifluoromethanesulfonate (88 mg) as a white powder.

IR (KBr) 2958, 1785, 1697, 1608, 1523, 1415, 1380, 1340, 1321, 1276, 1167, 1142, 1031, 1009, 984, 847, 738, and 641 cm$^{-1}$.

$^{1}$H NMR (DMSO-d$_{6}$, 500 MHz) δ0.55 (q, CH$_{3}$CH$_{2}$Si), 0.89 (t, CH$_{3}$CH$_{2}$Si), 1.08 (d, 1-CH$_{3}$), 1.13 (d, CH$_{3}$CHOSi), 3.64 (dd, H-6), 3.83 (dq, H-1), 4.20 (br s, N(CH$_{2}$CH$_{2}$)$_{3}$N), 4.26 (m, CH$_{3}$CHOSi), 4.30 (s, NCH$_{2}$CONH$_{2}$), 4.41 (dd, H-5), 5.38 and 5.47 (two d's, CH$_{2}$C$_{6}$H$_{4}$NO$_{2}$), 7.70 and 8.17 (two d's, C$_{6}$H$_{4}$NO$_{2}$), 7.90 and 8.09 (two br s's, CONH$_{2}$), 8.03 (d, ArH-6'), 8.33 (d, ArH-7'), and 8.63 (s, ArH-4').

Step 4: (1R,5S,6S)-2-{5-[(4—Carbamoylmethyl-1,4-diazoniabicyclo[ 2.2.2]oct-1-yl)acetyl]benzothiazol-2-ylthio -6-[1(R)-hydroxyethyl]- 1-methylcarbapen-2-em-3—Carboxylate chloride A solution of p-nitrobenzyl (1R,5S,6S)-2-{5-[(4-carbamoylmethyl- 1,4-diazoniabicyclo[2.2.2]oct-1 yl)acetyl]benzothiazol-2-ylthio}-6-[1(R)-hydroxyethyl]-1-methylcarbapen- 2-em-3-carboxylate bromide trifluoromethanesulfonate (80 mg, 0.075 mmol) in 2:1 tetrahydrofuran:water (2.3 mL) was stirred at room temperature while the pH of the solution was adjusted to 2.3 by addition of 1M aqueous trifluoromethanesulfonic acid (0.025 mL). The resulting solution was stirred at room temperature for 35 minutes then neutralized by addition of 1M aqueous sodium bicarbonate (0.025 mL). The reaction mixture was added to a mixture of n-butanol (1.5 mL), ethyl acetate (0.7 5 mL), 1M pH 7 phosphate buffer (0.4 mL), and water(1.9 mL). 5% Rhodium on carbon (16 mg) was added and the resulting mixture was cooled in an ice-water bath at 7° C. and stirred under a hydrogen atmosphere for 80 minutes. The lower aqueous phase o was separated and filtered through a tetrahydrofuran/water washed pad of Celite. The upper organic phase was extracted with water (2×1 mL) and the extracts were used to wash the filter pad. The combined aqueous filtrate was diluted with water (5 mL), washed with 1:1 ether-ethyl acetate (2×5 mL), and concentrated in vacuo to 5 mL volume. The aqueous solution was loaded onto a column of Bio-Rad Macro-Prep CM resin (3 mL) and the column eluted with water (15 mL) followed by 5% aqueous sodium chloride (10×1.5 mL fractions). The product-containing, sodium chloride fractions 3–7 were cooled in ice then loaded onto a column of TosoHaas Amberchrom CG-161 resin (3 mL). The column was eluted with ice-cold water (15 mL) followed by 20% aqueous isopropanol (3×3 mL fractions). The second isopropanol fraction was diluted with water, concentrated in vacuo to 2.5 mL volume, and lyophilized to afford (1R,5S,6S)-2-{5-[(4-carbamoylmethyl- 1,4-diazoniabicyclo[2.2.2]oct-1 yl)acetyl]benzothiazol-2-ylthio}-6-[1(R)-hydroxyethyl]-1-methylcarbapen-2-em-3-carboxylate chloride (20 mg) as an off-white, amorphous solid.

IR (KBr) 2969, 1761, 1696, 1597, 1460, 1387, 1278, 1254, 1140, 1076, 990, 845, 816, and 643 cm$^{-1}$. UV (0.1M pH 7.0 MOPS buffer) λ$_{max}$ 292.5 nm (ε 21,010) and 260.5 nm (ε 24,420).

$^{1}$H NMR (D2O, 500 MHz) δ1.08 (d, 1-CH$_{3}$), 1.22 (d, CH$_{23}$CHOH), 3.49 (dq, H-1 ), 3.53 (dd, H-6), 4.22 (p, CH$_{3}$CHOH), 4.32 (dd, H-5), 4.35–4.46 (m, N(CH$_{2}$CH$_{2}$)$_{3}$N), 7.94 (dd, ArH-6'), 8.06 (d, ArH-7'), and 8.37 (d, ArH-4'). ArCOCH$_{2}$N and NCH$_{2}$CONH$_{2}$ are not visible due to D-exchange.

EXAMPLES 73–76

By appropriately modifying the procedure of Steps 3 and 4 of Example 72, p-nitrobenzyl (1R,5S,6S)-2-[5-(bromoacetyl)benzothiazol- 2-ylthio]-6-[(1R)-(triethylsilyloxy)ethyl]-1-methylcarbapen- 2-em-3-carboxylate (compound A4) is reacted with compound Q* as set forth in the following Table to produce compounds of formula IIa in which Het is as defined in the following Table and X$^{-}$ a pharmaceutically acceptable counterion.

TABLE

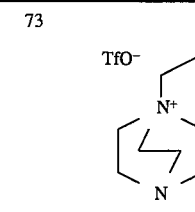

| Ex. # | Q* | Het (of Product IIa) |
|---|---|---|
| 73 | 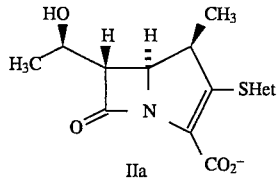 | |

TABLE-continued

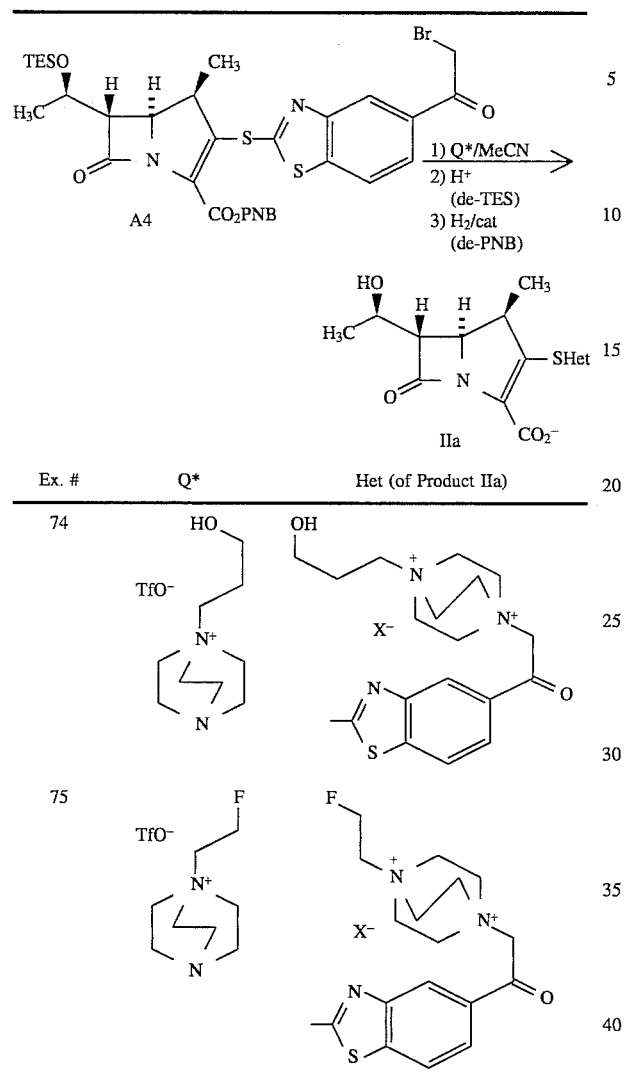

| Ex. # | Q* | Het (of Product IIa) |
|---|---|---|
| 74 | (HO-propyl-N+ quinuclidinium, TfO−) | (HO-propyl-N+-CH2CH2CH2-N+-CH2-C(O)-benzothiazol-2-yl-methyl, X−) |
| 75 | (F-ethyl-N+ quinuclidinium, TfO−) | (F-ethyl-N+-CH2CH2CH2-N+-CH2-C(O)-2-methylbenzothiazol-5-yl, X−) |

TABLE-continued

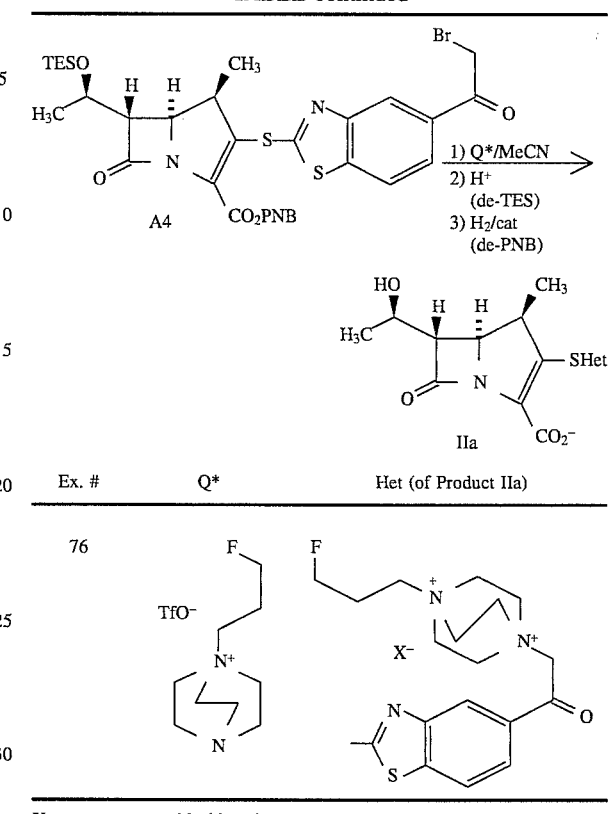

| Ex. # | Q* | Het (of Product IIa) |
|---|---|---|
| 76 | (F-propyl-N+ quinuclidinium, TfO−) | (F-propyl-N+-CH2CH2CH2-N+-CH2-C(O)-2-methylbenzothiazol-5-yl, X−) |

X− represents a chloride anion.

EXAMPLES 77–163

By appropriately modifying the procedures of Examples 1 compounds A1, LiSHet* and Q* as set forth in the following Table are reacted to produce compounds of formula Ia in which Het is as defined in the following Table and X− is a pharmaceutically acceptable counterion.

TABLE

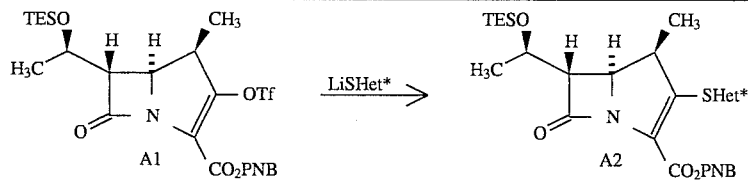

TES = triethylsilyl
PNB = p-nitrobenzyl

1) Tf2O
2) Q*
   or
1) MsCl, base
2) Q*
   or
1) MsCl, base
2) NaI or KI
3) Q*, AgOTf TABLE-continued
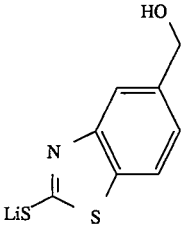

5,496,816

TABLE-continued

| | | | |
|---|---|---|---|
| 82 | (structure with OH, benzothiazole, LiS) | H₂N-C(O)-O-CH₂CH₂CH₂-N⁺(DABCO), TfO⁻ | H₂N-C(O)-O-CH₂CH₂CH₂-N⁺...N⁺-CH₂CH₂-(2-methylbenzothiazole), X⁻ |
| 83 | (structure with OH, benzothiazole, LiS) | H₂N-C(O)-O-CH₂CH₂-N⁺(DABCO), TfO⁻ | H₂N-C(O)-O-CH₂CH₂-N⁺...N⁺-CH₂CH₂-(2-methylbenzothiazole), X⁻ |
| 84 | (structure with OH, benzothiazole, LiS) | H₂N-C(O)-NH-CH₂CH₂-N⁺(DABCO), TfO⁻ | H₂N-C(O)-NH-CH₂CH₂-N⁺...N⁺-CH₂CH₂-(2-methylbenzothiazole), X⁻ |
| 85 | (structure with OH, benzothiazole, LiS) | CH₃CH₂-S(O)-CH₂-N⁺(DABCO), TfO⁻ | H₃C-CH₂-S(O)-CH₂-N⁺...N⁺-CH₂CH₂-(2-methylbenzothiazole), X⁻ |
| 86 | (structure with OH, benzothiazole, LiS) | H₃C-S(O)₂-CH₂CH₂-N⁺(DABCO), TfO⁻ | CH₃-S(O)₂-CH₂CH₂-N⁺...N⁺-CH₂CH₂-(2-methylbenzothiazole), X⁻ |
| 87 | (structure with OH, benzothiazole, LiS) | Ph-S(O)₂-CH₂-N⁺(DABCO), TfO⁻ | Ph-S(O)₂-CH₂-N⁺...N⁺-CH₂CH₂-(2-methylbenzothiazole), X⁻ |

TABLE-continued
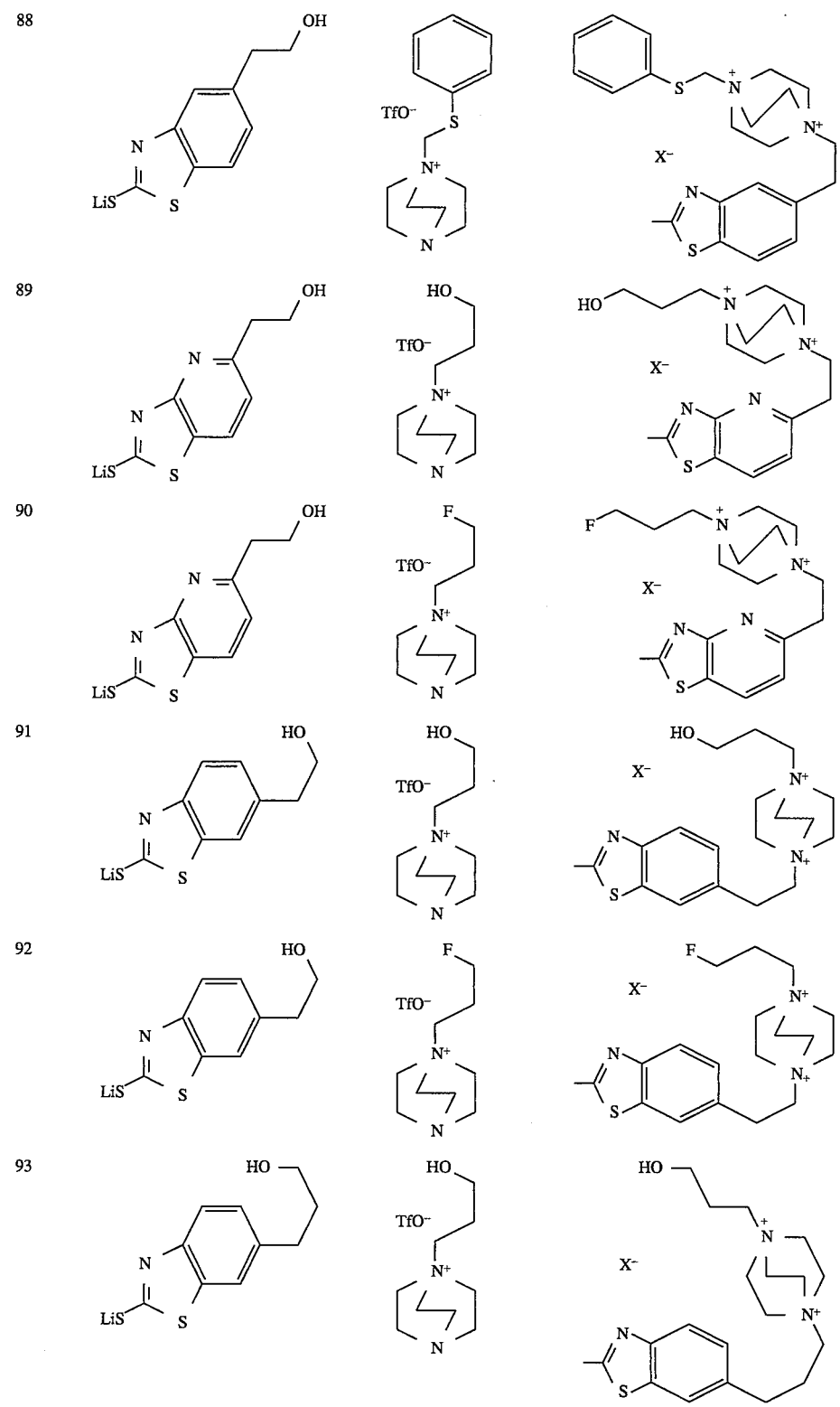

TABLE-continued
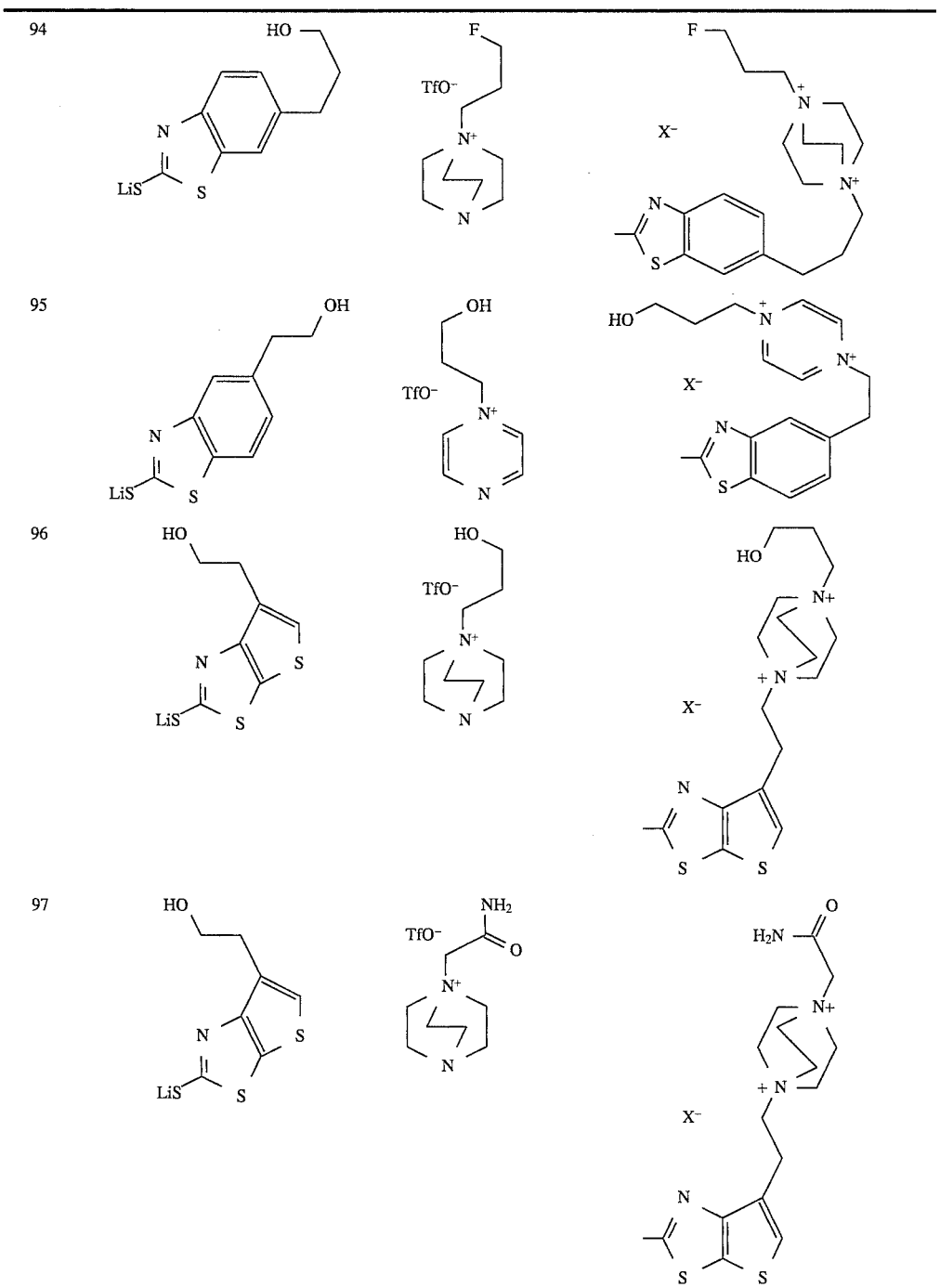

TABLE-continued

TABLE-continued
| | | | |
|---|---|---|---|
| 103 | 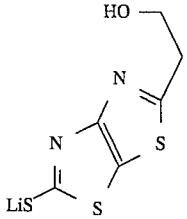 | 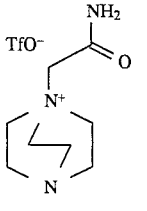 | 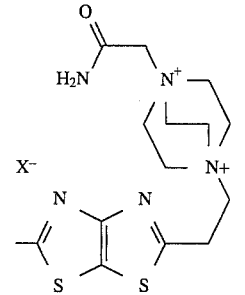 |
| 104 | 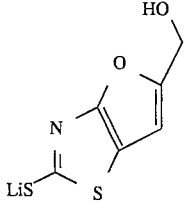 | 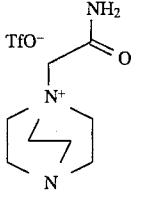 | 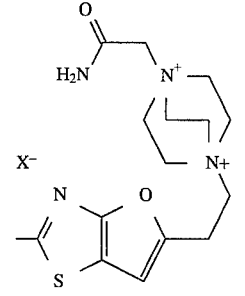 |
| 105 | 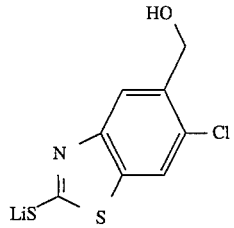 | 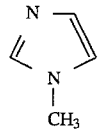 | 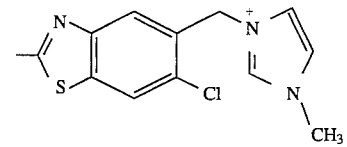 |
| 106 | 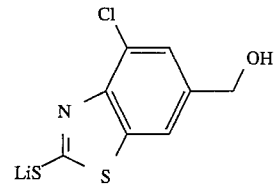 | 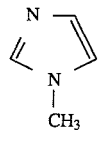 | 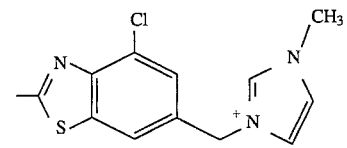 |
| 107 | 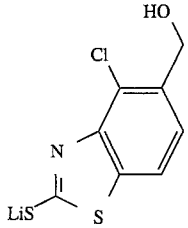 | 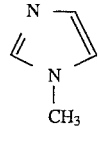 | 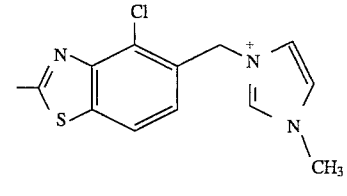 |
| 108 | 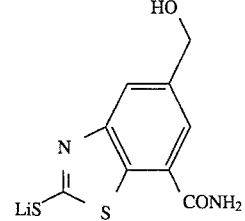 | 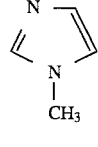 | 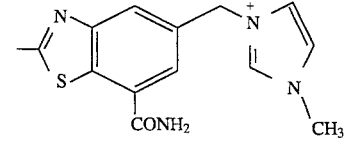 |

TABLE-continued

TABLE-continued

TABLE-continued 5,496,816
173                                                                                                   174
TABLE-continued
| 129 | 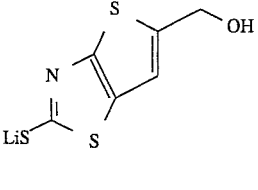 | 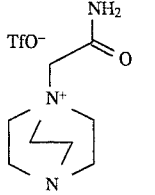 | 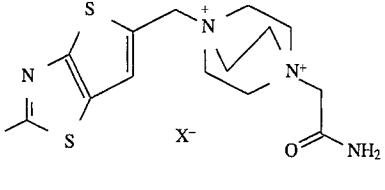 |
| 130 | 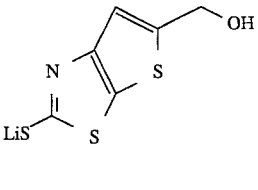 | 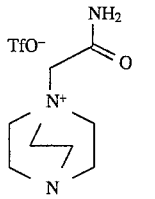 | 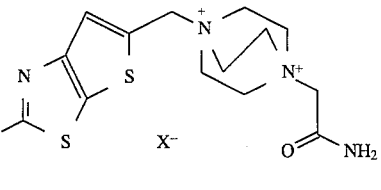 |
| 131 | 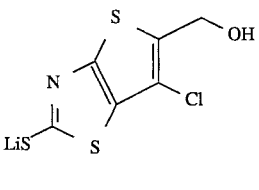 | 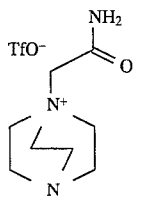 | 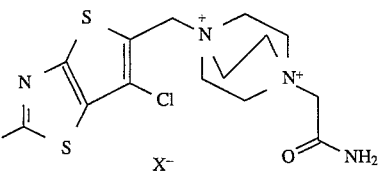 |
| 132 | 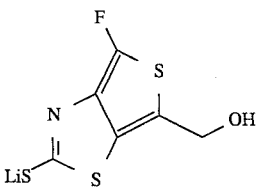 | 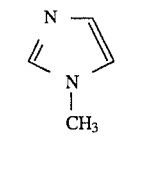 | 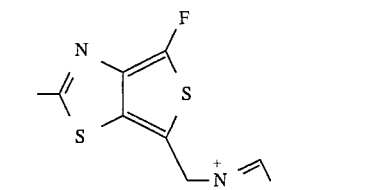 |
| 133 | 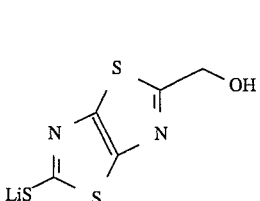 | 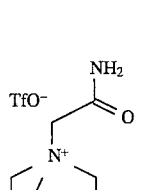 | 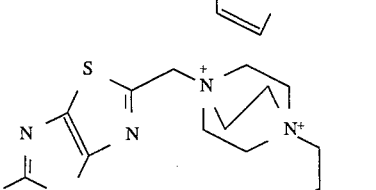 |
| 134 | 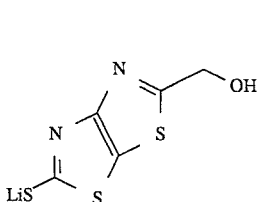 | 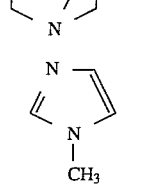 | 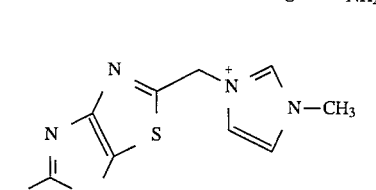 |
| 135 | 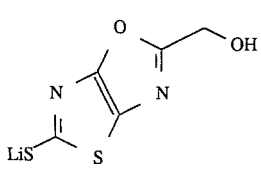 | 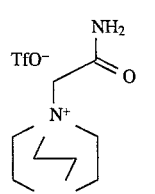 | 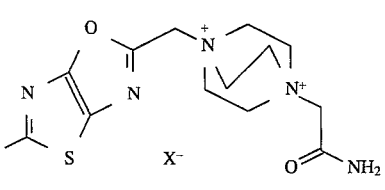 |
| 136 | 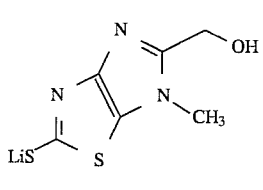 | 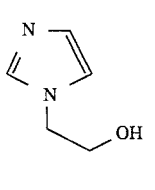 | 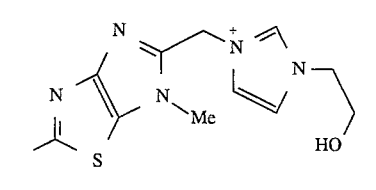 |

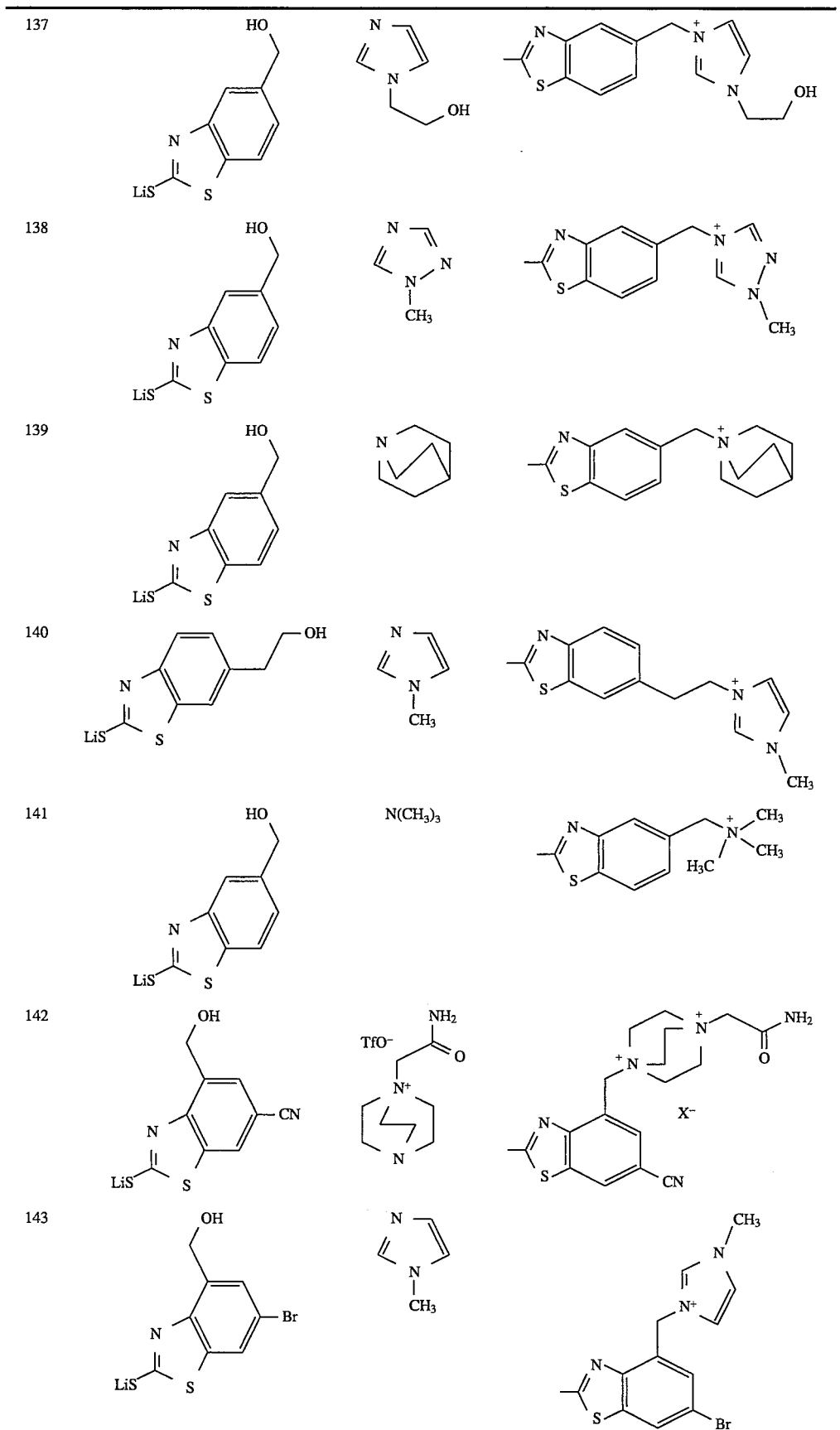

TABLE-continued

TABLE-continued
| | | | |
|---|---|---|---|
| 150 | 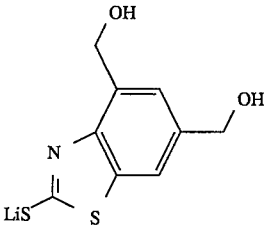 | N(CH₃)₃ | 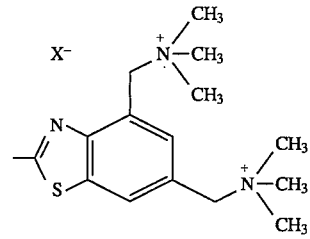 |
| 151 | 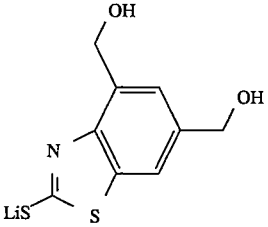 | 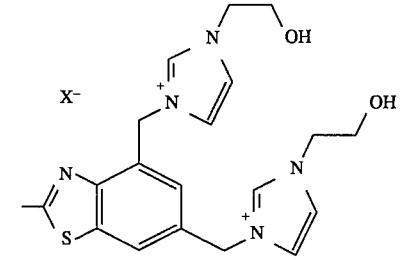 | 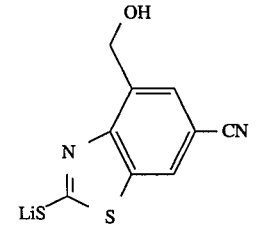 |
| 152 | 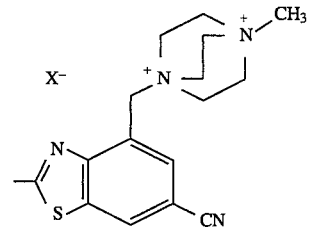 | 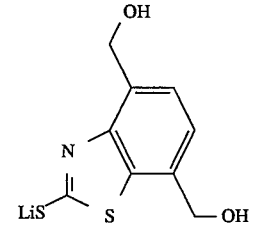 | 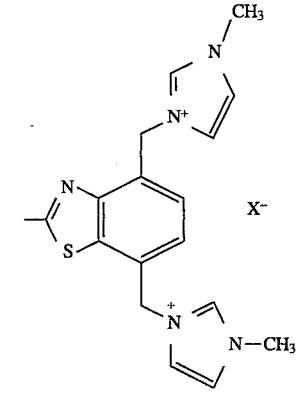 |
| 153 | 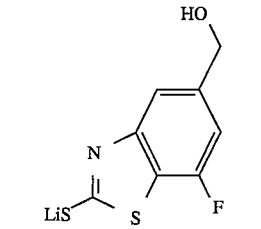 | 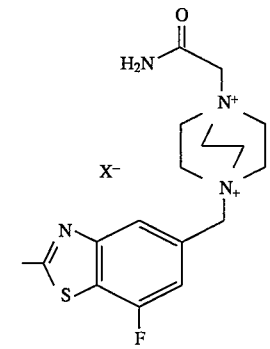 | |
| 154 | | | |

TABLE-continued

| # | | | |
|---|---|---|---|
| 155 | (2-imino-benzothiazole with CH2OH, F substituents, LiS) | TfO⁻ salt of DABCO-CH2C(O)NH2 | X⁻ salt of bis-DABCO linked to 2-methyl-6-fluoro-benzothiazol-4-ylmethyl, with CH2C(O)NH2 |
| 156 | (analogous with CF3) | same | 2-methyl-6-CF3-benzothiazole analog |
| 157 | (analogous with SO2NH2) | same | 2-methyl-6-SO2NH2-benzothiazole analog |
| 158 | (analogous with CONH2) | same | 2-methyl-6-CONH2-benzothiazole analog |
| 159 | (pyridine analog) | same | 2-methyl-thiazolo[pyridine] analog |

TABLE-continued
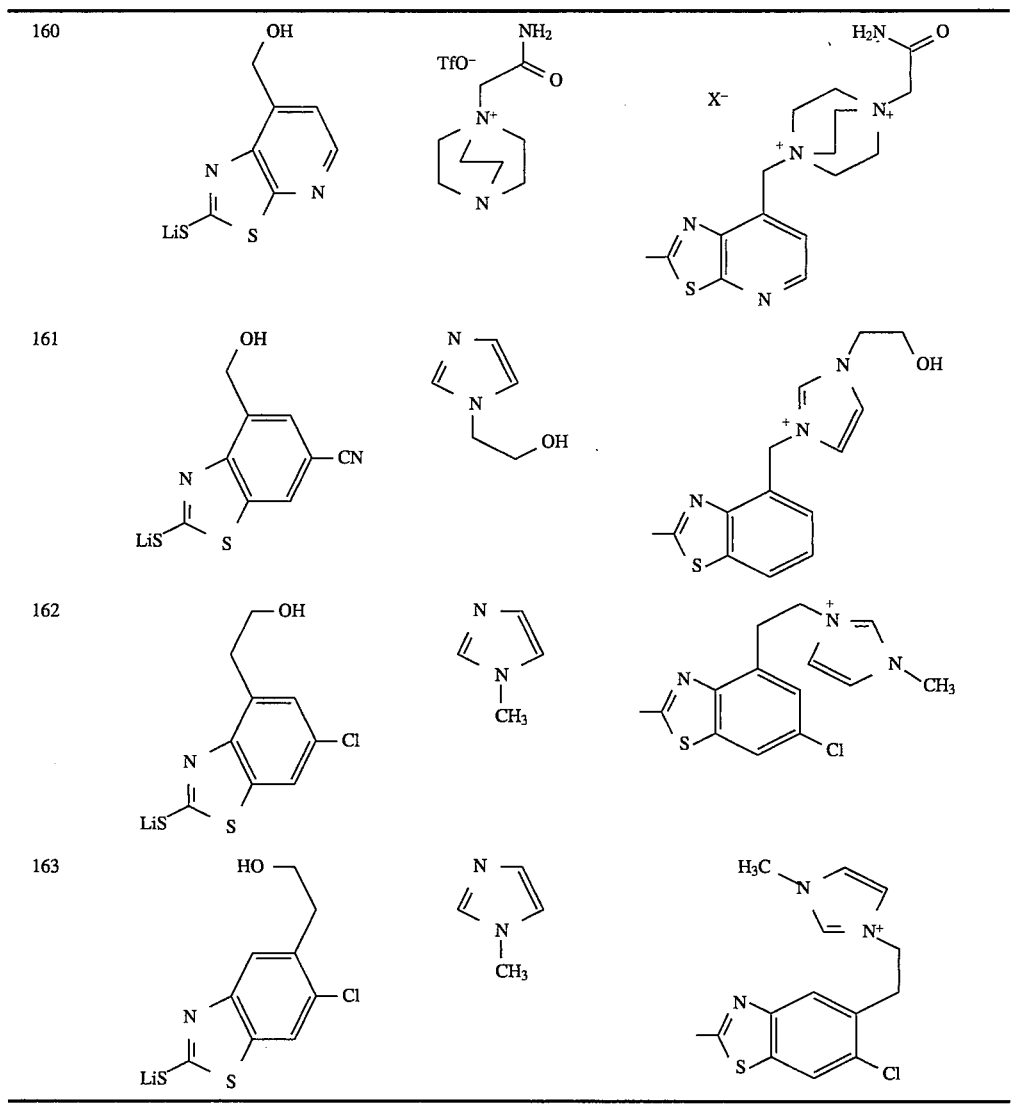
X⁻ represents a chloride anion.
EXAMPLES 164–167
By appropriately modifying the procedures of Examples 1–71 compounds A1, LiSHet* and Q* as set forth in the following Table are reacted to produce compounds of formula Ia in which Het is as defined in the following Table and X⁻ is a pharmaceutically acceptable counterion.

TABLE
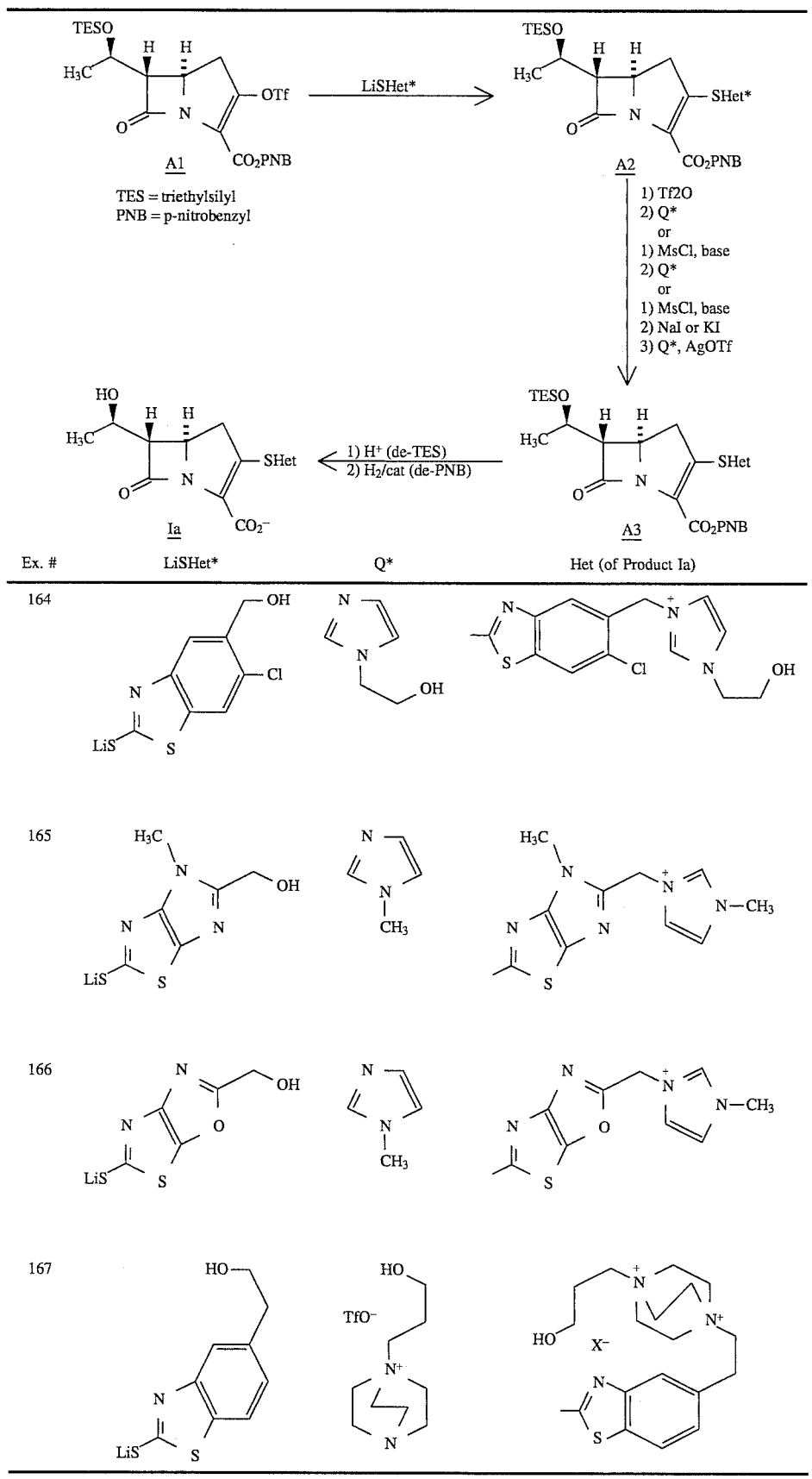

EXAMPLE 168

(1R,5S,6S)-2-(5-((1,3-DIMETHYL)IMIDAZOL-2-IUM)BENZOTHIAZOL-2-YL)THIO-6-[(1R)-HYDROXYETHYL]-1-METHYLCARBAPEN-2-EM-3-CARBOXYLATE

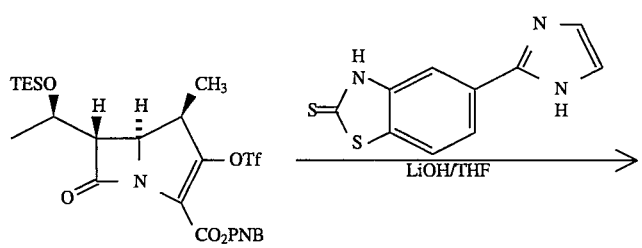

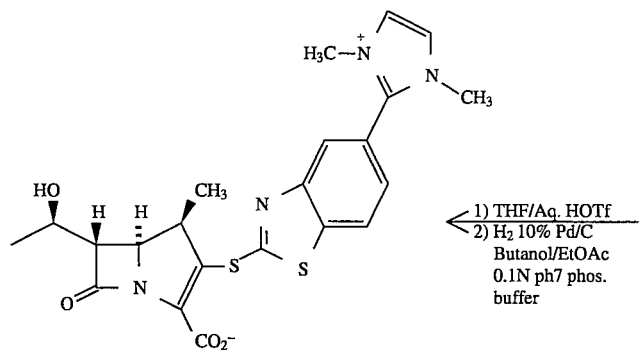

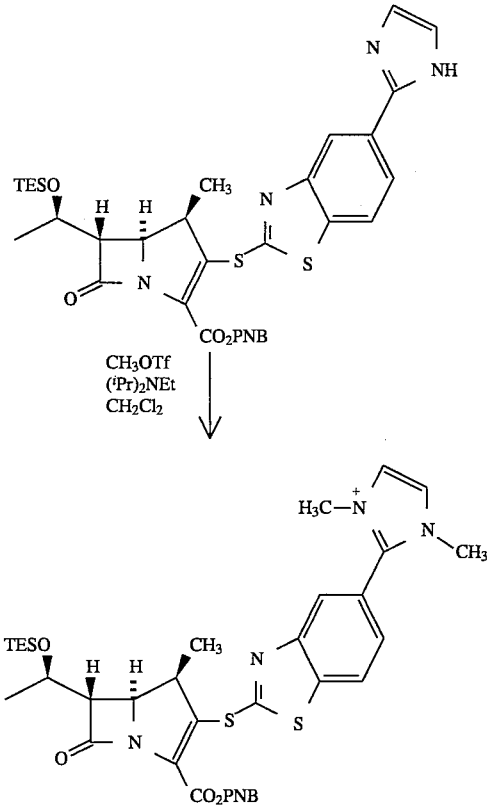

Step 1: p-Nitrobenzyl (1R,5S,6S)-2-(5-(imidazol-2-yl)benzothiazol-2-yl)thio- 6-[(1R )-((triethyl)silyl)oxyethyl]-1-methylcarbapen-2-em-3-carboxylate A solution of 5-(imidazol-2-yl)-2-thioxo-2,3-dihydrobenzothiazole (50 mg, 0.214 mmol), p-Nitrobenzyl (1R,5R,6S)-2-(trifluoromethanesulfono)oxy- 6-[(1R)-((triethyl)silyl)oxyethyl]-1-methylcarbapen- 2-em-3-carboxylate (130 mg, 0.214 mmol) and powdered lithium hydroxide monohydrate (0.01 1 g, 0.257 mmol) in tetrahydrofuran (2 mL) was stirred for 1 hour at room temperature. The mixture was partitioned between methylene chloride (10 mL) and water (10 mL). The aqueous layer was re-extracted with more methylene chloride (3×10 mL), and the combined methylene chloride extracts were dried with magnesium sulfate, were filtered and evaporated to an oil (0.13 g). The oil was chromatographed on preparative silica plates (2×1000 micron, 5% methanol/methylene chloride, 20×20cm). The product band was removed, eluted with 5% methanol/methylene chloride and evaporated to give the title compound as a clear oil (58 mg).

$^1$H NMR (CDCl$_3$, 500 MHz) δ0.61 (q, Si(CH$_2$CH$_3$)$_3$, 0.94 (t, Si(CH$_2$CH$_3$)$_3$, 1.12 (d, 1-CH$_3$), 1.22 (d, CH$_3$CHOH), 3.33 (dd, H-6), 3.86 (dq, H-1), 4.30 (p, CH$_3$CHOH), 4.41 (dd, H-5), 5.29 and 5.47 (two d's, CH$_2$C$_6$H$_4$NO$_2$), 7.20 (s, 2ImH), 7.64 and 8.20 (two m's, CH$_2$ C$_6$H$_4$NO$_2$), 7.80 (d, Ar7'H), 8.00 (dd, Ar6'H) and 8.39 (d, Ar4'H).

Step 2: p-Nitrobenzyl (1R,5S,6S)-2-(5-(1,3-dimethyl)imidazol- 2-ium)benzothiazol-2-yl)thio-6-[(1R)-((triethyl)silyl)oxyethyl]- 1-methylcarbapen-2-em-3-carboxylate trifluoromethanesulfonate p-Nitrobenzyl (1R,5S,6S)-2-(5-(imidazol-2-yl)benzothiazol- 2-yl)thio-6-[(1R )-((triethyl)silyl)oxyethyl]-1-methylcarbapen- 2-em-3-carboxylate (58 mg, 0.084 mmol) and diisopropylethylamine (0.016 mL, 0.092 mmol) were dissolved in methylene chloride (3 mL) trader a nitrogen atmosphere. The mixture was cooled in an ice bath and was treated with methyl trifluoromethanesulfonate (0.019 mL, 0.168 mmol). After 20 minutes, an additional amount of methyl trifluoromethanesulfonate (0.005 mL, 0.044 mmol) was added and 7 minutes later the mixture was removed from the cooling bath and allowed to warm to room temperature. After a total of 34 minutes, the clear solution was partitioned between methylene chloride (10 mL) and 0.1N pH$_7$ potassium phosphate buffer (20 mL). The methylene chloride layer was washed again with 0.1N pH7 potassium phosphate buffer (20 mL), was dried with magnesium sulfate, filtered and evaporated to give the title compound as a white solid (67 mg).

$^1$H NMR (CDCl$_3$, 500 MHz) δ0.60 (q, Si(CH$_2$CH$_3$)$_3$, 0.94 (t, Si(CH$_2$CH$_3$)$_3$, 1.17 (d, 1-CH$_3$), 1.23 (d, CH$_3$CHOH), 3.38 (dd, H-6), 3.83 (s, 2Me), 4.03 (dq, H-1), 4.32 (p, CH$_3$CHOH), 4.50 (dd, H-5), 5.31 and 5.49 (two d's, CH$_2$C$_6$H$_4$NO$_2$), 7.65 (s, 2ImH), 7.67 and 8.21 (two m's, CH$_2$C$_6$H$_4$NO$_2$), 7.70 (dd, Ar6'H), 8.14 (d, Ar7'H) and 8.16 (d, Ar4'H).

Step 3: (1R,5 S, 6 S )-2-(5-( (1,3-dimethyl)imidazol-2-ium)benzothiazol-2-yl)thio-6-[(1R)-hydroxyethyl]-1-methylcarbapen-2-em-3-carboxylate The pH of a solution of p-nitrobenzyl (1 R,5S,6S)-2-(5-(1,3-dimethyl)imidazol- 2-ium)benzothiazol-2-yl)thio-6-[(1R)-((triethyl)silyl)oxyethyl]- 1-methylcarbapen-2-em-3-carboxylate trifluoromethanesulfonate (67 mg, 0.077 mmol)

in a mixture of tetrahydrofuran (1 mL) and water (0.5 mL), was adjusted to 2.3 with 1N aqueous trifluoromethanesulfonic acid. After stirring for 60 minutes at room temperature, the pH was adjusted to 6 with 1.0M aqueous sodium bicarbonate. Butanol (1 .5 mL), ethyl acetate (1 mL), and 0.1N pH₇ potassium phosphate buffer (4 mL) were added and the rapidly stirred mixture was hydrogenated (atmospheric pressure) in the presence of 10% palladium on carbon (20 mg). After 120 minutes, the s mixture was filtered through a pad of solka-floc, the aqueous layer was removed and the organic layer was extracted with water (1×5 mL). The combined aqueous layers were sparged with nitrogen and the volatile organics were evaporated under vacuum. The aqueous layer (ca. 5 mL) was loaded onto an amberchrom 161 column (5 mL), and the column was washed with water (5×5 mL) and then eluted with 20% isopropanol/water (5×5 mL). Fractions 1–3 were combined, evaporated and freeze-dried to give the title compound as a white solid (29 mg).

UV (water) $\lambda_{max}$ 314 nm ($\epsilon$ 13,900).

$^1$H NMR (D$_2$O, 500 MHz) $\delta$1.03 (d, 1-CH$_3$), 1.21 (d, CH$_3$CHOH), 3.49 (dq, H-1 ), 3.50 (dd, H-6), 3.71 (s, 2ImMe), 4.21 (p, CH$_3$CHOH), 4.32 (dd, H-5), 7.53 (s, 2ImH), 7.49 (s, ImH), 7.54 (dd, Ar6'H), 8.00 (d, Ar7'H) and 8.13 (d, Ar4 'H).

EXAMPLES 169–173

By appropriately modifying the procedures of Examples 1– 71 compounds A1, LiSHet* and Q* as set forth in the following Table were reacted to produce compounds of formula Ia in which Het is as defined in the following Table and X⁻ is as defined in the comments accompanying the table.

TABLE

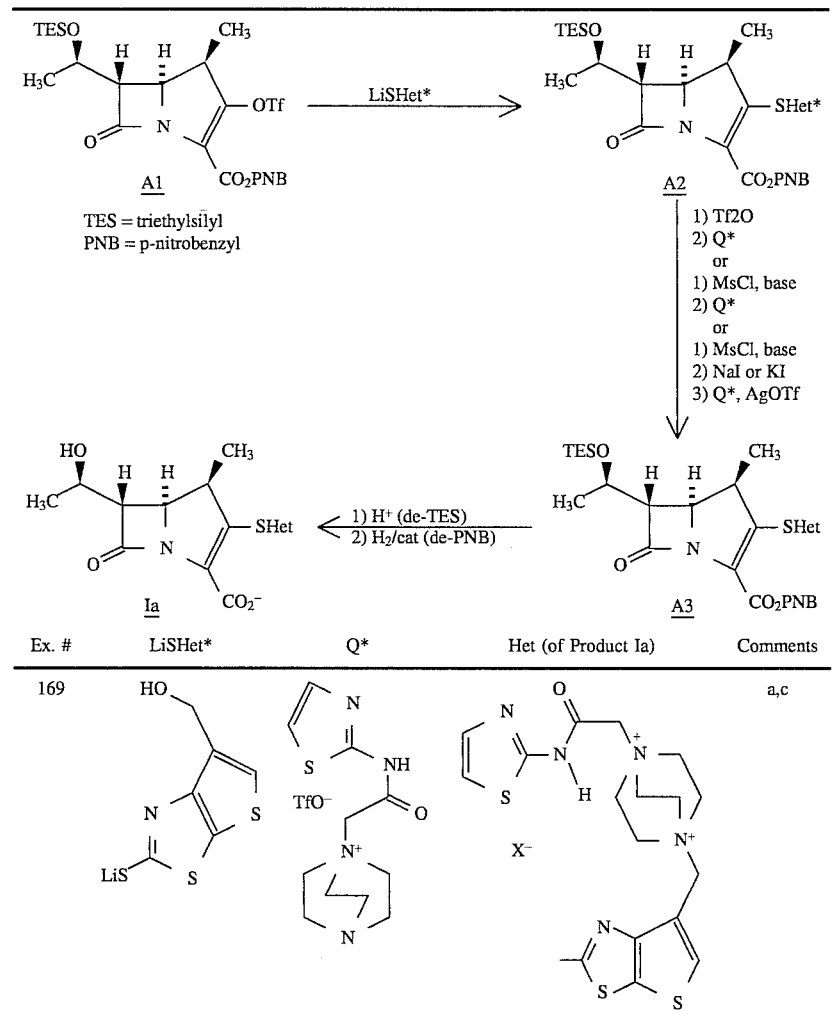

TABLE-continued

TES = triethylsilyl
PNB = p-nitrobenzyl

| Ex. # | LiSHet* | Q* | Het (of Product Ia) | Comments |
|---|---|---|---|---|
| 170 | | | | b,c |
| 171 | | | | b,c |
| 172 | | | | b,d |

TABLE-continued

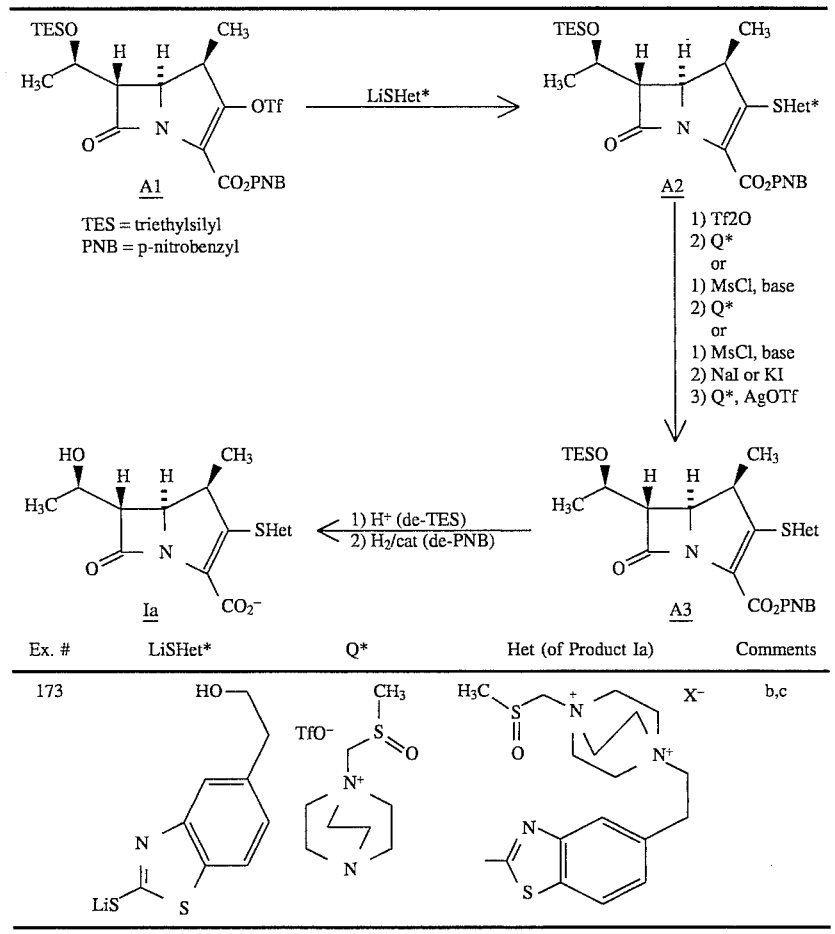

a) The final product was obtained as a mixture of chloride and trifluormethanesulfonate salts (X = a mixture of Cl & TfO) following purification on TosoHaas Amberchrom ® CG-161 resin.
b) The final product was obtained as the chloride salt (X = Cl) by ion exchange chroatography on Bio-Rad Macro-Prep CM resin followed by desalting on TosoHaas Amberchrom CG-161 resin (see Step 2 of Example 2 for details).
c) Hydrochloric acid was used in the step which removes the TES hydroxyl-protecting group.
d) Trifluoromethanesulfonic acid was used in the step which removes the TES hydroxyl-protecting group.

Data for the final product of Example 169 ((1R,5S,6S)-2-{4-[(4-(-N- 2-thiazolyl)-carbamoylmethyl-1,4-diazoniabicyclo[2.2.2]oct- 1-yl)methyl]thienothiazol-2-ylthio}-6-[1(R)-hydroxyethyl]- 1-methylcarbapen-2-em-3-carboxylate chloride/trifluoromethanesulfonate): UV (0.1M pH 7.0 MOPS buffer) $\lambda_{max}$ 292 nm ($\epsilon$ 17900).

$^1$H NMR (D$_2$O, 500 MHz) 5 1.09 (d), 1.20 (d), 3.24 (d), 4.12 (d), 4.20 (m), 4.28 (br s), .4.45 (d), 5.00 (dd), 7.14 (d), 7.42 (d), 8.11 (s).

Data for the final product of Example 170 ((1R,5S,6S)-2-{4-[(4-(-N- 2(1-methyl-imidazolyl))-carbamoylmethyl-1,4-diazoniabicyclo[2.2.2]oct-1-yl)methyl]thienothiazol-2-ylthio}-6-[1(R)-hydroxyethyl]-1-methylcarbapen- 2-em-3-carboxylate chloride):

UV (0.1M pH 7.0 MOPS buffer) $\lambda_{max}$ 310 nm ($\epsilon$ 8087).

$^1$H NMR (D$_2$O, 500 MHz) $\delta$1.09 (d), 1.22 (d), 3.25 (dq), 3.47 (dd), 4.05 (s), 4.22 (m), 4.89 (s), 4.97 (dd), 7.16 (s), 7.28 (s), 8.09 (s).

Data for the final product of Example 171 ((1R,5S,6S)-2-{5-[(4-(3-cyclopentoxy- 2(S)-hydroxy-propyl)-1,4-diazoniabicyclo[2.2.2]oct-1-yl)methyl]benzothiazol-2-ylthio}-6-[1(R)-hydroxyethyl]-1-methylcarbapen- 2-em-3-carboxylate chloride):

UV (0.1M pH 7.0 MOPS buffer) $\lambda_{max}$ 315 nm ($\epsilon$ 12,967).

$^1$H NMR (DMSO-d6, 500 MHz) $\delta$1.03 (d), 1.42–1.70 (m), 3.15–2.60 (m), 3.78 (dq), 3.95–4.20 (m), 4.30 (m), 4.60 (m), 5.03 (m), 6.22 (m), 7.38 (d), 7.81 (s), 7.96 (d).

Data for the final product of Example 172 ((1R,5S,6S)-2-{5-[(4-( 3,3,3-trifluoropropyl)-1,4-diazoniabicyclo[2.2.2]oct-1-yl)methyl]benzothiazol-2-ylthio}-6-[1(R)-hydroxyethyl]-1-methylcarbapen- 2-em-3-carboxylate chloride):

UV (water) $\lambda_{max}$ 318 nm ($\epsilon$ 12,700).

1H NMR (D$_2$O, 500 MHz) $\delta$0.91 (d, 1-CH$_3$), 1.16 (d, CH$_3$CHOH), 3.00 (m, CH$_2$CH$_2$CF3), 3.26 (dq, H-1 ), 3.31 (m, CH$_2$CH$_2$Ar), 3.42 (dd, H-6), 3.89 (m, CH$_2$CH$_2$CF3), 3.90 (m, CH$_2$CH$_2$Ar), 4.10 (dd, H-5), 4.13 (p, CH$_3$CHOH), 4.15 (m, N(CH$_2$CH$_2$)$_3$N), 7.29 (dd, Ar5'H), 7.62 (d, Ar4'H) and 7.73 (d, Ar6'H).

Data for the final product of Example 173 ((1R,5S,6S)-2-{5-[(4-(methylsulfonylmethyl)- 1,4-diazoniabicyclo[2.2.2]oct-1-yl)methyl]benzothiazol-2-ylthio}-6-[1(R)-hydroxyethyl]-1-methylcarbapen- 2-em-3-carboxylate chloride):

UV (0.1M pH 7.0 MOPS buffer) $\lambda_{max}$ 318 nm ($\epsilon$ 13,600).

$^1$H NMR (D$_2$O, 500 MHz) $\delta$0.87 (d), 1.12 (d), 2.93 (s), 2.96 (s), 3.18 o (dq), 3.31 (m), 3.36 (dd), 3.93 (m), 4.03 (dd), 4.12 (m), 4.25 (m), 4.41 (m), 5.02 (s), 5.03 (s), 7.28 (d), 7.61 (s), 7.66 (d).

What is claimed is:

1. A compound or a pharmaceutically acceptable salt thereof represented by formula I:

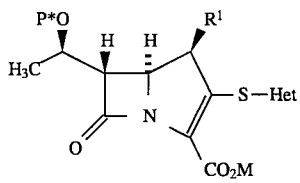

wherein:

$R^1$ represents H or methyl;

$CO_2M$ represents a carboxylic acid, a carboxylate anion, a pharmaceutically acceptable ester group or a carboxylic acid protected by a protecting group;

P* represents H or a hydroxyl protecting group;

Het has substituent groups which contain from one to three positively charged atoms and is selected from:

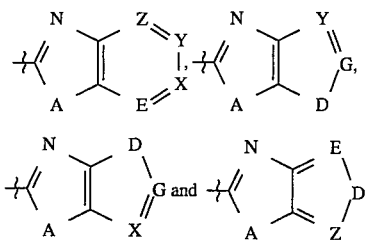

wherein:

A is O or S;

D is O, S or $NR^a$;

E, G, X, Y and Z represent CR or N;

each R is independently selected from: —R*; hydrogen; halo; —CN; —$NO_2$; —$OR^c$; —$SR^c$; —$CONR^aR^b$; —$COOR^h$; —$SOR^c$; —$SO_2R^c$; —$SO_2NR^aR^b$; —$NR^aSO_2R^b$; —$COR^a$; —$OCOR^a$; —$OCONR^aR^b$; —$NR^aCONR^bR^c$; —$NR^aCO_2R^h$; —$OCO_2R^h$; —$C_{1-6}$ straight- or branched-chain alkyl, unsubstituted or substituted with one to four $R^d$ groups; and —$C_{3-7}$ cycloalkyl, unsubstituted or substituted with one to four $R^d$ groups, $R^a$, $R^b$ and $R^c$ represent hydrogen, —$C_{1-6}$ straight- or branched-chain alkyl, unsubstituted or substituted with one to four $R^d$ groups; —$C_{3-7}$ cycloalkyl, unsubstituted or substituted with one to four $R^d$ groups; or -R * or $R^a$ and $R^b$ taken together with any intervening atoms represent a 4–6 membered saturated ring optionally interrupted by one or more of O, S, $NR^c$, with $R^c$ as defined above, or —C(O)—, said ring being unsubstituted or substituted with one to four $R^i$ groups;

or $R^b$ and $R^c$ taken together with any intervening atoms represent a 4–6 membered saturated ring optionally interrupted by one to three of O, S, $NR^a$, with $R^a$ as defined above, or —C(O)—, said ring being unsubstituted or substituted with one to four $R^i$ groups;

each $R^d$ independently represents halo; —CN; —$NO_2$; —$NR^eR^f$; —$OR^g$; —$SR^g$; —$CONR^eR^f$; —$COOR^g$; —$SOR^g$; —$SO_2R^g$; —$SO_2NR^eR^f$; —$NR^eSO_2R^f$; —$COR^e$; —$NR^eCOR^f$; —$OCOR^e$; —$OCONR^eR^f$; —$NR^eCONR^fR^g$; —$NR^eCO_2R^h$; —$OCO_2R^h$; —$C(NR^e)NR^fR^g$; —$NR^eC(NH)NR^fR^g$; —$NR^eC(NR^f)R^g$; —R* or —Q;

with the proviso that from 1 to 3 R groups are present which contain R* or Q, said R* and Q being defined below;

$R^e$, $R^f$ and $R^g$ represent hydrogen; —$C_{1-6}$ straight- or branched-chain alkyl unsubstituted or substituted with one to four $R^i$ groups, or —R*;

or $R^e$ and $R^f$ taken together with any intervening atoms represent a 4–6 membered saturated ring optionally interrupted by one to three of O, S, —C(O)— or $NR^g$ with $R^g$ as defined above, said ring being unsubstituted or substituted with one to four $R^i$ groups;

each $R^i$ independently represents halo; —CN; —$NO_2$; phenyl; —$NHSO_2R^h$; —$OR^h$, —$SR^h$; —$N(R^h)_2$; —$N^+(R^h)_3$; —$C(O)N(R^h)_2$; —$SO_2N(R^h)_2$; heteroaryl; heteroarylium; —$CO_2R^h$; —$C(O)R^h$; —$OCOR^h$; —$NHCOR^h$; guanidinyl; carbamimidoyl or ureido;

each $R^h$ independently represents H, a —$C_{1-6}$ straight or branched-chain alkyl group, a —$C_3$-$C_6$ cycloalkyl group or phenyl, or when two $R^h$ groups are present, said $R^h$ groups may be taken in combination and represent a 4–6 membered saturated ring, optionally interrupted by one or two of O, S, $SO_2$, —C(O)—, NH and $NCH_3$;

Q is selected from the group consisting of:

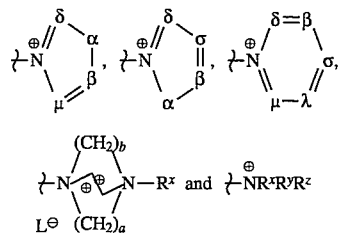

wherein:

a and b are 1, 2 or 3;

L– is a pharmaceutically acceptable counterion;

α represents O, S or $NR^s$;

β, δ, λ, μ and σ represent $CR^t$, N or $N^+R^s$, provided that no more than one of β, δ, λ, μ and σ is $N^+R^s$;

R* is selected from the group consisting of:

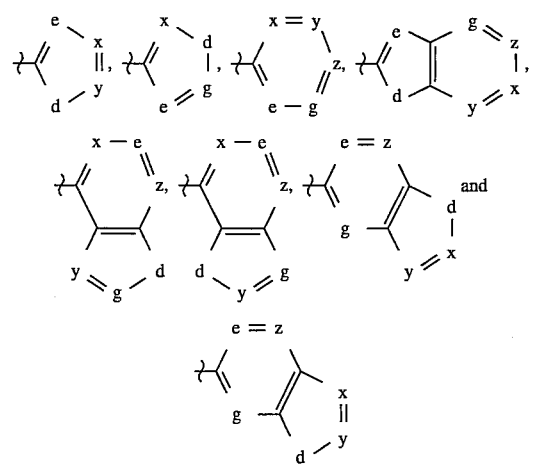

wherein:

each d independently represents O, S or $NR^k$;

e, g, x, y and z represent $CR^m$, N or $N^+R^k$, provided that no more than one of e, g, x, y and z in any given structure represents $N^+R^k$;

$R^k$ represents hydrogen; —$C^{1-6}$ straight- or branched-chain alkyl, unsubstituted or substituted with one to four $R^i$ groups; or —$(CH_2)_nQ$ where n=1, 2 or 3 and Q is as previously defined;

each $R^m$ independently represents a member selected from the group consisting of: hydrogen; halo; —CN;

—NO₂; —NR"R°; —OR"; —SR"; —CONR"R°; —COOR^h; —SOR"; —SO₂R"; —SO₂NR"R°; —NR"SO₂R°; —COR"; —NR"COR°; —OCOR"; —OCONR"R°; —NR"CO₂R^h; —NR"CONR°R^h; —OCO₂R^h; —CNR"NR°R^h; —NR"CNHNR°R^h; —NR"C(NR°)R^h; —C₁₋₆ straight- or branched-chain alkyl, unsubstituted or substituted with one to four R^i groups; —C₃₋₇ cycloalkyl, unsubstituted or substituted with one to four R^i groups; and —(CH₂)ₙQ where n and Q are as defined above;

R" and R° represent hydrogen, phenyl; —C₁₋₆ straight- or branched-chain alkyl unsubstituted or substituted with one to four R^i groups;

each R^s independently represents hydrogen; phenyl; —C₁₋₆ straight- or branched-chain alkyl, unsubstituted or substituted with one to four R^i groups;

each R^t independently represents hydrogen; halo; phenyl; —CN; —NO₂; —NR"R^v; —OR"; —SR"; —CONR"R^v; —COOR^h; —SOR"; —SO₂R"; —SO₂NR"R^v; —NR"SO₂R^v; —COR"; —NR"COR^v; —OCOR"; —OCONR"R^v; —NR"CO₂R^v; —NR"CONR^v R"; —OCO₂R^v; heteroaryl; heteroarylium; —C₁₋₆ straight- or branched-chain alkyl, unsubstituted or substituted with one to four R^i groups;

R^u and R^v represent hydrogen or —C₁₋₆ straight- or branched-chain alkyl, unsubstituted or substituted with one to four R^i groups;

or R_u and R^v together with any intervening atoms represent a 4–6 membered saturated ring optionally interrupted by one or more of O, S, NR^w or —C(O)—, said ring being unsubstituted or substituted with one to four R^i groups;

each R^w independently represents hydrogen or —C₁₋₆ straight- or branched-chain alkyl, unsubstituted or substituted with one to four R^i groups; C₃₋₆ cycloalkyl optionally substituted with one to four R^i groups; phenyl optionally substituted with one to four R^i groups or R^h and R^w taken together with any intervening atoms represent a 5–6 membered saturated ring, optionally interrupted by one or two of O, S, SO₂, NH or NCH₃;

R^x represents hydrogen or a C₁₋₈ straight- or branched-chain alkyl, optionally interrupted by one or two of O, S, SO, SO₂, NR^w, N⁺R^h R^w, or —C(O)—, said chain being unsubstituted or substituted with one to four of halo, CN, NO₂, OR^w, SR^w, SOR^w, SO₂R^w, NR^h R^w, N⁺(R^h)₂R^w, —C(O)—R^w, C(O)NR^h R^w, SO₂NR^h R^w, CO₂R^w, OC(O)R^w, OC(O)NR^h R^w, NR^h C(O)R^w, NR^h C(O)NR^h R^w, or a phenyl or heteroaryl group which is in turn optionally substituted with from one to four R^i groups or with one to two C₁₋₃ straight- or branched-chain alkyl groups, said alkyl groups being unsubstituted or substituted with one to four R^i groups;

R^y and R^z represent hydrogen; phenyl; —C₁₋₆ straight or branched chain alkyl, unsubstituted or substituted with one to four R^i groups, and optionally interrupted by O, S, NR^w, N⁺R^h R^w or —C(O)—;

or R^x and R^y together with any intervening atoms represent a 4–6 membered saturated ring optionally interrupted by O, S, SO₂, NR^w, N⁺R^h R^w or —C(O)—, unsubstituted or substituted with 1–4 Ri groups, and when R^x and R^y together represent a 4–6 membered ring as defined above, R^z is as defined above or R^z represents an additional saturated 4–6 membered ring fused to the ring represented by R^x and R^y taken together, optionally interrupted by O, S, NR^w or —C(O)—, said rings being unsubstituted or substituted with one to four R^i groups.

2. A compound in accordance with claim 1 wherein A represents S.

3. A compound in accordance with claim 1 wherein A represents O.

4. A compound in accordance with claim 1 represented by formula Ia:

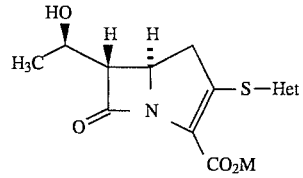

wherein:

CO₂M represents a carboxylic acid, a carboxylate anion or a pharmaceutically acceptable ester group;

Het has substituent groups which contain from one to three positively charged atoms and is selected from:

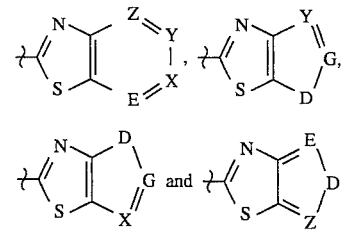

wherein:

D is O, S or NR^a;

E, G, X, Y and Z represent CR or N;

each R is independently selected from: —R*; hydrogen; halo; —CN; OR^e; —SR^c; —CONR^a R^b; —COOR^h; —SOR^c; —SO₂R^c; —SO₂NR^a R^b; —COR^a; —OCOR^a; —OCONR^a R^b; —OCO₂R^h; —C₁₋₆ straight- or branched-chain alkyl, unsubstituted or substituted with one to four R^d groups; —C₃₋₇ cycloalkyl, unsubstituted or substituted with one to four R^d groups, with the proviso that one to three R groups contain R* or Q;

and R* and Q are as defined above.

5. A compound in accordance with claim 4 represented by formula Ia:

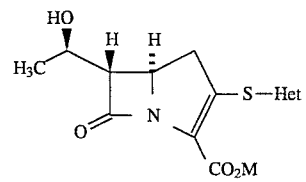

wherein:

CO₂M represents a carboxylic acid or a carboxylate anion;

Het has substituent groups which contain one or two positively charged atoms and is selected from:

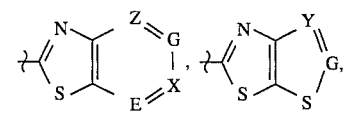

-continued

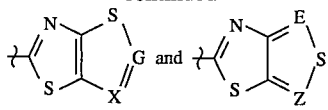

wherein:

E, G, X, Y and Z represent CR or N;

each R is independently selected from the group consisting of —R*; hydrogen; halo; —CN; —CONR$^a$R$^u$; —COOR$^h$; —SOR$^c$; —SO$_2$R$^c$; —SO$_2$NR$^a$R$^b$; —OC(O)R$^a$; —COR$^a$; —C$_{1-6}$ straight-or branched-chain alkyl, unsubstituted or substituted with one to three R$^d$ groups; —C$_{3-7}$ cycloalkyl, unsubstituted or substituted with one to three R$^d$ groups, with the proviso that one or two R groups contain R* or Q;

R$^a$, R$^b$ and R$^c$ independently represent —R*; hydrogen, —C$_{1-6}$ straight- or branched-chain alkyl, unsubstituted or substituted with one to four R$^d$ groups; —C$_{3-7}$ cycloalkyl, unsubstituted or substituted with one to four R$^d$ groups;

or R$^a$ and R$^b$ taken together with any intervening atoms represent a 4–6 membered saturated ring optionally interrupted by one or more of O, S, NR$^c$ with R$^c$ as defined above, or —C(O)—, said ring being unsubstituted or substituted with one to four R$^i$ groups;

Q represents a member selected from the group consisting of:

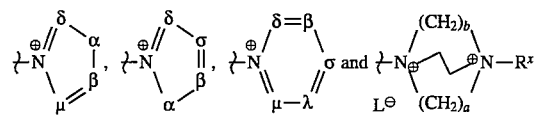

wherein:

a and b are 2 or 3;

L– is a pharmaceutically acceptable counterion;

α represents O, S or NR$^s$;

β, δ, λ, μ and σ represent CR$^t$, N or N$^+$R$^s$, provided that no more than one of β, δ, λ, μ and σ is N$^+$R$^s$;

R* is selected from:

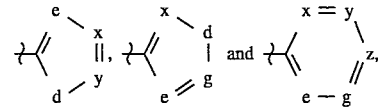

wherein each d independently represents O, S or NR$^k$;

e, g, x, y and z represent CR$^m$, N or N$^+$R$^k$, provided that no more than one of e, g, x, y and z in any given structure represents N$^+$R$^k$;

and R$^k$ is as previously defined.

6. A compound in accordance with claim 5 represented by formula Ic:

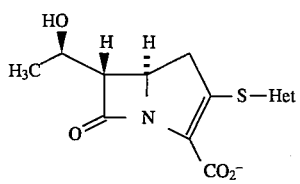

wherein:

Het has substituent groups which contain one or two positively charged atoms and is selected from the group consisting of:

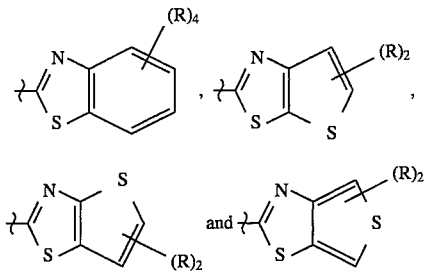

each R is independently selected from: hydrogen, —C$_{1-6}$ straight- or branched-chain alkyl, unsubstituted or substituted with one to three R$^d$ groups; and —R*, with the proviso that one or two R groups contain R* or Q;

R$^d$ represents —CN; —NR$^e$R$^f$; —OR$^g$; —CONR$^e$R$^f$; —COOR$^g$; —SOR$^g$; —SO$_2$R$^g$; —SO$_2$NR$^e$R$^f$; —NR$^e$SO$_2$R$^f$; —COR$^e$; —NR$^e$COR$^f$; —OCONR$^e$R$^f$; —NR$^e$CONR$^f$R$^g$; —NR$^e$CO$_2$R$^h$; —C(NR$^e$)NR$^f$R$^g$; —NR$^e$C(NH)NR$^f$R$^g$; —NR$^e$C(NR$^f$)R$^g$; —R* or —Q;

R$^e$, R$^f$ and R$^g$ represent hydrogen; —C$_{1-6}$ straight- or branched-chain alkyl or —R*;

or R$^e$ and R$^f$ taken together represent a 4–6 membered saturated ring optionally interrupted by one or more of O, S, —C(O)— or NR$^g$ with R$^g$ as defined above, said ring being unsubstituted or substituted with one to four R$^i$ groups;

each R$^h$ independently represents H, a —C$_{1-6}$ straight or branched-chain alkyl group, a —C$_3$–C$_6$ cycloalkyl group or phenyl, or when two R$^h$ groups are present, said R$^h$ groups may be taken in combination and represent a 4–6 membered saturated ring, optionally interrupted by one or two of O, S, SO$_2$, —C(O)—, NH and NCH$_3$;

each R$^i$ independently represents halo; —CN; —NO$_2$; phenyl; —NHSO$_2$R$^h$; —OR$^h$, —SR$^h$; —N (R$^h$)$_2$; —N$^+$(R$^h$)$_3$; —C(O)N(R$^h$ )$_2$; —SO$_2$N(R$^h$)$_2$; heteroaryl; heteroarylium; —CO$_2$R$^h$; —C(O)R$^h$; —OCOR$^h$; —NHCOR$^h$; guanidinyl; carbamimidoyl or ureido;

Q is selected from:

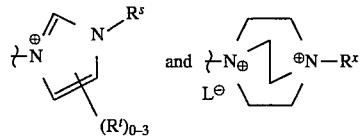

wherein:

L– is as previously defined;

R$^x$ represents hydrogen or a C$_{1-8}$ straight- or branched-chain alkyl, optionally interrupted by one or two of O, S, SO, SO$_2$, NR$^w$, N$^+$R$^h$R$^w$, or —C(O)—, said chain being unsubstituted or substituted with one to four of halo, CN, NO$_2$, OR$^w$, SR$^w$, SOR$^w$, SO$_2$R$^w$, NR$^h$R$^w$, N$^+$(R$^h$)$_2$R$^w$, —C(O)—R$^w$, C(O)NR$^h$R$^w$, SO$_2$NR$^h$R$^w$, CO$_2$R$^w$, OC(O)R$^w$, OC(O)NR$^h$R$^w$, NR$^h$C(O)R$^w$, NR$^h$C(O)NR$^h$R$^w$, or a phenyl or heteroaryl group which is in turn optionally substituted with from one to four R$^i$ groups or with one to two C$_{1-3}$ straight- or branched-chain alkyl groups, said alkyl groups being unsubstituted or substituted with one to four R$^i$ groups;

R$^s$ represents hydrogen; phenyl; —C$_{1-6}$ straight- or branched-chain alkyl, unsubstituted or substituted with one to four R$^i$ groups;

$R^t$ is selected from the group consisting of: halo; phenyl; —CN; —NO$_2$; —NR$^u$R$^v$; —OR$^u$; —SR$^u$; —CONR$^u$R$^v$; —COOR$^h$; —SOR$^u$; —SO$_2$R$^u$; —SO$_2$NR$^u$R$^v$; —NR$^u$SO$_2$R$^v$; —COR$^u$; —NR$^u$COR$^v$; —OCOR$^u$; —OCONR$^u$R$^v$; —NR$^u$CO$_2$R$^v$; —NR$^u$CONR$^v$R$^w$; —OCO$_2$R$^v$; —C$_{1-6}$ straight- or branched-chain alkyl, unsubstituted or substituted with one to four R$^i$ groups, and the remaining R$^t$ groups are hydrogen;

R* is

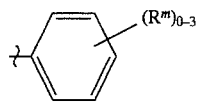

wherein each R$^m$ is selected from the group consisting of: halo; —CN; —NR$^n$R$^o$; —OR$^n$; —SR$^n$; —CONR$^n$R$^o$; —COOR$^h$; —SOR$^n$; —SO$_2$R$^n$; —SO$_2$NR$^n$R$^o$; —NR$^n$SO$_2$R$^o$; —COR$^n$; —NR$^n$COR$^o$; —OCOR$^n$; —OCONR$^n$R$^o$; —NR$^n$CO$_2$R$^h$; —NR$^n$CONR$^o$R$^h$; —OCO$_2$R$^h$; —C$_{1-6}$ straight- or branched-chain alkyl, unsubstituted or substituted with one to four R$^i$ groups; —C$_{3-7}$ cycloalkyl, unsubstituted or substituted with one to four R$^i$ groups; or —(CH$_2$)$_n$Q where n=1–3;

R$^n$ and R$^o$ represent hydrogen, phenyl; —C$_{1-6}$ straight- or branched-chain alkyl unsubstituted or substituted with one to four R$^i$ groups;

R$^u$ and R$^v$ independently represent hydrogen; —C$_{1-6}$ straight- or branched-chain alkyl unsubstituted or substituted with one to four R$^i$ groups;

or R$^u$ and R$^v$ together with any intervening atoms represent a 4–6 membered saturated ring optionally interrupted by one or more of O, S, NR$^w$ or —C(O)—, said ring being unsubstituted or substituted with one to four R$^i$ groups, and R$^w$ represents hydrogen or —C$_{1-6}$ straight- or branched-chain alkyl, unsubstituted or substituted with one to four R$^i$ groups, C$_{3-6}$ cycloalkyl optionally substituted with one to four R$^i$ groups; or phenyl optionally substituted with one to four R$^i$ groups;

or R$^h$ and R$^w$ taken together with any intervening atoms represent a 5–6 membered saturated ring, optionally interrupted by one or two of O, S, SO$_2$, NH or NCH$_3$.

7. A compound in accordance with claim 1 represented by formula Ib:

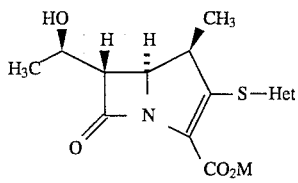

wherein:

CO$_2$M represents a carboxylic acid, a carboxylate anion or a pharmaceutically acceptable ester group;

and Het is as previously defined with respect to the compounds of formula I.

8. A compound in accordance with claim 7 represented by formula Ib:

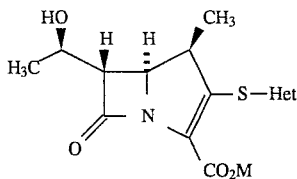

wherein:

CO$_2$M represents a carboxylic acid or a carboxylate anion;

Het has substituent groups which contain one to three positively charged atoms and is selected from the group consisting of:

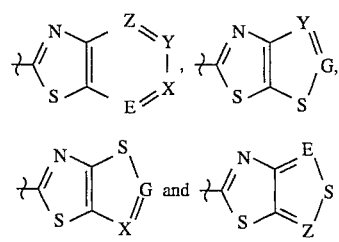

wherein:

E, G, X, Y and Z independently represent CR or N;

each R is selected from the group consisting of hydrogen; halo; —CN; —CONR$^a$R$^b$; —COOR$^h$; —SOR$^c$; —SO$_2$R$^c$; —SO$_2$NR$^a$R$^b$; —COR$^a$; —C$_{1-6}$ straight- or branched-chain alkyl, unsubstituted or substituted with one to three R$^d$ groups; —C$_{3-7}$ cycloalkyl, unsubstituted or substituted with one to three R$^d$ groups; and —R*, with the proviso that one to three R groups contain R* or Q;

Q is selected from the group consisting of:

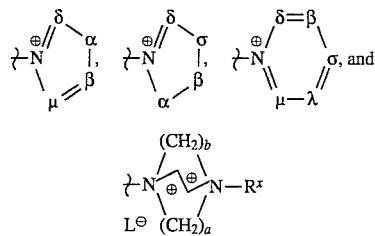

wherein:

L– represents a pharmaceutically acceptable counterion;

a and b independently represent 2 or 3;

α represents O, S or NR$^s$;

β, δ, λ, μ and σ independently represent CR', N or N$^+$R$^s$ provided that no more than one of β, δ, λ, μ and σ is N$^+$R$^s$;

R* is selected from the group consisting of:

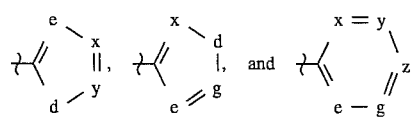

wherein:

d represents O, S or NR$^k$;

e, g, x, y and z independently represent CR$^m$, N or N$^+$R$^k$, provided that no more than one of e, g, x, y and z represents N$^+$R$^k$;

$R^a$, $R^b$ and $R^c$ independently represent hydrogen, —$C_{1-6}$ straight- or branched-chain alkyl, unsubstituted or substituted with one to four $R^d$ groups; —$C_{3-7}$ cycloalkyl, unsubstituted or substituted with one to four $R^d$ groups, or —R*;

or $R^a$ and $R^b$ taken together with any intervening atoms represent a 4–6 membered saturated ring optionally interrupted by one or more of O, S, $NR^c$, with $R^c$ as defined above, or —C(O)—, said ring being unsubstituted or substituted with one to four $R^i$ groups; and each $R^d$ independently represents halo; —CN; —$NO_2$; —$NR^eR^f$; —$OR^g$; —$SR^g$; —$CONR^eR^f$; —$COOR^g$; —$SOR^g$; —$SO_2R^g$; —$SO_2NR^eR^f$; —$NR^eSO_2R^f$; —$COR^e$; —$NR^e$ $COR^f$; —$OCOR^e$; —$OCONR^eR^f$; —$NR^eCONR^fR^g$; —$NR^eCO_2R^h$; —$OCO_2R^h$; —C(N-$R^e$)$NR^fR^g$; —$NR^eC(NH)NR^fR^g$; —$NR^eC(NR^f)R^g$; —R* or —Q;

$R^e$, $R^f$ and $R^g$ represent hydrogen; —$C_{1-6}$ straight- or branched-chain alkyl unsubstituted or substituted with one to four $R^i$ groups, or —R*;

or $R^e$ and $R^f$ taken together represent a 4–6 membered saturated ring optionally interrupted by one to three of O, S, —C(O)— or $NR^g$ with $R^g$ as defined above, said ring being unsubstituted or substituted with one to four $R^i$ groups;

each $R^i$ independently represents halo; —CN; —$NO_2$; phenyl; —$NHSO_2R^h$; —$OR^h$; —$SR^h$; —$N(R^h)_2$; —$N^+(R^h)_3$; —$C(O)N(R^h)_2$; —$SO_2N(R^h)_2$; heteroaryl; heteroarylium; —$CO_2R^h$; —$C(O)R^h$; —$OCOR^h$; —$NHCOR^h$; guanidinyl; carbamimidoyl or ureido;

each $R^h$ independently represents H, a —$C_{1-6}$ straight or branched-chain alkyl group, a —$C_3$-$C_6$ cycloalkyl group or phenyl, or when two $R^h$ groups are present, said $R^h$ groups may be taken in combination and represent a 4–6 membered saturated ring, optionally interrupted by one or two of O, S, $SO_2$, —C(O)—, NH and $NCH_3$;

$R^k$ represents hydrogen; —$C_{1-6}$ straight— or branched-chain alkyl, unsubstituted or substituted with one to four $R^i$ groups; or —$(CH_2)_n$Q where n and Q are as previously defined;

each $R^m$ independently represents a member selected from the group consisting of: hydrogen; halo; —CN; —$NO_2$; —$NHR^n$; —$NR^nR^o$; —$OR^n$; —$SR^n$; —CON-$R^nR^o$; —$COOR^h$; —$SOR^n$; —$SO_2R^n$; —$SO_2NR^nR^o$; —$NR^nSO_2R^o$; —$COR^n$; —$NR^nCOR^o$; —$OCOR^nR^o$; —$NR^nCO_2R^h$; —$NR^nCONR^oR^h$; —$OCO_2R^h$; —CN-$R^nNR^oR^h$; —$NR^nCNHNR^oR^h$; —$NR^nC(NR^o)R^h$; —$C_{1-6}$ straight— or branched-chain alkyl, unsubstituted or substituted with one to four $R^i$ groups; —$C_{3-7}$ cycloalkyl, unsubstituted or substituted with one to four $R^i$ groups; and —$(CH_2)_n$Q where n=1–3;

$R^n$ and $R^o$ represents hydrogen, phenyl; —$C_{1-6}$ straight— or branched-chain alkyl, unsubstituted or substituted with one to four $R^i$ groups;

each $R^t$ independently represents hydrogen; halo; phenyl; —CN; —$NO_2$; —$NHR^u$; —$NR^uR^v$; —$OR^u$; —$SR^u$; —$CONR^uR^v$; —$COOR^h$; —$SOR^u$; —$SO_2R^u$; —$SO_2NR^uR^v$; —$NR^uSO_2R^v$; —$COR^u$; —$NR^uCOR^v$; —$OCOR^u$; —$OCONR^uR^v$; —$NR^uCO_2R^v$; —$NR^u$-$CONR^vR^w$; —$OCO_2R^v$; heteroaryl; heteroarylium; —$C_{1-6}$ straight—or branched-chain alkyl, unsubstituted or substituted with one to four $R^i$ groups;

$R^u$ $R^v$ represent hydrogen or —$C_{1-6}$ straight—or branched-chain alkyl, unsubstituted or substituted with one to four $R^i$ groups;

or $R^u$ and $R^v$ together represent a 4–6 membered saturated ring optionally interrupted by one or more of O, S, $NR^w$ or —C(O)—, said ring being unsubstituted or substituted with one or four $R^i$ groups;

$R^x$ represents hydrogen or a $C_{1-8}$ straight— or branched-chain alkyl, optionally interrupted by one or two of O, S, SO, $SO_2$, $NR^w$, $N^+R^hR^w$, or —CO)—, said chain being unsubstituted with one to four of halo, CN, $NO_2$, $OR^w$, $SR^w$, $SOR^w$, $SO_2R^w$, $NR^hR^w$, $N^+(R^h)_2R^w$, —C(O)—$R^w$, $C(O)NR^hR^w$, $SO_{2\cdot NR}{}^hR^w$, $CO_2R^w$, $OC(O)R^w$, $OC(O)R^w$, $NR^hC(O)R^w$, $NR^hC(O)NR^hR^w$, or a phenyl or heteroaryl group which is turn optionally substituted with from one to four $R^1$ groups or with one to two $C_{1-3}$ straight— or branched-chain alkyl groups, said alkyl groups being unsubstituted or substituted with one to four $R^i$ groups;

each $R^w$ independently represents hydrogen or —$C_{1-6}$ straight— or branched-chain alkyl, unsubstituted or substituted with one to four $R^i$ groups, $C_{3-6}$ cycloalkyl optionally substituted with one to four $R^i$ groups; phenyl optionally substituted with one to four $R^i$ groups or $R^h$ are $R^w$ taken together with any intervening atoms represent a 5–6 membered saturated ring, optionally interrupted by one or two of O, S, $SO_2$, NH or $NCH_3$.

9. A compound in accordance with claim 8 represented by formula Ic:

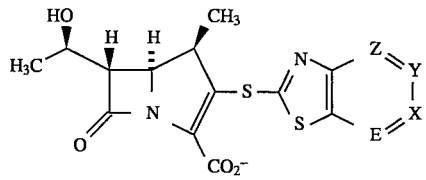

each R is independently selected from: —R*; hydrogen; halo; —CN; —$NO_2$; —$OR^c$; —$SR^c$; —$CONR^aR^b$; —$COOR^h$; —$SOR^c$; —$SO_2R$ $^c$; —$SO_2NR_{NR}{}^aR^b$; —$NR^aSO_2R^b$; —$OCOR^a$; —$OCONR^aR^b$; —$NR^a$-$CONR^bR^c$; —$NR^aCO_2R^h$;—$C_{1-6}$ straight- or branched-chained alkyl, unsubstituted or substituted with one or to four $R^d$ groups; and —$C_{3-7}$ cycloalkyl, unsubstituted or substituted with one to four $R^d$ groups, with the proviso that from one to three positively charged atoms are contained in said R groups, and one to three R groups are present which contain R* or Q;

Q is selected from the group consisting of:

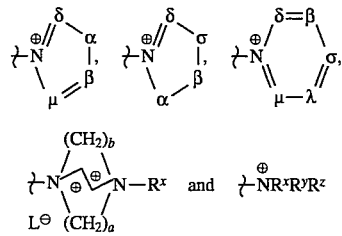

a and b are 1, 2 or 3;

$L^-$ is a pharmaceutically acceptable counterion;

α represents O, S, or $NR^s$:

β, δ, λ, µ and σ represent $Cr^t$, N or $N^{30}$ $R^s$, provided that no more than one of β, δ, λ, µ and σ is $N^+R^s$;

R* is selected from the group consisting of;

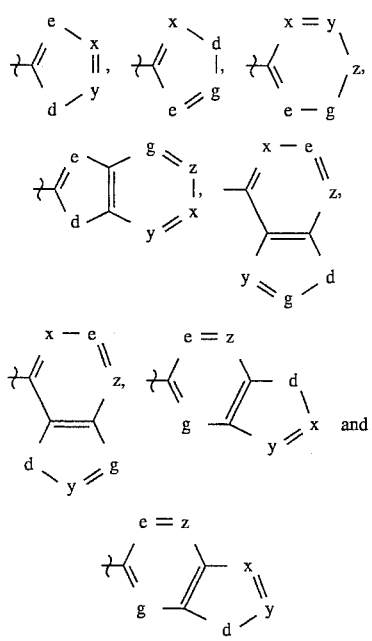

each d independently represents O, S, or $NR^K$;

e, g, x, y and z represent $CR^m$, N or $N^+R^k$, provided that no more than one of e, g, x, y and z in any given structure represents $N^{+Rk}$;

$R^a$, $R^b$ and $R^c$ represent hydrogen, —$C_{1-6}$ straight— or branched-chain alkyl, unsubstituted or substituted with one to four Rgroups; —$C_{3-7}$ cycloalkyl, unsubstituted or substituted with one to four $R^d$ groups; or —R*;

or $R^a$ and $R^b$ taken together with any intervening atoms represent a 4–6 membered saturated ring optionally interrupted by one or more of O, S, $NR^c$, with $R^c$ as defined above, or —C(O)—, said ring being unsubstituted or substituted with one to four $R^i$ groups;

or $R^b$ and $R^c$ taken together with any intervening atoms represent a 4–6 membered saturated ring optionally interrupted by one to three of O, S, $NR^a$, with $R^a$ as defined above, or —C(O)—, said ring being unsubstituted or substituted with one to four $r^i$ groups;

each $R^d$ independently represents halo; —CN; —$NO^2$; —$NR^eR^f$; —$OR^g$; —$SR^g$; —$CONR^eR^f$; —$COOR^h$; —$SOR^g$; —$SO_2R^g$; —$SO_2NR^eR^f$; —$NR^eSO_2R^f$; —$COR^e$; —$OCOR^eR^f$; —$NR^eCONR^fR^g$; —$NR^eCO^2R^h$; —$OCO_2R^h$; —$C(NR^e)NR^fR^g$; —$NR^eC(NH)NR^fR^g$; —$NR^eC(NR^f)R^g$; —R* or —Q;

$R^e$, $R^f$ and $R^g$ represent hydrogen; —$C_{1-6}$ straight— or branched-chain alkyl unsubstituted or substituted with one to four $R^i$ groups, or —R*;

or $R^e$ and $R^f$ taken together represent a 4–6 membered saturated ring optionally interrupted by one to three of O, S, —C(O)— or $NR^g$ with $R^g$ as defined above, said ring being substituted or substituted with one to four $R^i$ groups;

each $R^i$ independently represent halo; —CN; —$NO_2$; phenyl; —$NHSO_2R^h$; —$OR^h$, —$SR^h$; —$N(R^h)_2$; —$N^{+(Rh)}_3$; —$C(O)N(R^h)_2$; —$SO^2N(R^h)_2$; heteroaryl; heteroarylium; —$CO_2R^h$; —$OCOR^h$; —$NHCOR^h$; guanidinyl; carbamimidoyl or ureido;

each $R^h$ independently represents H, a —$C_{1-6}$ straight or branched-chain alkyl group, a —$C_3$–$C_6$ cycloalkyl group or phenyl, or when two $R^h$ groups are present, said $R^h$ groups may be taken in combination and represent a 4–6 membered saturated ring, optionally interrupted by one or two of O, S, $SO_2$, —C(O)—, NH and $NCH_3$;

$R^k$ represents hydrogen; —$C_{1-6}$ straight—or branched-chain alkyl, unsubstituted or substituted with one to four $R^i$ groups; or —$(CH_2)_nQ$ where n and Q are as previously defined;

each $R^m$ independently represents a member selected from the group consisting of: hydrogen; halo; —CN; —$NO_2$; —$NHR^n$; —$NR^nR^o$; —$OR^n$; —$SR^n$; —$CONR^nR^o$; —$COOR^h$; —$SOR^n$; —$SO_2R^n$; —$SO_2NR^nR^o$; —$NR^nSO_2R^o$; —$COR^n$; —$NR^nCOR^o$; —$OCOR^n$; —$OCONR^nR^o$; —$NR^nCO_2R^h$; —$NR^nCONR^oR^h$; —$OCO_2R^h$; —$CNR^nNR^oR^h$; —$NR^nCNHNR^oR^h$; —$NR^nC(NR^o)R^n$; —$C_{1-6}$ straight—or branched-chain alkyl, unsubstituted or substituted with one to four $R^i$ groups; —$C_{3-7}$ cycloalkyl, unsubstituted or substituted with one to four $R^i$ groups; and —$(CH_2)_nQ$ where n=1–3;

$R^n$ and $R^o$ represent hydrogen, phenyl; —$C_{1-6}$ straight— or branched-chain alkyl unsubstituted with one to four $R^i$ groups;

$R^n$ and $R^o$ represent hydrogen, phenyl; —$C_{1-6}$ straight— or branched-chain alkyl unsubstituted or substituted with one to four $r^i$ groups;

each $R^s$ independently represents hydrogen; phenyl; —$C_{1-6}$ straight— or branched alkyl, unsubstituted or substituted with one to four $R^i$ groups;

each $R^t$ independently represents hydrogen; halo; phenyl; —CN; —$NO_2$: —$NHR^u$; —$NR^uR^v$; —$OR^u$; —$SR^u$; —$CONR^uR^v$; —$COOR^h$; —$SOR^u$; —$SO_2R^u$; —$SO_2NR^uR^v$; —$NR^uSO_2R^v$; —$COR^u$; —$NR^uCOR^v$; —$OCOR^u$; —$OCONR^uR^v$; —$NR^uCO_2R^v$; —$NR^u$-$CONR^vR^w$; —$OCO_2R^v$; heteroaryl; heteroarylium; —$C_{1-6}$ straight— or branched-chain alkyl, unsubstituted or substituted with one to four $R^i$ groups;

$R^u$ and $R^v$ represents hydrogen or —$C_{1-6}$ straight— or branched-chain alkyl, unsubstituted or substituted with one to four $R^i$ groups;

or $R^u$ and $R^v$ together represent a 4–6 membered saturated ring optionally interrupted by one or more of O, S, $NR^w$ or —C(O)—, said ring being unsubstituted or substituted with one to four $R^i$ groups; $R^x$ represents hydrogen or a $C_{1-8}$ straight— or branched-chained alkyl, optionally interrupted by one or two of O, S, SO, $SO_2$, $NR^w$, $N^+R^hR^w$, or —C(O)—, said chain being unsubstituted or substituted with one to four of halo, CN, $NO_2OR^w$, $SR^w$, $SOR^w$, $SO_2R^w$, $NR^hR^w$, $N^+(R^h)_2R^w$, —C(O)—$R^w$, $C(O)NR^hR^w$, $SO_2NR^hR^w$, $CO_2R^w$, $OC(O)R^w$, $OC(O)NR^hR^w$, $NR^hC(O)R^w$, $NR^hC(O)N$-$R^hR^w$, or a phenyl or heteroaryl group which is in turn optionally substituted with from one to four $R^i$ groups or with one to two $C_{1-3}$ straight— or branched-chain alkyl groups, said alkyl groups being unsubstituted or substituted with one to four $r^i$ groups;

$R^y$, and $R^z$ represent; phenyl; —$C_{1-6}$ straight— or branched-chain alkyl, unsubstituted or substituted with one to four $R^i$ groups and optionally interrupted by O, S, $NR^w$, $N^+R^hR^w$ or —C(O)—;

or $R^x$ and $R^y$ together with any intervening atoms represent a 4–6 membered saturated ring optionally interrupted by O, S, $SO_2$, $NR^2$, $N^{+R^h}R^w$ or —C(O)—, and, when $R^x$ and $R^y$ together represent a 4–6 membered ring as defined above, $R^z$ is as defined above or $R^z$ represents an additional saturated 4–6 membered ring fused to the ring represented by $R^x$ and $R^y$ taken together, optionally interrupted by O, S, $NR^w$ or —C(O)—, said rings being unsubstituted or substituted with one to four $r^i$ groups each $R^w$ independently represents hydrogen or —$C_{1-6}$ straight— branched-chain alkyl, unsubstituted with one to four $R^i$ groups, $C_{3-6}$ cycloalkyl optionally substituted with one to four $R^i$ groups; or phenyl optionally substituted with one to four $R^i$ groups;

or $R^h$ and $R^w$ taken together with any intervening atoms represent a 5–6 membered saturated ring, optionally interrupted by one or two of O, S, $SO_2$, NH or $NCH_3$.

10. A compound in accordance with claim 9 represented by formula Id:

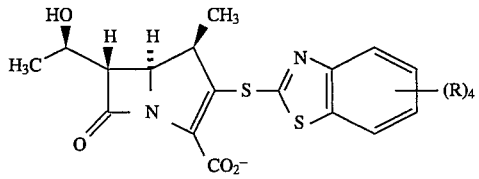

wherein:

$(R)_4$ contains from one to three positively charged atoms, and each R is selected from the group consisting of hydrogen; halo; —CN; —$CONR^aR^b$; —$COOR^h$; —$SOR^c$; —$SO_2R^c$; —$SO_2NR^aR^b$; —$COR^a$; —$C_{1-6}$ straight- or branched-chain alkyl, unsubstituted or substituted with one to three $R^d$ groups; or —R*, with the proviso that from 1–3 R groups are present which contain R* or Q;

$R^a$, $R^b$ and $R^c$ independently represent hydrogen, —$C_{1-6}$ straight- or branched-chain alkyl, unsubstituted or substituted with one to four $R^d$ groups; or —R*;

or $R^a$ and $R^b$ taken together with any intervening atoms represent a 4–6 membered saturated ring optionally interrupted by one or more of O, S, $NR^c$, with $R^c$ as defined above, or —C(O)—, said ring being unsubstituted or substituted with one to four $R^i$ groups;

each $R^d$ independently represents halo; —CN; —$NO_2$; —$NR^eR^f$; —$OR^g$; —$SR^g$; —$CONR^eR^f$; —$COOR^g$; —$SOR^g$; —$SO_2R^g$; —$SO_2NR^eR^f$; —$NR^eSO_2R^f$; —$COR^e$; —$NR^eCOR^f$; —$OCOR^e$; —$OCONR^eR^f$; —$NR^eCONR^fR^g$; —$NR^eCO_2R^h$; —$OCO_2R^h$; —C(N-$R^e$)$NR^fR^g$; —$NR^eC(NH)NR^fR^g$; —$NR^eC(NR^f)R^g$; —R* or —Q;

Q represents

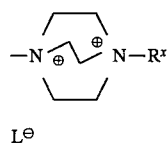

wherein $L^-$ is a pharmaceutically acceptable counterion;

$R^x$ represents hydrogen or a $C_{1-8}$ straight- or branched-chain alkyl, optionally interrupted by one or two of O, S, SO, $SO_2$, $NR^w$, $N^+R^hR^w$, or —C(O)—, said chain being unsubstituted or substituted with one to four of halo, CN, $NO_2$, $OR^w$, $SR^w$, $SOR^w$, $SO_2R^w$, $NR^hR^w$, $N^+(R^h)_2R^w$, —C(O)—$R^w$, C(O)$NR^hR^w$, $SO_2NR^hR^w$, $CO_2R^w$, OC(O)$R^w$, OC(O)$NR^hR^w$, $NR^hC(O)R^w$, $NR^hC(O)NR^hR^w$, or a phenyl or heteroaryl group which is in turn optionally substituted with from one to four $R^i$ groups or with one to two $C_{1-3}$ straight- or branched-chain alkyl groups, said alkyl groups being unsubstituted or substituted with one to four $R^i$ groups;

each $R^h$ independently represents H, a —$C_{1-6}$ straight or branched-chain alkyl group, a —$C_3$-$C_6$ cycloalkyl group or phenyl, or when two $R^h$ groups are present, said $R^h$ groups may be taken in combination and represent a 4–6 membered saturated ring, optionally interrupted by one or two of O, S, $SO_2$, —C(O)—, NH and $NCH_3$;

each $R^i$ independently represents halo; —CN; —$NO_2$; phenyl; —$NHSO_2R^h$; —$OR^h$, —$SR^h$; —$N(R^h)_2$; —C(O)N$(R^h)_2$; —$SO_2N(R^h)_2$; heteroaryl; heteroarylium; —$CO_2R^h$; —C(O)$R^h$; —$OCOR^h$; —$NHCOR^h$; guanidinyl; carbamimidoyl or ureido;

$R^w$ represents hydrogen or —$C_{1-6}$ straight- or branched-chain alkyl, unsubstituted or substituted with one to four $R^i$ groups; $C_{3-6}$ cycloalkyl optionally substituted with one to four $R^i$ groups; or phenyl optionally substituted with one to four $R^i$ groups;

or $R^h$ and $R^w$ taken together with any intervening atoms represent a 5–6 membered saturated ring, optionally interrupted by one or two or O, S, $SO_2$, NH or $NCH_3$;

R* is selected from the group consisting of:

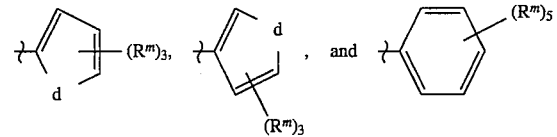

wherein:

d is O, S or $NR^k$;

$R^k$ represents hydrogen; —$C_{1-6}$ straight- or branched-chain alkyl, unsubstituted or substituted with one to four $R^i$ groups; or —$(CH_2)_n$—Q;

$R^m$ is selected from the group consisting of: hydrogen; halo; —CN; —$NO_2$; —$NHR^n$; —$NR^nR^o$; —$OR^n$; —$SR^n$; —$CONR^nR^o$; —$SOR^n$; —$SO_2R^n$; —$SO_2NR^nR^o$; —$NR^nSO_2R^o$; —$COR^n$; —$NR^nCOR^o$; —$NR^nCO_2R^h$; —$NR^nCONR^oR^h$; —$C_{1-6}$ straight- or branched-chain alkyl, unsubstituted or substituted with one to four $R^i$ groups; and —$(CH_2)_n$—Q;;

$R^d$ represents —R* as defined above or Q; and $R^n$ and $R^o$ represent hydrogen, phenyl; —$C_{1-6}$ straight- or branched-chain alkyl unsubstituted or substituted with one to four $R^i$ groups.

11. A compound in accordance with claim 9 represented by formula Id:

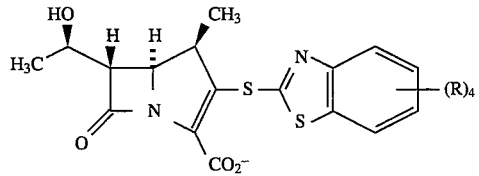

wherein:

each R is selected from the group consisting of hydrogen; halo; —CN; —$CONR^aR^b$; —$COOR^h$; —$SOR^c$; —$SO_2R^c$; —$SO_2NR^aR^b$; —$COR^a$; —$C_{1-6}$ straight- or branched-chain alkyl, unsubstituted or substituted with one to three $R^d$ groups; and —R*, with the proviso that one or two R groups contain R* or Q and —$(R)_4$ contains from one to two positively charged atoms;

Q represents a member selected from the group consisting of:

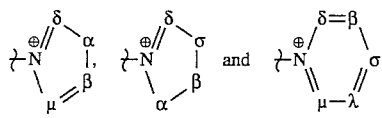

wherein:

α represents O, S or $NR^s$;

β, δ, λ, μ and σ independently represent $CR^t$, N or $N^+R^s$ provided that no more than one of β, δ, λ, μ, and σ may be $N^+R^S$;

R* is selected from the group consisting of:

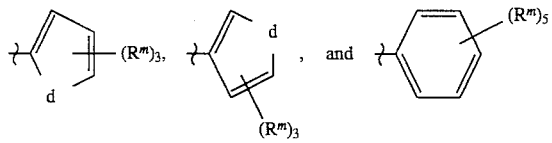

wherein:

d represents O, S or $NR^k$;

$R^a$, $R^b$ and $R^c$ independently represent hydrogen, $—C_{1-6}$ straight- or branched-chain alkyl, unsubstituted or substituted with one to four $R^d$ groups; or —R*;

or $R^a$ and $R^b$ taken together with any intervening atoms represent a 4–6 membered saturated ring optionally interrupted by one or more of O, S, $NR^c$, with $R^c$ as defined above, or —D(O)—, said ring being unsubstituted or substituted with one to four $R^i$ groups;

$R^d$ represents —R* or —Q;

each $R^h$ independently represents H, a $—C_{1-6}$ straight or branched-chain alkyl group, a $—C_3–C_6$ cycloalkyl group or phenyl, or when two $R^h$ groups are present, said $R^h$ groups may be taken in combination and represent a 4–6 membered saturated ring, optionally interrupted by one or two or O, S, $SO_2$, —C(O)—, NH and $NCH_3$;

$R^k$ represents hydrogen; $—C_{1-6}$ straight- or branched-chain alkyl, unsubstituted or substituted with one to four $R^i$ groups; or $—(CH_2)_n—Q$;

each $R^i$ independently represents halo; —CN; $—NO_2$; phenyl; $—NHSO_2R^h$; $—OR^h$; $—SR^h$; $—N(R^h)_3$; $—C(O)N(R^h)_2$; $—SO_2N(R^h)_2$; heteroaryl; heteroarylium; $—CO_2R^h$; $—C(O)R^h$; $—OCOR^h$; $—NHCOR^h$; guanidinyl; carbamimidoyl or ureido;

$R^m$ is selected from the group consisting of: hydrogen; halo; —CN; $—NO_2$; $—NHR^n$; $—NR^nR^o$; $—OR^n$; $—SR^n$; $—CONR^nR^o$; $—SOR^n$; $—SO_2R^n$; $—SO_2NR^nR^o$; $—NR^nSO_2R^o$; $—COR^n$; $—NR^n$-$COR^o$—$NR^nCO_2R^h$; $—NR^nCONR^oR^h$; $—C_{1-6}$ straight- or branched-chain alkyl, unsubstituted or substituted with one to four $R^i$ groups; and $—(CH_2)_n—Q$;

$R^n$ and $R^o$ represent hydrogen, phenyl; $—C_{1-6}$ straight- or branched-chain alkyl unsubstituted or substituted with one to four $R^i$ groups;

$R^n$ represents hydrogen; phenyl; $—C_{1-6}$ straight- or branched-chain alkyl, unsubstituted or substituted with one to four $R^i$ groups;

$R^t$ represents hydrogen; halo; phenyl; —CN; $—NHR^u$; $—NR^uR^v$; $—OR^u$; $—SR^u$; $—CONR^uR^v$; $—COOR^h$; $—SOR^u$; $—SO_2R^u$; $—SO_2NR^uR^v$; $—NR^uSO_2R^v$; $—COR^u$; $—NR^uCOR^v$; $—OCOR^u$; $—OCONR^uR^v$; $—NR^uCO_2R^v$; $—NR^uCONR^vR^w$; $—OCO_2R^v$; $—C_{1-6}$ straight-or branched-chain alkyl, unsubstituted or substituted with one to four $R^i$ groups;

$R^u$ and $R^v$ represent hydrogen or $—C_{1-6}$ straight- or branched-chain alkyl, unsubstituted or substituted with one to four $R^i$ groups;

or $R^u$ and $R^V$ together represent a 4–6 membered saturated ring optionally interrupted by one or more of O, S, $NR^w$ or —C(O)—, said ring being unsubstituted or substituted with one to four $R^i$ groups;

each $R^w$ independently represents hydrogen or $—C_{1-6}$ straight- or branched-chain alkyl, unsubstituted or substituted with one to four $R^i$ groups, $C_{3-6}$ cycloalkyl optionally substituted with one to four $R^i$ groups; or phenyl optionally substituted with one to four $R^i$ groups;

or $R^h$ and $R^w$ taken together with any intervening atoms represent a 5–6 membered saturated ring, optionally interrupted by one or two or O, S, $SO_2$, NH or $NCH_3$.

12. A compound in accordance with claim 8 represented by formula Ie;

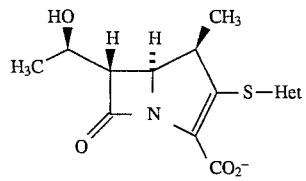

wherein:

Het has substituents which contain one to three positively charged atoms and is selected from the group consisting of:

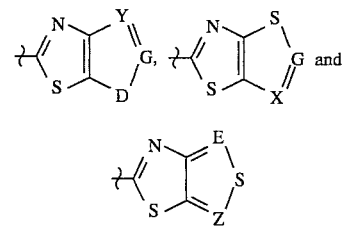

wherein:

E, G, X, Y and Z independently represent CR or N;

each R is selected from the group consisting of hydrogen; halo; —CN; $—CONR^aR^b$; $—COOR^h$; $—SOR^c$; $—SO_2R^c$; $—SO_2NR^aR^b$; $—COR^a$; $—C_{1-6}$ straight- or branched-chain alkyl, unsubstituted or substituted with one to three $R^d$ groups; $—C_{3-7}$ cycloalkyl, unsubstituted or substituted with one to three $R^d$ groups, and —R*, with the proviso that one or two R groups are present which contain R* or Q;

Q is selected from the group consisting of:

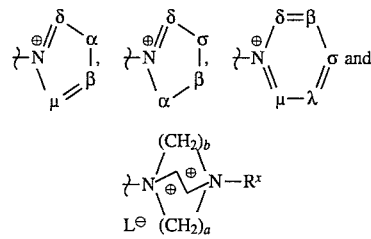

wherein:

L⁻ represents a pharmaceutically acceptable counterion;

a and b independently represent 2 or 3:

α represents O, S or $NR^s$;

β, δ, λ, μ and σ independently represent CR$^t$, N or N$^+$R$^s$ provided that no more that one of β, δ, λ, μ, and σ is N$^+$R$^s$;

R* is selected from the group consisting of;

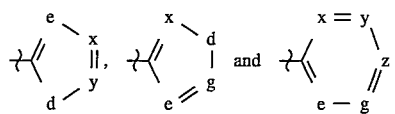

wherein:

O, S or NR$^k$;

e, g, x, y and z independently represent CR$^m$, N or N$^+$R$^k$, provided that no more that one of e, g, x, y and z represents N$^+$R$^k$;

R$^a$, R$^b$ and R$^c$ independently represent hydrogen —C$_{1-6}$ straight- or branched-chain alkyl, unsubstituted or substituted with one to four R$^d$ groups; —C$_{3-7}$ cycloalkyl, unsubstituted or substituted with one to four R$^d$ groups; or —R*;

or R$^a$ and R$^b$ taken together with any intervening atoms represent a 4–6 membered saturated ring optionally interrupted by one or more of O, S, NR$^c$, with R$^c$ as defined above, or —C(O)—, said ring being unsubstituted or substituted with one to four R$^i$ groups; and each R$^d$ independently represents halo; —CN; —NO$_2$; —NR$^e$R$^f$; —OR$^g$; —SR$^g$; —CONR$^e$R$^f$; COOR$^g$; —SOR$^g$; —SO$_2$NR$^e$R$^f$; —NR$^e$SO$_2$R$^f$; —COR$^e$; —NR$^e$COR$^f$; —OCOR$^e$; —OCONR$^e$R$^f$; —NR$^e$CONR$^f$R$^g$; —NR$^e$CO$_2$R$^h$; —OCO$_2$R$^h$; —C(NR$^e$)NR$^f$R$^g$; —NR$^e$C(NH)NR$^f$R$^g$; —NR$^e$C(NR$^f$)R$^g$; —R* or —Q;

R$^e$, R$^f$ and R$^g$ represent hydrogen; —C$_{1-6}$ straight- or branched-chain alkyl unsubstituted or substituted with one to four R$^i$ groups, or —R*;

or R$^e$ and R$^f$ taken together represent a 4–6 membered saturated ring optionally interrupted by one to three of O, S, —C(O)— or NR$^g$ with r$^g$ as defined above, said ring being unsubstituted or substituted with one to four R$^i$ groups;

each R$^h$ independently represents H, a —C$_{1-6}$ straight or branched-chain alkyl group, a —C$_3$-C$_6$ cycloalkyl group or phenyl, or when two R$^h$ groups are present, said R$^h$ groups may be taken in combination and represent a 4–6 membered saturated ring, optionally interrupted by one or two of O, S, SO$_2$, —C(O)—, NH and NCH$_3$;

each R$^i$ independently represents halo; —CN; —NO$_2$; phenyl; —NHSO$_2$R$^h$; —OR$^h$, —SR$^h$; —N(R$^h$)$_2$; —N$^+$(R$^h$)$_3$; —C(O)N(R$^h$)$_2$; —SO$_2$N(R$^h$)$_2$; heteroaryl, heteroarylium; —CO$_2$R$^h$; —C(O)R$^h$; —OCOR$^h$; —NHCOR$^h$; guanidinyl; carbamimidoyl or ureido;

R$^k$ represents hydrogen; —C$_{1-6}$ straight- or branched-chain alkyl, unsubstituted or substituted with one to four R$^i$ groups; or —(CH$_2$)$_n$—Q;

R$^s$ represents hydrogen; phenyl; —C$_{1-6}$ straight- or branched-chain alkyl, unsubstituted or substituted with one to four R$^i$ groups;

R$^t$ represents hydrogen; halo; phenyl; —CN; —NR$^u$R$^v$; —OR$^u$; —SR$^u$; —CONR$^u$R$^v$; —COOR$^h$; —SOR$^u$; —SO$_2$R$^u$; —SO$_2$NR$^u$R$^v$; — NR$^u$SO$_2$R$^v$; —COR$^u$; —NR$^u$COR$^v$; —OCOR$^u$; —OCONR$^u$R$^v$; —NR$^u$CO$_2$R$^v$; —NR$^u$CONR$^v$R$^w$; —OCO$_2$R$^v$; —C$_{1-6}$ straight- or branched-chain alkyl, unsubstituted or substituted with one to four R$^i$ groups;

R$^u$ and R$^v$ represent hydrogen or —C$_{1-6}$ straight- or branch-chain alkyl, unsubstituted or substituted with one to four R$^i$ groups;

or R$^u$ and R$^v$ together represent a 4–6 membered saturated ring optionally interrupted by one or more of O, S, NR$^w$ or —C(O)—, said ring being unsubstituted or substituted with one to four R$^i$ groups, and each R$^w$ independently represents hydrogen or —C$_{1-6}$ straight- or branched-chain alkyl, unsubstituted or substituted with one to four R$^i$ groups; C$_{3-6}$ cycloalkyl optionally substituted with one to four R$^i$ groups; or phenyl optionally substituted with one to four R$^i$ groups.

13. A compound in accordance with claim 12 represented by formula Ie:

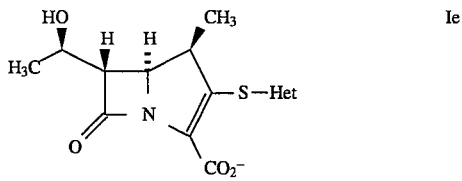

wherein:

Het has substituents which contain from one to three positively charged atoms and is selected from the group consisting of:

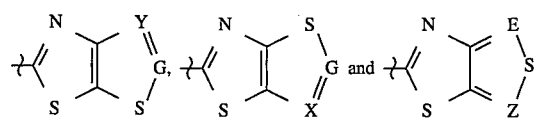

wherein:

E, G, X, Y and Z independently represent CR or N;

each R is selected from the group consisting of hydrogen; halo; —CN; —CONR$^a$R$^b$; —COOR$^h$; —SOR$^c$; —SO$_2$R$^c$; —SO$_2$NR$^a$R$^b$; —COR$^a$; —C$_{1-6}$ straight- or branched-chain alkyl, unsubstituted or substituted with one to three R$^d$ groups; —C$_{3-7}$ cycloalkyl, unsubstituted or substituted with one to three R$^d$ groups; and —R*;

with the proviso that one R group contains Q;

R* is selected from the group consisting of:

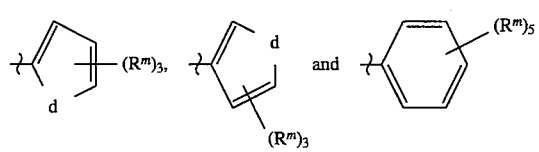

wherein:

d is O, S or NR$^k$;

Q represents

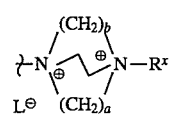

wherein a and b are 2,

L– is a pharmaceutically acceptable counterion, and

R$^x$ represents hydrogen or a C$_{1-8}$ straight- or branched-chain alkyl, optionally interrupted by one or two of O, S, SO, SO$_2$, NR$^w$, N$^+$R$^h$R$^w$, or —C(O)—, said chain being unsubstituted or substituted with one to four of halo, CN, NO$_2$, OR$^w$, SR$^w$, SOR$_w$, SO$_2$R$^w$, NR$^h$R$^w$, N$^+$(R$^h$)$_2$R$^w$, —C(O)—R$^w$, C(O)NR$^h$R$^w$, SO$_2$NR$^h$R$^w$, CO$_2$R$^w$, OC(O)R$^w$, OC(O)NR$^h$R$^w$, NR$^h$C(O)R$^w$, NR$^h$C(O)NR$^h$R$^w$, or a phenyl or heteroaryl group which is in turn optionally substituted with from one to four R$^i$ groups or with one to two C$_{1-3}$ straight- or branched-chain alkyl groups, said alkyl groups being unsubstituted or substituted with one to four R$^i$ groups;

each R$^h$ independently represents H, a —C$_{1-6}$ straight or branch-chain alkyl group, a —C$_3$-C$_6$ cycloalkyl group or phenyl, or when two R$^h$ groups are present, said R$^h$ groups may be taken in combination and represent a 4–6 membered saturated ring, optionally interrupted by one or two of O, S, SO$_2$, —C(O)—, NH and NCH$_3$;

each R$^i$ independently represents halo; —CN; —NO$_2$; phenyl; —NHSO$_2$R$^h$; —OR$^h$; —SR$^h$; —N(R$^h$)$_2$; —N$^+$(R$^h$)$_3$; —C(O)N(R$^h$)$_2$; —SO$_2$N(R$^h$)$_2$; heteroaryl, heteroarylium; —CO$_2$R$^h$; —C(O)R$^h$; —OCOR$^h$; —NHCOR$^h$; guanidinyl; carbamimidoyl or ureido;

R$^k$ represents hydrogen; —C$_{1-6}$ straight- or branched-chain alkyl, unsubstituted or substituted with one to four R$^i$ groups; or —(CH$_2$)$_n$—Q, wherein n=1, 2 or 3 and Q is as defined above;

R$^m$ is selected from the group consisting of: hydrogen; halo; —CN; —NO$_2$; —NHR$^n$; —NR$^n$R$^o$; —OR$^n$; —SR$^n$; — CONR$^n$R$^o$; —SOR$^n$; —SO$_2$R$^n$; —SO$_2$NR$^n$R$^o$; —NR$^n$SO$_2$R$^o$; —COR$^n$; —NR$^n$COR$^o$; —NR$^n$CO$_2$R$^h$; —NR$^n$CONR$^o$R$^h$; —C$_{1-6}$ straight- or branched-chain alkyl, unsubstituted or substituted with one to four R$^i$ groups; and —(CH$_2$)$_{1-3}$Q;

R$^a$, R$^b$ and R$^c$ independently represent hydrogen, —C$_{1-6}$ straight- or branched-chain alkyl, unsubstituted or substituted with one of four R$_d$ groups; or —R$^*$;

or R$^a$ and R$^b$ taken together with any intervening atoms represent a 4–6 membered saturated ring optionally interrupted by one or more of O, S, NR$^c$, with R$^c$ as defined above, or —C(O)—, said ring being unsubstituted or substituted with one to four R$^i$ groups;

R$^d$ represents R$^*$ or Q;

R$^n$ and R$^o$ represent hydrogen, phenyl, —C$_{1-6}$ straight- or branched-chain alkyl unsubstituted or substituted with one to four R$^i$ groups, and R$^w$ represents hydrogen or —C$_{1-6}$ straight- or branched-chain alkyl, unsubstituted or substituted with one to four R$^i$ groups; C$_{3-6}$ cycloalkyl optionally substituted with one to four R$^i$ groups; or phenyl optionally substituted with one to four R$^i$ groups, or R$^h$ and R$^w$ taken together with any intervening atoms represent a 5–6 membered saturated ring, optionally interrupted by one or two of O, S, SO$_2$, NH or NCH$_3$.

14. A compound in accordance with claim 12 represented by formula Ie:

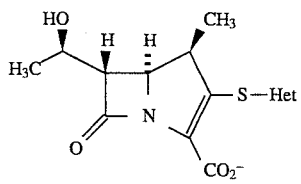

Ie wherein

Het has substituent groups which contain from one to three positively charged atoms and is selected from the group consisting of:

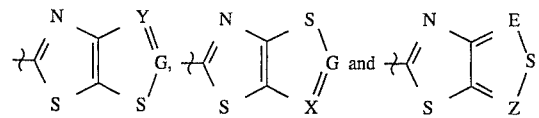

wherein

E, G, X, Y and Z independently represent CR of N;

R represents a member selected from the group consisting of hydrogen; halo; —CN; —CONR$^a$R$^b$; —COOR$^h$; —SOR$^c$; —SO$_2$R$^c$; —SO$_2$NR$^a$R$^b$; —COR$^a$; —C$_{1-6}$ straight- or branched-chain alkyl unsubstituted or substituted with one to three R$^d$ groups; and —R$^*$, with the proviso that one or two R groups contain R$^*$ or Q;

Q represents a member selected from the group consisting of:

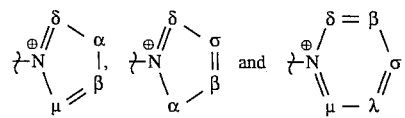

α represents O, S, or NR$^s$;

β, δ, λ, μ and σ independently represent CR$^t$, N or N$^+$R$^s$ provided that no more than one of β, δ, λ, μ, and σ may be N$^+$R$^s$;

R$^*$ is selected from the group consisting of:

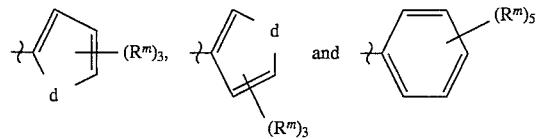

wherein:

d represents O, S, or NR$^k$;

R$^a$, R$^b$ and R$^c$ independently represent hydrogen, —C$_{1-6}$ straight- or branched-chain alkyl, unsubstituted or substituted with one to four R$^d$ groups; or —R$^*$;

or R$^a$ and R$^b$ taken together with any intervening atoms represent a 4–6 membered saturated ring optionally interrupted by one or more of O, S, NR$^c$, with R$^c$ as defined above, or —C(O)—, said ring being unsubstituted or substituted with one to four R$^i$ groups;

R$^d$ represents —R$^*$ or —Q;

each R$^h$ independently represents H, a —C$_{1-6}$ straight or branched-chain alkyl group, a —C$_3$-C$_6$ cycloalkyl group or phenyl, or when two R$^h$ groups are present, said R$^h$ groups may be taken in combination and represent a 4–6 membered saturated ring, optionally interrupted by one or two of O, S, SO$_2$, —C(O)—, NH and NCH$_3$;

each R$^i$ independently represents halo; —CN; —NO$_2$; phenyl —NHSO$_2$R$^h$; —OR$^h$; —SR$^h$; —N(R$^h$)$_2$; —N$^+$(R$^h$)$_3$; —C(O)N(R$^h$)$_2$; —SO$_2$N(R$^h$)$_2$; heteroaryl, heteroarylium, —CO$_2$R$^h$; —C(O)R$^h$; —OCOR$_h$; —NHCOR$^h$; guanidinyl; carbamimidoyl or ureido;

R$^k$ represents hydrogen; —C$_{1-6}$ straight- or branched-chain alkyl, unsubstituted or substituted with one to four R$^i$ groups; or —(CH$_2$)$_n$—Q, wherein n and Q are as previously defined;

R$^m$ is selected from the group consisting of: hydrogen; halo; —CN; —NO$_2$; —NHR$^n$; —NR$^n$R$^o$; —OR$^n$; —SR$^n$; —CONR$^n$R$^o$; —SOR$^n$; —SO$_2$R$^n$;

—SO$_2$NR$^n$R$^o$; —NR$^n$SO$_2$R$^o$; —COR$^n$; —NR$^n$COR$^o$; —NR$^n$CO$_2$R$^h$; —NR$^n$CONR$^o$R$^h$; —C$_{1-6}$ straight- or branched-chain alkyl, unsubstituted or substituted with one to four R$^i$ groups; and —(CH$_2$)$_n$—Q, wherein n and Q are as previously defined;

R$^n$ and R$^o$ represent hydrogen, phenyl; —C$_{1-6}$ straight- or branched-chain alkyl unsubstituted or substituted with one to four R$^i$ groups;

R$^s$ represents hydrogen; phenyl; —C$_{1-6}$ straight- or branched-chain alkyl, unsubstituted or substituted with one to four R$^i$ groups;

R$^t$ represents hydrogen; halo; phenyl; —CN; —NHR$^u$; —NR$^u$R$^v$; —OR$^u$; —SR$^u$; —CONR$^u$R$^v$; —COOR$^h$; —SOR$^u$; —SO$_2$R$^u$; —SO$_2$NR$^u$R$^v$; —NR$^u$SO$_2$R$^v$; —COR$^u$; —NR$^u$COR$^v$; —OCOR$^u$; — OCONR$^u$R$^v$; —NR$^u$CO$_2$R$^v$; —NR$^u$CONR$^v$R$^w$, —OCO$_2$R$^v$; —C$_{1-6}$ straight- or branched-chain alkyl unsubstituted or substituted with one to four R$^i$ groups;

R$^u$ and R$^v$ represent hydrogen or —C$_{1-6}$ straight- or branched-chain alkyl, unsubstituted or substituted with one to four R$^i$ groups;

or R$^u$ and R$^v$ together represent a 4–6 membered saturated ring optionally interrupted by one or more of O, S, NR$^w$ or —C(O)—, said ring being unsubstituted or substituted with one to four R$^i$ groups each R$^w$ independently represents hydrogen or —C$_{1-6}$ straight- or branched-chain alkyl, unsubstituted or substituted with one to four R$^i$ groups; C$_{3-6}$ cycloalkyl optionally substituted with one to four R$^i$ groups; or phenyl optionally substituted with one to four R$^i$ groups.

15. A compound in accordance with claim 10 represented by the formula If:

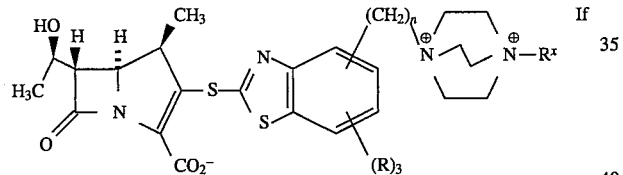

wherein:

L— is a pharmaceutically acceptable counterion:

n is 1–3;

R$^x$ represents hydrogen or a C$_{1-8}$ straight- or branched-chain alkyl, optionally interrupted by one or two of O, S, SO, SO$_2$, NR$^w$, N$^+$R$^w$R$^w$, or —C(O)—, said chain being unsubstituted or substituted with one of four of halo, CN, NO$_2$, OR$^w$, SR$^w$, SOR$^w$, SO$_2$R$^w$, NR$^h$R$^w$, N$^+$(R$^h$)$_2$R$^w$, —C(O)—R$^w$, C(O)NR$^h$R$^w$, SO$_2$NR$^h$R$^w$, CO$_2$R$^w$, OC(O)R$^w$, OC(O)NR$^h$R$^w$, NR$^h$C(O)R$^w$, NR$^h$R$^w$, or a phenyl or heteroaryl group which is in turn optionally substituted with from one to four R$^i$ groups or with one to two C$_{1-3}$ straight- or branched- chain alkyl groups, said alkyl groups being unsubstituted or substituted with one to four R$^i$ groups;

each R is independently selected from: hydrogen; halo; —CN; ≦NO$_2$; —OR$^c$; —SR$^c$; —CONR$^a$R$^b$; —CO-OR$^h$; —SOR$^c$j; —SO$_2$ R$^c$; —SO$_2$NR$^a$R$^b$; —NR$^a$SO$_2$R$^b$; ≦COR$^a$; —OCOR$^a$; —OCONR$^a$R$^b$; —NR$^a$CONR$^b$R$^c$; —NR$^a$CO$_2$R$^h$; —OCO$_2$R$^h$; —C$_{1-6}$ straight- or branched- chain alkyl, unsubstituted or substituted with one to four R$^d$ groups; and —C$_{3-7}$ cycloalkyl, unsubstituted or substituted with one of four R$^d$ groups, each R$^d$ independently represents halo; —CN; —NO$_2$; —NR$^e$R$^f$; —OR$^g$; —SR$^g$; —CONR$^e$R$^f$; —COOR$^g$; —SOR$^g$; —SO$_2$NR$^e$R$^f$; —NR$^e$SO$_2$R$^f$; —COR$^e$; —NR$^e$COR$^f$; —OCOR$^e$; —OCONR$^e$R$^f$; —NR$^e$CON-R$^f$R$^g$; —NR$^e$CO$_2$R$^h$; —OCO$_2$R$^h$; —C(NR$^e$)NR$^f$R$^g$; —NR$^e$C(NH)NR$^f$R$^g$; or —NR$^e$C(NR$^f$)R$^g$;

R$^e$, R$^f$ and R$^g$ represent hydrogen; or C$_{1-6}$ straight- or branched-chain alkyl unsubstituted or substituted with one to four R$^i$ groups;

or R$^e$ and R$^f$ taken together with any intervening atoms represent a 4–6 membered saturated ring optionally interrupted by one to three of O, S, —C(O)— or NR$^g$ with R$^g$ as defined above, said ring being unsubstituted or substituted with one to four R$^i$ groups;

each R$^h$ independently represents H, a —C$_{1-6}$ straight or branched-chain alkyl group, a —C$_3$-C$_6$ cycloalkyl group or phenyl, or when two R$^h$ groups are present, said R$^h$ groups may be taken in combination and represent a 4–6 membered saturated ring, optionally interrupted by one or two of O, S, SO$_2$, —C(O)—, NH and NCH$_3$;

each R$^i$ independently represents halo; —CN; —NO$_2$; phenyl; —NHSO$_2$R$^h$; —OR$^h$, —SR$^h$; —N(R$^h$)$_2$; —N$^+$(R$^h$)$_3$; —C(O)N(R$^h$)$_2$; —SO$_2$N(R$^h$)$_2$; heteroaryl; heteroarylium; —CO$_2$R$^h$; —C(O)R$^h$; —OCOR$^h$; —NHCOR$^h$; guanidinyl; carbamimidoyl or ureido;

R$^w$ represents hydrogen or —C$_{1-6}$ straight- or branched-chain alkyl, unsubstituted or substituted with one to four R$^i$ groups; C$_{3-6}$ cycloalkyl optionally substituted with one to four R$^i$ groups; or phenyl optionally substituted with one to four R$^i$ groups, or R$^h$ and R$^w$ taken together with any intervening atoms represent a 5–6 membered saturated ring, optionally interrupted by one or two of O, S, SO$_2$, NH or NCH$_3$.

16. A compound in accordance with claim 15 represented by formula Ig:

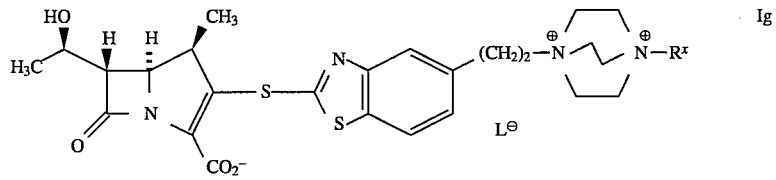

wherein:

L— is a pharmaceutically acceptable counterion;

R$^x$ represents hydrogen or a C$_{1-8}$ straight- or branched-chain alkyl, optionally interrupted by one or two of O, S,SO, SO$_2$, NR$^w$, N$^+$R$^h$R$^w$, or ≦C(O)—, said chain being unsubstituted or substituted with one to four of halo, CN, NO$_2$, OR$^w$, SR$^w$, SOR$^w$, SO$_2$R$^w$, OC(O)R$^w$, OC(O)NR$^h$R$^w$, NR$^h$C(O)R$^w$, NR$^h$C(O)NR$^h$R$^w$, or a phenyl of heteroaryl group which is in turn optionally substituted with from one to four R$^i$ groups or with one to two C$_{1-3}$ straight- or branched- chain alkyl groups, said alkyl groups being unsubstituted or substituted with one to four R$^i$ groups;

each R$^h$ independently represents H, a —C$_{1-6}$ straight or branched-chain alkyl group, a —C$_3$-C$_6$ cycloalkyl group or phenyl, or when two R$^h$ groups are present, said $R^h$ groups may be taken in combination and represent a 4-6 membered saturated ring, optionally interrupted by one or two of O, S, $SO_2$m —C(O)—NH and $NCH_3$; p1 $R^w$ represents hydrogen or —$C_{1-6}$ straight- or branched-chain alkyl, unsubstituted or substituted with one to four $R^i$ groups, $C_{3-6}$ cycloalkyl optionally substituted with one to four $R^i$ groups; or phenyl optionally substituted with one to four $R^i$ groups, or $R^h$ and $R^w$ taken together with any intervening atoms represent at 5-6 membered saturated ring, optionally interrupted by one or two of O, S, $SO_2$, NH or $NCH_3$; and each $R^i$ independently represents halo; —CN; —$NO_2$; phenyl; —$NHSO_2R^h$; —$OR^h$, —$SR^h$; —$N(R^h)_2$; —$N^{+(Rh)}{}_3$; —$C(O)N(R^h)_2$; —$SO_2N(R^h)_2$; heteroaryl; heteroarylium; —$CO_2R^h$; —$C(O)R^h$; —$OCOR^h$; —$NHCOR^h$; guanidinyl; carbamimidoyl or ureido.

17. A compound in accordance with claim 15 represented by formula Ih:

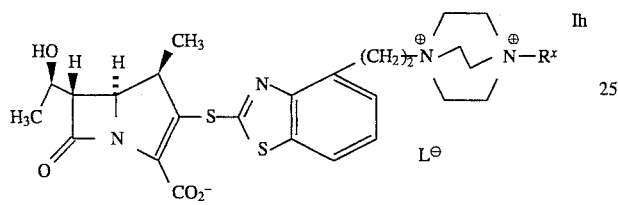

wherein:

L– is a pharmaceutically acceptable counterion;

$R^x$ represents hydrogen or a $C_{1-8}$ straight- or branched-chain alkyl, optionally interrupted by one or two of O, S, SO, $SO_2$, $NR^w$, $N^+R^hR^w$, or —C(O)—, said chain being unsubstituted or substituted with one to four of halo, CN, $NO_2$, $OR^w$, $SR^w$, $SOR^w$, $SO_2R^w$, $NR^hR^w$, $N^{+(Rh)}{}_2R^w$, —C(O)—$R^w$, $C(O)NR^hR^w$, $SO_2NR^hR^w$, $CO_2R^w$, $OC(O)R^w$, $OC(O)NR^hR^w$, $NR^hC(O)R^w$, $NR^hC(O)NR^hR^w$, or a phenyl or heteroaryl group which is in turn optionally substituted with from one to four $R^i$ groups or with one to two $C_{1-3}$ straight- or branched- chain alkyl groups, said alkyl groups being unsubstituted or substituted with one to four $R^i$ groups;

each $R^h$ independently represents H, a —$C_{1-6}$ straight or branched-chain alkyl group, a —$C_3$-$C_6$ cycloalkyl group or phenyl, or when two $R^h$ groups are present, said $R^h$ groups may be taken in combination and represent a 4-6 membered saturated ring, optionally interrupted by one or two of O, S, $SO_2$, —C(O)—, NH and $NCH_3$;

$R^w$ represents hydrogen or —$C_{1-6}$ straight- or branched-chain alkyl, unsubstituted or substituted with one to four $R^i$ groups, $C_{3-6}$ cycloalkyl optionally substituted with one to four $R^i$ groups; or phenyl optionally substituted with one to four $R^i$ groups;

or $R^h$ and $R^w$ taken together with any intervening atoms represent a 5-6 membered saturated ring, optionally interrupted by one or two of O, S, $SO_2$, NH or $NCH_3$, and each $R^i$ independently represents halo; —CN; —$NO_2$; phenyl; —$NHSO_2R^h$; —$OR^h$—$SR^h$; —$N(R^h)_2$; $N^+(R^h)_3$; —$C(O)N(R^h)_2$; —$SO_2N(R^h)_2$; heteroaryl; heteroarylium; —$CO_2R^h$; —$C(O)R^h$; —$OCOR^h$; —$NHCOR^h$; guanidinyl; carbamimidoyl or ureido.

18. A compound i accordance with claim 11 represented by formula Ii:

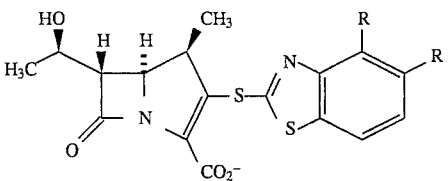

wherein:

each R independently represents a member selected from the group consisting of hydrogen or —$C_{1-6}$ straight- or branched-chain alkyl, unsubstituted or substituted with one to three $R^d$ groups;

$R^d$ represents —Q;

Q represents a member selected from the group consisting

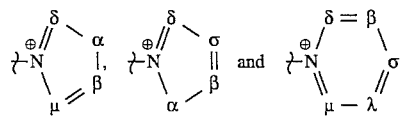

wherein:

α represents O, S or $NR^s$;

β, δ, λ, μ and σ independently represent $CR^t$, N or $N^+R^s$ provided that no more than one of β, δ, λ, μ, and σ may be $N^+R^s$ and further provided that from one to three positively charged atoms are contained in the R groups;

$R^s$ represents hydrogen; halo; phenyl; ≦CN; —$NHR^u$; —$NR^uR^v$; —$OR^u$; —$SR^u$; —$CONR^uR^v$; —$COOR^h$; —$SOR^u$; —$SO_2R^u$; —$SO_2NR^uR^v$; —$NR^uSO_2R^v$; —$COR^u$; —$NR^uCOR^v$; —$OCOR^u$; —$OCONR^uR^v$; —$NR^uCO_2R^v$; —$NR^uCONR^vR^w$; —$OCO_2R^v$; —$C_{1-6}$ straight- or branched-chain alkyl, unsubstituted or substituted with one to four $R^i$ groups;

each $R^i$ independently represents halo; —CN; —$NO_2$; phenyl; —$NHSO_2R^h$; —$OR^h$, —$SR^h$; —$N(R^h)_2$; —$N^+(R^h)_3$; —$C(O)N(R^h)_2$; —$SO_2N(R^h)_2$; heteroaryl; heteroarylium; —$CO_2R^h$; —$C(O)R^h$; —$OCOR^h$; —$NHCOR^h$; guanidinyl; carbamimidoyl or ureido.

each $R^h$ independently represents H, a —$C_{1-6}$ straight or branched-chain alkyl group, a —$C_3$-$C_6$ cycloalkyl group or phenyl or when two $R^h$ groups are present, said $R^h$ groups may be taken in combination and represent a 4-6 membered saturated ring, optionally interrupted by one or two of O, $S_2$, —C(O)—, NH and $NCH_3$;

$R^u$ and $R^v$ represent hydrogen or —$C_{1-6}$ straight- or branched-chain alkyl, unsubstituted or substituted wit one to four $R^i$ groups;

$R^u$ and $R^v$ together represent a 4-6 membered saturated ring optionally interrupted by one or more of O, S, $NR^w$ or —C(O)—, said ring being unsubstituted or substituted with one to four $R^i$ groups;

and each $R^w$ independently represents hydrogen or —$C_{1-6}$ straight- or branched-chain alkyl, unsubstituted or substituted with one to four $R^i$ groups; $C_{3-6}$ cycloalkyl optionally substituted with one to four $R^i$ groups; or phenyl optionally substituted with one to four $R^i$ groups.

19. A compound in accordance with claim 13 represented by formula Ie:

219

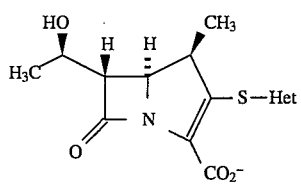

wherein:

Het has substituent groups which contain from two to three positively charged atoms and is selected from the group consisting of:

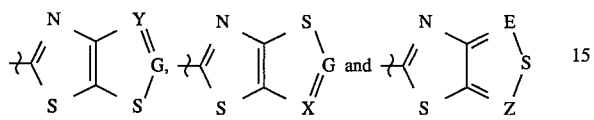

wherein:

E, G and Y independently represent CR or N;

X and Z independently represent CH or N;

R represents a member selected from the group consisting of hydrogen; —$C_{1-6}$ straight- or branched-chain alkyl, unsubstituted or substituted with $R^d$;

with the proviso that one R group is present which contains Q;

$R^d$ represents Q:

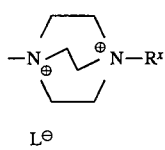

Q represents wherein L— is a pharmaceutically acceptable counterion;

$R^x$ represents hydrogen or a $C_{1-8}$ straight- or branched-chain alkyl, optionally interrupted by one or two of O, S, SO, $SO_2$, $NR^w$, $N^+R^hR^w$, or —C(O)—, said chain being unsubstituted or substituted with one to four of halo, CN, $NO_2$, $OR^w$, $SR^w$, $SOR^w$, $SO_2R^w$, $NR^hR^w$, $N^+(R^h)_2R^w$, $C(O)NR^hR^w$, $SO_2NR^hR^w$, $CO_2R^w$, $OC(O)R^w$, $OC(O)NR^hR^w$, $NR^hC(O)R^w$, $NR^hC(O)N$-$R^hR^w$, or a phenyl or heteroaryl group which is in turn optionally substituted with from one to four $R^i$ groups or with one to two $C_{1-3}$ straight- or branched-chain alkyl groups, said alkyl groups being unsubstituted or substituted with one to four $R^i$ groups;

each $R^h$ independently represents H, a —$C_{1-6}$ straight or branched-chain alkyl group, a —$C_3$-$C_6$ cycloalkyl group or phenyl, or when two $R^h$ groups are present, said $R^h$ groups may be taken in combination and represent a 4–6 membered saturated ring, optionally interrupted by one or two of O, S, $SO_2$, —C(O)—, NH and $NCH_3$;

each $R^i$ independently represents halo; —CN; —$NO_2$; phenyl; —$NHSO_2R^h$; —$OR^h$, —$SR^h$; —$N(R^h)_2$; —N+$(R^h)_3$; —$C(O)N(R^h)_2$; —$SO_2N(R^h)_2$; heteroaryl; heteroarylium; —$CO_2R^h$; —$C(O)R^h$; —$OCOR^h$; —$NHCOR^h$; guanidinyl; carbamimidoyl or ureido, and $R^w$ represents hydrogen or —$C_{1-6}$ straight- or branched-chain alkyl, unsubstituted or substituted with one to

220 four $R^i$ groups; $C_{3-6}$ cycloalkyl optionally substituted with one to four $R^i$ groups; or phenyl optionally substituted with one to four $R^i$ groups, or $R^h$ and $R^w$ taken together with any intervening atoms represent a 5–6 membered saturated ring, optionally interrupted by one or two of O, S, $SO_2$, NH or $NCH_3$.

20. A compound in accordance with claim 14 represented by formula Ie:

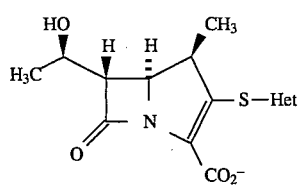

wherein:

Het has substituents which contain from one to three positively charged atoms and is selected from the group consisting of:

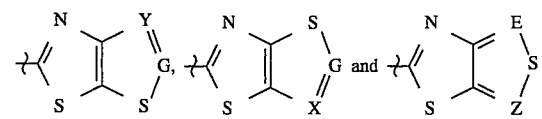

wherein:

E, G, X, Y and Z independently represent CR or N;

R represents a member selected from the group consisting of hydrogen; —$C_{1-6}$ straight- or branched-chain alkyl, unsubstituted or substituted with one to three $R^d$ groups;

with the proviso that from one to three R groups are present which contains Q;

$R^d$ represents Q;

Q is selected from the group consisting of:

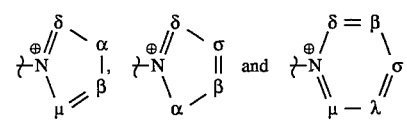

wherein:

α represents O, S or $NR^s$;

β, δ, λ, μ and σ independently represent $CR^t$, N or $N^{+Rs}$ provided that no more than one of β, δ, λ, μ, and σ may be $N^+R^s$;

$R^s$ represents hydrogen; phenyl; —$C_{1-6}$ straight- or branched-chain alkyl, unsubstituted or substituted with one to four $R^i$ groups;

each $R^i$ independently represents halo; —CN; —$NO_2$; phenyl; —$NHSO_2R^h$; —$OR^h$, —$SR^h$; —$N(R^h)_2$; —$N^+(R^h)_3$; —$C(O)N(R^h)_2$; —$SO_2N(R^h)_2$; heteroaryl; heteroarylium; —$CO_2R^h$; —$C(O)R^h$; —$OCOR^h$; —$NHCOR^h$; guanidinyl; carbamimidoyl or ureido;

each $R^h$ independently represents H, a —$C_{1-6}$ straight or branched-chain alkyl group, a —$C_3$-$C_6$ cycloalkyl group or phenyl, or when two $R^h$ groups are present, said $R^h$ groups may be taken in combination and represent a 4–6 membered saturated ring, optionally interrupted by one or two of O, S, $SO_2$, —C(O)—, NH and $NCH_3$;

$R^t$ represents hydrogen; halo; phenyl; —CN; —NHR$^u$; —NR$^u$R$^v$; —OR$^u$; —SR$^u$; —CONR$^u$R$^v$; —COOR$^h$; —SOR$^u$; —SO$_2$R$^u$; —SO$_2$NR$^u$R$^v$; —NR$^u$SO$_2$R$^v$; —COR$^u$; —NR$^u$COR$^v$; —OCOR$^u$; —OCONR$^u$R$^v$; —NR$^u$CO$_2$R$^v$; —NR$^u$CONR$^v$R$^w$; —OCO$_2$R$^v$; —C$_{1-6}$ straight- or branched-chain alkyl, unsubstituted or substituted with one to four R$^i$ groups;

R$^u$ and R$^v$ represent hydrogen or —C$_{1-6}$ straight- or branched-chain alkyl, unsubstituted or substituted with one to four R$^i$ groups;

or R$^u$ and R$^v$ together represent a 4–6 membered saturated ring optionally interrupted by one or more of O, S, NR$^w$ or —C(O)—, said ring being unsubstituted or substituted with one to four R$^i$ groups;

and each R$^w$ independently represents hydrogen or —C$_{1-6}$ straight- or branched-chain alkyl, unsubstituted or substituted with one to four R$^i$ groups; C$_{3-6}$ cycloalkyl optionally substituted with one to four R$^i$ groups; or phenyl optionally substituted with one to four R$^i$ groups.

21. A compound in accordance with claim 16 wherein Het is selected from the group consisting of:

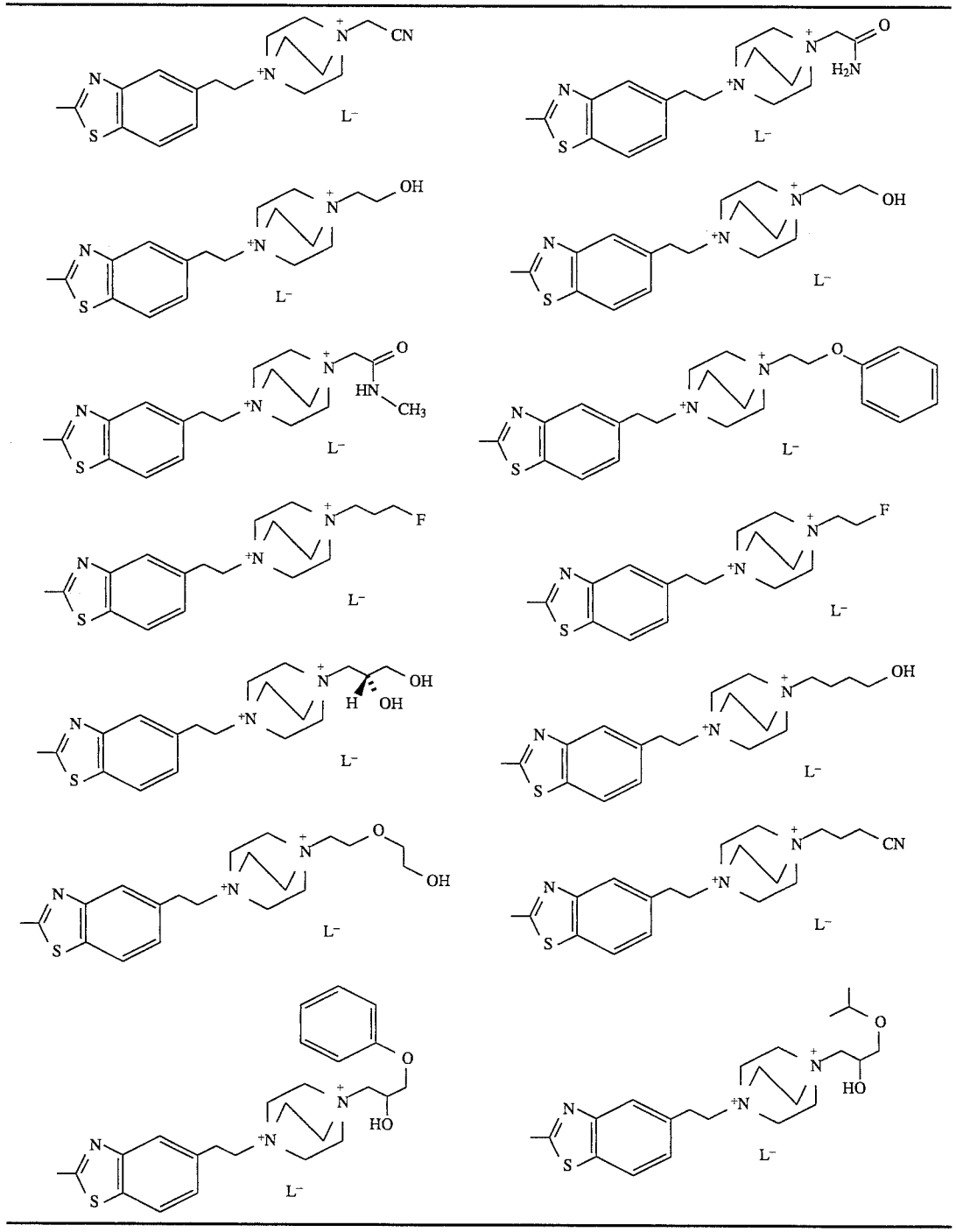

22. A compound in accordance with claim 7 wherein Het is selected from the following:
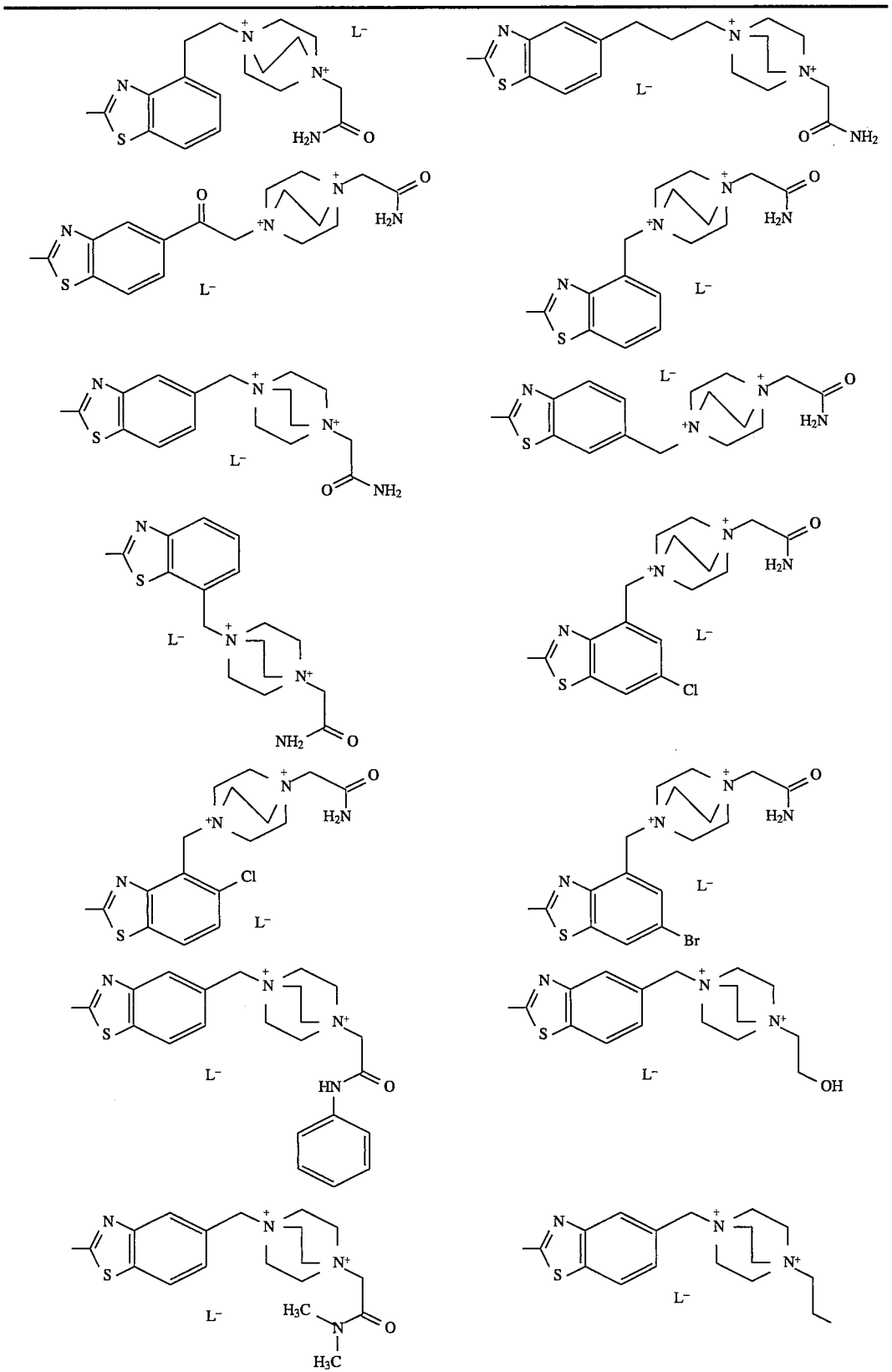

| 225 | 226 |
|---|---|
| 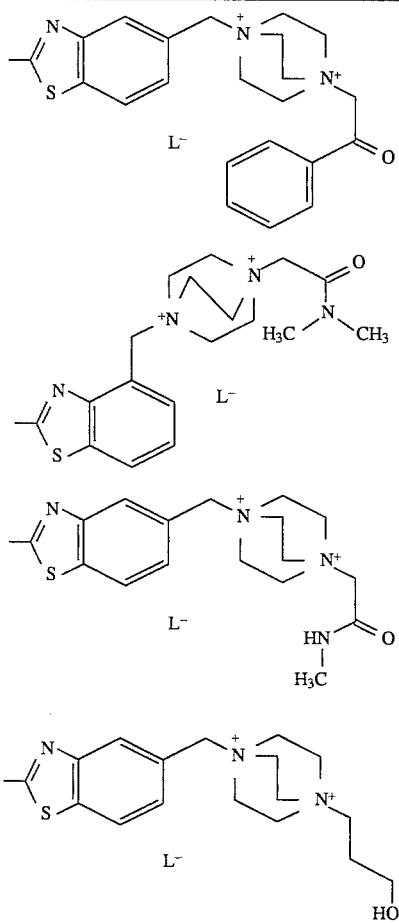 | 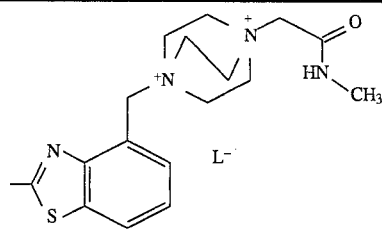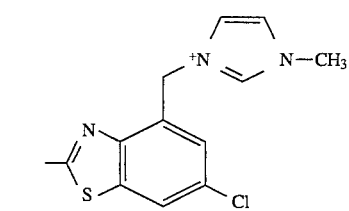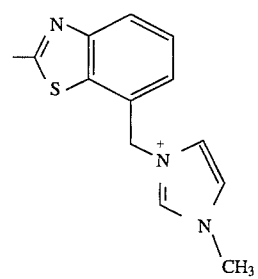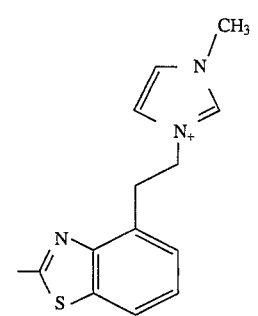 |
| 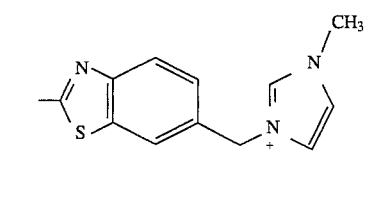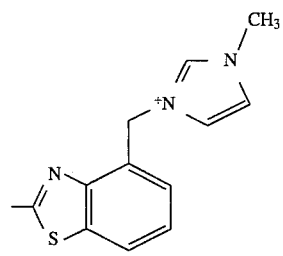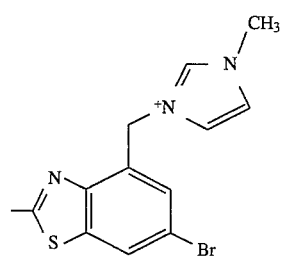 | |

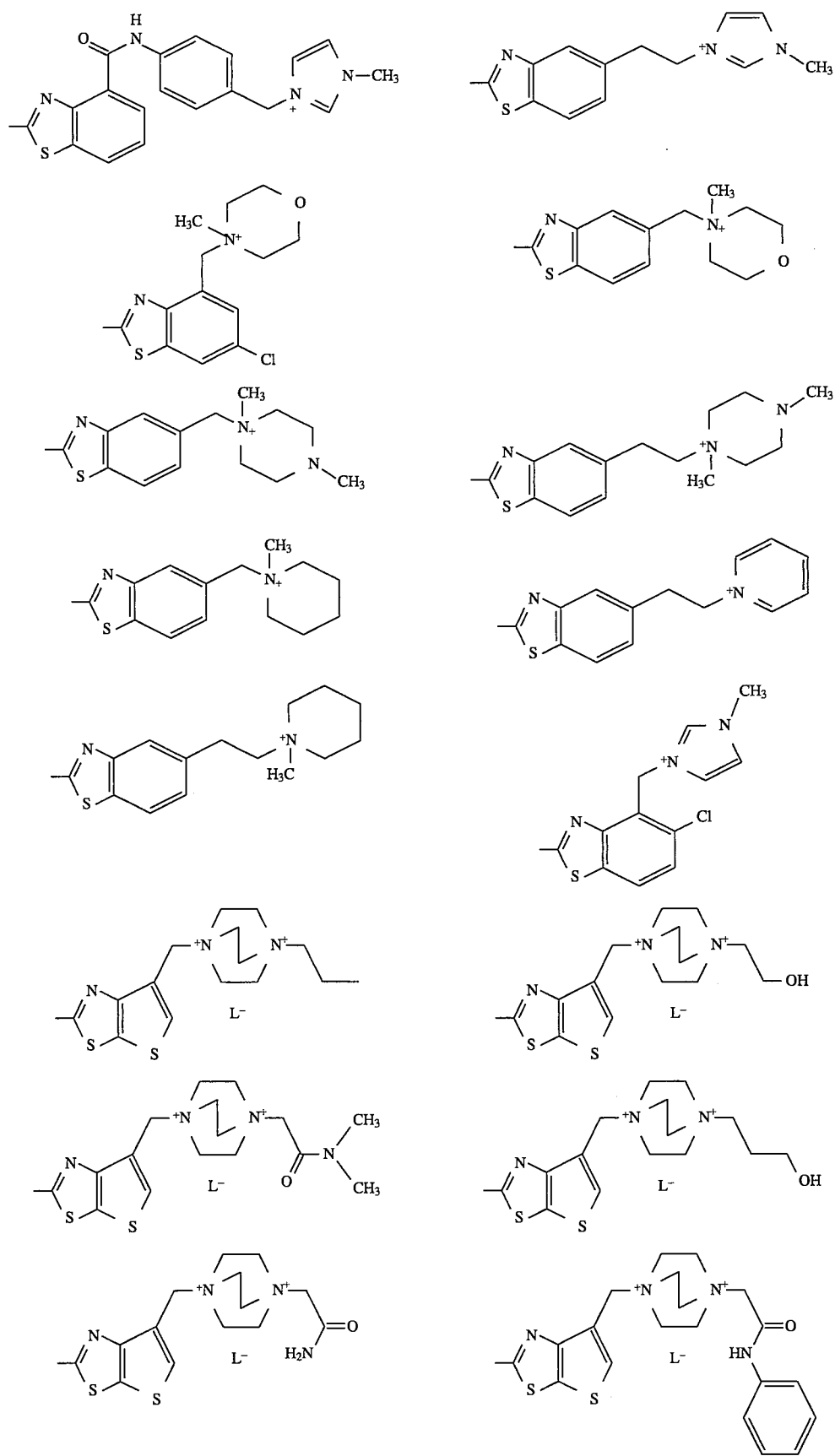

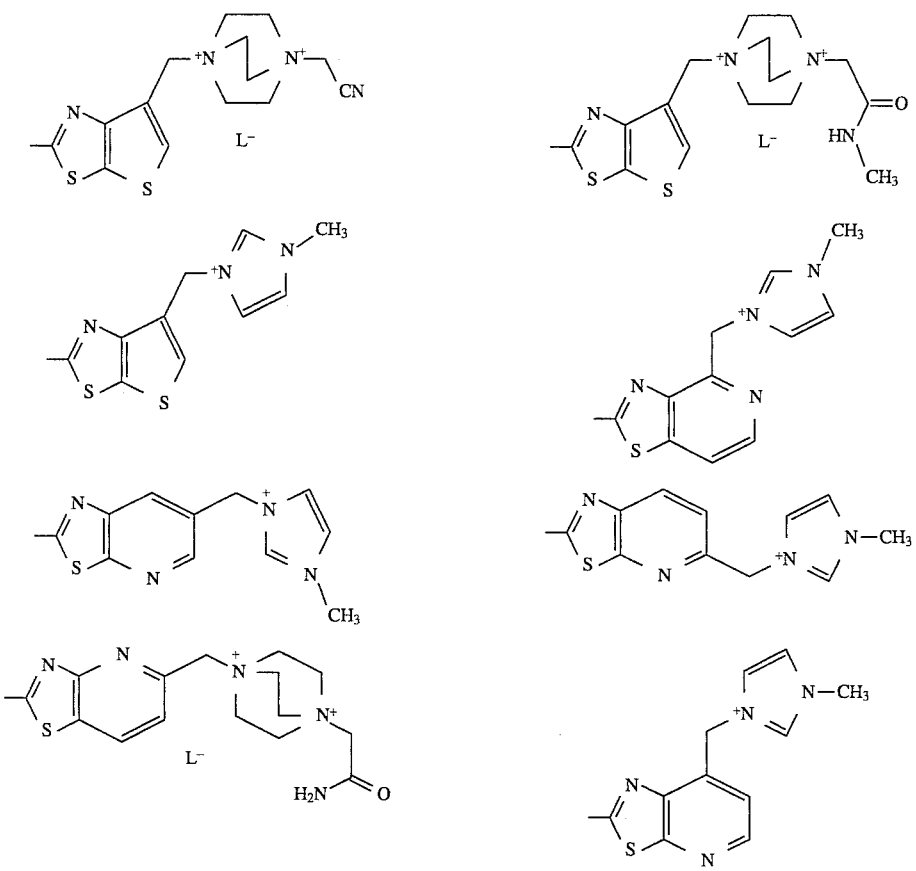
23. A compound in accordance with claim 1 wherein Het is selected from the group consisting of:
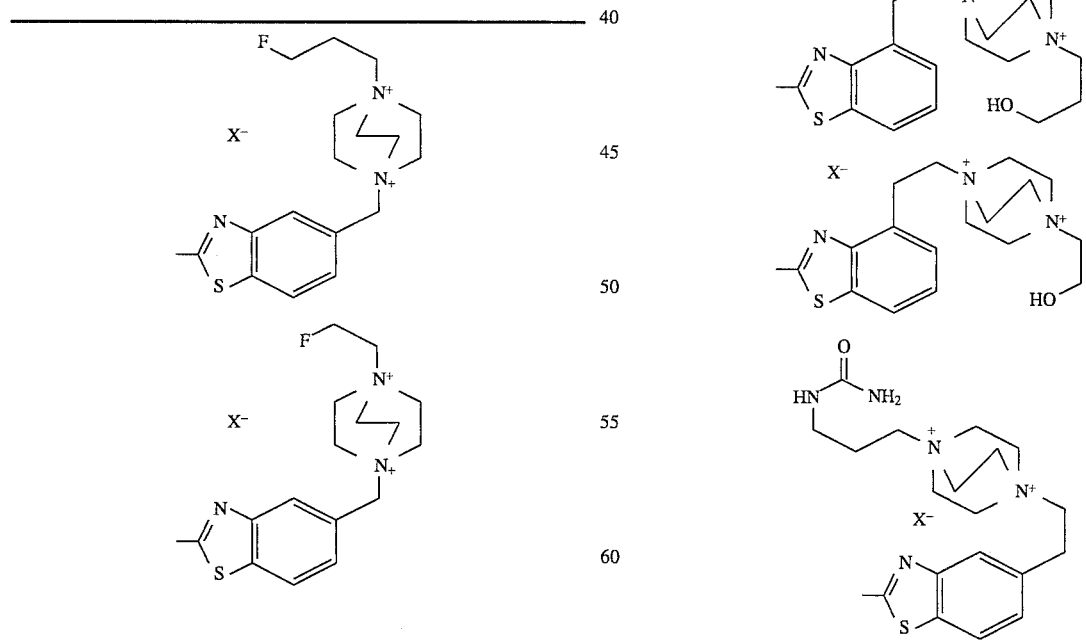

231
-continued
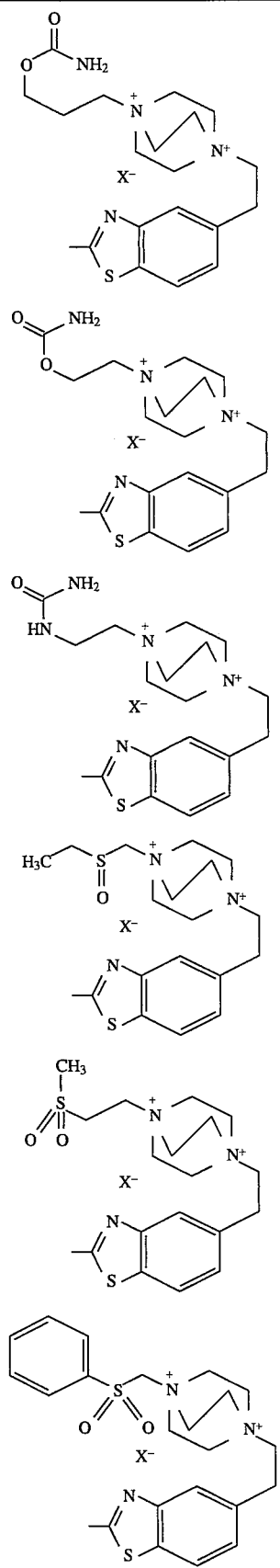
232
-continued
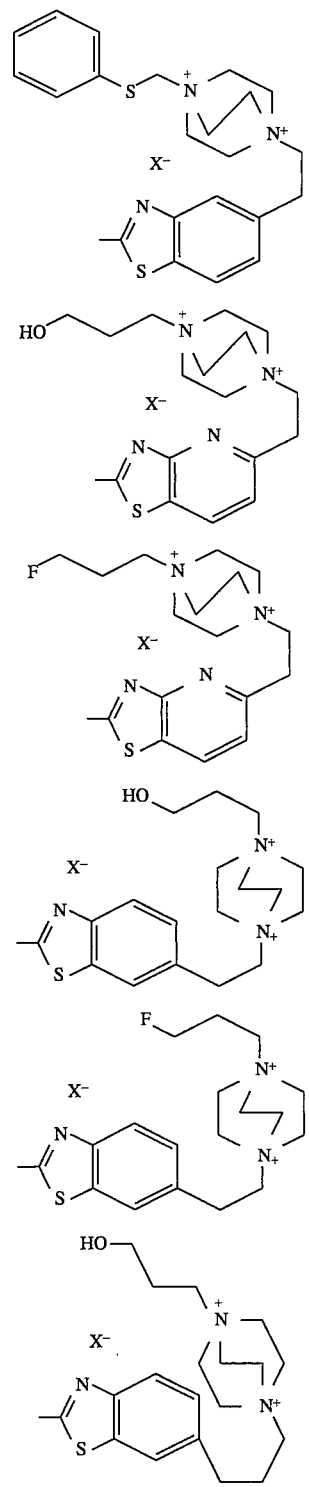

233
-continued
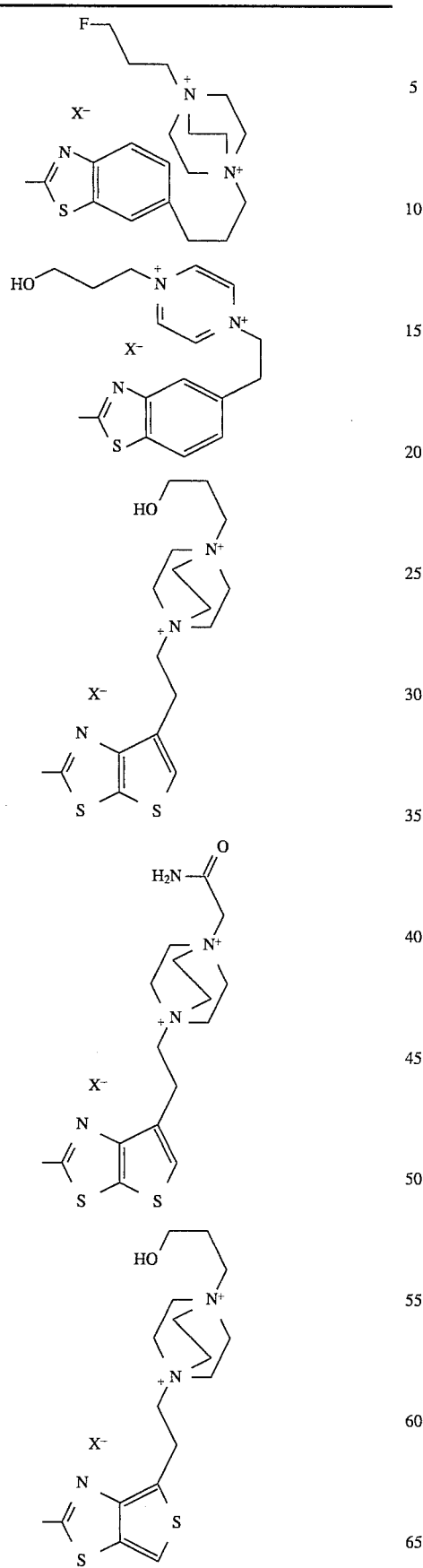
234
-continued
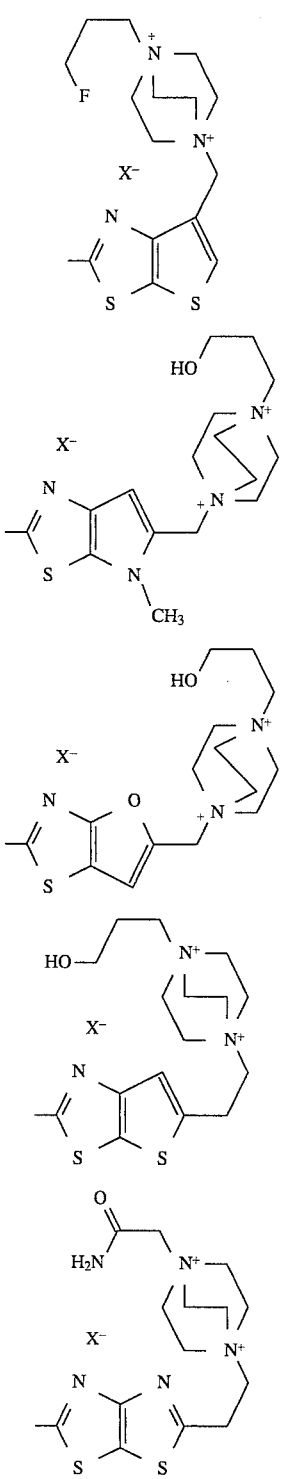

235
-continued
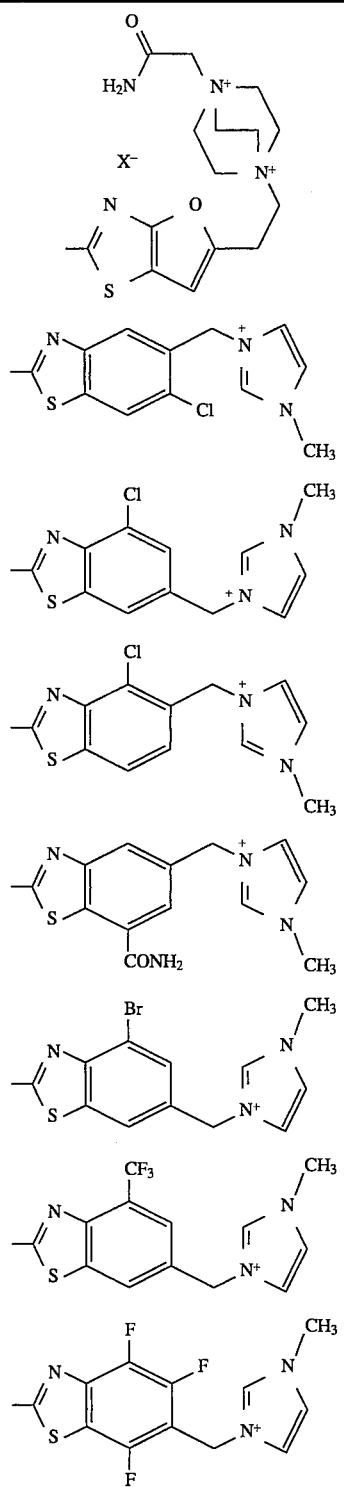
236
-continued
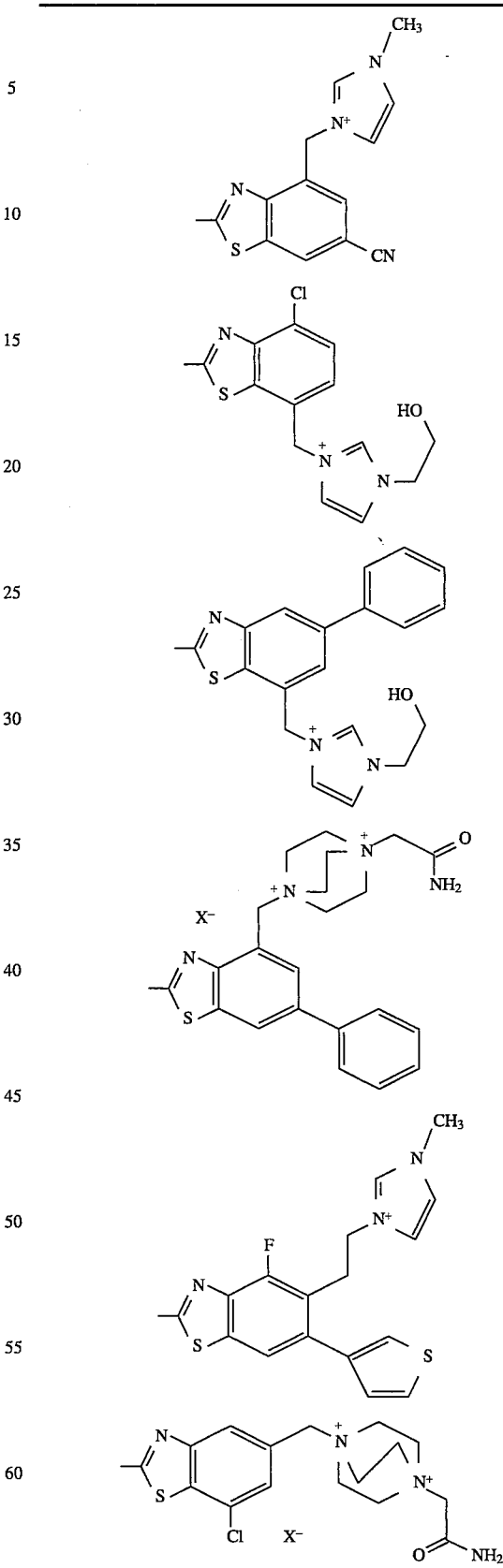

5,496,816
237
-continued
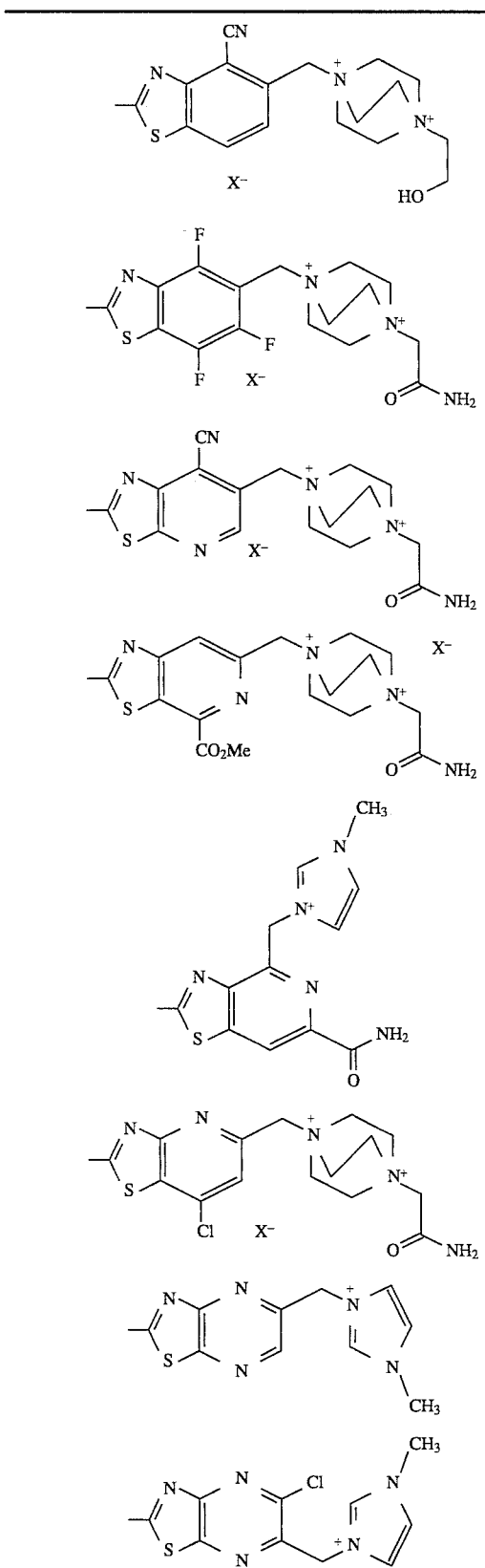
238
-continued
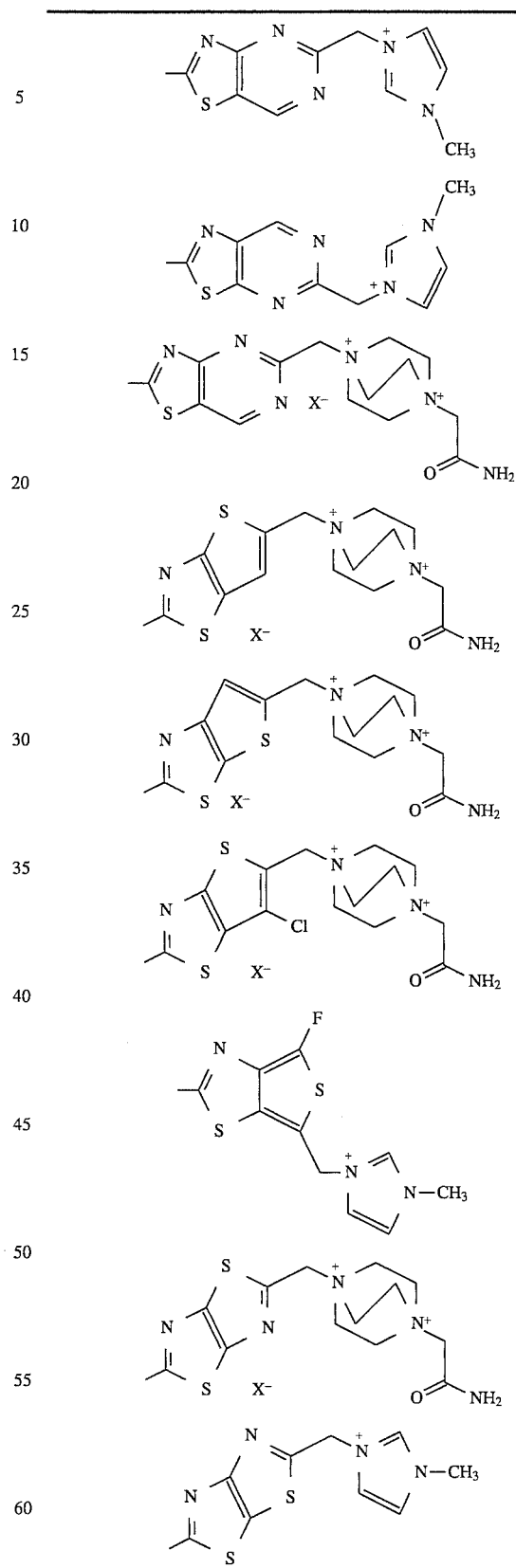

239
-continued
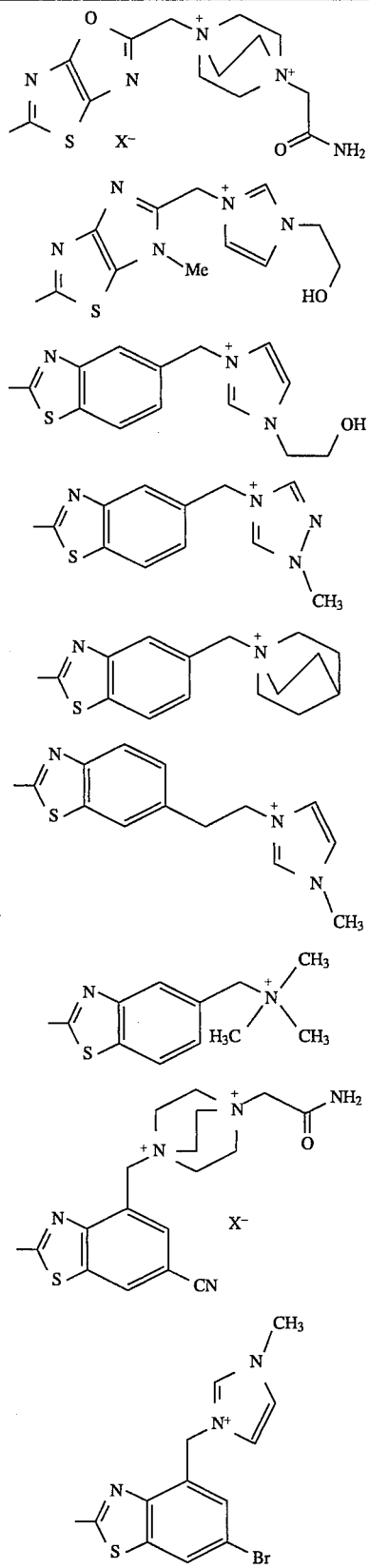
240
-continued
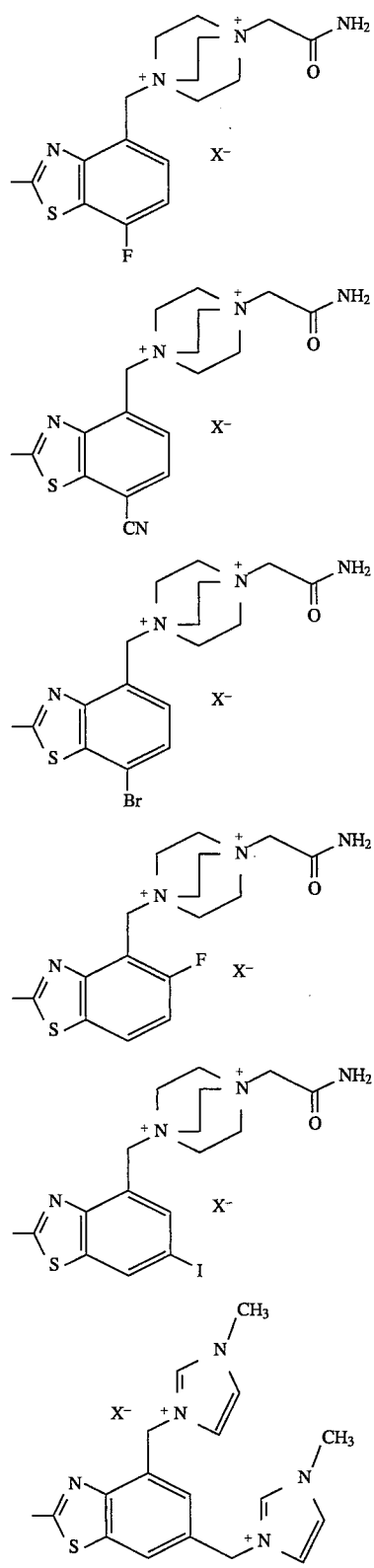

241
-continued
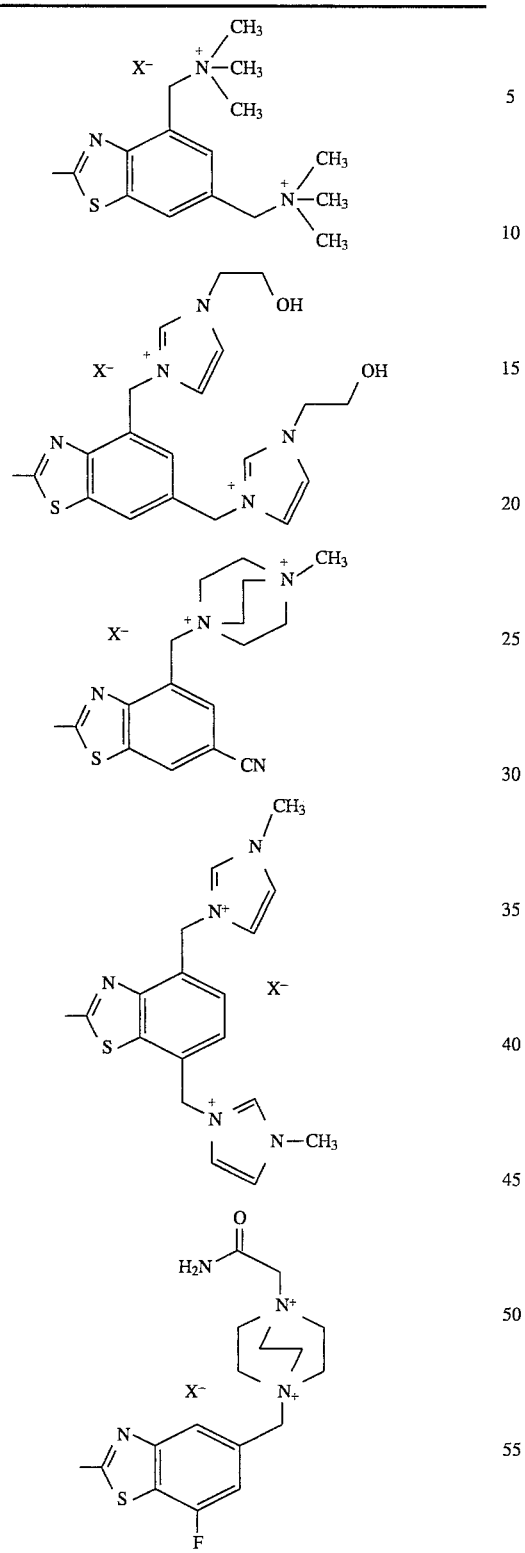
242
-continued
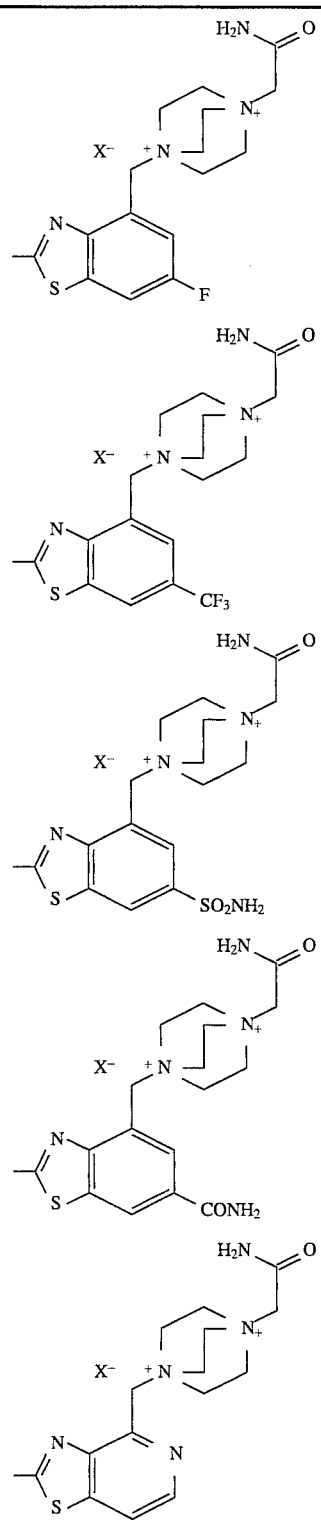

-continued

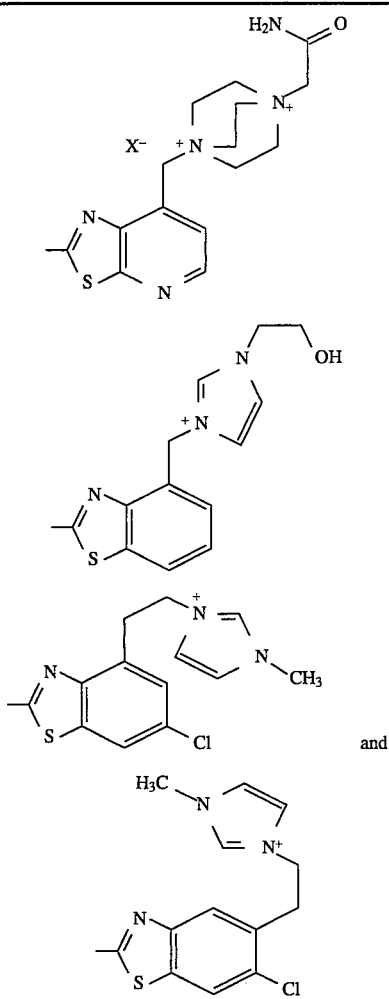

wherein X⁻ equals L⁻ and L⁻ represents a pharmaceutically acceptable counterion.

24. A compound represented by the formula:

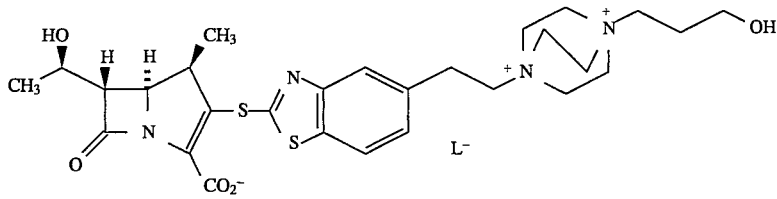

wherein L⁻ represents a pharmaceutically acceptable counterion.

25. A pharmaceutical composition comprising a pharmaceutically effective amount of the compound of claim 1 in combination with a pharmaceutically acceptable carrier.

26. A pharmaceutical composition in accordance with claim 25 in the form of a tablet, capsule, solution or suspension.

27. A pharmaceutical composition in accordance with claim 25 in the form of an injectable liquid or lyophillized solid.

28. A pharmaceutical composition in accordance with claim 25, further comprised of a DHP inhibitor.

29. A pharmaceutical composition in accordance with claim 28 wherein the DHP inhibitor is 7-(L-2-amino-2-carboxyethylthio)- 2-(2,2-dimethylcyclopropanecarboxamide)-2-heptenoic acid.

30. A method of treating a bacterial infection in a mammal in need of such treatment comprising administering to said mammal a compound of claim 1 in an amount effective to treat said bacterial infection.

31. A method of treating a bacterial infection in accordance with claim 30 wherein the compound is administered orally.

32. A method of treating a bacterial infection in accordance with claim 30 wherein the compound is administered by injection.

33. A method of treating a bacterial infection in a mammalian subject in need of such treatment, comprising administering to such subject an antibacterially effective amount of a compound of claim 1 and an inhibitorily effective amount of a DHP inhibitor.

34. The method according to claim 33, wherein the DHP inhibitor is 7-(L-2-amino-2-carboxyethyl-thio)-2-( 2,2-dimethylcyclopropanecarboxamide)-2-heptenoic acid.

* * * * *

UNITED STATES PATENT AND TRADEMARK OFFICE
CERTIFICATE OF CORRECTION

PATENT NO. : 5,496,816
DATED : Mar. 5, 1996
INVENTOR(S) : Timothy A. Hlizzard, et al.

Page 1 of 28

It is certified that error appears in the above-identified patent and that said Letters Patent is hereby corrected as shown below:

Col.195-244 should be deleted and substituted with col. 195-248 as per attached.

Signed and Sealed this

Eighth Day of July, 1997

Attest:

BRUCE LEHMAN

Attesting Officer

Commissioner of Patents and Trademarks

1. A compound or a pharmaceutically acceptable salt thereof represented by formula I:

[Structure of formula I showing a carbapenem core with P*O-CH(H₃C)- group, R¹, S-Het substituent, N, O, and CO₂M groups]

wherein:
$R^1$ represents H or methyl;
$CO_2M$ represents a carboxylic acid, a carboxylate anion, a pharmaceutically acceptable ester group or a carboxylic acid protected by a protecting group;
$P^*$ represents H or a hydroxyl protecting group;
Het has substituent groups which contain from one to three positively charged atoms and is selected from:

[Four heterocyclic ring structures with labeled positions N, Z, Y, E, X, A, D, G]

wherein:
A is O or S;
D is O, S or $NR^a$;
E, G, X, Y and Z represent CR or N;
each R is independently selected from: —$R^*$; hydrogen; halo; —CN; —$NO_2$; —$OR^c$; —$SR^c$; —CON$R^aR^b$; —COO$R^h$; —SO$R^c$; —SO$_2R^c$; —SO$_2$N$R^aR^b$; —N$R^a$SO$_2R^b$; —CO$R^a$; —OCO$R^a$; —OCONR$^a$R$^b$; —NR$^a$CONR$^b$R$^c$; —NR$^a$CO$_2$R$^h$; —OCO$_2$R$^h$; —$C_{1-6}$ straight- or branched-chain alkyl, unsubstituted or substituted with one to four $R^d$ groups; and —$C_{3-7}$ cycloalkyl, unsubstituted or substituted with one to four $R^d$ groups,
$R^a$, $R^b$ and $R^c$ represent hydrogen, —$C_{1-6}$ straight- or branched-chain alkyl, unsubstituted or substituted with one to four $R^d$ groups; —$C_{3-7}$ cycloalkyl, unsubstituted or substituted with one to four $R^d$ groups; or -$R^*$
or $R^a$ and $R^b$ taken together with any intervening atoms represent a 4–6 membered saturated ring optionally interrupted by one or more of O, S, $NR^c$, with $R^c$ as defined above, or —C(O)—, said ring being unsubstituted or substituted with one to four $R^i$ groups;
or $R^b$ and $R^c$ taken together with any intervening atoms represent a 4–6 membered saturated ring optionally interrupted by one to three of O, S, $NR^a$, with $R^a$ as defined above, or —C(O)—, said ring being unsubstituted or substituted with one to four $R^i$ groups;
each $R^d$ independently represents halo; —CN; —$NO_2$; —NR$^e$R$^f$; —OR$^g$; —SR$^g$; —CONR$^e$R$^f$; —COOR$^g$; —SOR$^g$; —SO$_2$R$^g$; —SO$_2$NR$^e$R$^f$; —NR$^e$SO$_2$R$^f$; —COR$^e$; —NR$^e$COR$^f$; —OCOR$^e$; —OCONR$^e$R$^f$; —NR$^e$CONR$^f$R$^g$; —NR$^e$CO$_2$R$^h$; —OCO$_2$R$^h$; —C(NR$^e$)NR$^f$R$^g$; —NR$^e$C(NH)NR$^f$R$^g$; —NR$^e$C(NR$^f$)R$^g$; —$R^*$ or —Q;
with the proviso that from 1 to 3 R groups are present which contain $R^*$ or Q, said $R^*$ and Q being defined below:
$R^e$, $R^f$ and $R^g$ represent hydrogen; —$C_{1-6}$ straight- or branched-chain alkyl unsubstituted or substituted with one to four $R^i$ groups, or —$R^*$;
or $R^e$ and $R^f$ taken together with any intervening atoms represent a 4–6 membered saturated ring optionally interrupted by one to three of O, S, —C(O)— or NR$^g$ with R$^g$ as defined above, said ring being unsubstituted or substituted with one to four $R^i$ groups;
each $R^i$ independently represents halo; —CN; —$NO_2$; phenyl; —NHSO$_2$R$^h$; —OR$^h$; —SR$^h$; —N(R$^h$)$_2$; —N$^+$(R$^h$)$_3$; —C(O)N(R$^h$)$_2$; —SO$_2$N(R$^h$)$_2$; heteroaryl; heteroarylium; —CO$_2$R$^h$; —C(O)R$^h$; —O-COR$^h$; —NHCOR$^h$; guanidinyl; carbamimidoyl or ureido;
each $R^h$ independently represents H, a —$C_{1-6}$ straight or branched-chain alkyl group, a —$C_3$-$C_6$ cycloalkyl group or phenyl, or when two $R^h$ groups are present, said $R^h$ groups may be taken in combination and represent a 4–6 membered saturated ring, optionally interrupted by one or two of O, S, SO$_2$, —C(O)—, NH and NCH$_3$;
Q is selected from the group consisting of:

[Structures showing heterocyclic cationic groups with labeled positions α, β, δ, λ, μ, σ]

wherein:
a and b are 1, 2 or 3;
$L^-$ is a pharmaceutically acceptable counterion;
α represents O, S or NR$^s$;
β, δ, λ, μ and σ represent CR$^t$, N or N$^+$R$^s$, provided that no more than one of β, δ, λ, μ and σ is N$^+$R$^s$;
$R^*$ is selected from the group consisting of:

[Several heterocyclic ring structures with labeled positions]

wherein:

each d independently represents O, S or $NR^h$;

e, g, x, y and z represent $CR^m$, N or $N^+R^k$, provided that no more than one of e, g, x, y and z in any given structure represents $N^+R^k$;

$R^k$ represents hydrogen; —$C^{1-6}$ straight- or branched-chain alkyl, unsubstituted or substituted with one to four $R^i$ groups; or —$(CH_2)_nQ$ where n = 1, 2 or 3 and Q is as previously defined;

each $R^m$ independently represents a member selected from the group consisting of: hydrogen; halo; —CN; —$NO_2$; —$NR^nR^o$; —$OR^n$; —$SR^n$; —$CONR^nR^o$; —$COOR^h$; —$SOR^n$; —$SO_2R^n$; —$SO_2NR^nR^o$; —$NR^nSO_2R^o$; —$COR^n$; —$NR^nCOR^o$; —$OCOR^n$; —$OCONR^nR^o$; —$NR^nCO_2R^h$; —$NR^nCONR^oR^h$; —$OCO_2R^h$; —$CNR^nNR^oR^h$; —$NR^nCNHNR^oR^h$; —$NR^nC(NR^o)R^h$; —$C_{1-6}$ straight- or branched-chain alkyl, unsubstituted or substituted with one to four $R^i$ groups; —$C_{3-7}$ cycloalkyl, unsubstituted or substituted with one to four $R^i$ groups; and —$(CH_2)_nQ$ where n and Q are as defined above;

$R^n$ and $R^o$ represent hydrogen, phenyl; —$C_{1-6}$ straight- or branched-chain alkyl unsubstituted or substituted with one to four $R^i$ groups;

each $R^s$ independently represents hydrogen; phenyl; —$C_{1-6}$ straight- or branched-chain alkyl, unsubstituted or substituted with one to four $R^i$ groups;

each $R^t$ independently represents hydrogen; halo; phenyl; —CN; —$NO_2$; —$NR^uR^v$; —$OR^u$; —$SR^u$; —$CONR^uR^v$; —$COOR^h$; —$SOR^u$; —$SO_2R^u$; —$SO_2NR^uR^v$; —$NR^uSO_2R^v$; —$COR^u$; —$NR^uCOR^v$; —$OCOR^u$; —$OCONR^uR^v$; —$NR^uCO_2R^v$; —$NR^uCONR^vR^w$; —$OCO_2R^v$; heteroaryl; heteroarylium; —$C_{1-6}$ straight- or branched-chain alkyl, unsubstituted or substituted with one to four $R^i$ groups;

$R^u$ and $R^v$ represent hydrogen or —$C_{1-6}$ straight- or branched-chain alkyl, unsubstituted or substituted with one to four $R^i$ groups;

or $R_u$ and $R^v$ together with any intervening atoms represent a 4–6 membered saturated ring optionally interrupted by one or more of O, S, $NR^w$ or —C(O)—, said ring being unsubstituted or substituted with one to four $R^i$ groups;

each $R^w$ independently represents hydrogen or —$C_{1-6}$ straight- or branched-chain alkyl, unsubstituted or substituted with one to four $R^i$ groups; $C_{3-6}$ cycloalkyl optionally substituted with one to four $R^i$ groups; phenyl optionally substituted with one to four $R^i$ groups or $R^h$ and $R^w$ taken together with any intervening atoms represent a 5–6 membered saturated ring, optionally interrupted by one or two of O, S, $SO_2$, NH or $NCH_3$;

$R^x$ represents hydrogen or a $C_{1-8}$ straight- or branched-chain alkyl, optionally interrupted by one or two of O, S, SO, $SO_2$, $NR^w$, $N^+R^hR^w$, or —C(O)—, said chain being unsubstituted or substituted with one to four of halo, CN, $NO_2$, $OR^w$, $SR^w$, $SOR^w$, $SO_2R^w$, $NR^hR^w$, $N^+(R^h)_2R^w$, —C(O)—$R^w$, C(O)$NR^hR^w$, $SO_2NR^hR^w$, $CO_2R^w$, OC(O)$R^w$, OC(O)$NR^hR^w$, $NR^hC(O)R^w$, $NR^hC(O)NR^hR^w$, or a phenyl or heteroaryl group which is in turn optionally substituted with from one to four $R^i$ groups or with one to two $C_{1-3}$ straight- or branched-chain alkyl groups, said alkyl groups being unsubstituted or substituted with one to four $R^i$ groups;

$R^y$ and $R^z$ represent hydrogen; phenyl; —$C_{1-6}$ straight or branched chain alkyl, unsubstituted or substituted with one to four $R^i$ groups, and optionally interrupted by O, S, $NR^w$, $N^+R^hR^w$ or —C(O)—;

or $R^x$ and $R^y$ together with any intervening atoms represent a 4–6 membered saturated ring optionally interrupted by O, S, $SO_2$, $NR^w$, $N^+R^hR^w$ or —C(O)—, unsubstituted or substituted with 1–4 Ri groups, and when $R^x$ and $R^y$ together represent a 4–6 membered ting as defined above, $R^z$ is as defined above or $R^z$ represents an additional saturated 4–6 membered ring fused to the ring represented by $R^x$ and $R^y$ taken together, optionally interrupted by O, S, $NR^w$ or —C(O)—, said rings being unsubstituted or substituted with one to four $R^i$ groups.

2. A compound in accordance with claim 1 wherein A represents S.

3. A compound in accordance with claim 1 wherein A represents O.

4. A compound in accordance with claim 1 represented by formula Ia:

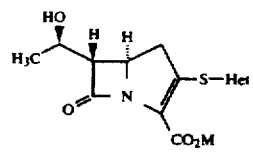

wherein:

$CO_2M$ represents a carboxylic acid, a carboxylate anion or a pharmaceutically acceptable ester group;

Het has substituent groups which contain from one to three positively charged atoms and is selected from:

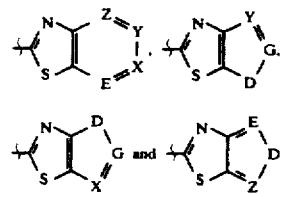

wherein:

D is O, S or $NR^a$;

E, G, X, Y and Z represent CR or N;

each R is independently selected from: —R*; hydrogen; halo; —CN; $OR^c$; —$SR^c$; —$CONR^aR^b$; —$COOR^h$; —$SOR^c$; —$SO_2R^c$; —$SO_2NR^aR^b$; —$COR^a$; —$OCOR^a$; —$OCONR^aR^b$; —$OCO_2R^h$; —$C_{1-6}$ straight- or branched-chain alkyl, unsubstituted or substituted with one to four $R^d$ groups; —$C_{3-7}$ cycloalkyl, unsubstituted or substituted with one to four $R^d$ groups, with the proviso that one to three R groups contain R* or Q;

and R* and Q are as defined above.

5. A compound in accordance with claim 4 represented by formula Ia:

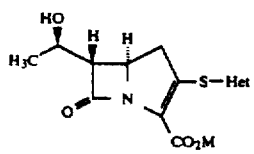

wherein:
CO₂M represents a carboxylic acid or a carboxylate anion;
Het has substituent groups which contain one or two positively charged atoms and is selected from:

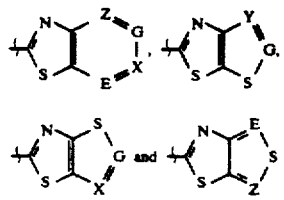

wherein:
E, G, X, Y and Z represent CR or N;
each R is independently selected from the group consisting of —R*; hydrogen; halo; —CN; —CONR$^a$R$^b$; —COOR$^h$; —SOR$^c$; —SO₂R$^c$; —SO₂NR$^a$R$^b$; —OC(O)R$^a$; —COR$^a$; —C$_{1-6}$ straight-or branched-chain alkyl, unsubstituted or substituted with one to three R$^d$ groups; —C$_{3-7}$ cycloalkyl, unsubstituted or substituted with one to three R$^d$ groups, with the proviso that one or two R groups contain R* or Q;
R$^a$, R$^b$ and R$^c$ independently represent —R*; hydrogen, —C$_{1-6}$ straight- or branched-chain alkyl, unsubstituted or substituted with one to four R$^d$ groups; —C$_{3-7}$ cycloalkyl, unsubstituted or substituted with one to four R$^d$ groups;
or R$^a$ and R$^b$ taken together with any intervening atoms represent a 4-6 membered saturated ring optionally interrupted by one or more of O, S, NR$^c$ with R$^c$ as defined above, or —C(O)—, said ring being unsubstituted or substituted with one to four R$^i$ groups;
Q represents a member selected from the group consisting of:

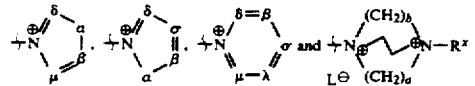

wherein:
a and b are 2 or 3;
L− is a pharmaceutically acceptable counterion;
α represents O, S or NR$^s$;
β, δ, λ, μ and σ represent CR$^t$, N or N+R$^s$, provided that no more than one of β, δ, λ, μ and σ is N+R$^s$;
R* is selected from:

wherein each d independently represents O, S or NR$^k$;
e, g, x, y and z represent CR$^m$, N or N+R$^k$, provided that no more than one of e, g, x, y and z in any given structure represents N+R$^k$;
and R$^k$ is as previously defined.

6. A compound in accordance with claim 5 represented by formula Ic:

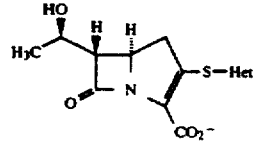

wherein:
Het has substituent groups which contain one or two positively charged atoms and is selected from the group consisting of:

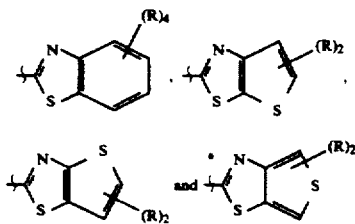

each R is independently selected from: hydrogen, —C$_{1-6}$ straight- or branched-chain alkyl, unsubstituted or substituted with one to three R$^d$ groups; and —R*, with the proviso that one or two R groups contain R* or Q;
R$^d$ represents —CN; —NR$^e$R$^f$; —OR$^s$; —CONR$^e$R$^f$; —COOR$^s$; —SOR$^s$; —SO₂R$^s$; —SO₂NR$^e$R$^f$; —NR$^e$SO₂R$^f$; —COR$^e$; —NR$^e$COR$^f$; —OCONR$^e$R$^f$; —NR$^e$CONR$^f$R$^s$; —NR$^e$CO₂R$^h$; —C(NR$^e$)NR$^f$R$^s$; —NR$^e$C(NH)NR$^f$R$^s$; —NR$^e$C(NR$^f$)R$^s$; —R * or —Q;
R$^e$, R$^f$ and R$^s$ represent hydrogen; —C$_{1-6}$ straight- or branched-chain alkyl or —R*;
or R$^e$ and R$^f$ taken together represent a 4-6 membered saturated ring optionally interrupted by one or more of O, S, —C(O)— or NR$^s$ with R$^s$ as defined above, said ring being unsubstituted or substituted with one to four R$^i$ groups;
each R$^h$ independently represents H, a —C$_{1-6}$ straight or branched-chain alkyl group, a —C$_3$-C$_6$ cycloalkyl group or phenyl, or when two R$^h$ groups are present, said R$^h$ groups may be taken in combination and represent a 4-6 membered saturated ring, optionally interrupted by one or two of O, S, SO₂, —C(O)—, NH and NCH₃;
each R$^i$ independently represents halo; —CN; —NO₂; phenyl; —NHSO₂R$^h$; —OR$^h$; —SR$^h$; —N (R$^h$)₂;

—N+(R$^h$)$_3$; —C(O)N(R$^h$)$_2$; —SO$_2$N(R$^h$)$_2$; heteroaryl; heteroarylium; —CO$_2$R$^h$; —C(O)R$^h$; —O-COR$^h$; —NHCOR$^h$; guanidinyl; carbamimidoyl or ureido;

Q is selected from:

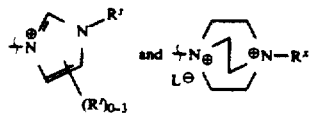

wherein:

L— is as previously defined;

R$^x$ represents hydrogen or a C$_{1-8}$ straight- or branched-chain alkyl, optionally interrupted by one or two of O, S, SO, SO$_2$, NR$^w$, N+R$^h$R$^w$, or —C(O)—, said chain being unsubstituted or substituted with one to four of halo, CN, NO$_2$, OR$^w$, SR$^w$, SOR$^w$, SO$_2$R$^w$, NR$^h$R$^w$, N+(R$^h$)$_2$R$^w$, —C(O)—R$^w$, C(O)NR$^h$R$^w$, SO$_2$NR$^h$R$^w$, CO$_2$R$^w$, OC(O)R$^w$, OC(O)NR$^h$R$^w$, NR$^h$C(O)R$^w$, NR$^h$C(O)NR$^h$R$^w$, or a phenyl or heteroaryl group which is in turn optionally substituted with from one to four R$^i$ groups or with one to two C$_{1-3}$ straight- or branched-chain alkyl groups, said alkyl groups being unsubstituted or substituted with one to four R$^i$ groups;

R$^s$ represents hydrogen; phenyl; —C$_{1-6}$ straight- or branched-chain alkyl, unsubstituted or substituted with one to four R$^i$ groups;

R$^t$ is selected from the group consisting of: halo; phenyl; —CN; —NO$_2$; —NR$^u$R$^v$; —OR$^u$; —SR$^u$; —CONR$^u$R$^v$; —COOR$^h$; —SOR$^u$; —SO$_2$R$^u$; —SO$_2$NR$^u$R$^v$; —NR$^u$SO$_2$R$^v$; —COR$^u$; —NR$^u$COR$^v$; —OCOR$^u$; —OCONR$^u$R$^v$; —NR$^u$CO$_2$R$^v$; —NR$^u$CONR$^v$R$^w$; —OCO$_2$R$^v$; —C$_{1-6}$ straight- or branched-chain alkyl, unsubstituted or substituted with one to four R$^i$ groups, and the remaining R$^i$ groups are hydrogen;

R* is

wherein each R$^m$ is selected from the group consisting of: halo; —CN; —NR$^n$R$^o$; —OR$^n$; —SR$^n$; —CONR$^n$R$^o$; —COOR$^h$; —SOR$^n$; —SO$_2$R$^n$; —SO$_2$NR$^n$R$^o$; —NR$^n$SO$_2$R$^o$; —COR$^n$; —NR$^n$COR$^o$; —OCOR$^n$; —OCONR$^n$R$^o$; —NR$^n$CO$_2$R$^h$; —NR$^n$CONR$^o$R$^h$; —OCO$_2$R$^h$; —C$_{1-6}$ straight- or branched-chain alkyl, unsubstituted or substituted with one to four R$^i$ groups; —C$_{3-7}$ cycloalkyl, unsubstituted or substituted with one to four R$^i$ groups; or —(CH$_2$)$_n$Q where n=1–3;

R$^n$ and R$^o$ represent hydrogen, phenyl; —C$_{1-6}$ straight- or branched-chain alkyl unsubstituted or substituted with one to four R$^i$ groups;

R$^u$ and R$^v$ independently represent hydrogen; —C$_{1-6}$ straight- or branched-chain alkyl, unsubstituted or substituted with one to four R$^i$ groups;

or R$^u$ and R$^v$ together with any intervening atoms represent a 4–6 membered saturated ring optionally interrupted by one or more of O, S, NR$^w$ or —C(O)—, said ring being unsubstituted or substituted with one to four R$^i$ groups, and R$^w$ represents hydrogen or —C$_{1-6}$ straight- or branched-chain alkyl, unsubstituted or substituted with one to four R$^i$ groups, C$_{3-6}$ cycloalkyl optionally substituted with one to four R$^i$ groups; or phenyl optionally substituted with one to four R$^i$ groups;

or R$^h$ and R$^w$ taken together with any intervening atoms represent a 5–6 membered saturated ring, optionally interrupted by one or two of O, S, SO$_2$, NH or NCH$_3$.

7. A compound in accordance with claim 1 represented by formula Ib:

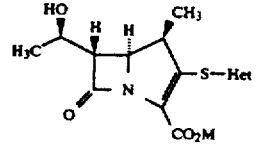

wherein:

CO$_2$M represents a carboxylic acid, a carboxylate anion or a pharmaceutically acceptable ester group;

and Het is as previously defined with respect to the compounds of formula I.

8. A compound in accordance with claim 7 represented by formula Ib:

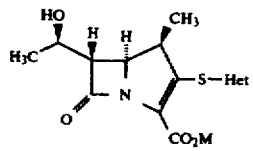

wherein:

CO$_2$M represents a carboxylic acid or a carboxylate anion;

Het has substituent groups which contain one to three positively charged atoms and is selected from the group consisting of:

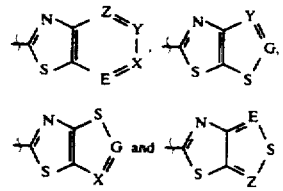

wherein:

E, G, X, Y and Z independently represent CR or N;

each R is selected from the group consisting of hydrogen; halo; —CN; —CONR$^a$R$^b$; —COOR$^h$; —SOR$^c$; —SO$_2$R$^c$; —SO$_2$NR$^a$R$^b$; —COR$^a$; —C$_{1-6}$ straight- or branched-chain alkyl, unsubstituted or substituted with one to three R$^d$ groups; —C$_{3-7}$ cycloalkyl, unsubstituted or substituted with one to three R$^d$ groups; and —R*, with the proviso that one to three R groups contain R* or Q;

Q is selected from the group consisting of:

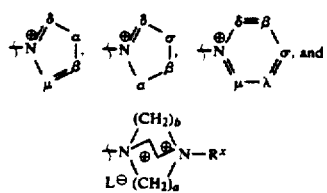

wherein:
L— represents a pharmaceutically acceptable counterion;
a and b independently represent 2 or 3;
α represents O, S or $NR^k$;
β, δ, λ, μ and σ independently represent $CR^t$, N or $N^+R^s$ provided that no more than one of β, δ, λ, μ and σ is $N^+R^s$;
$R^*$ is selected from the group consisting of:

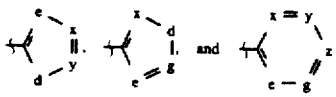

wherein:
d represents O, S or $NR^k$;
e, g, x, y and z independently represent $CR^m$, N or $N^+R^k$, provided that no more than one of e, g, x, y and z represents $N^+R^k$;
$R^a$, $R^b$ and $R^c$ independently represent hydrogen, —$C_{1-6}$ straight- or branched-chain alkyl, unsubstituted or substituted with one to four $R^d$ groups; —$C_{3-7}$ cycloalkyl, unsubstituted or substituted with one to four $R^d$ groups, or —$R^*$;
or $R^a$ and $R^b$ taken together with any intervening atoms represent a 4–6 membered saturated ring optionally interrupted by one or more of O, S, $NR^c$, with $R^c$ as defined above, or —C(O)—, said ring being unsubstituted or substituted with one to four $R^i$ groups; and
each $R^d$ independently represents halo; —CN; —NO$_2$; —$NR^eR^f$; —$OR^g$; —$SR^g$; —$CONR^eR^f$; —$COOR^g$; —$SOR^g$; —$SO_2R^g$; —$SO_2NR^eR^f$; —$NR^eSO_2R^f$; —$COR^e$; —$NR^e COR^f$; —$OCOR^e$; —$OCONR^eR^f$; —$NR^eCONR^fR^g$; —$NR^eCO_2R^h$; —$OCO_2R^h$; —$C(NR^e)NR^fR^g$; —$NR^eC(NH)NR^fR^g$; —$NR^eC(NR^f)R^g$; —$R^*$ or —Q;
$R^e$, $R^f$ and $R^g$ represent hydrogen; —$C_{1-6}$ straight- or branched-chain alkyl unsubstituted or substituted with one to four $R^i$ groups, or —$R^*$;
or $R^e$ and $R^f$ taken together represent a 4–6 membered saturated ring optionally interrupted by one to three of O, S, —C(O)— or $NR^g$ with $R^g$ as defined above, said ring being unsubstituted or substituted with one to four $R^i$ groups;
each $R^i$ independently represents halo; —CN; —NO$_2$; phenyl; —$NHSO_2R^h$; —$OR^h$; —$SR^h$; —$N(R^h)_2$; —$N^+(R^h)_3$; —$C(O)N(R^h)_2$; —$SO_2N(R^h)_2$; heteroaryl; heteroarylium; —$CO_2R^h$; —$C(O)R^h$; —O-$COR^h$; —$NHCOR^h$; guanidinyl; carbamimidoyl or ureido;
each $R^h$ independently represents H, a —$C_{1-6}$ straight or branched-chain alkyl group, a —$C_3$–$C_6$ cycloalkyl group or phenyl, or when two $R^h$ groups are present, said $R^h$ groups may be taken in combination and represent a 4–6 membered saturated ring, optionally interrupted by one or two of O, S, SO$_2$, —C(O)—, NH and NCH$_3$;
$R^k$ represents hydrogen; —$C_{1-6}$ straight— or branched-chain alkyl, unsubstituted or substituted with one to four $R^i$ groups; or —(CH$_2$)$_n$Q where n and Q are as previously defined;
each $R^m$ independently represents a member selected from the group consisting of: hydrogen; halo; —CN; —NO$_2$; —$NHR^n$; —$NR^nR^o$; —$OR^n$; —$SR^n$; —$CONR^nR^o$; —$COOR^h$; —$SOR^n$; —$SO_2R^n$; —$SO_2NR^nR^o$; —$NR^nSO_2R^o$; —$COR^n$; —$NR^nCOR^o$; —$OCOR^n$; —$OCONR^nR^o$; —$NR^nCO_2R^h$; —$NR^nCONR^oR^h$; —$OCO_2R^h$; —$CNR^nNR^oR^h$; —$NR^nCNHNR^oR^h$; —$NR^nC(NR^o)R^h$; —$C_{1-6}$ straight— or branched-chain alkyl, unsubstituted or substituted with one to four $R^i$ groups; —$C_{3-7}$ cycloalkyl, unsubstituted or substituted with one to four $R^i$ groups; and —(CH$_2$)$_n$Q where n=1–3;
$R^n$ and $R^o$ represents hydrogen, phenyl; —$C_{1-6}$ straight— or branched-chain alkyl, unsubstituted or substituted with one to four $R^i$ groups;
each $R^s$ independently represents hydrogen; phenyl; —$C_{1-6}$ straight- or branched-chain alkyl, unsubstituted or substituted with one to four $R^i$ groups;
each $R^t$ independently represents hydrogen; halo; phenyl; —CN; —NO$_2$; —$NHR^u$; —$NR^uR^v$; —$OR^u$; —$SR^u$; —$CONR^uR^v$; —$COOR^h$; —$SOR^u$; —$SO_2R^u$; —$SO_2NR^uR^v$; —$NR^uSO_2R^v$; —$COR^u$; —$NR^uCOR^v$; —$OCOR^u$; —$OCONR^uR^v$; —$NR^uCO_2R^v$; —$NR^uCONR^vR^h$; —$OCO_2R^h$; heteroaryl; heteroarylium; —$C_{1-6}$ straight—or branched-chain alkyl, unsubstituted or substituted with one to four $R^i$ groups;
$R^u$ and $R^v$ represent hydrogen or —$C_{1-6}$ straight—or branched-chain alkyl, unsubstituted or substituted with one to four $R^i$ groups;
or $R^u$ and $R^v$ together represent a 4–6 membered saturated ring optionally interrupted by one or more of O, S, $NR^w$ or —C(O)—, said ring being unsubstituted or substituted with one or four $R^i$ groups;
$R^x$ represents hydrogen or a $C_{1-8}$ straight— or branched-chain alkyl, optionally interrupted by one or two of O, S, SO, SO$_2$, $NR^w$, $N^+R^hR^w$, or —CO)—, said chain being unsubstituted with one to four of halo, CN, NO$_2$, $OR^w$, $SR^w$, $SOR^w$, $SO_2R^w$, $NR^hR^w$, $N^+(R^h)_2R^w$, —C(O)—$R^w$, C(O)$NR^hR^w$, $SO_2NR^hR^w$, $CO_2R^w$, $OC(O)R^w$, $OC(O)NR^hR^w$, $NR^hC(O)R^w$, $NR^hC(O)NR^hR^w$, or a phenyl or heteroaryl group which is turn optionally substituted with from one to four $R^1$ groups or with one to two $C_{1-3}$ straight— or branched-chain alkyl groups, said alkyl groups being unsubstituted or substituted with one to four $R^i$ groups;
each $R^w$ independently represents hydrogen or —$C_{1-6}$ straight— or branched-chain alkyl, unsubstituted or substituted with one to four $R^i$ groups, $C_{3-6}$ cycloalkyl optionally substituted with one to four $R^i$ groups; phenyl optionally substituted with one to four $R^i$ groups
or $R^h$ are $R^w$ taken together with any intervening atoms represent a 5–6 membered saturated ring, optionally interrupted by one or two of O, S, SO$_2$, NH or NCH$_3$.

9. A compound in accordance with claim 8 represented by formula Ic:

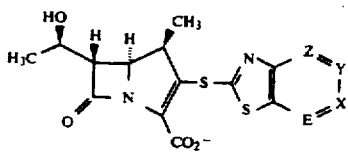

Ic

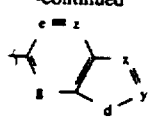

—continued wherein:

E, X, Y and Z independently represent CR or N; and each R is independently selected from: —R*; hydrogen; halo; —CN; —NO₂; —OR$^c$; —SR$^c$; —CONR$^a$R$^b$; —COOR$^h$; —SOR$^c$; —SO₂R $^c$; —SO₂NR$^a$R$^b$; —NR$^a$SO₂R$^b$; —COR$^a$; OCOR$^e$; —OCONR$^a$R$^b$; —NR$^a$CONR$^b$R$^c$; —NR$^a$CO₂R$^h$; —O-CO₂R$^h$; —C$_{1-6}$ straight- or branched-chained alkyl, unsubstituted or substituted with one or to four R$^d$ groups; and —C$_{3-7}$ cycloalkyl, unsubstituted or substituted with one to four R$^d$ groups, with the proviso that from one to three positively charged atoms are contained in said R groups, and one to three R groups are present which contain R* or Q;

Q is selected from the group consisting of:

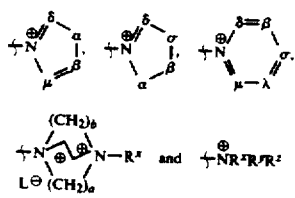

wherein a and b are 1, 2 or 3;

L$^-$ is a pharmaceutically acceptable counterion;

α represents O, S, or NR$^s$;

β, δ, λ, μ and σ represent Cr$^t$, N or N+R$^s$, provided that no more than one of β, δ, λ, μ and σ is N+R$^s$;

R* is selected from the group consisting of:

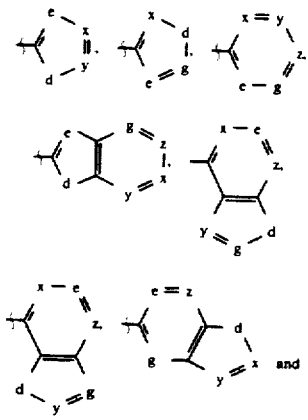

wherein each d independently represents O, S, or NR$^k$;

e, g, x, y and z represent CR$^m$, N or N+R$^k$, provided that no more than one of e, g, x, y and z in any given structure represents N+R$^k$;

R$^a$, R$^b$ and R$^c$ represent hydrogen, —C$_{1-6}$ straight— or branched-chain alkyl, unsubstituted or substituted with one to four R$^d$ groups; —C$_{3-7}$ cycloalkyl, unsubstituted or substituted with one to four R$^d$ groups; or —R*;

or R$^a$ and R$^b$ taken together with any intervening atoms represent a 4-6 membered saturated ring optionally interrupted by one or more of O, S, NR$^c$, with R$^c$ as defined above, or —C(O)—, said ring being unsubstituted or substituted with one to four R$^f$ groups;

or R$^b$ and R$^c$ taken together with any intervening atoms represent a 4-6 membered saturated ring optionally interrupted by one to three of O, S, NR$^a$, with R$^a$ as defined above, or —C(O)—, said ring being unsubstituted or substituted with one to four r$^f$ groups;

each R$^d$ independently represents halo; —CN; —NO₂; —NR$^e$R$^f$; —OR$^g$; —SR$^g$; —CONR$^e$R$^f$; —COOR$^g$; —SOR$^g$; —SO₂R$^g$; —SO₂NR$^e$R$^f$; —NR$^e$SO₂R$^f$; —COR$^e$; —NR$^e$COR$^f$; —OCOR$^e$; —OCONR$^e$R$^f$; —NR$^e$CONR$^f$R$^g$; —NR$^e$CO₂R$^h$; —OCO₂R$^h$; —C(NR$^e$)NR$^f$R$^g$; —NR$^e$C(NH)NR$^f$R$^g$; —NR$^e$C(NR$^f$)R$^g$; —R* or —Q;

R$^e$, R$^f$ and R$^g$ represent hydrogen; —C$_{1-6}$ straight— or branched-chain alkyl unsubstituted or substituted with one to four R$^i$ groups, or —R*;

or R$^e$ and R$^f$ taken together represent a 4-6 membered saturated ring optionally interrupted by one to three of O, S, —C(O)— or NR$^g$ with R$^g$ as defined above, said ring being substituted or substituted with one to four R$^i$ groups;

each R$^i$ independently represent halo; —CN; —NO₂; phenyl; —NHSO₂R$^h$; —OR$^h$, —SR$^h$; —N(R$^h$)₂; —N+(R$^h$)₃; —C(O)N(R$^h$)₂; —SO₂N(R$^h$)₂; heteroaryl; heteroarylium; —CO₂R$^h$; —C(O)R$^h$; —O-COR$^h$; —NHCOR$^h$; guanidinyl; carbamimidoyl or ureido;

each R$^h$ independently represents H, a —C$_{1-6}$ straight or branched-chain alkyl group, a —C$_3$-C$_6$ cycloalkyl group or phenyl, or when two R$^h$ groups are present, said R$^h$ groups may be taken in combination and represent a 4-6 membered saturated ring, optionally interrupted by one or two of O, S, SO₂, —C(O)—, NH and NCH₃;

R$^k$ represents hydrogen; —C$_{1-6}$ straight—or branched-chain alkyl, unsubstituted or substituted with one to four R$^i$ groups; or —(CH₂)$_n$Q where n and Q are as previously defined;

each R$^m$ independently represents a member selected from the group consisting of: hydrogen; halo; —CN; —NO₂; —NHR$^n$; —NR$^n$R$^o$; —OR$^n$; —SR$^n$; —CONR$^n$R$^o$; —COOR$^h$; —SOR$^n$; —SO₂R$^n$; —SO₂NR$^n$R$^o$; —NR$^n$SO₂R$^o$; —COR$^n$; —NR$^n$COR$^o$; —OCOR$^n$; —OCONR$^n$R$^o$; —NR$^n$CO₂R$^h$;

—NR"CONR°R^h; —OCO_2R^h; —CNR^nNR°R^h; —NR"CNHNR°R^h; —NR"C(NR°)R^h; —C_{1-6} straight— or branched-chain alkyl, unsubstituted or substituted with one to four R^i groups; —C_{3-7} cycloalkyl, unsubstituted or substituted with one to four R^i groups; and —(CH_2)_nQ where n=1–3;

R^n and R° represent hydrogen, phenyl; —C_{1-6} straight—or branched-chain alkyl unsubstituted or substituted with one to four r^i groups;

each R^s independently represents hydrogen; phenyl; —C_{1-6} straight— or branched alkyl, unsubstituted or substituted with one to four R^i groups;

each R^t independently represents hydrogen; halo; phenyl; —CN; —NO_2; —NHR"; —NR"R"; —OR"; —SR"; —CONR"R"; —COOR^h; —SOR"; —SO_2R"; —SO_2NR"R"; —NR"SO_2R"; —COR"; —NR"COR"; —OCOR"; —OCONR"R"; —NR"CO_2R"; —NR"CONR"R"; —OCO_2R"; heteroaryl; heteroarylium; —C_{1-6} straight— or branched-chain alkyl, unsubstituted or substituted with one to four R^i groups;

R^u and R^v represents hydrogen or —C_{1-6} straight— or branched-chain alkyl, unsubstituted or substituted with one to four R^i groups;

or R^u and R^v together represent a 4–6 membered saturated ring optionally interrupted by one or more of O, S, NR^w or —C(O)—, said ring being unsubstituted or substituted with one to four R^i groups;

R^x represents hydrogen or a C_{1-8} straight— or branched-chained alkyl, optionally interrupted by one or two of O, S, SO, SO_2, NR^w, N+R^hR^w, or —C(O)—, said chain being unsubstituted or substituted with one to four of halo, CN, NO_2; OR^w, SR^w, SOR^w, SO_2R^w, NR^hR^w, N+(R^h)_2R^w, —C(O)—R^w, C(O)NR^hR^w, SO_2NR^hR^w, CO_2R^w, OC(O)R^w, OC(O)NR^hR^w, NR^hC(O)R^w, NR^hC(O)NR^hR^w, or a phenyl or heteroaryl group which is in turn optionally substituted with from one to four R^i groups or with one to two C_{1-3} straight— or branched-chain alkyl groups, said alkyl groups being unsubstituted or substituted with one to four R^i groups;

R^y, and R^z represent; phenyl; —C_{1-6} straight— or branched-chain alkyl, unsubstituted or substituted with one to four R^i groups and optionally interrupted by O, S, NR^w, N+R^hR^w or —C(O)—;

or R^x and R^y together with any intervening atoms represent a 4–6 membered saturated ring optionally interrupted by O, S, SO_2, NR^w, N+R^hR^w or —C(O)—, and, when R^x and R^y together represent a 4–6 membered ring as defined above, R^z is as defined above or R^z represents an additional saturated 4–6 membered ring fused to the ring represented by R^x and R^y taken together, optionally interrupted by O, S, NR^w or —C(O)—, said rings being unsubstituted or substituted with one to four R^i groups each R^w independently represents hydrogen or —C_{1-6} straight— or branched-chain alkyl, unsubstituted or substituted with one to four R^i groups, C_{3-6} cycloalkyl optionally substituted with one to four R^i groups; or phenyl optionally substituted with one to four R^i groups;

or R^h and R^w taken together with any intervening atoms represent a 5–6 membered saturated ring, optionally interrupted by one or two of O, S, SO_2, NH or NCH_3.

10. A compound in accordance with claim 9 represented by formula Id:

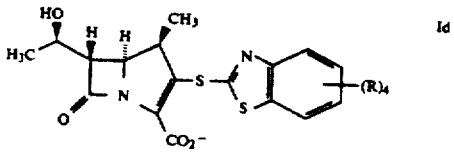

wherein:

(R)_4 contains from one to three positively charged atoms, and each R is selected from the group consisting of hydrogen; halo; —CN; —CONR^aR^b; —COOR^a; —SOR^a; —SO_2R^c; —SO_2NR^aR^b; —COR^a; —C_{1-6} straight- or branched-chain alkyl, unsubstituted or substituted with one to three R^d groups; or —R^a, with the proviso that from 1–3 R groups are present which contain R^a or Q;

R^a, R^b and R^c independently represent hydrogen, —C_{1-6} straight- or branched-chain alkyl, unsubstituted or substituted with one to four R^d groups; or —R^a;

or R^a and R^b taken together with any intervening atoms represent a 4–6 membered saturated ring optionally interrupted by one or more of O, S, NR^c, with R^c as defined above, or —C(O)—, said ring being unsubstituted or substituted with one to four R^i groups;

each R^d independently represents halo; —CN; —NO_2; —NR^eR^f; —OR^e; —SR^e; —CONR^eR^f; —COOR^e; —SOR^e; —SO_2R^e; —SO_2NR^eR^f; —NR^eSO_2R^f; —COR^e; —NR^eCOR^f; —OCOR^e; —OCONR^eR^f; —NR^eCONR^eR^f; —NR^eCO_2R^h; —OCO_2R^h; —C(NR^e)NR^fR^g; —NR^eC(NH)NR^fR^g; —NR^eC(NR^f)R^g; —R^a or —Q;

Q represents

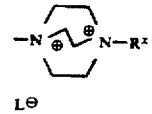

wherein L^- is a pharmaceutically acceptable counterion;

R^x represents hydrogen or a C_{1-8} straight- or branched-chain alkyl, optionally interrupted by one or two of O, S, SO, SO_2, NR^w, N+R^hR^w, or —C(O)—, said chain being unsubstituted or substituted with one to four of halo, CN, NO_2, OR^w, SR^w, SOR^w, SO_2R^w, NR^hR^w, N+(R^h)_2R^w, —C(O)—R^w, C(O)NR^hR^w, SO_2NR^hR^w, CO_2R^w, OC(O)R^w, OC(O)NR^hR^w, NR^hC(O)R^w, NR^hC(O)NR^hR^w, or a phenyl or heteroaryl group which is in turn optionally substituted with from one to four R^i groups or with one to two C_{1-3} straight- or branched-chain alkyl groups, said alkyl groups being unsubstituted or substituted with one to four R^i groups;

each R^h independently represents H, a —C_{1-6} straight or branched-chain alkyl group, a —C_3–C_6 cycloalkyl group or phenyl, or when two R^h groups are present, said R^h groups may be taken in combination and represent a 4–6 membered saturated ring, optionally interrupted by one or two of O, S, SO$_2$, —C(O)—, NH and NCH$_3$;

each R$^i$ independently represents halo; —CN; —NO$_2$; phenyl; —NHSO$_2$R$^h$; —OR$^h$, —SR$^h$; —N(R$^h$)$_2$; —N$^+$(R$^h$)$_3$; —C(O)N(R$^h$)$_2$; —SO$_2$N(R$^h$)$_2$; heteroaryl; heteroarylium; —CO$_2$R$^h$; —C(O)R$^h$; —O-COR$^h$; —NHCOR$^h$; guanidinyl; carbamimidoyl or ureido;

R$^w$ represents hydrogen or —C$_{1-6}$ straight- or branched-chain alkyl, unsubstituted or substituted with one to four R$^i$ groups; C$_{3-6}$ cycloalkyl optionally substituted with one to four R$^i$ groups; or phenyl optionally substituted with one to four R$^i$ groups;

or R$^h$ and R$^w$ taken together with any intervening atoms represent a 5–6 membered saturated ring, optionally interrupted by one or two or O, S, SO$_2$, NH or NCH$_3$;

R* is selected from the group consisting of:

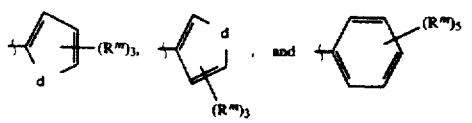

wherein:
d is O, S or NR$^k$;

R$^k$ represents hydrogen; —C$_{1-6}$ straight- or branched-chain alkyl, unsubstituted or substituted with one to four R$^i$ groups; or —(CH$_2$)$_n$—Q;

R$^m$ is selected from the group consisting of: hydrogen; halo; —CN; —NO$_2$; —NHR$^n$; —NR$^n$R$^o$; —OR$^n$; —SR$^n$; —CONR$^n$R$^o$; —SOR$^n$; —SO$_2$R$^n$; —SO$_2$NR$^n$R$^o$; —NR$^n$SO$_2$R$^o$; —COR$^n$; —NR$^n$COR$^o$; —NR$^n$CO$_2$R$^h$; —NR$^n$CONR$^o$R$^h$; —C$_{1-6}$ straight- or branched-chain alkyl, unsubstituted or substituted with one to four R$^i$ groups; and —(CH$_2$)$_n$—Q;;

R$^d$ represents —R* as defined above or Q; and

R$^n$ and R$^o$ represent hydrogen, phenyl; —C$_{1-6}$ straight- or branched-chain alkyl unsubstituted or substituted with one to four R$^i$ groups.

11. A compound in accordance with claim 9 represented by formula Id:

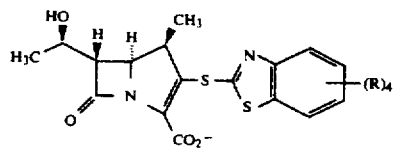

wherein:
each R is selected from the group consisting of hydrogen; halo; —CN; —CONR$^a$R$^b$; —COOR$^h$; —SOR$^c$; —SO$_2$R$^c$; —SO$_2$NR$^a$R$^b$; —COR$^a$; —C$_{1-6}$ straight- or branched-chain alkyl, unsubstituted or substituted with one to three R$^d$ groups; and —R*, with the proviso that one or two R groups contain R* or Q and —(R)$_4$ contains from one to two positively charged atoms;

Q represents a member selected from the group consisting of:

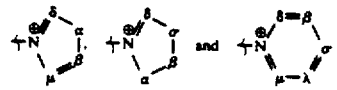

wherein:
α represents O, S or NR$^s$;
β, δ, λ, μ and σ independently represent CR$^t$, N or N$^+$R$^s$ provided that no more than one of β, δ, λ, μ, and σ may be N$^+$R$^s$;

R* is selected from the group consisting of:

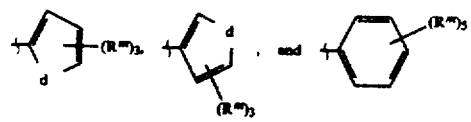

wherein:
d represents O, S or NR$^k$;

R$^a$, R$^b$ and R$^c$ independently represent hydrogen, —C$_{1-6}$ straight- or branched-chain alkyl, unsubstituted or substituted with one to four R$^d$ groups; or —R*;

or R$^a$ and R$^b$ taken together with any intervening atoms represent a 4–6 membered saturated ring optionally interrupted by one or more of O, S, NR$^c$, with R$^c$ as defined above, or —C(O)—, said ring being unsubstituted or substituted with one to four R$^i$ groups;

R$^d$ represents —R* or —Q;

each R$^h$ independently represents H, a —C$_{1-6}$ straight or branched-chain alkyl group, a —C$_3$–C$_6$ cycloalkyl group or phenyl, or when two R$^h$ groups are present, said R$^h$ groups may be taken in combination and represent a 4–6 membered saturated ring, optionally interrupted by one or two or O, S, SO$_2$, —C(O)—, NH and NCH$_3$;

R$^k$ represents hydrogen; —C$_{1-6}$ straight- or branched-chain alkyl, unsubstituted or substituted with one to four R$^i$ groups; or —(CH$_2$)$_n$—Q;

each R$^i$ independently represents halo; —CN; —NO$_2$; phenyl; —NHSO$_2$R$^h$; —OR$^h$, —SR$^h$; —N(R$^h$)$_2$; —N$^+$(R$^h$)$_3$; —C(O)N(R$^h$)$_2$; —SO$_2$N(R$^h$)$_2$; heteroaryl; heteroarylium; —CO$_2$R$^h$; —C(O)R$^h$; —O-COR$^h$; —NHCOR$^h$; guanidinyl; carbamimidoyl or ureido;

R$^m$ is selected from the group consisting of: hydrogen; halo; —CN; —NO$_2$; —NHR$^n$; —NR$^n$R$^o$; —OR$^n$; —SR$^n$; —CONR$^n$R$^o$; —SOR$^n$; —SO$_2$R$^n$; —SO$_2$NR$^n$R$^o$; —NR$^n$SO$_2$R$^o$; —COR$^n$; —NR$^n$COR$^o$; —NR$^n$CO$_2$R$^h$; —NR$^n$CONR$^o$R$^h$; —C$_{1-6}$ straight- or branched-chain alkyl, unsubstituted or substituted with one to four R$^i$ groups; and —(CH$_2$)$_n$—Q;

R$^n$ and R$^o$ represent hydrogen, phenyl; —C$_{1-6}$ straight- or branched-chain alkyl unsubstituted or substituted with one to four R$^i$ groups;

R$^s$ represents hydrogen; phenyl; —C$_{1-6}$ straight- or branched-chain alkyl, unsubstituted or substituted with one to four R$^i$ groups;

R$^t$ represents hydrogen; halo; phenyl; —CN; —NHR$^u$; —NR$^u$R$^v$; —OR$^u$; —SR$^u$; —CONR$^u$R$^v$; —COOR$^h$; —SOR$^u$; —SO$_2$R$^u$; —SO$_2$NR$^u$R$^v$; —N-R$^u$SO$_2$R$^v$; —COR$^u$; —NR$^u$COR$^v$; —OCOR$^u$;

—OCONR"R"; —NR"CO₂R"; —NR"CONR'R"; —OCO₂R"; —C₁₋₆ straight-or branched-chain alkyl, unsubstituted or substituted with one to four R' groups;

R" and R" represent hydrogen or —C₁₋₆ straight- or branched-chain alkyl, unsubstituted or substituted with one to four R' groups;

or R" and R" together represent a 4–6 membered saturated ring optionally interrupted by one or more of O, S, NR" or —C(O)—, said ring being unsubstituted or substituted with one to four R' groups;

each R" independently represents hydrogen or —C₁₋₆ straight- or branched-chain alkyl, unsubstituted or substituted with one to four R' groups, C₃₋₆ cycloalkyl optionally substituted with one to four R' groups; or phenyl optionally substituted with one to four R' groups;

or R" and R" taken together with any intervening atoms represent a 5–6 membered saturated ring, optionally interrupted by one or two or O, S, SO₂, NH or NCH₃.

12. A compound in accordance with claim 8 represented by formula Ie;

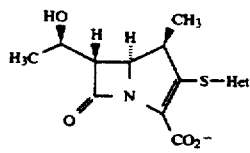

wherein:
Het has substituents which contain one to three positively charged atoms and is selected from the group consisting of:

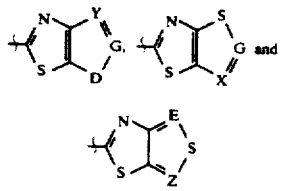

wherein:
E, G, X, Y and Z independently represent CR or N; each R is selected from the group consisting of hydrogen; halo; —CN; —CONR"R"; —COOR"; —SOR"; —SO₂R"; —SO₂NR"R"; —COR"; —C₁₋₆ straight- or branched-chain alkyl, unsubstituted or substituted with one to three R" groups; —C₃₋₇ cycloalkyl, unsubstituted or substituted with one to three R" groups, and —R*, with the proviso that one or two R groups are present which contain R* or Q;

Q is selected from the group consisting of:

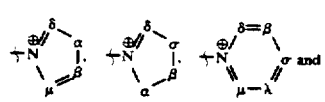

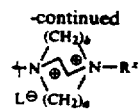

wherein:
L⁻ represents a pharmaceutically acceptable counterion;
a and b independently represent 2 or 3;
α represents O, S or NR";
β, δ, λ, μ and σ independently represent CR', N or N⁺R" provided that no more that one of β, δ, λ, μ, and σ is N⁺R";
R* is selected from the group consisting of;

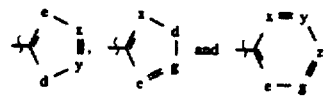

wherein:
d represents O, S or NR";
e, g, x, y and z independently represent CR", N or N⁺R", provided that no more that one of e, g, x, y and z represents N⁺R";
R", R" and R" independently represent hydrogen —C₁₋₆ straight- or branched-chain alkyl, unsubstituted or substituted with one to four R" groups; —C₃₋₇ cycloalkyl, unsubstituted or substituted with one to four R" groups; or —R*;

or R" and R" taken together with any intervening atoms represent a 4–6 membered saturated ring optionally interrupted by one or more of O, S, NR", with R" as defined above, or —C(O)—, said ring being unsubstituted or substituted with one to four R" groups; and each R" independently represents halo; —CN; —NO₂; —NR"R"; —OR"; —SR"; —CONR"R"; COOR"; —SOR"; —SO₂R"; —SO₂NR"R"; —NR"SO₂R"; —COR"; —NR"COR"; —OCOR"; —OCONR"R"; —NR"CONR"R"; —NR"CO₂R"; —OCO₂R"; —C(NR")NR"R"; —NR"C(NH)NR"R"; —NR"C(NR")R"; —R* or —Q;

R", R" and R" represent hydrogen; —C₁₋₆ straight- or branched-chain alkyl unsubstituted or substituted with one to four R" groups, or —R*;

or R" and R" taken together represent a 4–6 membered saturated ring optionally interrupted by one to three of O, S, —C(O)— or NR" with R" as defined above, said ring being unsubstituted or substituted with one to four R" groups;

each R" independently represents H, a —C₁₋₆ straight or branched-chain alkyl group, a —C₃–C₆ cycloalkyl group or phenyl, or when two R" groups are present, said R" groups may be taken in combination and represent a 4–6 membered saturated ring, optionally interrupted by one or two of O, S, SO₂, —C(O)—, NH and NCH₃;

each R" independently represents halo; —CN; —NO₂; phenyl; —NHSO₂R"; —OR"; —SR"; —N(R")₂; —N⁺(R")₃; —C(O)N(R")₂; —SO₂N(R")₂; heteroaryl, heteroarylium; —CO₂R"; —C(O)R"; —OCOR"; —NHCOR"; guanidinyl; carbamimidoyl or ureido;

$R^k$ represents hydrogen; —$C_{1-6}$ straight- or branched-chain alkyl, unsubstituted or substituted with one to four $R^i$ groups; or —$(CH_2)_n$—Q;

$R^j$ represents hydrogen; phenyl; —$C_{1-6}$ straight- or branched-chain alkyl, unsubstituted or substituted with one to four $R^i$ groups;

$R^i$ represents hydrogen; halo; phenyl; —CN; —$NR^uR^v$; —$OR^u$; —$SR^u$; —$CONR^uR^v$; —$COOR^h$; —$SOR^u$; —$SO_2R^u$; —$SO_2NR^uR^v$; —$NR^uSO_2R^v$; —$COR^u$; —$NR^uCOR^v$; —$OCOR^u$; —$OCONR^uR^v$; —$NR^uCO_2R^v$; —$NR^uCONR^vR^w$; —$OCO_2R^v$; —$C_{1-6}$ straight- or branched-chain alkyl, unsubstituted or substituted with one to four $R^i$ groups;

$R^u$ and $R^v$ represent hydrogen or —$C_{1-6}$ straight- or branch-chain alkyl, unsubstituted or substituted with one to four $R^i$ groups;

or $R^u$ and $R^v$ together represent a 4-6 membered saturated ring optionally interrupted by one or more of O, S, $NR^w$ or —C(O)—, said ring being unsubstituted or substituted with one to four $R^i$ groups, and each $R^w$ independently represents hydrogen or —$C_{1-6}$ straight- or branched-chain alkyl, unsubstituted or substituted with one to four $R^i$ groups; $C_{3-6}$ cycloalkyl optionally substituted with one to four $R^i$ groups; or phenyl optionally substituted with one to four $R^i$ groups.

13. A compound in accordance with claim 12 represented by formula Ie:

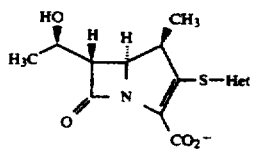

wherein:
Het has substituents which contain from one to three positively charged atoms and is selected from the group consisting of:

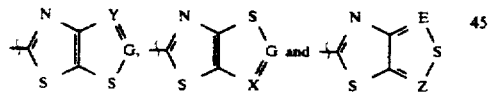

wherein:
E, G, X, Y and Z independently represent CR or N;
each R is selected from the group consisting of hydrogen; halo; —CN; —$CONR^aR^b$; —$COOR^h$; —$SOR^c$; —$SO_2R^c$; —$SO_2NR^aR^b$; —$COR^a$; —$C_{1-6}$ straight- or branched-chain alkyl, unsubstituted or substituted with one to three $R^d$ groups; —$C_{3-7}$ cycloalkyl, unsubstituted or substituted with one to three $R^d$ groups; and —$R^*$;
with the proviso that one R group contains Q;
$R^*$ is selected from the group consisting of:

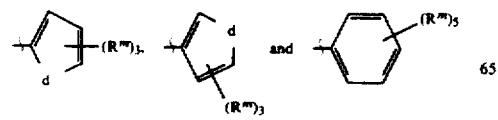

wherein:
d is O, S or $NR^k$;
Q represents

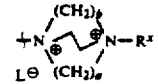

wherein a and b are 2,
$L^-$ is a pharmaceutically acceptable counterion, and
$R^x$ represents hydrogen or a $C_{1-8}$ straight- or branched-chain alkyl, optionally interrupted by one or two of O, S, SO, $SO_2$, $NR^w$, $N^+R^hR^w$, or —C(O)—, said chain being unsubstituted or substituted with one to four of halo, CN, $NO_2$, $OR^w$, $SR^w$, $SOR^w$, $SO_2R^w$, $NR^hR^w$, $N^+(R^h)_2R^w$, —C(O)—$R^w$, $C(O)NR^hR^w$, $SO_2NR^hR^w$, $CO_2R^w$, OC(O)$R^w$, OC(O)$NR^hR^w$, $NR^hC(O)R^w$, $NR^hC(O)NR^hR^w$, or a phenyl or heteroaryl group which is in turn optionally substituted with from one to four $R^i$ groups or with one to two $C_{1-3}$ straight- or branched-chain alkyl groups, said alkyl groups being unsubstituted or substituted with one to four $R^i$ groups;

each $R^h$ independently represents H, a —$C_{1-6}$ straight or branch-chain alkyl group, a —$C_3$-$C_6$ cycloalkyl group or phenyl, or when two $R^h$ groups are present, said $R^h$ groups may be taken in combination and represent a 4-6 membered saturated ring, optionally interrupted by one or two of O, S, $SO_2$, —C(O)—, NH and $NCH_3$;

each $R^i$ independently represents halo; —CN; —$NO_2$; phenyl; —$NHSO_2R^h$; —$OR^h$; —$SR^h$; —$N(R^h)_2$; —$N^+(R^h)_3$; —$C(O)N(R^h)_2$; —$SO_2N(R^h)_2$; heteroaryl, heteroarylium; —$CO_2R^h$; —$C(O)R^h$; —$OCOR^h$; —$NHCOR^h$; guanidinyl; carbamimidoyl or ureido;

$R^k$ represents hydrogen; —$C_{1-6}$ straight- or branched-chain alkyl, unsubstituted or substituted with one to four $R^i$ groups; or —$(CH_2)_n$—Q, wherein n = 1, 2 or 3 and Q is as defined above;

$R^m$ is selected from the group consisting of: hydrogen; halo; —CN; —$NO_2$; —$NHR^a$; —$NR^aR^o$; —$OR^a$; —$SR^a$; —$CONR^aR^o$; —$SOR^a$; —$SO_2R^a$; —$SO_2NR^aR^o$; —$NR^aSO_2R^o$; —$COR^a$; —$NR^aCOR^o$; —$NR^aCO_2R^h$; —$NR^aCONR^oR^h$; —$C_{1-6}$ straight- or branched-chain alkyl, unsubstituted or substituted with one to four $R^i$ groups; and —$(CH_2)_{1-3}Q$;

$R^a$, $R^b$ and $R^c$ independently represent hydrogen, —$C_{1-6}$ straight- or branched-chain alkyl, unsubstituted or substituted with one of four $R^d$ groups; or —$R^*$;

or $R^a$ and $R^b$ taken together with any intervening atoms represent a 4-6 membered saturated ring optionally interrupted by one or more of O, S, $NR^c$, with $R^c$ as defined above, or —C(O)—, said ring being unsubstituted or substituted with one to four $R^i$ groups;

$R^d$ represents $R^*$ or Q;

$R^n$ and $R^o$ represent hydrogen, phenyl, —$C_{1-6}$ straight- or branched-chain alkyl unsubstituted or substituted with one to four $R^i$ groups, and $R^w$ represents hydrogen or —$C_{1-6}$ straight- or branched-chain alkyl, unsubstituted or substituted with one to four $R^i$ groups; $C_{3-6}$ cycloalkyl optionally substituted with one to four R$^i$ groups; or phenyl optionally substituted with one to four R$^i$ groups, or R$^h$ and R$^w$ taken together with any intervening atoms represent a 5–6 membered saturated ring, optionally interrupted by one or two of O, S, SO$_2$, NH or NCH$_3$.

14. A compound in accordance with claim 12 represented by formula Ie:

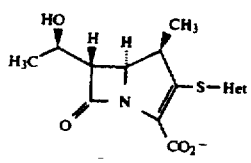

Ie wherein

Het has substituent groups which contain from one to three positively charged atoms and is selected from the group consisting of:

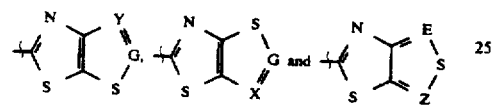

wherein

E, G, X, Y and Z independently represent CR or N;

R represents a member selected from the group consisting of hydrogen; halo; —CN; —CONR$^a$R$^b$; —COOR$^h$; —SOR$^c$; —SO$_2$R$^c$; —SO$_2$NR$^a$R$^b$; —COR$^a$; —C$_{1-6}$ straight- or branched-chain alkyl unsubstituted or substituted with one to three R$^d$ groups; and —R$^*$, with the proviso that one or two R groups contain R$^*$ or Q;

Q represents a member selected from the group consisting of:

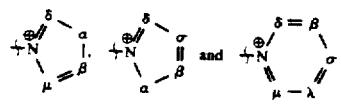

wherein:

α represents O, S, or NR$^s$;

β, δ, λ, μ and σ independently represent CR$^t$, N or N$^+$R$^s$ provided that no more than one of β, δ, λ, μ, and σ may be N$^+$R$^s$;

R$^*$ is selected from the group consisting of:

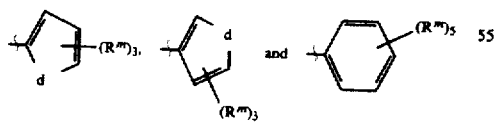

wherein:

d represents O, S, or NR$^k$;

R$^a$, R$^b$ and R$^c$ independently represent hydrogen, —C$_{1-6}$ straight- or branched-chain alkyl, unsubstituted or substituted with one to four R$^d$ groups; or —R$^*$;

or R$^a$ and R$^b$ taken together with any intervening atoms represent a 4–6 membered saturated ring optionally interrupted by one or more of O, S, NR$^c$, with R$^c$ as defined above, or —C(O)—, said ring being unsubstituted or substituted with one to four R$^i$ groups;

R$^d$ represents —R$^*$ or —Q;

each R$^h$ independently represents H, a —C$_{1-6}$ straight or branched-chain alkyl group, a —C$_3$–C$_6$ cycloalkyl group or phenyl, or when two R$^h$ groups are present, said R$^h$ groups may be taken in combination and represent a 4–6 membered saturated ring, optionally interrupted by one or two of O, S, SO$_2$, —C(O)—, NH and NCH$_3$;

each R$^i$ independently represents halo; —CN; —NO$_2$; phenyl —NHSO$_2$R$^h$; —OR$^h$; —SR$^h$; —N(R$^h$)$_2$; —N$^+$(R$^h$)$_3$; —C(O)N(R$^h$)$_2$; —SO$_2$N(R$^h$)$_2$; heteroaryl, heteroarylium; —CO$_2$R$^h$; —C(O)R$^h$; —O-COR$^h$; —NHCOR$^h$; guanidinyl; carbamimidoyl or ureido;

R$^k$ represents hydrogen; —C$_{1-6}$ straight- or branched-chain alkyl, unsubstituted or substituted with one to four R$^i$ groups; or —(CH$_2$)$_n$—Q, wherein n and Q are as previously defined;

R$^m$ is selected from the group consisting of: hydrogen; halo; —CN; —NO$_2$; —NHR$^n$; —NR$^n$R$^o$; —OR$^n$; —SR$^n$; —CONR$^n$R$^o$; —SOR$^n$; —SO$_2$R$^n$; —SO$_2$NR$^n$R$^o$; —NR$^n$SO$_2$R$^o$; —COR$^n$; —NR$^n$COR$^o$; —NR$^n$CO$_2$R$^h$; —NR$^n$CONR$^o$R$^h$; —C$_{1-6}$ straight- or branched-chain alkyl, unsubstituted or substituted with one to four R$^i$ groups; and —(CH$_2$)$_n$—Q, wherein n and Q are as previously defined;

R$^n$ and R$^o$ represent hydrogen, phenyl; —C$_{1-6}$ straight- or branched-chain alkyl unsubstituted or substituted with one to four R$^i$ groups;

R$^s$ represents hydrogen; phenyl; —C$_{1-6}$ straight- or branched-chain alkyl, unsubstituted or substituted with one to four R$^i$ groups;

R$^t$ represents hydrogen; halo; phenyl; —CN; —NHR$^u$; —NR$^u$R$^v$; —OR$^u$; —SR$^u$; —CONR$^u$R$^v$; —COOR$^h$; —SOR$^u$; —SO$_2$R$^u$; —SO$_2$NR$^u$R$^v$; —NR$^u$SO$_2$R$^v$; —COR$^u$; —NR$^u$COR$^v$; —OCOR$^u$; —OCONR$^u$R$^v$; —NR$^u$CO$_2$R$^v$; —NR$^u$CONR$^v$R$^w$, —OCO$_2$R$^v$; —C$_{1-6}$ straight- or branched-chain alkyl unsubstituted or substituted with one to four R$^i$ groups;

R$^u$ and R$^v$ represent hydrogen or —C$_{1-6}$ straight- or branched-chain alkyl, unsubstituted or substituted with one to four R$^i$ groups;

or R$^u$ and R$^v$ together represent a 4–6 membered saturated ring optionally interrupted by one or more of O, S, NR$^w$ or —C(O)—, said ring being unsubstituted or substituted with one to four R$^i$ groups;

each R$^w$ independently represents hydrogen or —C$_{1-6}$ straight- or branched-chain alkyl, unsubstituted or substituted with one to four R$^i$ groups; C$_{3-6}$ cycloalkyl optionally substituted with one to four R$^i$ groups; or phenyl optionally substituted with one to four R$^i$ groups.

15. A compound in accordance with claim 10 represented by the formula If:

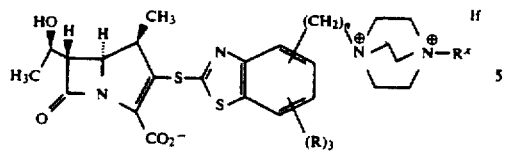

wherein:

L— is a pharmaceutically acceptable counterion;
n is 1–3;

$R^x$ represents hydrogen or a $C_{1-8}$ straight- or branched-chain alkyl, optionally interrupted by one or two of O, S, SO, $SO_2$, $NR^w$, $N+R^hR^w$, or —C(O)—, said chain being unsubstituted or substituted with one of four of halo, CN, $NO_2$, $OR^w$, $SR^w$, $SOR^w$, $SO_2R^w$, $NR^hR^w$, $N+(R^h)_2R^w$, —C(O)—$R^w$, $C(O)NR^hR^w$, $SO_2NR^hR^w$, $CO_2R^w$, OC(O)$R^w$, OC(O)$NR^hR^w$, $NR^hC(O)R^w$, $NR^hC(O)NR^hR^w$, or a phenyl or heteroaryl group which is in turn optionally substituted with from one to four $R^i$ groups or with one to two $C_{1-3}$ straight- or branched-chain alkyl groups, said alkyl groups being unsubstituted or substituted with one to four $R^i$ groups;

each R is independently selected from: hydrogen; halo; —CN; —$NO_2$; —$OR^c$; —$SR^c$; —$CONR^aR^b$; —$COOR^b$; —$SOR^c$; —$SO_2R^c$; —$SO_2NR^aR^b$; —$N-R^aSO_2R^b$; —$COR^a$; —$OCOR^a$; —$OCONR^aR^b$; —$NR^aCONR^bR^c$; —$NR^aCO_2R^b$; —$OCO_2R^b$; —$C_{1-6}$ straight- or branched-chain alkyl, unsubstituted or substituted with one to four $R^d$ groups; and —$C_{3-7}$ cycloalkyl, unsubstituted or substituted with one of four $R^d$ groups, each $R^d$ independently represents halo; —CN; —$NO_2$; —$NR^eR^f$; —$OR^g$; —$SR^g$; —$CONR^eR^f$; —$COOR^g$; —$SOR^g$; —$SO_2R^g$; —$SO_2NR^eR^f$; —$N-R^gSO_2R^f$; —$COR^e$; —$NR^eCOR^f$; —$OCOR^e$; —$OCONR^eR^f$; —$NR^eCONR^fR^g$; —$NR^eCO_2R^h$; —$OCO_2R^h$; —$C(NR^e)NR^fR^g$; —$N-R^eC(NH)NR^fR^g$; or —$NR^eC(NR^f)R^g$;

$R^e$, $R^f$ and $R^g$ represent hydrogen; or $C_{1-6}$ straight- or branched-chain alkyl unsubstituted or substituted with one to four $R^i$ groups;

or $R^e$ and $R^f$ taken together with any intervening atoms represent a 4–6 membered saturated ring optionally interrupted by one to three of O, S, —C(O)— or $NR^g$ with $R^g$ as defined above, said ring being unsubstituted or substituted with one to four $R^i$ groups;

each $R^h$ independently represents H, a —$C_{1-6}$ straight or branched-chain alkyl group, a —$C_3$–$C_6$ cycloalkyl group or phenyl, or when two $R^h$ groups are present, said $R^h$ groups may be taken in combination and represent a 4–6 membered saturated ring, optionally interrupted by one or two of O, S, $SO_2$, —C(O)—, NH and $NCH_3$;

each $R^i$ independently represents halo; —CN; —$NO_2$; phenyl; —$NHSO_2R^h$; —$OR^h$, —$SR^h$; —$N(R^h)_2$; —$N+(R^h)_3$; —C(O)$N(R^h)_2$; —$SO_2N(R^h)_2$; heteroaryl; heteroarylium; —$CO_2R^h$; —C(O)$R^h$; —O-$COR^h$; —$NHCOR^h$; guanidinyl; carbamimidoyl or ureido;

$R^w$ represents hydrogen or —$C_{1-6}$ straight- or branched-chain alkyl, unsubstituted or substituted with one to four $R^i$ groups; $C_{3-6}$ cycloalkyl optionally substituted with one to four $R^i$ groups; or phenyl optionally substituted with one to four $R^i$ groups, or $R^h$ and $R^w$ taken together with any intervening atoms represent a 5–6 membered saturated ring, optionally interrupted by one or two of O, S, $SO_2$, NH or $NCH_3$.

16. A compound in accordance with claim 15 represented by formula Ig:

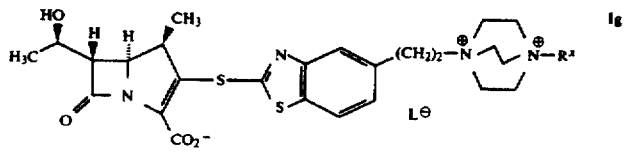

wherein:

L— is a pharmaceutically acceptable counterion;

$R^x$ represents hydrogen or a $C_{1-8}$ straight- or branched-chain alkyl, optionally interrupted by one or two of O, S, SO, $SO_2$, $NR^w$, $N+R^hR^w$, or —C(O)—, said chain being unsubstituted or substituted with one to four of halo, CN, $NO_2$, $OR^w$, $SR^w$, $SOR^w$, $SO_2R^w$, $NR^hR^w$, $N+(R^h)_2R^w$, —C(O)—$R^w$, $C(O)NR^hR^w$, $SO_2NR^hR^w$, $CO_2R^w$, OC(O)$R^w$, OC(O)$NR^h$, $R^w$, $NR^hC(O)R^w$, $NR^hC(O)NR^hR^w$, or a phenyl of heteroaryl group which is in turn optionally substituted with from one to four $R^i$ groups or with one to two $C_{1-3}$ straight- or branched-chain alkyl groups, said alkyl groups being unsubstituted or substituted with one to four $R^i$ groups;

each $R^h$ independently represents H, a —$C_{1-6}$ straight or branched-chain alkyl group, a —$C_3$–$C_6$ cycloalkyl group or phenyl, or when two $R^h$ groups are present, said $R^h$ groups may be taken in combination and represent a 4–6 membered saturated ring, optionally interrupted by one or two of O, S, $SO_2$, —C(O)—NH and $NCH_3$;

$R^w$ represents hydrogen or —$C_{1-6}$ straight- or branched-chain alkyl, unsubstituted or substituted with one to four $R^i$ groups, $C_{3-6}$ cycloalkyl optionally substituted with one to four $R^i$ groups; or phenyl optionally substituted with one to four $R^i$ groups, or $R^h$ and $R^w$ taken together with any intervening atoms represent a 5–6 membered saturated ring, optionally interrupted by one or two of O, S, $SO_2$, NH or $NCH_3$; and each $R^i$ independently represents halo; —CN; —$NO_2$; phenyl; —$NHSO_2R^h$; —$OR^h$, —$SR^h$; —$N(R^h)_2$; —$N+(R^h)_3$; —C(O)$N(R^h)_2$; —$SO_2N(R^h)_2$; heteroaryl; heteroarylium; —$CO_2R^h$; —C(O)$R^h$; —O-$COR^h$; —$NHCOR^h$; guanidinyl; carbamimidoyl or ureido.

17. A compound in accordance with claim 15 represented by formula Ih:

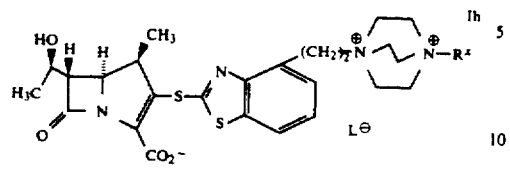

wherein:
L− is a pharmaceutically acceptable counterion;
$R^x$ represents hydrogen or a $C_{1-8}$ straight- or branched-chain alkyl, optionally interrupted by one or two of O, S, SO, $SO_2$, $NR^w$, $N^+R^hR^w$, or —C(O)—, said chain being unsubstituted or substituted with one to four of halo, CN, $NO_2$, $OR^w$, $SR^w$, $SOR^w$, $SO_2R^w$, $NR^hR^w$, $N^+(R^h)_2R^w$, —C(O)—$R^w$, $C(O)NR^hR^w$, $SO_2NR^hR^w$, $CO_2R^w$, OC(O)$R^w$, OC(O)$NR^hR^w$, $NR^hC(O)R^w$, $NR^hC(O)NR^hR^w$, or a phenyl or heteroaryl group which is in turn optionally substituted with from one to four $R^i$ groups or with one to two $C_{1-3}$ straight- or branched-chain alkyl groups, said alkyl groups being unsubstituted or substituted with one to four $R^i$ groups;
each $R^h$ independently represents H, a —$C_{1-6}$ straight or branched-chain alkyl group, a —$C_3$-$C_6$ cycloalkyl group or phenyl, or when two $R^h$ groups are present, said $R^h$ groups may be taken in combination and represent a 4–6 membered saturated ring, optionally interrupted by one or two of O, S, $SO_2$, —C(O)—, NH and $NCH_3$;
$R^w$ represents hydrogen or —$C_{1-6}$ straight- or branched-chain alkyl, unsubstituted or substituted with one to four $R^i$ groups, $C_{3-6}$ cycloalkyl optionally substituted with one to four $R^i$ groups; or phenyl optionally substituted with one to four $R^i$ groups;
or $R^h$ and $R^w$ taken together with any intervening atoms represent a 5–6 membered saturated ring, optionally interrupted by one or two of O, S, $SO_2$, NH or $NCH_3$, and
each $R^i$ independently represents halo; —CN; —$NO_2$; phenyl; —$NHSO_2R^h$; —$OR^h$; —$SR^h$; —$N(R^h)_2$; $N^+(R^h)_3$; —$C(O)N(R^h)_2$; —$SO_2N(R^h)_2$; heteroaryl; heteroarylium; —$CO_2R^h$; —$C(O)R^h$; —O-COR$^h$; —$NHCOR^h$; guanidinyl; carbamimidoyl or ureido.

18. A compound i accordance with claim 11 represented by formula Ii:

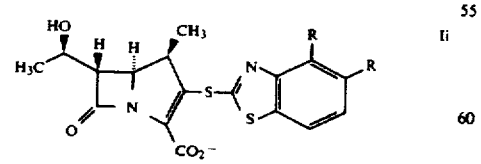

wherein:
each R independently represents a member selected from the group consisting of hydrogen or —$C_{1-6}$ straight- or branched-chain alkyl, unsubstituted or substituted with one to three $R^d$ groups;

$R^d$ represents —Q;
Q represents a member selected from the group consisting

wherein:
α represents O, S or $NR^s$;
β, δ, λ, μ and σ independently represent $CR^t$, N or $N^+R^s$ provided that no more than one of β, δ, λ, μ, and σ may be $N^+R^s$ and further provided that from one to three positively charged atoms are contained in the R groups;
$R^s$ represents hydrogen; phenyl; —$C_{1-6}$ straight- or branched-chain alkyl, unsubstituted or substituted with one to four $R^i$ groups;
$R^t$ represents hydrogen; halo; phenyl; —CN; —$NHR^u$; —$NR^uR^v$; —$OR^u$; —$SR^u$; —$CONR^uR^v$; —$COOR^h$; —$SOR^u$; —$SO_2R^u$; —$SO_2NR^uR^v$; —$NR^uSO_2R^v$; —$COR^u$; —$NR^uCOR^u$; —$OCOR^u$; —$OCONR^uR^v$; —$NR^uCO_2R^v$; —$NR^uCONR^vR^w$; —$OCO_2R^v$; —$C_{1-6}$ straight- or branched-chain alkyl, unsubstituted or substituted with one to four $R^i$ groups;
each $R^i$ independently represents halo; —CN; —$NO_2$; phenyl; —$NHSO_2R^h$; —$OR^h$; —$SR^h$; —$N(R^h)_2$; —$N^+(R^h)_3$; —$C(O)N(R^h)_2$; —$SO_2N(R^h)_2$; heteroaryl; heteroarylium; —$CO_2R^h$; —$C(O)R^h$; —O-COR$^h$; —$NHCOR^h$; guanidinyl; carbamimidoyl or ureido.
each $R^h$ independently represents H, a —$C_{1-6}$ straight or branched-chain alkyl group, a —$C_3$-$C_6$ cycloalkyl group or phenyl or when two $R^h$ groups are present, said $R^h$ groups may be taken in combination and represent a 4–6 membered saturated ring, optionally interrupted by one or two of O, S, $SO_2$, —C(O)—, NH and $NCH_3$;
$R^u$ and $R^v$ represent hydrogen or —$C_{1-6}$ straight- or branched-chain alkyl, unsubstituted or substituted with one to four $R^i$ groups;
or $R^u$ and $R^v$ together represent a 4–6 membered saturated ring optionally interrupted by one or more of O, S, $NR^w$ or —C(O)—, said ring being unsubstituted or substituted with one to four $R^i$ groups;
and each $R^w$ independently represents hydrogen or —$C_{1-6}$ straight- or branched-chain alkyl, unsubstituted or substituted with one to four $R^i$ groups; $C_{3-6}$ cycloalkyl optionally substituted with one to four $R^i$ groups; or phenyl optionally substituted with one to four $R^i$ groups.

19. A compound in accordance with claim 13 represented by formula Ie:

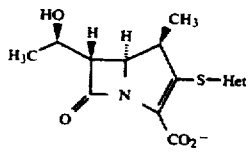

wherein:

221

Het has substituent groups which contain from two to three positively charged atoms and is selected from the group consisting of:

wherein:
E, G and Y independently represent CR or N;
X and Z independently represent CH or N;
R represents a member selected from the group consisting of hydrogen; —$C_{1-6}$ straight- or branched-chain alkyl, unsubstituted or substituted with $R^d$;
with the proviso that one R group is present which contains Q;
$R^d$ represents Q; Q represents

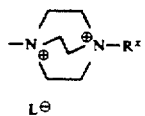

wherein L— is a pharmaceutically acceptable counterion;
$R^x$ represents hydrogen or a $C_{1-8}$ straight- or branched-chain alkyl, optionally interrupted by one or two of O, S, SO, $SO_2$, $NR^w$, $N^+R^hR^w$, or —C(O)—, said chain being unsubstituted or substituted with one to four of halo, CN, $NO_2$, $OR^w$, $SR^w$, $SOR^w$, $SO_2R^w$, $NR^hR^w$, $N^+(R^h)_2R^w$, C(O)—$R^w$, C(O)$NR^hR^w$, $SO_2NR^hR^w$, $CO_2R^w$, OC(O)$R^w$, OC(O)$NR^hR^w$, $NR^hC(O)R^w$, $NR^hC(O)NR^hR^w$, or a phenyl or heteroaryl group which is in turn optionally substituted with from one to four $R^i$ groups or with one to two $C_{1-3}$ straight- or branched-chain alkyl groups, said alkyl groups being unsubstituted or substituted with one to four $R^i$ groups;
each $R^h$ independently represents H, a —$C_{1-6}$ straight or branched-chain alkyl group, a —$C_3$-$C_6$ cycloalkyl group or phenyl, or when two $R^h$ groups are present, said $R^h$ groups may be taken in combination and represent a 4–6 membered saturated ring, optionally interrupted by one or two of O, S, $SO_2$, —C(O)—, NH and $NCH_3$;
each $R^i$ independently represents halo; —CN; —$NO_2$; phenyl; —$NHSO_2R^h$; —$OR^h$, —$SR^h$; —$N(R^h)_2$; —$N^+(R^h)_3$; —C(O)$N(R^h)_2$; —$SO_2N(R^h)_2$; heteroaryl; heteroarylium; —$CO_2R^h$; —C(O)$R^h$; —$OCOR^h$; —$NHCOR^h$; guanidinyl; carbamimidoyl or ureido, and
$R^w$ represents hydrogen or —$C_{1-6}$ straight- or branched-chain alkyl, unsubstituted or substituted with one to four $R^i$ groups; $C_{3-6}$ cycloalkyl optionally substituted with one to four $R^i$ groups; or phenyl optionally substituted with one to four $R^i$ groups,
or $R^h$ and $R^w$ taken together with any intervening atoms represent a 5–6 membered saturated ring, optionally interrupted by one or two of O, S, $SO_2$, NH or $NCH_3$.

20. A compound in accordance with claim 14 represented by formula Ie:

222

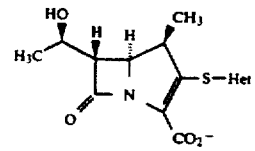

wherein:
Het has substituents which contain from one to three positively charged atoms and is selected from the group consisting of:

wherein:
E, G, X, Y and Z independently represent CR or N;
R represents a member selected from the group consisting of hydrogen; —$C_{1-6}$ straight- or branched-chain alkyl, unsubstituted or substituted with one to three $R^d$ groups;
with the proviso that from one to three R groups are present which contains Q;
$R^d$ represents Q;
Q is selected from the group consisting of:

wherein:
$\alpha$ represents O, S or $NR^s$;
$\beta$, $\delta$, $\lambda$, $\mu$ and $\sigma$ independently represent $CR^t$, N or $N^+R^s$ provided that no more than one of $\beta$, $\delta$, $\lambda$, $\mu$, and $\sigma$ may be $N^+R^s$;
$R^s$ represents hydrogen; phenyl; —$C_{1-6}$ straight- or branched-chain alkyl, unsubstituted or substituted with one to four $R^i$ groups;
each $R^i$ independently represents halo; —CN; —$NO_2$; phenyl; —$NHSO_2R^h$; —$OR^h$, —$SR^h$; —$N(R^h)_2$; —$N^+(R^h)_3$; —C(O)$N(R^h)_2$; —$SO_2N(R^h)_2$; heteroaryl; heteroarylium; —$CO_2R^h$; —C(O)$R^h$; —$OCOR^h$; —$NHCOR^h$; guanidinyl; carbamimidoyl or ureido;
each $R^h$ independently represents H, a —$C_{1-6}$ straight or branched-chain alkyl group, a —$C_3$-$C_6$ cycloalkyl group or phenyl, or when two $R^h$ groups are present, said $R^h$ groups may be taken in combination and represent a 4–6 membered saturated ring, optionally interrupted by one or two of O, S, $SO_2$, —C(O)—, NH and $NCH_3$;
$R^t$ represents hydrogen; halo; phenyl; —CN; —$NHR^u$; —$NR^uR^v$; —$OR^u$; —$SR^u$; —$CONR^uR^v$; —$COOR^h$; —$SOR^u$; —$SO_2R^u$; —$SO_2R^u$; —$SO_2NR^uR^v$; —$NR^uSO_2R^v$; —$COR^u$; —$NR^uCOR^v$; —$OCOR^u$; —$OCONR^uR^v$; —$NR^uCO_2R^v$; —$NR^uCONR^vR^w$; —$OCO_2R^v$; —$C_{1-6}$ straight- or branched-chain alkyl, unsubstituted or substituted with one to four $R^i$ groups;

$R^u$ and $R^v$ represent hydrogen or —$C_{1-6}$ straight- or branched-chain alkyl, unsubstituted or substituted with one to four $R^i$ groups;

or $R^u$ and $R^v$ together represent a 4–6 membered saturated ring optionally interrupted by one or more of O, S, $NR^w$ or —C(O)—, said ring being unsubstituted or substituted with one to four $R^i$ groups;

and each $R^w$ independently represents hydrogen or —$C_{1-6}$ straight- or branched-chain alkyl, unsubstituted or substituted with one to four $R^i$ groups; $C_{3-6}$ cycloalkyl optionally substituted with one to four $R^i$ groups; or phenyl optionally substituted with one to four $R^i$ groups.

21. A compound in accordance with claim 16 wherein Het is selected from the group consisting of:

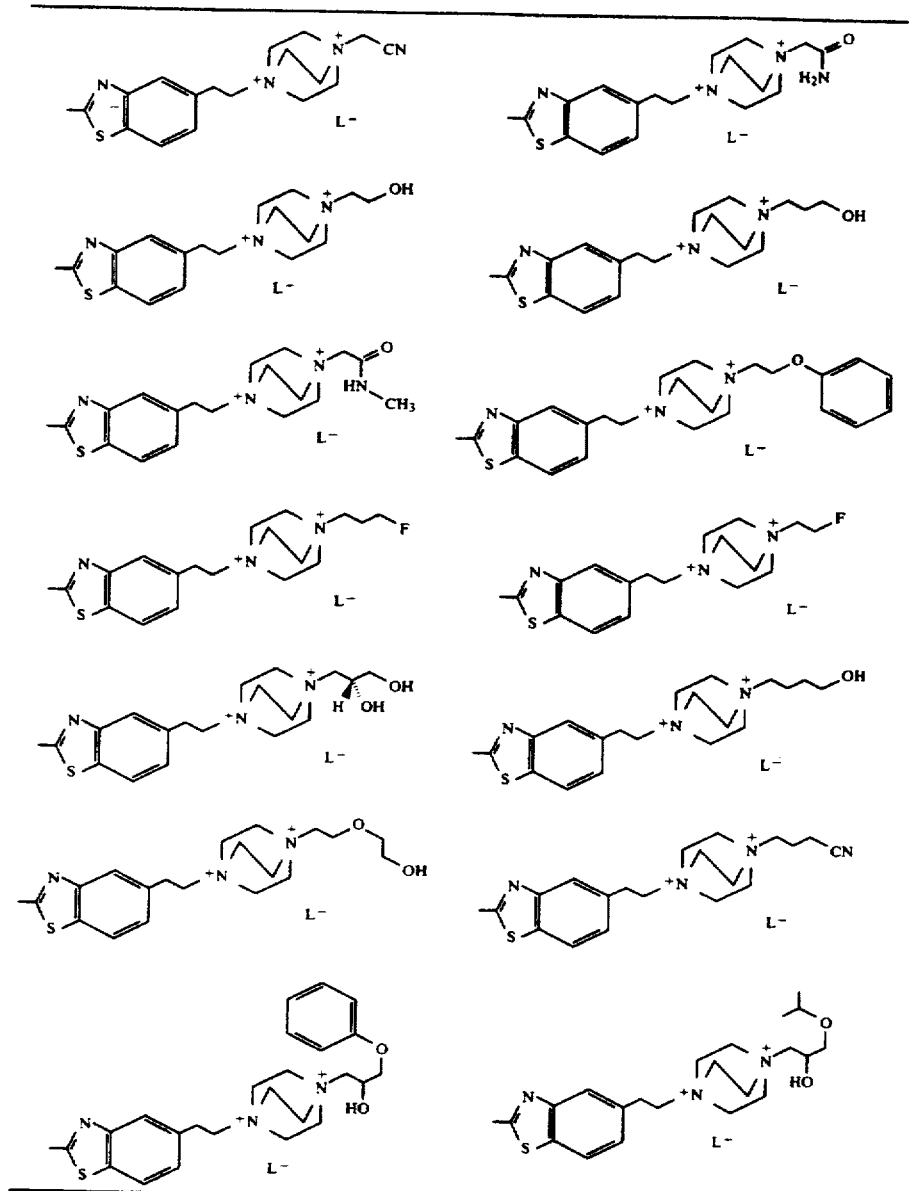

22. A compound in accordance with claim 7 wherein Het is selected from the following:

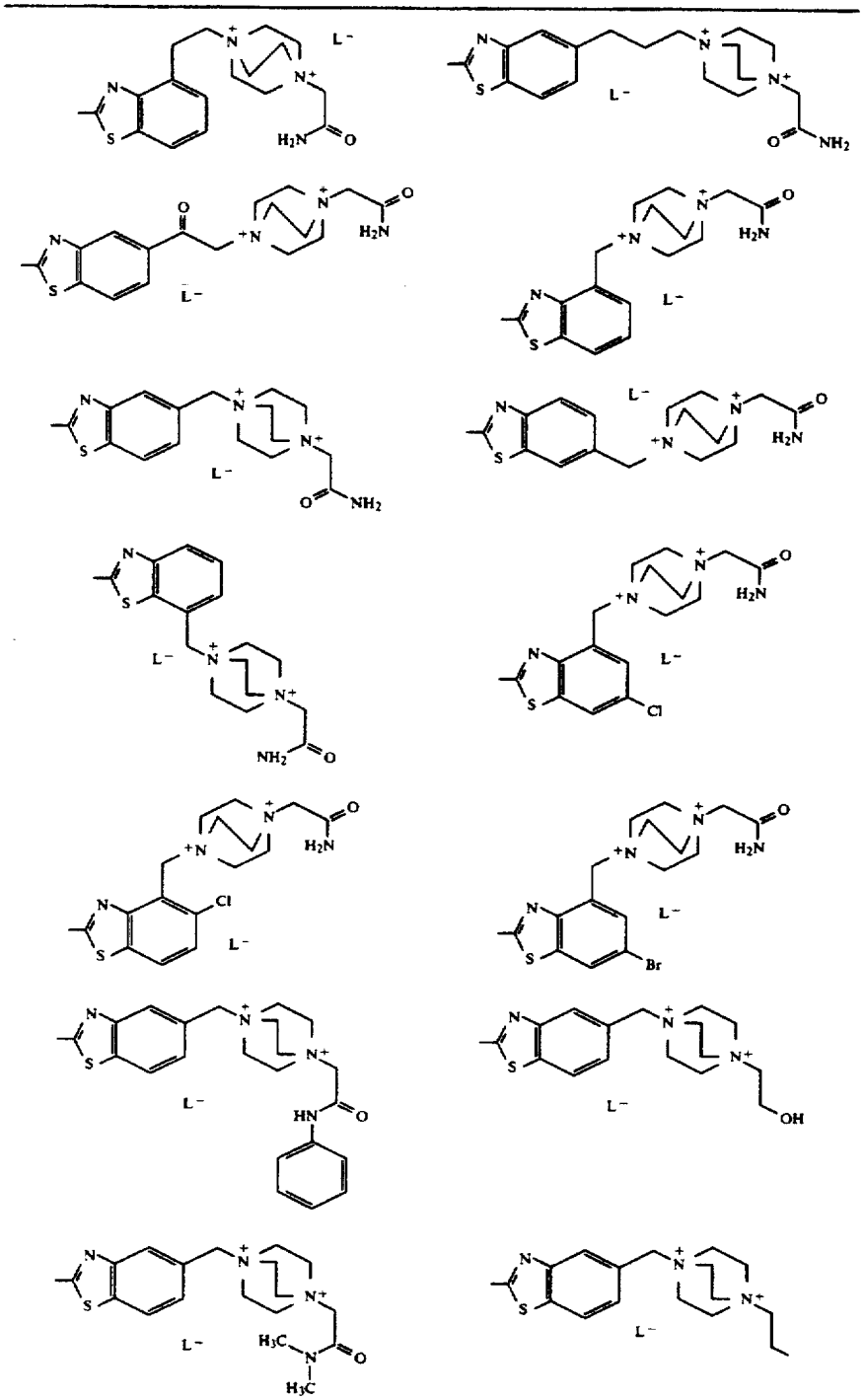

| 227 | 228 |
|---|---|
| 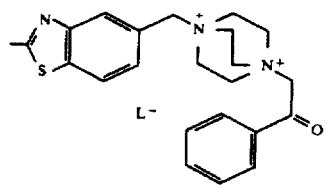 | 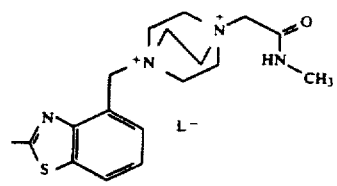 |
| 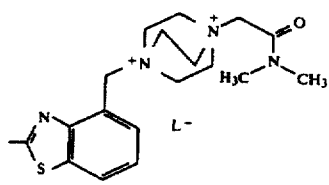 | 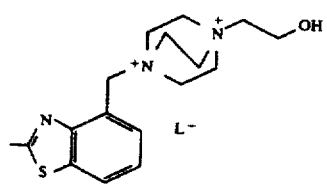 |
| 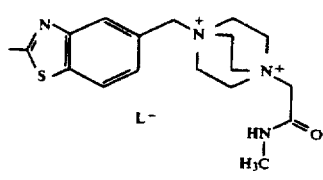 | 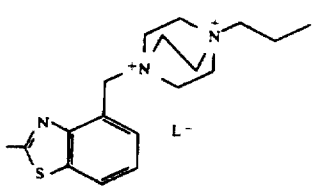 |
| 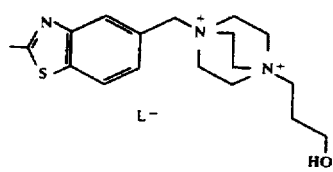 | 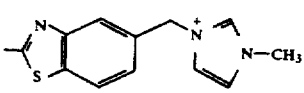 |
| 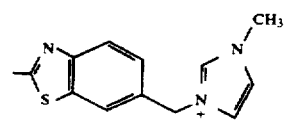 | 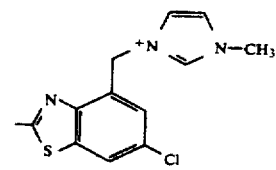 |
| 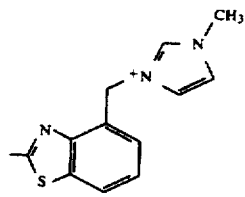 | 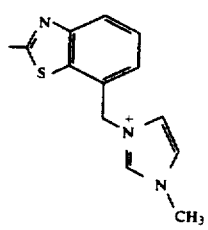 |

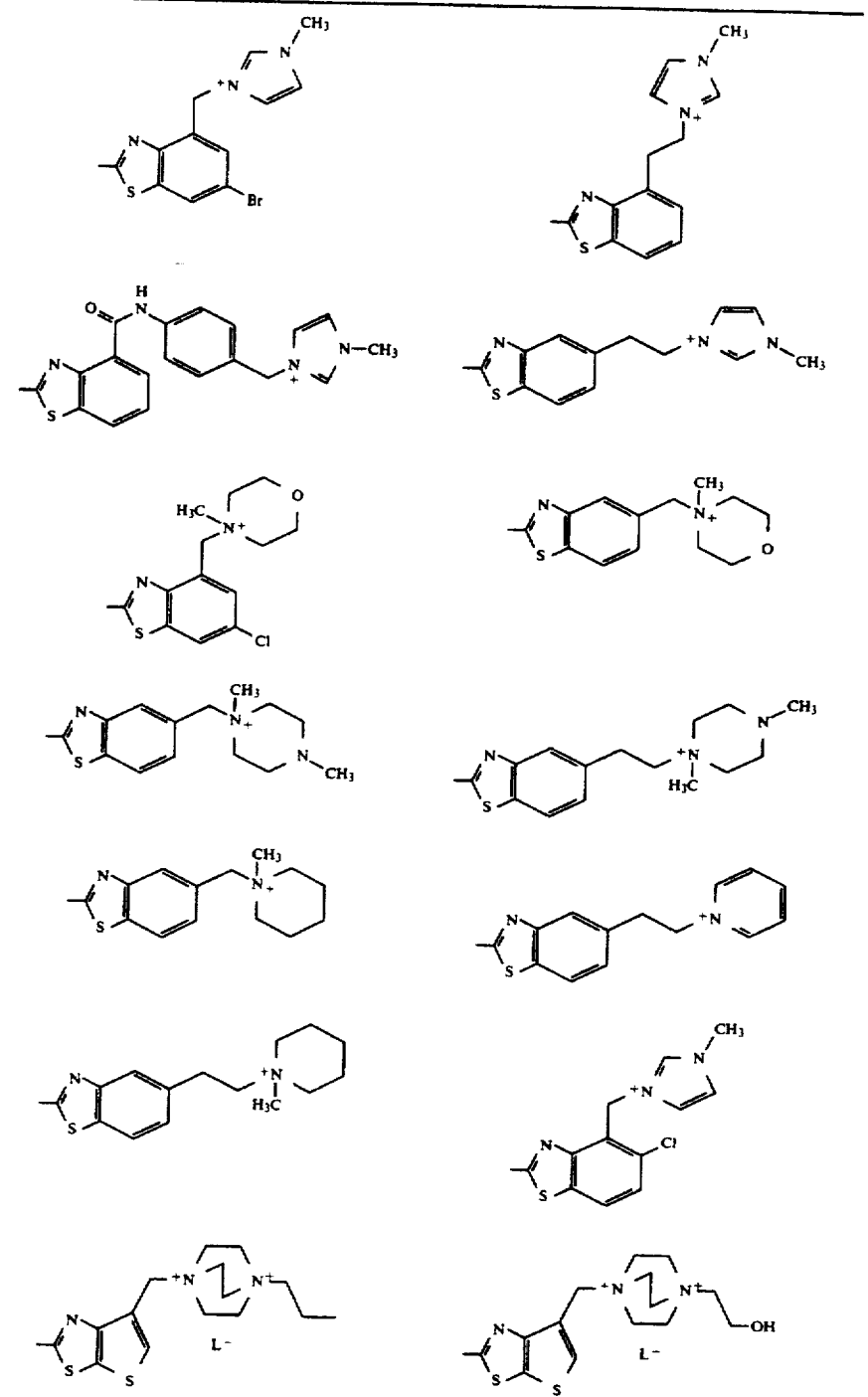

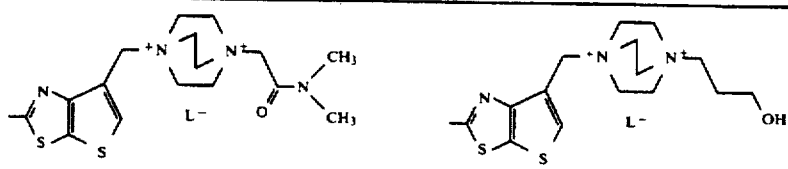
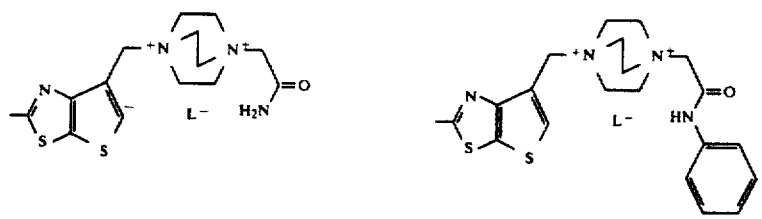
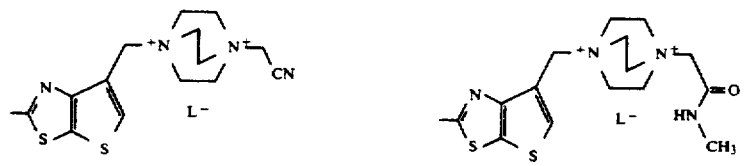
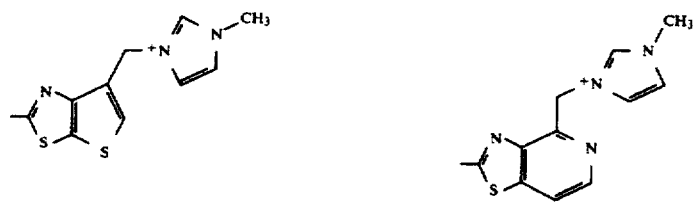
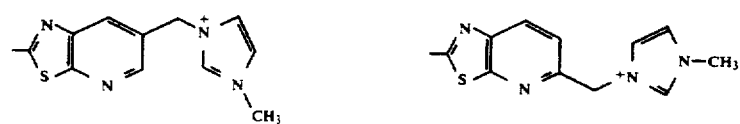
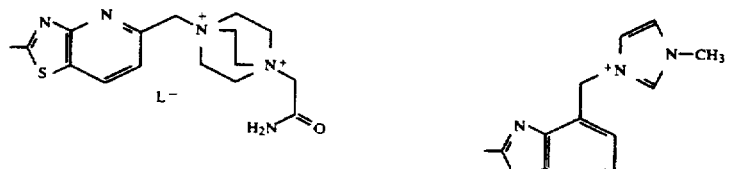
23. A compound in accordance with claim 1 wherein Het is selected from the group consisting of:
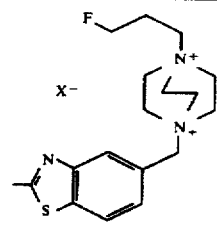

233
-continued
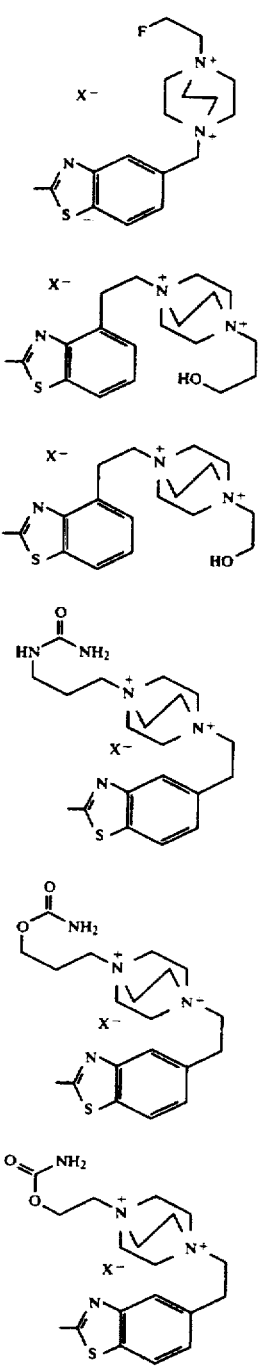
234
-continued
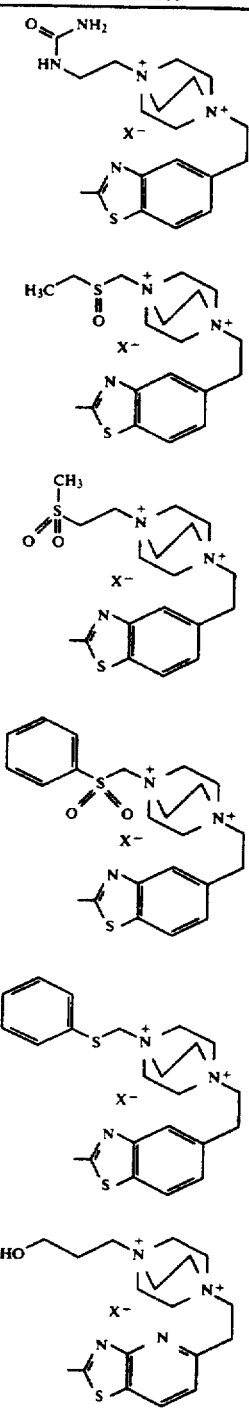

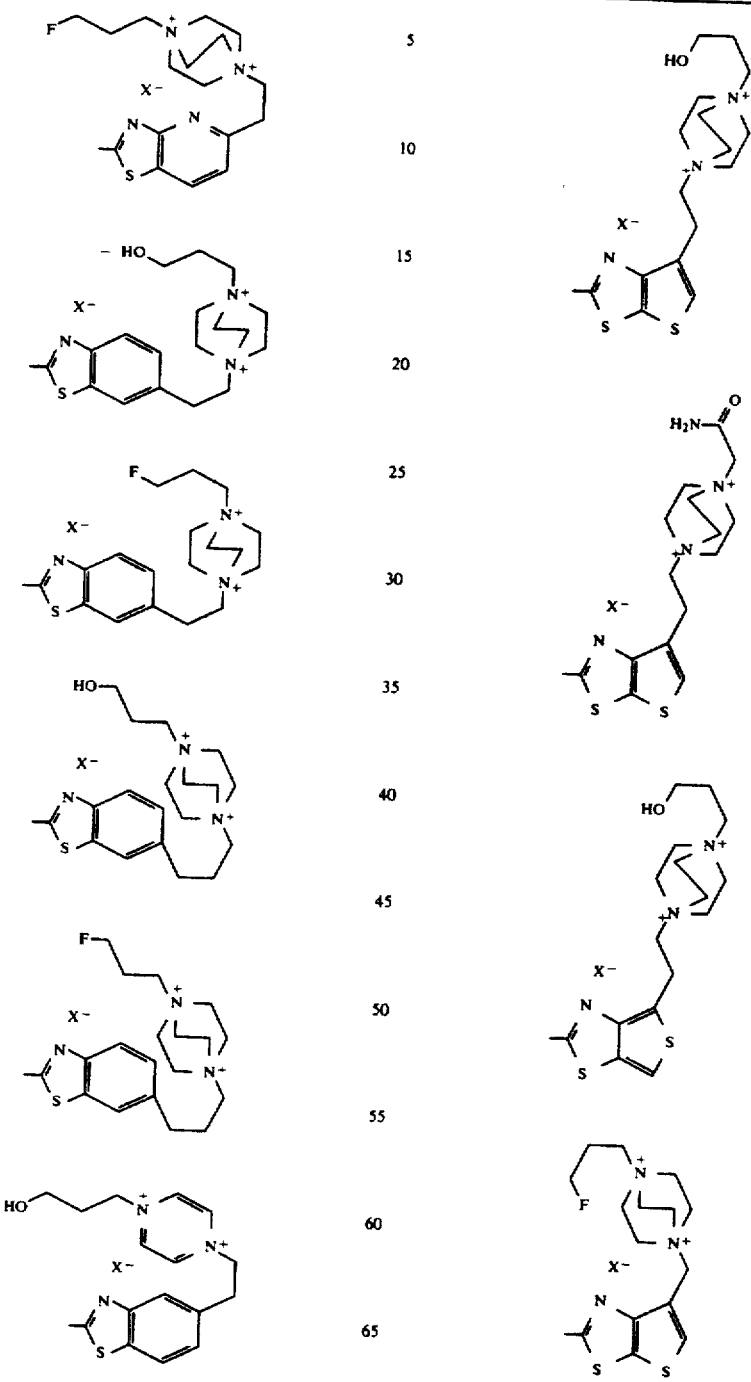

237
-continued
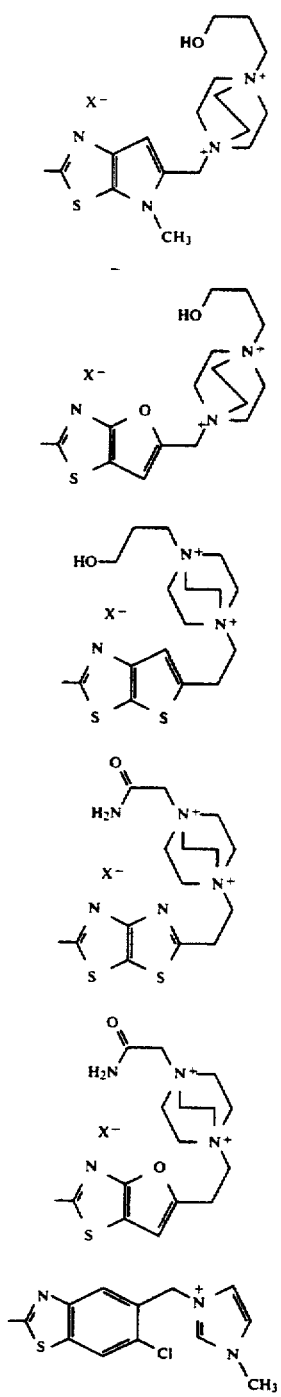
238
-continued
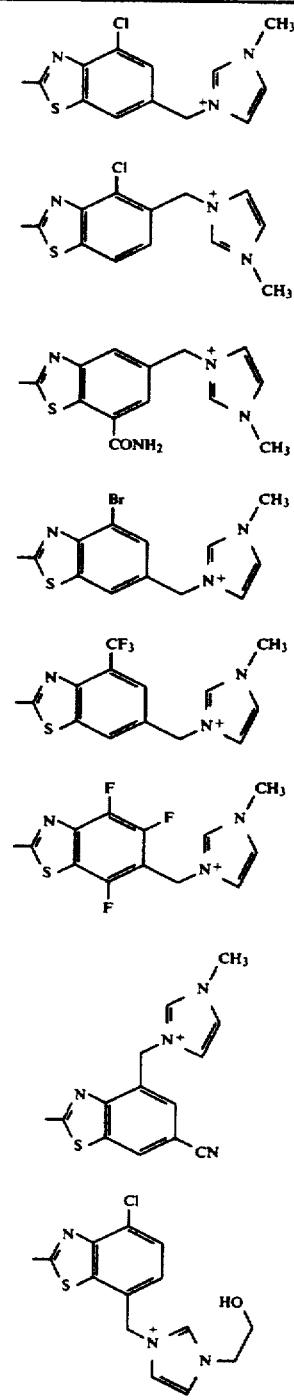

239
-continued
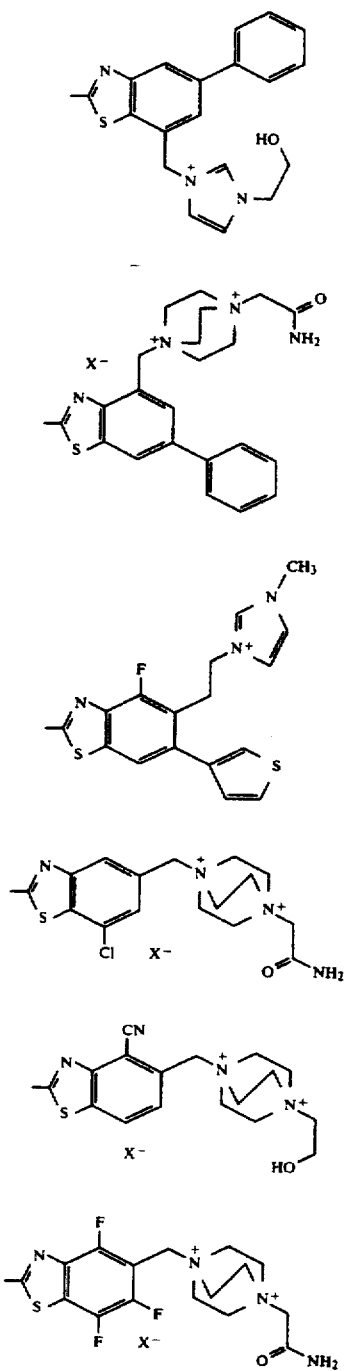
240
-continued
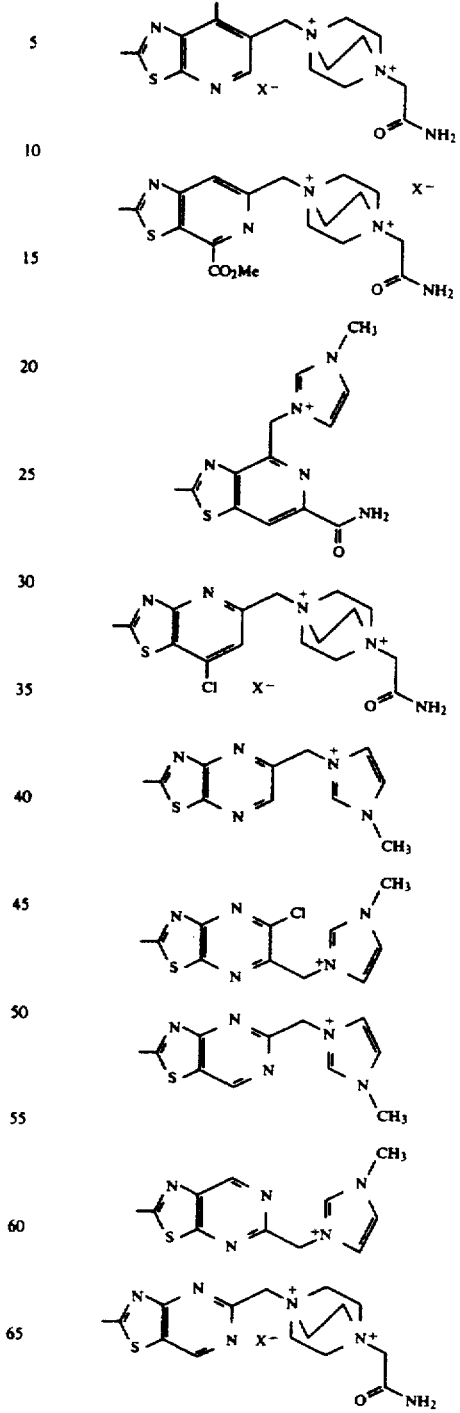

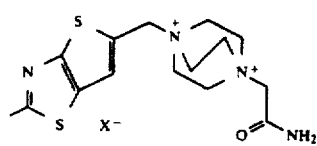
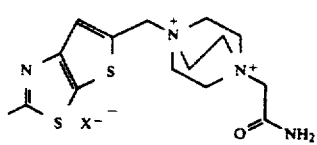
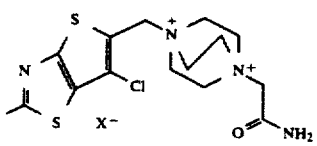
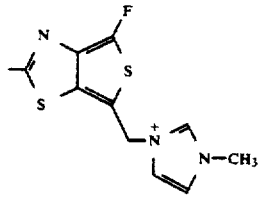
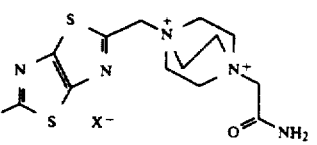
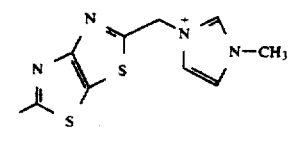
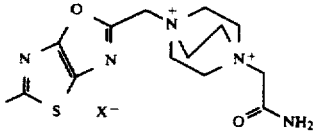
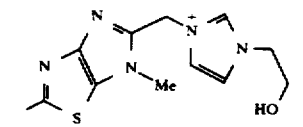
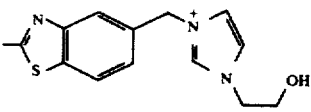
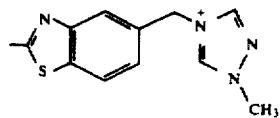
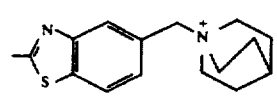
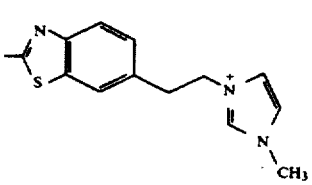
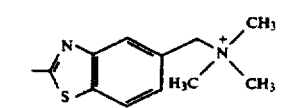
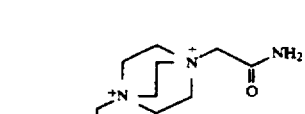

| 243 -continued | 244 -continued |
|---|---|
| 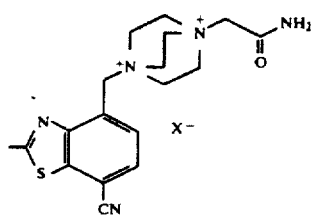 | 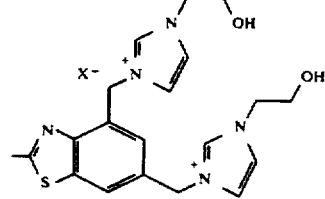 |
| 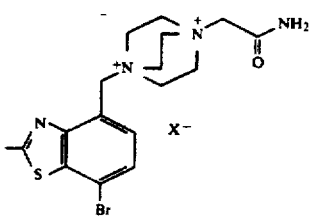 | 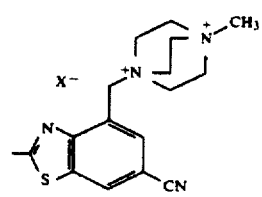 |
| 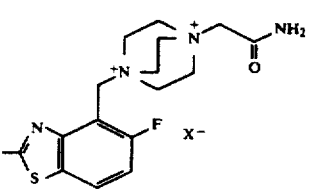 | 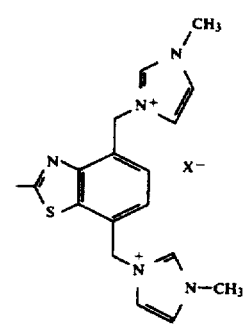 |
| 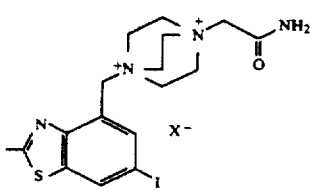 | |
| 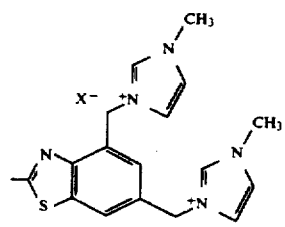 | 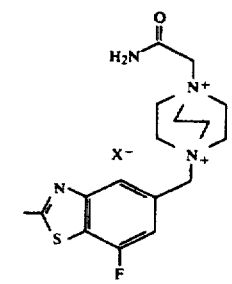 |
| 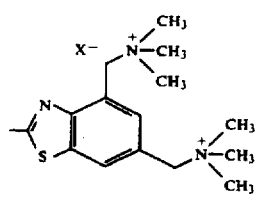 | 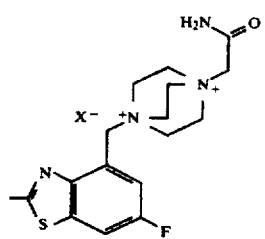 |

245
-continued

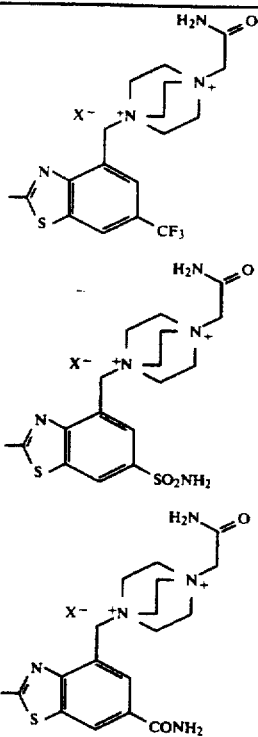

246
-continued

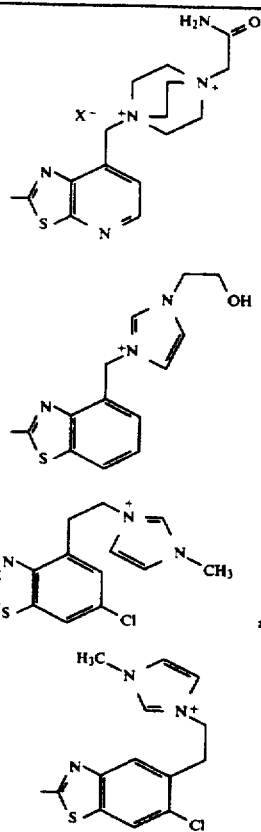

wherein X⁻ equals L⁻ and L⁻ represents a pharmaceutically acceptable counterion.

24. A compound represented by the formula:

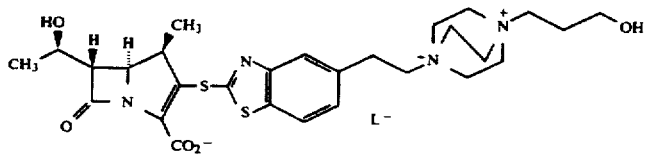

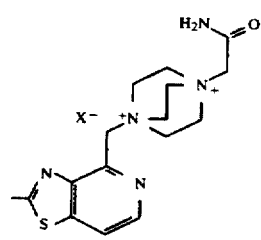

wherein L⁻ represents a pharmaceutically acceptable counterion.

25. A pharmaceutical composition comprising a pharmaceutically effective amount of the compound of claim 1 in combination with a pharmaceutically acceptable carrier.

26. A pharmaceutical composition in accordance with claim 25 in the form of a tablet, capsule, solution or suspension.

27. A pharmaceutical composition in accordance with claim 25 in the form of an injectable liquid or lyophillized solid.

28. A pharmaceutical composition in accordance with claim 25, further comprised of a DHP inhibitor.

29. A pharmaceutical composition in accordance with claim 28 wherein the DHP inhibitor is 7-(L-2-amino-2-carboxyethylthio)-2-(2,2-dimethylcyclopropanecarboxamide)-2-heptenoic acid.

30. A method of treating a bacterial infection in a mammal in need of such treatment comprising administering to said mammal a compound of claim 1 in an amount effective to treat said bacterial infection.

31. A method of treating a bacterial infection in accordance with claim 30 wherein the compound is administered orally.

32. A method of treating a bacterial infection in accordance with claim 30 wherein the compound is administered by injection.

33. A method of treating a bacterial infection in a mammalian subject in need of such treatment, comprising administering to such subject an antibacterially effective amount of a compound of claim 1 and an inhibitorily effective amount of a DHP inhibitor.

34. The method according to claim 33, wherein the DHP inhibitor is 7-(L-2-amino-2-carboxyethyl-thio)-2-(2,2-dimethylcyclopropanecarboxamide)-2-heptenoic acid.

* * * * *